(12) United States Patent
DeSimone et al.

(10) Patent No.: US 9,902,818 B2
(45) Date of Patent: *Feb. 27, 2018

(54) ISOLATED AND FIXED MICRO AND NANO STRUCTURES AND METHODS THEREOF

(71) Applicant: The University of North Carolina at Chapel Hill, Chapel Hill, NC (US)

(72) Inventors: Joseph M. DeSimone, Chapel Hill, NC (US); Ginger Denison Rothrock, Durham, NC (US); Benjamin W. Maynor, Durham, NC (US); Jason P. Rolland, Belmont, MA (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/704,047

(22) Filed: May 5, 2015

(65) Prior Publication Data
US 2015/0307669 A1 Oct. 29, 2015

Related U.S. Application Data

(63) Continuation of application No. 11/594,023, filed on Nov. 7, 2006, now Pat. No. 9,040,090, which is a continuation-in-part of application No. PCT/US2006/023722, filed on Jun. 19, 2006, said application No. 11/594,023 is a continuation-in-part of application No. PCT/US2006/034997, filed on Sep. 7, 2006, said application No. 11/594,023 is a continuation-in-part of application No. 10/583,570, filed as application No. PCT/US2004/042706 on Dec. 20, 2004, now Pat. No. 8,263,129.

(60) Provisional application No. 60/734,228, filed on Nov. 7, 2005, provisional application No. 60/762,802, filed on Jan. 27, 2006, provisional application No. 60/799,876, filed on May 12, 2006, provisional application No. 60/691,607, filed on Jun. 17, 2005, provisional application No. 60/714,961, filed on Sep. 7, 2005, provisional application No. 60/531,531, filed on Dec. 19, 2003, provisional application No. 60/583,170, filed on Jun. 25, 2004, provisional application No. 60/604,970, filed on Aug. 27, 2004.

(51) Int. Cl.
| A61K 9/14 | (2006.01) |
| C08J 5/00 | (2006.01) |
| A61K 9/51 | (2006.01) |
| B82Y 10/00 | (2011.01) |
| B82Y 40/00 | (2011.01) |
| G03F 7/00 | (2006.01) |
| B29C 59/00 | (2006.01) |
| A61K 9/00 | (2006.01) |

(52) U.S. Cl.
CPC ............... *C08J 5/00* (2013.01); *A61K 9/5138* (2013.01); *A61K 9/5192* (2013.01); *B29C 59/00* (2013.01); *B82Y 10/00* (2013.01); *B82Y 40/00* (2013.01); *G03F 7/0002* (2013.01); *A61K 9/0097* (2013.01); *A61K 9/14* (2013.01); *C08J 2335/02* (2013.01); *Y10T 428/2982* (2015.01)

(58) Field of Classification Search
None
See application file for complete search history.

(56) References Cited

U.S. PATENT DOCUMENTS

| 2,128,179 A | 7/1937 | Du Grenier |
| 3,810,874 A | 5/1974 | Mitsch et al. |
| 4,065,252 A | 12/1977 | Hemsath et al. |
| 4,131,064 A | 12/1978 | Ryan et al. |
| 4,191,321 A | 3/1980 | Samsing |
| 4,332,887 A | 6/1982 | Gerber |
| 4,352,874 A | 10/1982 | Land et al. |
| 4,353,977 A | 10/1982 | Gerber et al. |
| 4,356,257 A | 10/1982 | Gerber |
| 4,359,525 A | 11/1982 | Gerber |
| 4,359,526 A | 11/1982 | Walworth |
| 4,362,806 A | 12/1982 | Whitmore |
| 4,366,235 A | 12/1982 | Land |
| 4,512,848 A | 4/1985 | Deckman et al. |
| 4,663,274 A | 5/1987 | Slafer et al. |
| 4,697,514 A | 10/1987 | George et al. |
| 4,818,801 A | 4/1989 | Rice et al. |
| 5,041,359 A | 8/1991 | Kooi |
| 5,147,763 A | 9/1992 | Kamitakahara |
| 5,175,030 A | 12/1992 | Lu et al. |
| 5,259,926 A | 11/1993 | Kuwabara et al. |
| 5,279,689 A | 1/1994 | Shvartsman |
| 5,294,476 A | 3/1994 | Calhoun |

(Continued)

FOREIGN PATENT DOCUMENTS

| EP | 1 473 594 A2 | 11/2004 |
| EP | 1 517 181 A1 | 3/2005 |
| EP | 1 533 657 A1 | 5/2005 |
| EP | 1 551 066 A1 | 7/2005 |
| EP | 1 700 680 A1 | 9/2006 |

(Continued)

OTHER PUBLICATIONS

Ahn, S., et al., "Fabrication of a 50 nm Half-Pitch Wire Grid Polarizer Using Nanoimprint Lithography," *Nanotechnology*, 2005, pp. 1874-1877, vol. 16, Institute of Physics Publishing.

(Continued)

*Primary Examiner* — Jessica Worsham
(74) *Attorney, Agent, or Firm* — Alston & Bird LLP

(57) ABSTRACT

Discrete micro and nanoscale particles are formed in predetermined shapes and sizes and predetermined size dispersions. The particles can also be attached to a film to form arrays of particles on a film. The particles are formed from molding techniques that can include high throughput and continuous particle molding.

11 Claims, 46 Drawing Sheets

(56) References Cited

U.S. PATENT DOCUMENTS

| | | |
|---|---|---|
| 5,368,789 A | 11/1994 | Kamitakahara et al. |
| 5,425,848 A | 6/1995 | Haisma et al. |
| 5,460,831 A | 10/1995 | Kossovsky et al. |
| 5,512,131 A | 4/1996 | Kumar et al. |
| 5,630,902 A | 5/1997 | Galarneau et al. |
| 5,772,905 A | 6/1998 | Chou |
| 5,817,242 A | 10/1998 | Biebuyck et al. |
| 5,834,025 A | 11/1998 | de Garavilla et al. |
| 5,855,853 A | 1/1999 | Zauser et al. |
| 5,869,103 A | 2/1999 | Yeh et al. |
| 5,879,326 A | 3/1999 | Godshall et al. |
| 5,994,133 A | 11/1999 | Meijs et al. |
| 6,000,603 A | 12/1999 | Koskenmaki et al. |
| 6,027,595 A | 2/2000 | Suleski |
| 6,027,630 A | 2/2000 | Cohen |
| 6,083,971 A | 7/2000 | Diederich et al. |
| 6,228,318 B1 | 5/2001 | Nakamae et al. |
| 6,245,849 B1 | 6/2001 | Morales et al. |
| 6,247,986 B1 | 6/2001 | Chiu et al. |
| 6,284,072 B1 | 9/2001 | Ryan et al. |
| 6,284,345 B1 | 9/2001 | Ruoff |
| 6,294,450 B1 | 9/2001 | Chen et al. |
| 6,300,042 B1 | 10/2001 | Mancini et al. |
| 6,306,563 B1 | 10/2001 | Xu et al. |
| 6,334,960 B1 | 1/2002 | Willson et al. |
| 6,355,198 B1 | 3/2002 | Kim et al. |
| 6,375,870 B1 | 4/2002 | Visovsky et al. |
| 6,402,876 B1 | 6/2002 | McArdle et al. |
| 6,422,528 B1 | 7/2002 | Domeier et al. |
| 6,507,989 B1 | 1/2003 | Bowden et al. |
| 6,517,995 B1 | 2/2003 | Jacobson et al. |
| 6,518,189 B1 | 2/2003 | Chou |
| 6,555,221 B1 | 4/2003 | Komiyama et al. |
| 6,589,629 B1 | 7/2003 | Bao et al. |
| 6,607,683 B1 | 8/2003 | Harrington |
| 6,649,715 B1 | 11/2003 | Smith et al. |
| 6,653,030 B2 | 11/2003 | Mei et al. |
| 6,656,308 B2 | 12/2003 | Hougham et al. |
| 6,656,398 B2 | 12/2003 | Birch et al. |
| 6,660,151 B1 | 12/2003 | Lessmollmann et al. |
| 6,660,192 B1 | 12/2003 | Kim et al. |
| 6,663,820 B2 | 12/2003 | Arias et al. |
| 6,669,961 B2 | 12/2003 | Kim et al. |
| 6,686,184 B1 | 2/2004 | Anderson et al. |
| 6,696,220 B2 | 2/2004 | Bailey et al. |
| 6,699,347 B2 | 3/2004 | Lehrter et al. |
| 6,719,868 B1 | 4/2004 | Schueller et al. |
| 6,752,942 B2 | 6/2004 | Kim et al. |
| 6,753,131 B1 | 6/2004 | Rogers et al. |
| 6,755,984 B2 | 6/2004 | Lee et al. |
| 6,759,182 B2 | 7/2004 | Ikeda et al. |
| 6,770,721 B1 | 8/2004 | Kim |
| 6,783,717 B2 | 8/2004 | Hougham et al. |
| 6,808,646 B1 | 10/2004 | Jeans |
| 6,809,356 B2 | 10/2004 | Chou |
| 6,828,244 B2 | 12/2004 | Chou |
| 6,829,050 B2 | 12/2004 | Ikeda et al. |
| 6,849,558 B2 | 2/2005 | Schaper |
| 6,855,202 B2 | 2/2005 | Alivisatos et al. |
| 6,860,956 B2 | 3/2005 | Bao et al. |
| 6,869,557 B1 | 3/2005 | Wago et al. |
| 6,872,645 B2 | 3/2005 | Duan et al. |
| 6,899,827 B2 | 5/2005 | Lauf et al. |
| 6,900,881 B2 | 5/2005 | Sreenivasan et al. |
| 6,923,930 B2 | 8/2005 | Ling et al. |
| 6,929,899 B2 | 8/2005 | Pottebaum et al. |
| 6,932,934 B2 | 8/2005 | Choi et al. |
| 6,936,181 B2 | 8/2005 | Bulthaup et al. |
| 6,936,194 B2 | 8/2005 | Watts |
| 6,953,653 B2 | 10/2005 | Smith et al. |
| 6,964,793 B2 | 11/2005 | Willson et al. |
| 6,976,424 B2 | 12/2005 | Bruno et al. |
| 7,052,618 B2 | 5/2006 | Moll et al. |
| 7,056,409 B2 | 6/2006 | Dubrow |
| 7,056,834 B2 | 6/2006 | Mei et al. |
| 7,070,406 B2 | 7/2006 | Jeans |
| 7,081,269 B2 | 7/2006 | Yang et al. |
| 7,117,790 B2 | 10/2006 | Kendale et al. |
| 7,122,482 B2 | 10/2006 | Xu et al. |
| 7,141,275 B2 | 11/2006 | Chen |
| 7,142,363 B2 | 11/2006 | Sato et al. |
| 7,148,142 B1 | 12/2006 | Dakshina-Murthy et al. |
| 7,168,939 B2 | 1/2007 | Bietsch et al. |
| 7,195,733 B2 | 3/2007 | Rogers et al. |
| 7,235,464 B2 | 6/2007 | Bona et al. |
| 7,254,278 B2 | 8/2007 | Jung |
| 7,275,193 B1 | 9/2007 | Verma |
| 7,288,320 B2 | 10/2007 | Steenblik et al. |
| 7,294,294 B1 | 11/2007 | Wago et al. |
| 7,354,698 B2 | 4/2008 | Van Santen et al. |
| 2002/0172895 A1 | 11/2002 | Breen et al. |
| 2003/0006527 A1 | 1/2003 | Rabolt et al. |
| 2003/0062334 A1 | 4/2003 | Lee et al. |
| 2003/0071016 A1 | 4/2003 | Shih et al. |
| 2003/0114366 A1 | 6/2003 | Martin et al. |
| 2003/0139521 A1 | 7/2003 | Linert et al. |
| 2003/0205552 A1 | 11/2003 | Hansford et al. |
| 2004/0028804 A1 | 2/2004 | Anderson et al. |
| 2004/0046271 A1 | 3/2004 | Watts |
| 2004/0053009 A1 | 3/2004 | Ozin et al. |
| 2004/0065252 A1 | 4/2004 | Sreenivasan et al. |
| 2004/0067360 A1 | 4/2004 | Steenblik et al. |
| 2004/0097371 A1 | 5/2004 | Janbarwala |
| 2004/0110856 A1 | 6/2004 | Young et al. |
| 2004/0115239 A1 | 6/2004 | Shastri et al. |
| 2004/0115270 A1 | 6/2004 | Jani et al. |
| 2004/0115279 A1 | 6/2004 | Hansford et al. |
| 2004/0137734 A1 | 7/2004 | Chou et al. |
| 2004/0169791 A1 | 9/2004 | Nilsen et al. |
| 2004/0182820 A1 | 9/2004 | Motowaki et al. |
| 2004/0202865 A1 | 10/2004 | Homola et al. |
| 2004/0217085 A1 | 11/2004 | Jeans |
| 2004/0219246 A1 | 11/2004 | Jeans |
| 2005/0038180 A1 | 2/2005 | Jeans |
| 2005/0061773 A1 | 3/2005 | Choi et al. |
| 2005/0064209 A1 | 3/2005 | Haines et al. |
| 2005/0064452 A1 | 3/2005 | Schmid et al. |
| 2005/0120902 A1 | 6/2005 | Adams et al. |
| 2005/0133943 A1 | 6/2005 | Akutsu et al. |
| 2005/0176182 A1 | 8/2005 | Me et al. |
| 2005/0196702 A1 | 9/2005 | Bryant et al. |
| 2005/0202350 A1 | 9/2005 | Colburn et al. |
| 2005/0214661 A1 | 9/2005 | Stasiak et al. |
| 2006/0021533 A1 | 2/2006 | Jeans |
| 2006/0068128 A1 | 3/2006 | Greener et al. |
| 2006/0096477 A1 | 5/2006 | Bietsch et al. |
| 2006/0096949 A1 | 5/2006 | Watts et al. |
| 2006/0188598 A1 | 8/2006 | Jeans |
| 2006/0214326 A1 | 9/2006 | Kim et al. |
| 2006/0273480 A1 | 12/2006 | Stevenson et al. |
| 2006/0279025 A1 | 12/2006 | Heidari et al. |
| 2007/0009572 A1 | 1/2007 | Chan et al. |
| 2007/0031505 A1 | 2/2007 | Roy et al. |
| 2007/0054119 A1 | 3/2007 | Garstecki et al. |
| 2007/0243279 A1 | 10/2007 | McMackin et al. |
| 2007/0269747 A1 | 11/2007 | Bahadur et al. |
| 2008/0038398 A1 | 2/2008 | Wago et al. |

FOREIGN PATENT DOCUMENTS

| | | |
|---|---|---|
| JP | 57-025911 | 2/1982 |
| JP | 2001-158031 A | 6/2001 |
| JP | 2005-095733 | 4/2005 |
| KR | 2003-0062492 A | 7/2003 |
| WO | WO 96/017266 | 6/1996 |
| WO | WO 96/020698 | 7/1996 |
| WO | WO 96/031548 | 10/1996 |
| WO | WO 96/031791 | 10/1996 |
| WO | WO 99/34831 A1 | 7/1999 |
| WO | WO 02/014078 A2 | 2/2002 |
| WO | WO 02/024604 A1 | 3/2002 |
| WO | WO 02/029397 A2 | 4/2002 |
| WO | WO 03/005124 A1 | 1/2003 |
| WO | WO 03/031096 A2 | 4/2003 |

(56) References Cited

FOREIGN PATENT DOCUMENTS

| | | |
|---|---|---|
| WO | WO 03/072625 A1 | 9/2003 |
| WO | WO 03/092785 A1 | 11/2003 |
| WO | WO 03/098188 A2 | 11/2003 |
| WO | WO 04/033189 A1 | 4/2004 |
| WO | WO 04/096896 A2 | 11/2004 |
| WO | WO 04/097371 A2 | 11/2004 |
| WO | WO 05/047575 A1 | 5/2005 |
| WO | WO 05/054119 A2 | 6/2005 |
| WO | WO 05/059952 A2 | 6/2005 |
| WO | WO 05/089106 A2 | 9/2005 |
| WO | WO 05/101466 A2 | 10/2005 |
| WO | WO 05/104756 A2 | 11/2005 |
| WO | WO 06/012915 A1 | 2/2006 |
| WO | WO 06/030625 A1 | 3/2006 |
| WO | WO 06/041645 A2 | 4/2006 |
| WO | WO 06/071470 A2 | 7/2006 |
| WO | WO 06/083311 A2 | 8/2006 |
| WO | WO 06/121819 A1 | 11/2006 |
| WO | WO 07/021762 A2 | 2/2007 |
| WO | WO 07/024323 A2 | 3/2007 |
| WO | WO 07/030698 A2 | 3/2007 |
| WO | WO 07/043987 A2 | 4/2007 |

OTHER PUBLICATIONS

Bailey, T., et al., "Step and Flash Imprint Lithography: Template Surface Treatment and Defect Analysis," *J. Vac. Sci. Technol. B.*, 2000, pp. 3572-3577, vol. 18(6).

Barton, J.E. et. al., "Mass-Limited Growth in Zeptoliter Beakers: A General Approach for the Synthesis of Nanocrystals," *Nano Lett.*, Jul. 2004, pp. 1555-1528, vol. 4(8).

Becker, H. and C. Gartner, "Polymer Microfabrication Methods for Microfluidic Analytical Applications," *Electrophoresis*, 2000, pp. 12-26, vol. 21.

Bongiovanni, R., et al., "Fluorinated Networks Through Photopolymerisation Processes: Synthesis, Characterization and Properties," *J. Fluor. Chem.*, 2004, pp. 345-351, vol. 125, Elsevier.

Bongiovanni, R., et al., "Perfluoropolyether Structures as Surface Modifying Agents of UV-Curable Systems," *Macromol. Chem. Phys.*, 1998, pp. 1099-1105, vol. 199.

Chan-Park, M.B., et al., "Simulation and Investigation of Factors Affecting High Aspect Ratio UV Embossing," *Langmuir*, 2005, pp. 2000-2007, vol. 21, American Chemical Society.

Choi, S-J., et al., "An Ultraviolet-Curable Mold for Sub-100-Nm Lithography," *J. Am. Chem. Soc.*, 2004, pp. 7744-7745, vol. 126.

Choi, W.M. and O.O. Park, "A Soft-Imprint Technique for Direct Fabrication of Submicron Scale Patterns Using a Surface-Modified Pdms Mold," *Microelect. Eng.*, 2003, pp. 131-136, vol. 70, Elsevier.

Chou, S.Y. and P.R. Krauss, "Imprint Lithography with Sub-10 nm Feature Size and High Throughput," *Microelect. Eng.*, 1997, pp. 237-240, vol. 35.

Chou, S.Y., et al., "Imprint of Sub-25 nm Vias and Trenches in Polymers," *Appl. Phys. Lett.*, 1995, pp. 3114-3116, vol. 67(21).

Colburn, M., "Capillary Fill Time & Meniscus Shape: An Asymmetric, Nonequal Contact Angle, Coplanar Cavity Study," *ChE 385 Project Report*, Available Online at Willson.cm.utexas.edu- . . . -Surface_Phenomena-Spring1999Asymetric_Noon_equal_contact_angle_capillary_study, Dec. 3, 1998.

Cooper, K.P., "Layered Manufacturing: Challenges and Opportunities," *Mat. Res. Soc. Symp. Proc*, 2003, pp. LL1.4.1-LL1.4.12.

El-Sayed, M.A., "Some Interesting Properties of Metals Confined in Time and Nanometer Space of Different Shapes," *Accts. Chem. Res.*, 2001, pp. 257-264, vol. 34(4).

Gadegaard, N., et al., "Biomimetic Polymer Nanostructures by Injection Molding," *Macromol. Mater. Eng.*, 2003, pp. 76-83, vol. 288(1).

Gates, B., et al., "New Approaches to Nanofabrication: Molding, Printing and Other Techniques," *Chem. Rev.*, 2005, pp. 1171-1196, vol. 105(4).

Haatainen, T and J. Ahopelto, "Step & Stamp Imprint Lithography: A Versatile Method for Nanoimprinting," presented at the NNT Conference, Dec. 11-13, 2002 at San-Francisco, CA.

Haatainen, T., and J. Ahopelto, "Pattern Transfer Using Step & Stamp Imprint Lithography," *Physica. Scripta.*, 2003, pp. 357-360, vol. 67.

Haatainen, T., et. al., "Step & Stamp Imprint Lithography Using a Commercial Flip Chip Bonder," *Proceeding of SPIE's 25th Annual International Symposium of Microlithography, Emerging Lithographic Technologies IV* at Santa Clara, CA, 2000, pp. 1-10.

Haisma, J., et al., "Mold-Assisted Nanolithography: A Process for Reliable Pattern Replication," *J. Vac. Sci. Technol.*, 1996, pp. 4124-4128, vol. B14(6).

Hirai, Y., et al., "Mold Surface Treatment for Imprint Lithography," *Journal of Photopolymer Science and Technology*, 2001, pp. 457-462, vol. 14(3).

Hua, F., et al., "Polymer Imprint Lithography with Molecular-Scale Resolution," *Nano Letters*, 2004, pp. 2467-2471, vol. 4(12).

Hulteen, J.C. and C.R. Martin, "A General Template-Based Method for the Preparation of Nanomaterials," *J. Mater. Chem.*, 1997, pp. 1075-1087, vol. 7(7).

Jackman, R., et al., "Fabricating Large Arrays of Microwells with Arbitrary Dimensions and Filling Them Using Discontinuous Dewetting," *Analytical Chemistry*, 1998, pp. 2280-2287, vol. 70(11).

Jiang, P., et al., "A Lost-Wax Approach to Monodisperse Colloids and Their Crystals," *Science*, 2001, pp. 453-457, vol. 291.

Katz, E. and I. Willner, "Integrated Nanoparticle-Biomolecule Hybrid Systems: Synthesis, Properties, and Applications," *Angew. Chem. Int. Ed.*, 2004, pp. 6042-6108, vol. 43.

Khang, D. and H.L. Hong, "Pressure-Assisted Capillary Force Lithography," *Adv. Mater.*, 2004, pp. 176-179, vol. 16(2).

Krauss, P., et al., Fabrication of Nanodevices Using Sub-25 nm Imprint Lithography, *Presented at NanoStructure Laboratory, Department of Electrical Engineering, University of Minnesota, Minneapolis, MN*, pp. 194-195.

Lee, J.-H., et al., "Two-Polymer Microtransfer Molding for Highly Layered Microstructures," *Adv. Mater.*, 2005, pp. 2481-2485, vol. 17.

Marzolin, C., et al., "Fabrication of Glass Microstructures by Micro-Molding of Sol-Gel Precursors," *Adv.Mater.*, 1998, pp. 571-574, vol. 10(8).

Meiring, J. E., et al., "Hydrogel Biosensor Array Platform Indexed by Shape," *Chem. Mater.*, 2004, pp. 5574-5580, vol. 16.

Moran, P. M. and C. Robert, "Microstamping of Freestanding Bipolymer Features," *American Institute of Physics*, 2001, pp. 3741-3743, vol. 78(23).

Nicewarner-Peña, S., et al., "Submicrometer Metallic Barcodes," *Science*, 2001, pp. 137141., vol. 294.

Payne, E.K., et al., "Sacrificial Biological Templates for the Formation of Nanostructured Metallic Microshells," *Angew. Chem. Intl. Ed.*, 2005, pp. 5064-5067, vol. 44.

Pileni, M., "The Role of Soft Colloidal Templates in Controlling the Size and Shape of Inorganic Nanocrystals," *Nature Materials*, 2003, pp. 145-150, vol. 2, Nature Publishing Group.

Rejman, J., et al., "Size-Dependent Internalization of Particles Via the Pathways of Clathrin-and Caveolae-Mediated Endocytosis," *Biochem. J.*, 2004, pp. 159-169., vol. 377.

Rogers, J. A. and R.G. Nuzzo, "Recent Progress in Soft Lithography," *Materialstoday*, Feb. 2005, pp. 50-56, Elsevier Ltd.

Rolland, J. P., et al., "Direct Fabrication and Harvesting of Monodisperse, Shape-Specific Nanobliomaterials," *J. Am. Chem. Soc.*, 2005, pp. 10096-10100, vol. 127(28).

Rolland, J. P., et al., Solvent-Resistant Photocurable "Liquid Teflon" for Microfluidic Device Fabrication, *J. Am. Chem. Soc.*, 2004, pp. 2322-2323, vol. 126.

Rolland, J.P., et al., "High-Resolution Soft Lithography: Enabling Materials for Nanotechnologies," *Angew. Chem. Int. Ed.*, 2004, pp. 5796-5799, vol. 43.

(56) References Cited

OTHER PUBLICATIONS

Rolland, M.P., "Functional Perfluoropolyethers for Novel Applications," Dissertation Submitted to The Faculty of The University of North Carolina At Chapel Hill in Partial Fulfillment of the Requirements for The Degree of Doctorate of Philosophy in the Dept. of Chemistry, 2005, pp. 1-183.

Sosa, I. O., et al., "Optical Properties of Metal Nanoparticles with Arbitrary Shapes," *J. Phys. Chem.*, 2003, pp. 6269-6275, vol. 107.

Suh, D., et al., "Rigiflex Lithography for Nanostructure Transfer," *Adv. Mater.*, 2005, pp. 1554-1560, vol. 17.

Suh, K.Y., and H.H. Lee, "Capillary Force Lithography: Large-Area Patterning, Self-Organization, and Anisotropic Dewetting," *Adv. Funct. Mater.*, 2002, pp. 405-413, vol. 12(6+7).

Suh, K.Y., et al., "Capillary Force Lithography," *Adv. Mater.*, 2001, pp. 1386-1389, vol. 13(18).

Suh, K.Y., et al., "Observation of High-Aspect-Ratio Nanostructures Using Capillary Lithography," *Adv. Mater.*, 2005, pp. 560-564, vol. 17(5).

Sun, Y. and Y. Xia, "Shape-Controlled Synthesis of Gold and Silver Nanoparticles," *Science*, 2002, pp. 2176-2179, vol. 298.

Tan, H., et al., "Roller Nanoimprint Lithography," *J. Vac. Sci. Technol.*, 1998, pp. 3926-3928, vol. B16(6).

Tao, S.L. and T.A. Desai, "Microfabrication of Multilayer, Asymmetric, Polymeric Devices for Drug Delivery," *Adv. Mater.*, 2005, pp. 1625-1630, vol. 17.

Tien, J., et al., "Crystallization of Millimeter-Scale Objects with Use of Capillary Forces," *J. Am. Chem. Soc.*, 1998, pp. 12670-12671, vol. 120.

Trombetta, T., et al., "Novel Branched Fluorinated Oligourethane Cationomers for Low Surface Tension Treatments," *Progr. Colloid. Polym. Sci.*, 2004, pp. 47-53, vol. 124.

Turri, S., et al., "Novel Glass Fiber-Reinforced Composites Having a UV and Peroxy Curable Fluoropolymer Matrix," *Macromol. Mater. Eng.*, 2003, pp. 708-716, vol. 288(9).

Wood, C.D., et al., "New Fluoropolymer Materials," *J. Fluor. Chem.*, 2004, pp. 1671-1676, vol. 125, Elsevier.

Xia, Y. and G.M. Whitesides, "Soft Lithography," *Agnew. Chem. Ed.*, 1998, pp. 550-575, vol. 37.

Xia, Y., et al., "Complex Optical Surfaces by Replica Molding Against Elastomeric Masters," *Sci. New Series*, 1996, pp. 347-349, vol. 274(5273).

Yin, Y. and Y. Xia, "Self-Assembly of Monodispersed Spherical Colloids into Complex Aggregates with Well-Defined Sizes, Shapes, and Structures," *Adv. Mater.*, 2001, pp. 267-271, vol. 13(4).

Yin, Y., et al., "A soft lithography approach to the fabrication of nanostructures of single crystalline silicon with well-defined dimensions and shapes", *Advanced Materials*, 2000, pp. 1426-1430, vol. 12(19).

Zhao, X-M., et al., "Soft Lithographic Methods for Nano-Fabrication," *J. Mater. Chem.*, 1997, pp. 1069-1074, vol. 7(7).

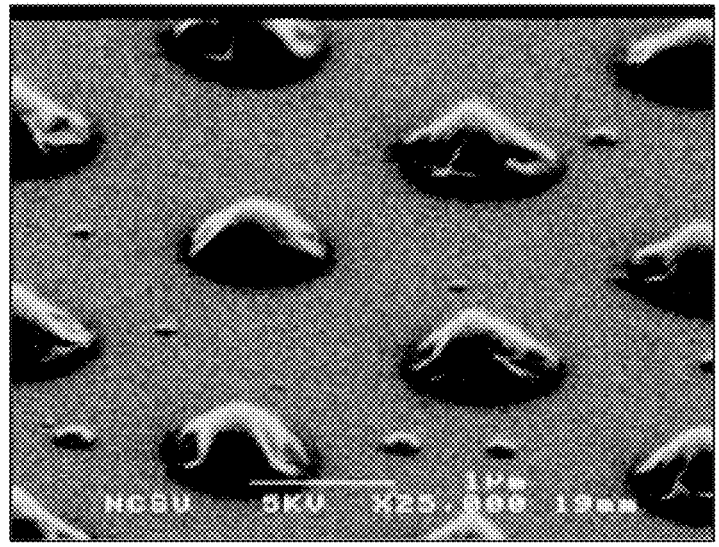
FIG. 27
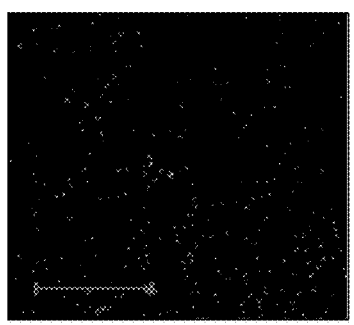 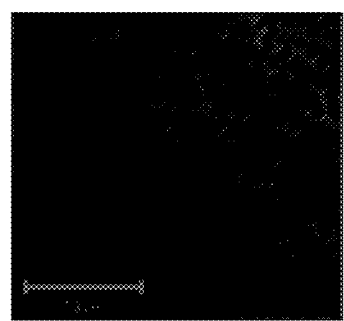 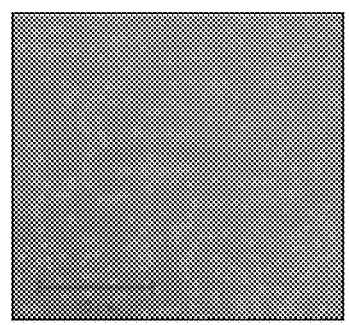
FIG. 28A     FIG. 28B     FIG. 28C

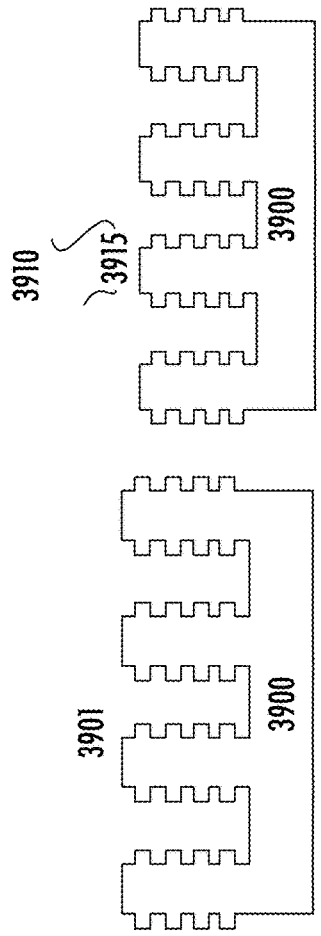
FIG. 39A
FIG. 39B
FIG. 39C
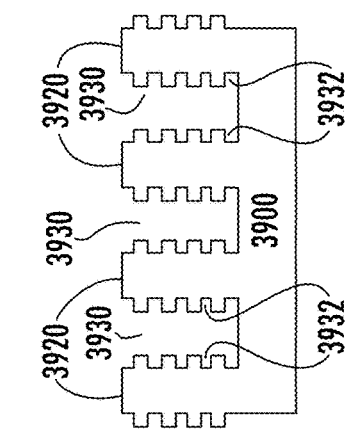
FIG. 39D
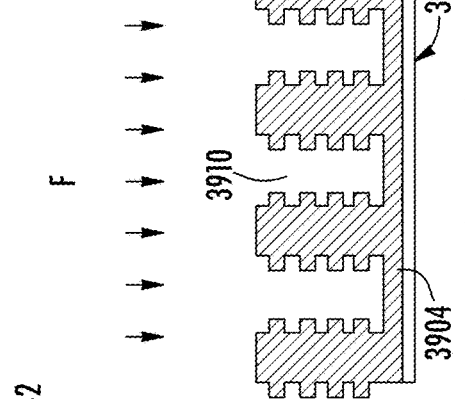
FIG. 39E
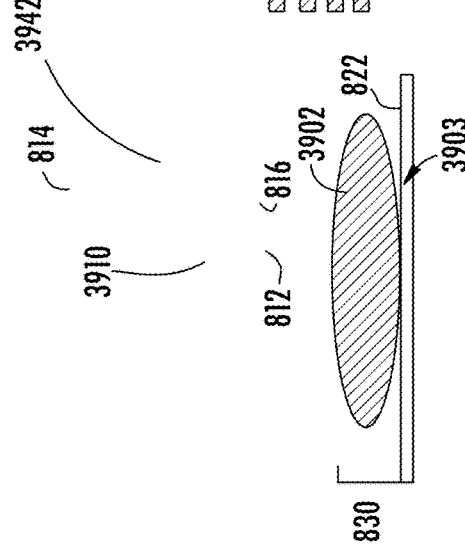
FIG. 39F

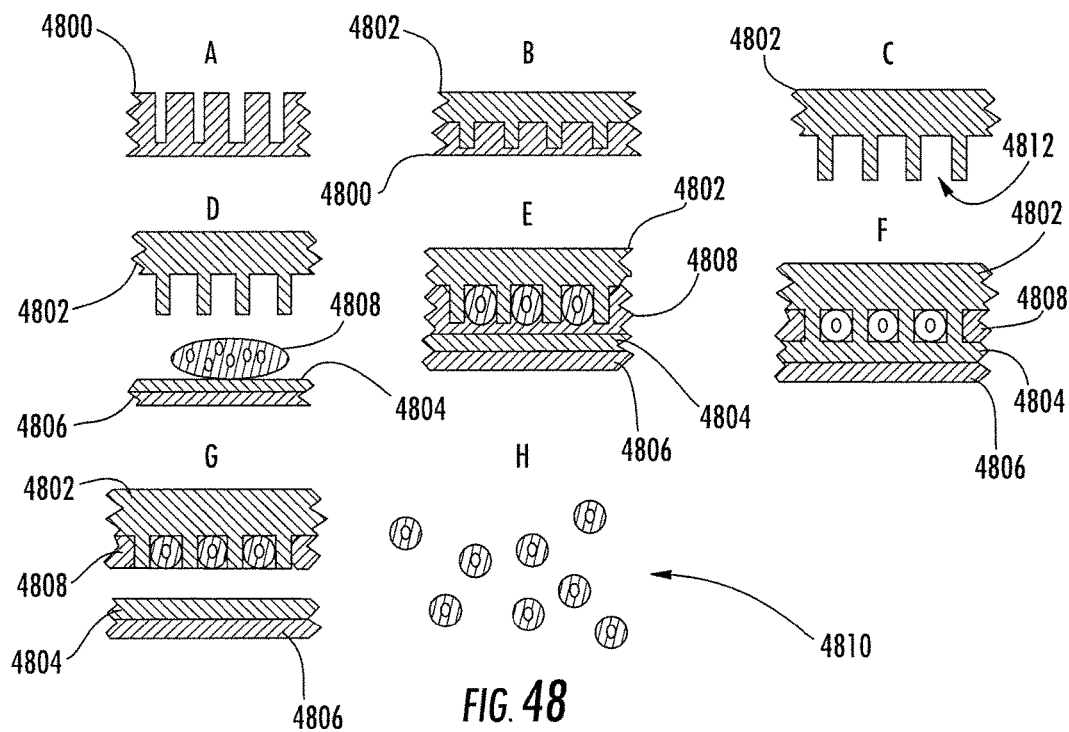
FIG. 48
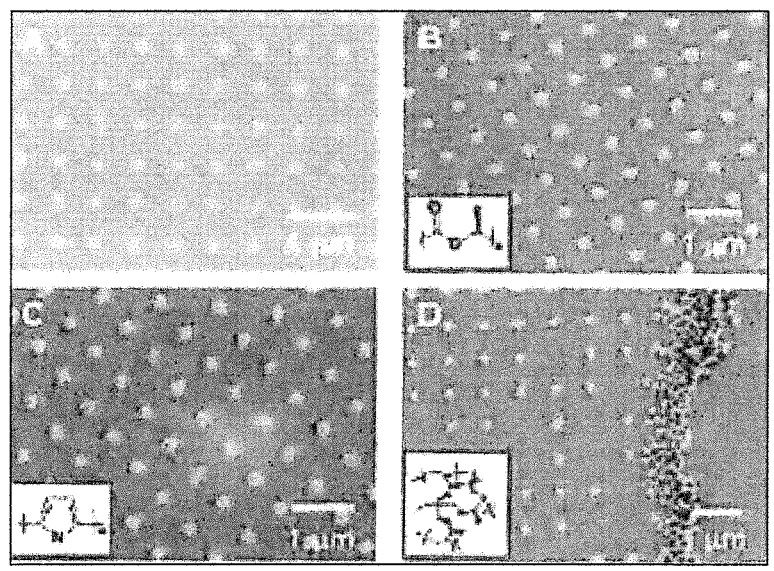
FIG. 49A-D

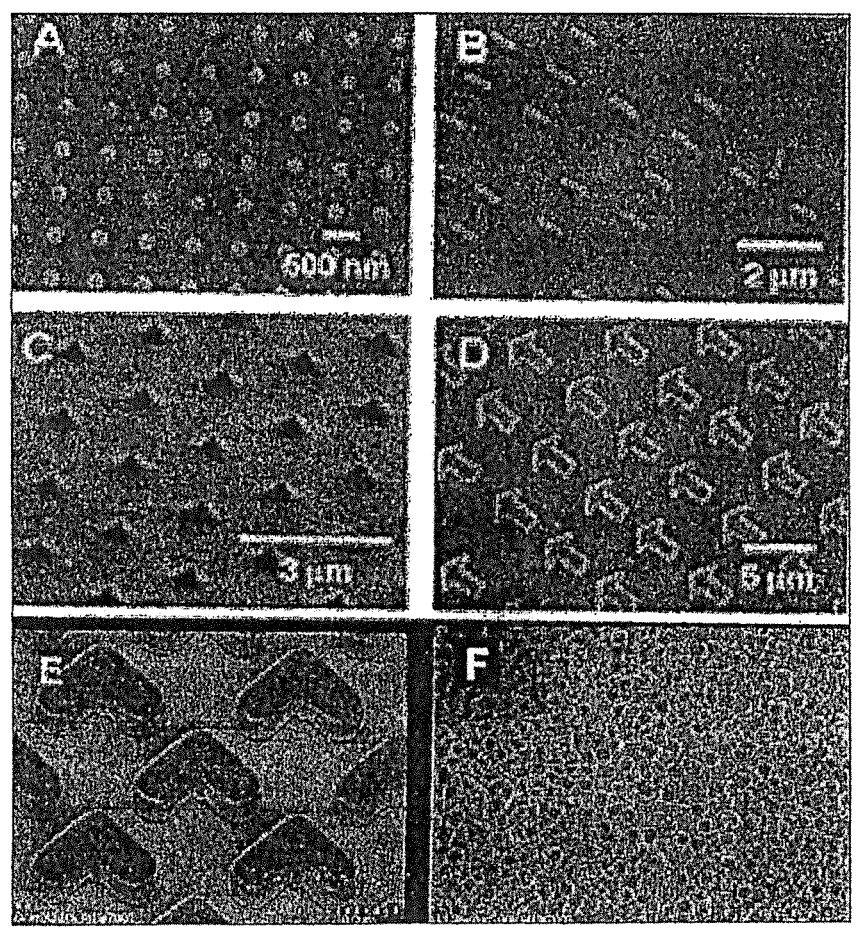
FIG. 50A-F

ISOLATED AND FIXED MICRO AND NANO STRUCTURES AND METHODS THEREOF

CROSS REFERENCE TO RELATED APPLICATIONS

This is a continuation of U.S. patent application Ser. No. 11/594,023, filed Nov. 7, 2006, which claims priority application to U.S. Provisional Patent Application Ser. No. 60/734,228, filed Nov. 7, 2005; U.S. Provisional Patent Application Ser. No. 60/762,802, filed Jan. 27, 2006; and U.S. Provisional Patent Application No. 60/799,876, filed May 12, 2006; the disclosure of each of which is incorporated herein by reference in its entirety.

This application is also a continuation-in-part of PCT International Application Serial No. PCT/US06/23722, filed Jun. 19, 2006, which is based on and claims priority to U.S. Provisional Patent Application Ser. No. 60/691,607, filed Jun. 17, 2005; U.S. Provisional Patent Application Ser. No. 60/714,961, filed Sep. 7, 2005; U.S. Provisional Patent Application Ser. No. 60/762,802, filed Jan. 27, 2006; and U.S. Provisional Patent Application No. 60/799,876, filed May 12, 2006; each of which is incorporated herein by reference in its entirety.

This application is also a continuation-in-part of PCT International Application Serial No. PCT/US06/34997, filed Sep. 7, 2006, which is based on and claims priority to U.S. Provisional Patent Application Ser. No. 60/714,961, filed Sep. 7, 2005; U.S. Provisional Patent Application Ser. No. 60/734,228, filed Nov. 7, 2005; U.S. Provisional Patent Application Ser. No. 60/762,802, filed Jan. 27, 2006; and U.S. Provisional Patent Application No. 60/799,876, filed May 12, 2006; each of which is incorporated herein by reference in its entirety.

This application is also a continuation-in-part of U.S. patent application Ser. No. 10/583,570, filed Jun. 19, 2006, which is based on and claims priority to PCT International Patent Application Serial No. PCT/US04/42706, filed Dec. 20, 2004, which is based on and claims priority to U.S. Provisional Patent Application Ser. No. 60/531,531, filed Dec. 19, 2003; U.S. Provisional Patent Application Ser. No. 60/583,170, filed Jun. 25, 2004; and U.S. Provisional Patent Application Ser. No. 60/604,970, filed Aug. 27, 2004, each of which is incorporated herein by reference in its entirety.

GOVERNMENT INTEREST

A portion of the disclosure contained herein was made with U.S. Government support from the Office of Naval Research Grant No. N00014210185 and the Science and Technology Center program of the National Science Foundation under Agreement No. CHE-9876674. The U.S. Government has certain rights to that portion of the disclosure.

INCORPORATION BY REFERENCE

All documents referenced herein are hereby incorporated by reference as if set forth in their entirety herein.

TECHNICAL FIELD

Generally, the present disclosure relates to micro and nanoscale particles and methods for forming the particles.

ABBREVIATIONS

° C.=degrees Celsius
cm=centimeter
DBTDA=dibutyltin diacetate
DMA=dimethylacrylate
DMPA=2,2-dimethoxy-2-phenylacetophenone
EIM=2-isocyanatoethyl methacrylate
FEP=fluorinated ethylene propylene
Freon 113=1,1,2-trichlorotrifluoroethane
g=grams
h=hours
Hz=hertz
IL=imprint lithography
kg=kilograms
kHz=kilohertz
kPa=kilopascal
MCP=microcontact printing
MEMS=micro-electro-mechanical system
MHz=megahertz
MIMIC=micro-molding in capillaries
mL=milliliters
mm=millimeters
mmol=millimoles
mN=milli-Newton
m.p.=melting point
mW=milliwatts
NCM=nano-contact molding
NIL=nanoimprint lithography
nm=nanometers
PDMS=polydimethylsiloxane
PEG poly(ethylene glycol)
PFPE=perfluoropolyether
PLA poly(lactic acid)
PP=polypropylene
Ppy=poly(pyrrole)
psi=pounds per square inch
PVDF=poly(vinylidene fluoride)
PTFE=polytetrafluoroethylene
SAMIM=solvent-assisted micro-molding
SEM=scanning electron microscopy
S-FIL="step and flash" imprint lithography
Si=silicon
Tg=glass transition temperature
Tm=crystalline melting temperature
TMPTA=trimethylolpropane triacrylate
μm=micrometers
UV=ultraviolet
W=watts
ZDOL=poly(tetrafluoroethylene oxide-co-difluoromethylene oxide)α,ω diol

BACKGROUND

The availability of viable nanofabrication processes is a key factor to realizing the potential of nanotechnologies. In particular, the availability of viable nanofabrication processes is important to the fields of photonics, electronics, and proteomics. Traditional imprint lithographic (IL) techniques are an alternative to photolithography for manufacturing integrated circuits, micro- and nano-fluidic devices, and other devices with micrometer and/or nanometer sized features. There is a need in the art, however, for new materials to advance IL techniques. See Xia, Y., et al., *Angew. Chem. Int. Ed.*, 1998, 37, 550-575; Xia, Y., et al., *Chem. Rev.*, 1999, 99, 1823-1848; Resnick, D. J., et al., *Semiconductor International*, 2002, June, 71-78; Choi, K. M., et al., *J. Am. Chem. Soc.*, 2003, 125, 4060-4061; McClelland, G. M., et al., *Appl. Phys. Lett.*, 2002, 81, 1483; Chou, S. Y., et al., *J. Vac. Sci. Technol. B*, 1996, 14, 4129; Otto, M., et al., *Microelectron. Eng.*, 2001, 57, 361; and Bailey, T., et al., *J. Vac. Sci. Technol., B*, 2000, 18, 3571.

Imprint lithography includes at least two areas: (1) soft lithographic techniques, see Xia, Y., et al., *Angew. Chem. Int. Ed.,* 1998, 37, 550-575, such as solvent-assisted micro-molding (SAMIM); micro-molding in capillaries (MIMIC); and microcontact printing (MCP); and (2) rigid imprint lithographic techniques, such as nano-contact molding (NCM), see McClelland, G. M., et al., *Appl. Phys. Lett.,* 2002, 81, 1483; Otto, M., et al., *Microelectron. Eng.,* 2001, 57, 361; "step and flash" imprint lithographic (S-FIL), see Bailey, T., et al., *J. Vac. Sci. Technol., B,* 2000, 18, 3571; and nanoimprint lithography (NIL), see Chou, S. Y., et al., *J. Vac. Sci. Technol. B,* 1996, 14, 4129.

Polydimethylsiloxane (PDMS) based networks have been the material of choice for much of the work in soft lithography. See Quake, S. R., et al., *Science,* 2000, 290, 1536; Y. N. Xia and G. M. Whitesides, *Angew. Chem. Int. Ed. Engl.* 1998, 37, 551; and Y. N. Xia, et al., *Chem. Rev.* 1999, 99, 1823.

The use of soft, elastomeric materials, such as PDMS, offers several advantages for lithographic techniques. For example, PDMS is highly transparent to ultraviolet (UV) radiation and has a very low Young's modulus (approximately 750 kPa), which gives it the flexibility required for conformal contact, even over surface irregularities, without the potential for cracking. In contrast, cracking can occur with molds made from brittle, high-modulus materials, such as etched silicon and glass. See Bietsch, A., et al., *J. Appl. Phys.,* 2000, 88, 4310-4318. Further, flexibility in a mold facilitates the easy release of the mold from masters and replicates without cracking and allows the mold to endure multiple imprinting steps without damaging fragile features. Additionally, many soft, elastomeric materials are gas permeable, a property that can be used to advantage in soft lithography applications.

Although PDMS offers some advantages in soft lithography applications, several properties inherent to PDMS severely limit its capabilities in soft lithography. First, PDMS-based elastomers swell when exposed to most organic soluble compounds. See Lee, J. N., et al., *Anal. Chem.,* 2003, 75, 6544-6554. Although this property is beneficial in microcontact printing (MCP) applications because it allows the mold to adsorb organic inks, see Xia, Y., et al., *Angew. Chem. Int. Ed.,* 1998, 37, 550-575, swelling resistance is critically important in the majority of other soft lithographic techniques, especially for SAMIM and MIMIC, and for IL techniques in which a mold is brought into contact with a small amount of curable organic monomer or resin. Otherwise, the fidelity of the features on the mold is lost and an unsolvable adhesion problem ensues due to infiltration of the curable liquid into the mold. Such problems commonly occur with PDMS-based molds because most organic liquids swell PDMS. Organic materials, however, are the materials most desirable to mold. Additionally, acidic or basic aqueous solutions react with PDMS, causing breakage of the polymer chain.

Secondly, the surface energy of PDMS (approximately 25 mN/m) is not low enough for soft lithography procedures that require high fidelity. For this reason, the patterned surface of PDMS-based molds is often fluorinated using a plasma treatment followed by vapor deposition of a fluoroalkyl trichlorosilane. See Xia, Y., et al., *Angew. Chem. Int. Ed.,* 1998, 37, 550-575. These fluorine-treated silicones swell, however, when exposed to organic solvents.

Third, the most commonly-used commercially available form of the material used in PDMS molds, e.g., Sylgard 184® (Dow Corning Corporation, Midland, Mich., United States of America) has a modulus that is too low (approximately 1.5 MPa) for many applications. The low modulus of these commonly used PDMS materials results in sagging and bending of features and, as such, is not well suited for processes that require precise pattern placement and alignment. Although researchers have attempted to address this last problem, see Odom, T. W., et al., *J. Am. Chem. Soc.,* 2002, 124, 12112-12113; Odom, T. W. et al., *Langmuir,* 2002, 18, 5314-5320; Schmid, H. et al. *Macromolecules,* 2000, 33, 3042-3049; Csucs, G., et al., *Langmuir,* 2003, 19, 6104-6109; Trimbach, D., et al., *Langmuir,* 2003, 19, 10957-10961, the materials chosen still exhibit poor solvent resistance and require fluorination steps to allow for the release of the mold.

Rigid materials, such as quartz glass and silicon, also have been used in imprint lithography. See Xia, Y., et al., *Angew. Chem. Int. Ed.,* 1998, 37, 550-575; Resnick, D. J., et al., *Semiconductor International,* 2002, June, 71-78; McClelland, G. M., et al., *Appl. Phys. Lett.,* 2002, 81, 1483; Chou, S. Y., et al., *J. Vac. Sci. Technol. B,* 1996, 14, 4129; Otto, M., et al., *Microelectron. Eng.,* 2001, 57, 361; and Bailey, T., et al., *J. Vac. Sci. Technol.,* B, 2000, 18, 3571; Chou, S. Y., et al., *Science,* 1996, 272, 85-87; Von Werne, T. A., et al., *J. Am. Chem. Soc.,* 2003, 125, 3831-3838; Resnick, D. J., et al., *J. Vac. Sci. Technol. B,* 2003, 21, 2624-2631. These materials are superior to PDMS in modulus and swelling resistance, but lack flexibility. Such lack of flexibility inhibits conformal contact with the substrate and causes defects in the mask and/or replicate during separation.

Another drawback of rigid materials is the necessity to use a costly and difficult to fabricate hard mold, which is typically made by using conventional photolithography or electron beam (e-beam) lithography. See Chou, S. Y., et al., *J. Vac. Sci. Technol. B,* 1996, 14, 4129. More recently, the need to repeatedly use expensive quartz glass or silicon molds in NCM processes has been eliminated by using an acrylate-based mold generated from casting a photopolymerizable monomer mixture against a silicon master. See McClelland, G. M., et al., *Appl. Phys. Lett.,* 2002, 81, 1483, and Jung, G. Y., et al., *Nanoletters,* 2004, ASAP. This approach also can be limited by swelling of the mold in organic solvents.

Despite such advances, other disadvantages of fabricating molds from rigid materials include the necessity to use fluorination steps to lower the surface energy of the mold, see Resnick, D. J., et al., *Semiconductor International,* 2002, June, 71-78, and the inherent problem of releasing a rigid mold from a rigid substrate without breaking or damaging the mold or the substrate. See Resnick, D. J., et al., *Semiconductor International,* 2002, June, 71-78; Bietsch, A., *J. Appl. Phys.,* 2000, 88, 4310-4318. Khang, D. Y., et al., *Langmuir,* 2004, 20, 2445-2448, have reported the use of rigid molds composed of thermoformed Teflon AF® (DuPont, Wilmington, Del., United States of America) to address the surface energy problem. Fabrication of these molds, however, requires high temperatures and pressures in a melt press, a process that could be damaging to the delicate features on a silicon wafer master. Additionally, these molds still exhibit the intrinsic drawbacks of other rigid materials as outlined hereinabove.

Further, a clear and important limitation of fabricating structures on semiconductor devices using molds or templates made from hard materials is the usual formation of a residual or "scum" layer that forms when a rigid template is brought into contact with a substrate. Even with elevated applied forces, it is very difficult to completely displace liquids during this process due to the wetting behavior of the liquid being molded, which results in the formation of a scum layer. Thus, there is a need in the art for a method of fabricating a pattern or a structure on a substrate, such as a semiconductor device, which does not result in the formation of a scum layer.

The fabrication of solvent resistant, microfluidic devices with features on the order of hundreds of microns from photocurable perfluoropolyether (PFPE) has been reported. See Rolland, J. P., et al., *J. Am. Chem. Soc.*, 2004, 126, 2322-2323. PFPE-based materials are liquids at room temperature and can be photochemically cross-linked to yield tough, durable elastomers. Further, PFPE-based materials are highly fluorinated and resist swelling by organic solvents, such as methylene chloride, tetrahydrofuran, toluene, hexanes, and acetonitrile among others, which are desirable for use in microchemistry platforms based on elastomeric microfluidic devices. There is a need in the art, however, to apply PFPE-based materials to the fabrication of nanoscale devices for related reasons.

Further, there is a need in the art for improved methods for forming a pattern on a substrate, such as method employing a patterned mask. See U.S. Pat. No. 4,735,890 to Nakane et al.; U.S. Pat. No. 5,147,763 to Kamitakahara et al.; U.S. Pat. No. 5,259,926 to Kuwabara et al.; and International PCT Publication No. WO 99/54786 to Jackson et al., each of which is incorporated herein by reference in their entirety.

There also is a need in the art for an improved method for forming isolated structures that can be considered "engineered" structures, including but not limited to particles, shapes, and parts. Using traditional IL methods, the scum layer that almost always forms between structures acts to connect or link structures together, thereby making it difficult, if not impossible, to fabricate and/or harvest isolated structures.

There also is a need in the art for an improved method for forming micro- and nanoscale charged particles, in particular polymer electrets. The term "polymer electrets" refers to dielectrics with stored charge, either on the surface or in the bulk, and dielectrics with oriented dipoles, frozen-in, ferrielectric, or ferroelectric. On the macro scale, such materials are used, for example, for electronic packaging and charge electret devices, such as microphones and the like. See Kressman, R., et al., *Space-Charge Electrets*, Vol. 2, Laplacian Press, 1999; and Harrison, J. S., et al., *Piezoelectic Polymers*, NASA/CR-2001-211422, ICASE Report No. 2001-43. Poly(vinylidene fluoride) (PVDF) is one example of a polymer electret material. In addition to PVDF, charge electret materials, such as polypropylene (PP), Teflon-fluorinated ethylene propylene (FEP), and polytetrafluoroethylene (PTFE), also are considered polymer electrets.

Further, there is a need in the art for improved methods for delivering therapeutic agents, such as drugs, non-viral gene vectors, DNA, RNA, RNAi, and viral particles, to a target. See *Biomedical Polymers*, Shalaby, S. W., ed., Harner/Gardner Publications, Inc., Cincinnati, Ohio, 1994; *Polymeric Biomaterials*, Dumitrin, S., ed., Marcel Dekkar, Inc., New York, N.Y., 1994; Park, K., et al., *Biodegradable Hydrogels for Drug Delivery*, Technomic Publishing Company, Inc., Lancaster, Pa., 1993; Gumargalieva, et al., *Biodegradation and Biodeterioration of Polymers: Kinetic Aspects*, Nova Science Publishers, Inc., Commack, N.Y., 1998; *Controlled Drug Delivery*, American Chemical Society Symposium Series 752, Park, K., and Mrsny, R. J., eds., Washington, D.C., 2000; *Cellular Drug Delivery: Principles and Practices*, Lu, D. R., and Oie, S., eds., Humana Press, Totowa, N.J., 2004; and *Bioreversible Carriers in Drug Design: Theory and Applications*, Roche, E. B., ed., Pergamon Press, New York, N.Y., 1987. For a description of representative therapeutic agents for use in such delivery methods, see U.S. Pat. No. 6,159,443 to Hallahan, which is incorporated herein by reference in its entirety.

There is also a need in the art for an improved method for forming super absorbent particles. These particles can be used for specialty packaging, wire waterblocking, filtration, medical markets, spill control, therapy packs, composites and laminates, water retention.

There is also a need in the art for improved methods to create polymorphs. Polymorphs exist when there is more than one way for the particles of a particular substance to arrange themselves into a crystalline array. Different polymorphs of the same substance can have vastly different physical and chemical properties. Invariably, one of the crystal forms may be more stable or easier to handle than another although the conditions under which the various crystal forms appears may be so close as to be very difficult to control on the large scale. This effect can create differences in the bioavailability of the drug which leads to inconsistencies in efficacy. See "Drug polymorphism and dosage form design: a practical perspective" *Adv. Drug Deliv. Rev.*, Singhal D, Curatolo W. 2004 Feb. 23; 56(3): 335-47; *Generic Drug Product Development: Solid Oral Dosage Forms*, Shargel, L., ed., Marcel Dekker, New York, 2005.

In sum, there exists a need in the art to identify new materials for use in imprint lithographic techniques. More particularly, there is a need in the art for methods for the fabrication of structures at the hundreds of micron level down to sub-100 nm feature sizes. Additionally, there is a need in the art for improved methods for polymorph creation.

SUMMARY

In some embodiments, the present invention includes a particle having a geometric solid shape, wherein a maximum cross-sectional dimension of the particle is less than about 1 micrometer. In alternative embodiments, the maximum cross-sectional dimension is between about 5 nanometers and about 1 micrometer; between about 10 nanometers and about 1 micrometer; less than about 800 nanometers; less than about 750 nanometers; less than about 500 nanometers; less than about 300 nanometers; less than about 250 nanometers; less than about 200 nanometers; less than about 150 nanometers; or less than about 100 nanometers. According to some embodiments, the present invention includes a plurality of substantially congruent particles. In some embodiments, the particles include a maximum cross-sectional dimension as described herein.

According to some embodiments, the particle includes a reaction product of a methacrylate; a reaction product of an acrylate; a reaction product of an epoxy; a reaction product of a free radical polymerization; a thermoplastic material; an organic material; an imaging agent; a drug; a treatment agent; an antibiotic; biologic material; a soluble material; a biodegradable material; a hydrophilic material; a hydrophobic material; an inorganic material; a polymer material; a small molecule; a ceramic; a metal; a material cured by applying actinic radiation, such as UV light; a material that hardens through evaporation, such as through evaporation of a solvent; a material that hardens through a chemical reaction; or a material that hardens through a change in temperature, such as through a melt transition of the material or a transitioning from between a flowable and non-flowable configuration. In some embodiments, the particle has a modulus from about 0.1 MPa to about 500 MPa. In other embodiments, the particle has a modulus of about 1 MPa to about 100 MPa. In some embodiments, the particle includes a porogen.

In other embodiments, a particle of the present invention has an engineered geometric shape and a volume of the particle is less than about 4200 cubic micrometers. In some embodiments, a particle of the present invention has a geometric solid shape, wherein a maximum cross-sectional dimension of the particle is less than about 10 micrometer and the particle includes a biologic material. In other embodiments, a particle of the present invention has a geometric solid shape, wherein a maximum cross-sectional dimension of the particle is less than about 10 micrometer and the particle includes a drug.

In alternative embodiments of the present invention, a nanostructure includes a layer of a first material and a structure having a geometric solid shape configured from a second material, wherein the structure is coupled with the layer and the structure has a maximum cross-sectional dimension of less than about 10 micrometers. In alternative embodiments, the structure includes a maximum cross-sectional dimension between about 5 nanometers and about 5 micrometers; between about 10 nanometers and about 2 micrometers; between about 10 nanometers and about 1 micrometer; less than about 1 micrometer; less than about 750 nanometers; less than about 500 nanometers; less than about 300 nanometers; less than about 250 nanometers; less than about 200 nanometers; less than about 150 nanometers; or less than about 100 nanometers.

According to some embodiments, a plurality of substantially congruent structures are coupled with the layer. In some embodiments, the plurality of structures are arranged in a substantially predetermined orientation and in other embodiments, the plurality of structures are arranged in a substantially ordered array.

According to some embodiments, the second material of the nanostructure includes a reaction product of a methacrylate; a reaction product of an acrylate; a reaction product of an epoxy; a reaction product of a free radical polymerization; a thermoplastic material; an organic material; an imaging agent; a drug; a treatment agent; an antibiotic; biologic material; a porogen; a soluble material; a biodegradable material; a hydrophilic material; a hydrophobic material; an inorganic material; a polymer material; a small molecule; a ceramic; a metal; a material cured by applying actinic radiation, such as UV light; a material that hardens through evaporation, such as through evaporation of a solvent; a material that hardens through a chemical reaction; or a material that hardens through a change in temperature, such as through a melt transition of the second material or a transitioning from between a flowable and non-flowable configuration. According to other embodiments, the first material and the second material include the same composition.

In some embodiments of the present invention, the layer of material includes a thickness of about twice a dimension of the structure. In other embodiments, the layer of material includes a thickness of about equal a dimension of the structure. In still other embodiments, the layer of material includes a thickness of about one half a dimension of the structure.

According to some embodiments, structures of more than one size are coupled with the layer. In some embodiments, structures of more than one shape are coupled with the layer. In other embodiments, an agent is configured to couple the structure to the layer by interactions such as covalent binding, ionic bonding, electrostatic binding, surface energy, hydrogen bonding, van der Waals forces, other intra- and inter-molecular forces, adhesives, or a magnetic force.

The present invention also includes methods for fabricating particles, particles attached to a scum layer and particles adhered to films. In some embodiments, a method of fabricating arrayed nanostructures includes placing a first material into a recess in a polymer mold where the recess is less than about 10 micrometers in a maximum cross-sectional dimension, hardening the first material to form a particle having a geometric solid shape substantially corresponding to the recess, removing the particle from the recess, and coupling the particle with a film. In alternative embodiments, the maximum cross-sectional dimension is between about 5 nanometers and about 5 micrometers; between about 10 nanometers and about 2 micrometers; between about 10 nanometers and about 1 micrometer; less than about 1 micrometer; less than about 750 nanometers; less than about 500 nanometers; less than about 300 nanometers; less than about 250 nanometers; less than about 200 nanometers; less than about 150 nanometers; or less than about 100 nanometers. In some embodiments, a plurality of substantially congruent particles are fabricated by placing the first material into a plurality of substantially congruent recesses in the polymer mold, wherein the recess is less than about 10 micrometers in a maximum cross-sectional dimension and hardening the first material to form a plurality of substantially congruent particles, each having a geometric solid shape substantially corresponding to the recess in which it was hardened. Next, the particles are removed from the recesses and coupled with a film. In some embodiments, the polymer mold includes a fluorinated polymer. In other embodiments, the fluorinated polymer includes a perfluoropolyether.

BRIEF DESCRIPTION OF THE DRAWINGS

Reference is made to the accompanying drawings in which are shown illustrative embodiments of the presently disclosed subject matter, from which its novel features and advantages will be apparent.

FIG. 4A represents the electrostatic charging of the molded particle during polymerization or crystallization; FIG. 4B represents a charged nano-disc; FIG. 4C represents typical random juxtapositioning of uncharged nano-discs; and FIG. 4D represents the spontaneous aggregation of charged nano-discs into chain-like structures;

FIG. 27 is a scanning electron micrograph of 500-nm conical shaped Ppy particles;

FIGS. 28A-28C are fluorescence confocal micrographs of 200-nm isolated trapezoidal particles of PEG diacrylate that contain fluorescently tagged DNA. FIG. 28A is a fluorescent confocal micrograph of 200 nm trapezoidal PEG nanoparticles which contain 24-mer DNA strands that are tagged with CY-3. FIG. 28B is optical micrograph of the 200-nm isolated trapezoidal particles of PEG diacrylate that contain fluorescently tagged DNA.

FIG. 28C is the overlay of the images provided in FIGS. 28A and 28B, showing that every particle contains DNA;

FIG. 31A is a scanning electron micrograph of silicon/silicon oxide masters of 3 micron arrows. FIG. 31B is a scanning electron micrograph of silicon/silicon oxide masters of 200-nm×800-nm bars;

FIG. 32A is a SU-8 master. FIG. 32B is a PFPE-DMA mold templated from a photolithographic master;

FIG. 33A is a master. FIG. 33B is a PFPE-DMA mold templated from a virus master;

FIG. 34A is a polystyrene-polyisoprene block copolymer micelle. FIG. 34B is a PFPE-DMA mold templated from a micelle master;

FIG. 35A is a brush polymer master. FIG. 35B is a PFPE-DMA mold templated from a brush polymer master;

FIGS. 39A-39F are schematic representations of one embodiment of one process of the presently disclosed subject matter for imprint lithography wherein 3-dimensional features are patterned;

FIG. 48 shows a process for coating a seed and seeds coated from the process according to some embodiments of the present invention;

FIG. 49A shows a silicon template having a 2-dimensional array of 200 nm trapezoid recesses;

FIG. 49B shows 200 nm trapezoidal PLA particles fabricated according to an embodiment of the present invention;

FIG. 49C shows 200 nm trapezoidal poly(pyrrole) (PPy) particles fabricated according to an embodiment of the present invention;

FIG. 49D shows 200 nm trapezoidal trimethylopropane triacrylate (TMPTA) particles fabricated according to an embodiment of the present invention;

FIGS. 50A-50F show PEG particles of different shapes and sizes fabricated according to embodiments of the present invention;

DETAILED DESCRIPTION

Figure 1A:
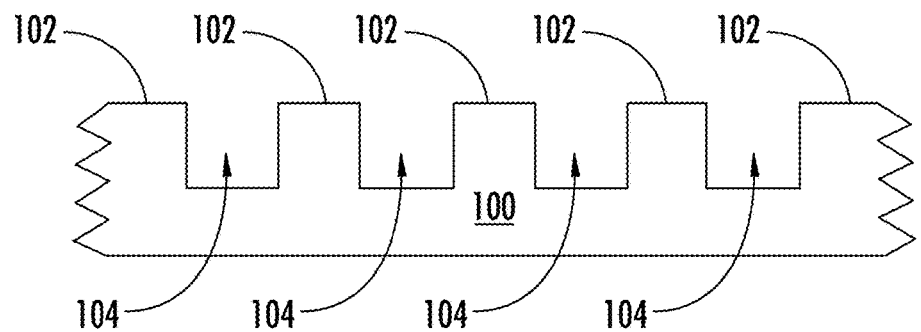
FIGS. 1A-1D are a schematic representation of an embodiment of the presently disclosed method for preparing a patterned template.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Materials

The presently disclosed subject matter broadly describes solvent resistant, low surface energy polymeric materials, derived from casting low viscosity liquid materials onto a master template and then curing the low viscosity liquid materials to generate a patterned template for use in high-resolution soft or imprint lithographic applications, such as micro- and nanoscale replica molding. In some embodiments, the patterned template includes a solvent resistant, elastomer-based material, such as but not limited to a fluorinated elastomer-based material.

Further, the presently disclosed subject matter describes the first nano-contact molding of organic materials to generate high fidelity features using an elastomeric mold. Accordingly, the presently disclosed subject matter describes a method for producing free-standing, isolated micro- and nanostructures of any shape using soft or imprint lithography techniques. Representative micro- and nano-structures include but are not limited to micro- and nano-particles, and micro- and nano-patterned substrates.

The nanostructures described by the presently disclosed subject matter can be used in several applications, including, but not limited to, semiconductor manufacturing, such as molding etch barriers without scum layers for the fabrication of semiconductor devices; crystals; materials for displays; photovoltaics; a solar cell device; optoelectronic devices; routers; gratings; radio frequency identification (RFID) devices; catalysts; fillers and additives; detoxifying agents; etch barriers; atomic force microscope (AFM) tips; parts for nano-machines; the delivery of a therapeutic agent, such as a drug or genetic material; cosmetics; chemical mechanical planarization (CMP) particles; and porous particles and shapes of any kind that will enable the nanotechnology industry.

Representative solvent resistant elastomer-based materials include but are not limited to fluorinated elastomer-based materials. As used herein, the term "solvent resistant" refers to a material, such as an elastomeric material that neither swells nor dissolves in common hydrocarbon-based organic solvents or acidic or basic aqueous solutions. Representative fluorinated elastomer-based materials include but are not limited to perfluoropolyether (PFPE)-based materials. A photocurable liquid PFPE exhibits desirable properties for soft lithography. A representative scheme for the synthesis and photocuring of functional PFPEs is provided in Scheme 1.

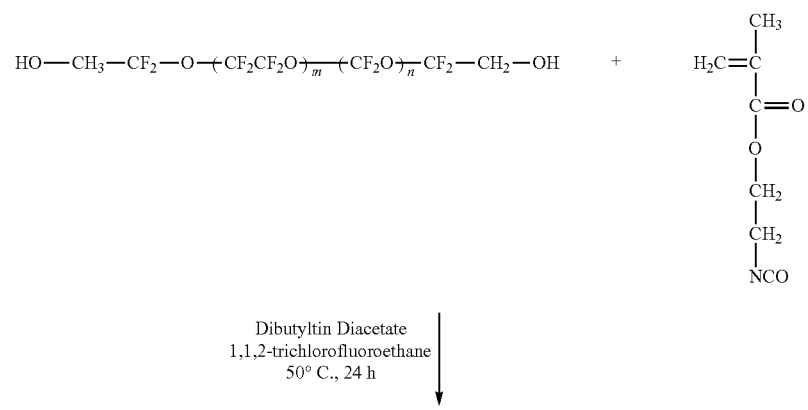

Scheme 1. Synthesis and Photocuring of Functional Perfluoropolyethers.

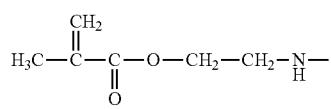
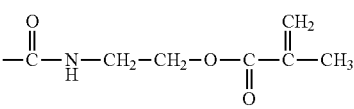
-continued

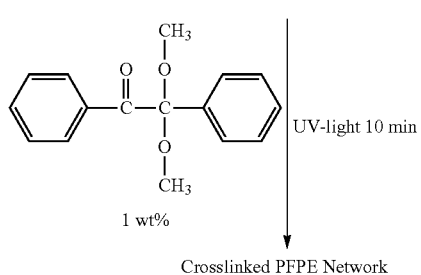

↓ UV-light 10 min 1 wt%

Crosslinked PFPE Network

According to another embodiment, a material according to the presently disclosed subject matter includes one or more of a photo-curable constituent, a thermal-curable constituent, and mixtures thereof. In one embodiment, the photo-curable constituent is independent from the thermal-curable constituent such that the material can undergo multiple cures. A material having the ability to undergo multiple cures is useful, for example, in forming layered devices. For example, a liquid material having photo-curable and thermal-curable constituents can undergo a first cure to form a first device through, for example, a photocuring process or a thermal curing process. Then the photocured or thermal cured first device can be adhered to a second device of the same material or any material similar thereto that will thermally cure or photocure and bind to the material of the first device. By positioning the first device and second device adjacent one another and subjecting the first and second devices to a thermalcuring or photocuring process, whichever component that was not activated on the first curing can be cured by a subsequent curing step. Thereafter, either the thermalcure constituents of the first device that was left un-activated by the photocuring process or the photocure constituents of the first device that were left un-activated by the first thermal curing, will be activated and bind the second device. Thereby, the first and second devices become adhered together. It will be appreciated by one of ordinary skill in the art that the order of curing processes is independent and a thermal-curing could occur first followed by a photocuring or a photocuring could occur first followed by a thermal curing.

According to yet another embodiment, multiple thermo-curable constituents can be included in the material such that the material can be subjected to multiple independent thermal-cures. For example, the multiple thermo-curable constituents can have different activation temperature ranges such that the material can undergo a first thermal-cure at a first temperature range and a second thermal-cure at a second temperature range.

Additional schemes for the synthesis of functional perfluoropolyethers are provided in Examples 7.1 through 7.6.

According to one embodiment this PFPE material has a surface energy below about 30 mN/m. According to another embodiment the surface energy of the PFPE is between about 10 mN/m and about 20 mN/m. According to a another embodiment, the PFPE has a low surface energy of between about 12 mN/m and about 15 mN/m. The PFPE is non-toxic, UV transparent, and highly gas permeable; and cures into a tough, durable, highly fluorinated elastomer with excellent release properties and resistance to swelling. The properties of these materials can be tuned over a wide range through the judicious choice of additives, fillers, reactive co-monomers, and functionalization agents. Such properties that are desirable to modify, include, but are not limited to, modulus, tear strength, surface energy, permeability, functionality, mode of cure, solubility and swelling characteristics, and the like. The non-swelling nature and easy release properties of the presently disclosed PFPE materials allows for nanostructures to be fabricated from any material. Further, the presently disclosed subject matter can be expanded to large scale rollers or conveyor belt technology or rapid stamping that allow for the fabrication of nanostructures on an industrial scale.

In some embodiments, the patterned template includes a solvent resistant, low surface energy polymeric material derived from casting low viscosity liquid materials onto a master template and then curing the low viscosity liquid materials to generate a patterned template. In some embodiments, the patterned template includes a solvent resistant elastomeric material.

In some embodiments, at least one of the patterned template and substrate includes a material selected from the group including a perfluoropolyether material, a fluoroolefin material, an acrylate material, a silicone material, a styrenic material, a fluorinated thermoplastic elastomer (TPE), a triazine fluoropolymer, a perfluorocyclobutyl material, a fluorinated epoxy resin, and a fluorinated monomer or fluorinated oligomer that can be polymerized or crosslinked by a metathesis polymerization reaction.

In some embodiments, the perfluoropolyether material includes a backbone structure selected from the group including:

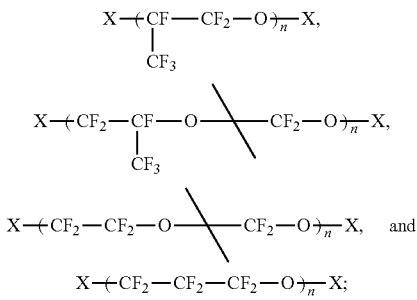

wherein X is present or absent, and when present includes an endcapping group.

In some embodiments, the fluoroolefin material is selected from the group including:

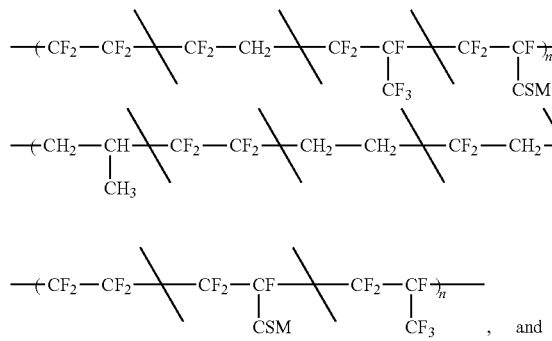

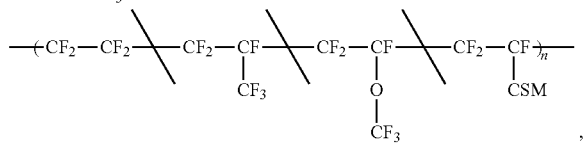

wherein CSM includes a cure site monomer.

In some embodiments, the fluoroolefin material is made from monomers which include tetrafluoroethylene, vinylidene fluoride, hexafluoropropylene, 2,2-bis(trifluoromethyl)-4,5-difluoro-1,3-dioxole, a functional fluoroolefin, functional acrylic monomer, and a functional methacrylic monomer.

In some embodiments, the silicone material includes a fluoroalkyl functionalized polydimethylsiloxane (PDMS) having the following structure:

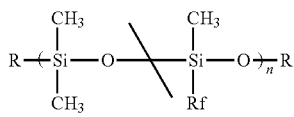

wherein:

R is selected from the group including an acrylate, a methacrylate, and a vinyl group; and Rf includes a fluoroalkyl chain.

In some embodiments, the styrenic material includes a fluorinated styrene monomer selected from the group including:

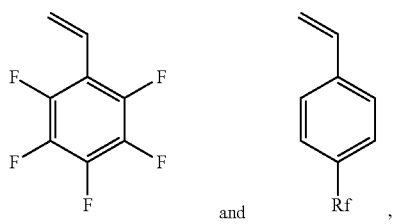

wherein Rf includes a fluoroalkyl chain.

In some embodiments, the acrylate material includes a fluorinated acrylate or a fluorinated methacrylate having the following structure:

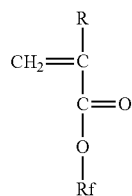

wherein:

R is selected from the group including H, alkyl, substituted alkyl, aryl, and substituted aryl; and Rf includes a fluoroalkyl chain.

In some embodiments, the triazine fluoropolymer includes a fluorinated monomer. In some embodiments, the fluorinated monomer or fluorinated oligomer that can be polymerized or crosslinked by a metathesis polymerization reaction includes a functionalized olefin. In some embodiments, the functionalized olefin includes a functionalized cyclic olefin.

In some embodiments, at least one of the patterned template and the substrate has a surface energy lower than about 18 mN/m. In some embodiments, at least one of the patterned template and the substrate has a surface energy lower than about 15 mN/m. According to a further embodiment the patterned template and/or the substrate has a surface energy between about 10 mN/m and about 20 mN/m. According to another embodiment, the patterned template and/or the substrate has a low surface energy of between about 12 mN/m and about 15 mN/m.

From a property point of view, the exact properties of these molding materials can be adjusted by adjusting the composition of the ingredients used to make the materials. In particular the modulus can be adjusted from low (approximately 1 MPa) to multiple GPa.

II. Formation of Isolated Micro- and/or Nanoparticles

In some embodiments, the presently disclosed subject matter provides a method for making isolated micro- and/or nanoparticles. In some embodiments, the process includes initially forming a patterned substrate. Turning now to FIG. 1A, a patterned master 100 is provided. Patterned master 100 includes a plurality of non-recessed surface areas 102 and a plurality of recesses 104. In some embodiments, patterned master 100 includes an etched substrate, such as a silicon wafer, which is etched in the desired pattern to form patterned master 100.

Figure 1B:
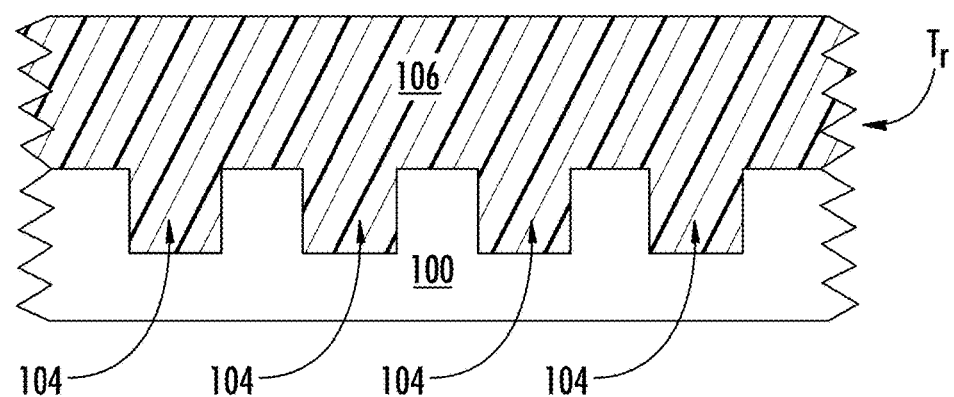

Referring now to FIG. 1B, a liquid material 106, for example, a liquid fluoropolymer composition, such as a PFPE-based precursor, is then poured onto patterned master 100. Liquid material 106 is treated by treating process $T_r$, for example exposure to UV light, actinic radiation, or the like, thereby forming a treated liquid material 108 in the desired pattern.

Figure 1C:
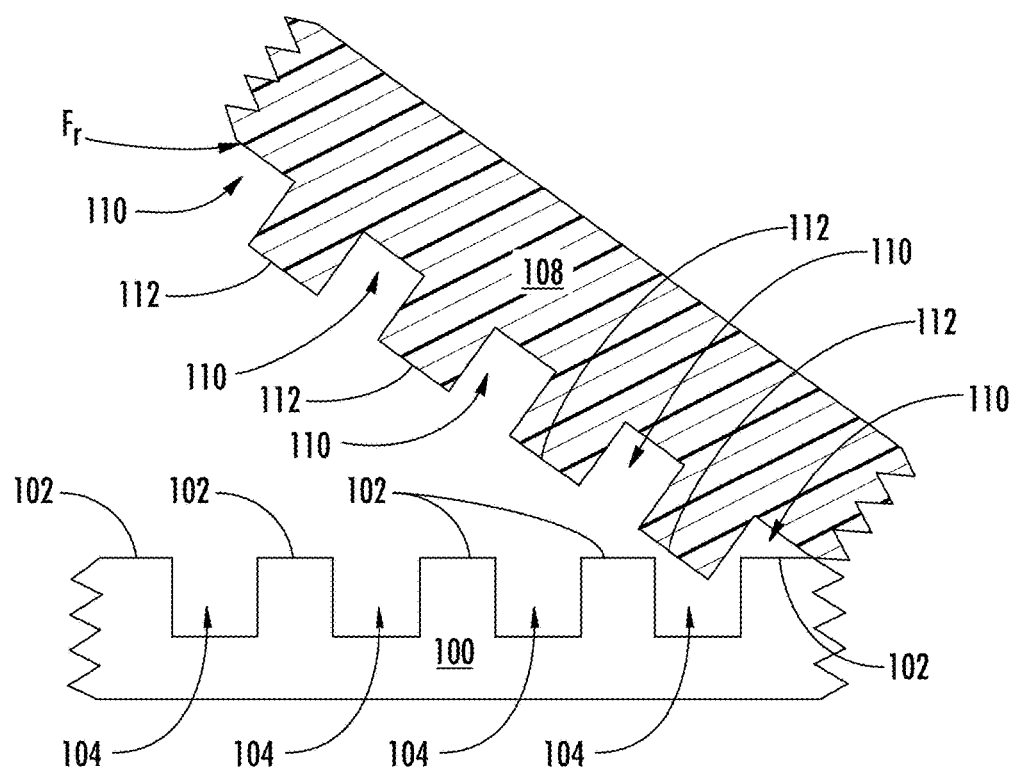
Figure 1D:
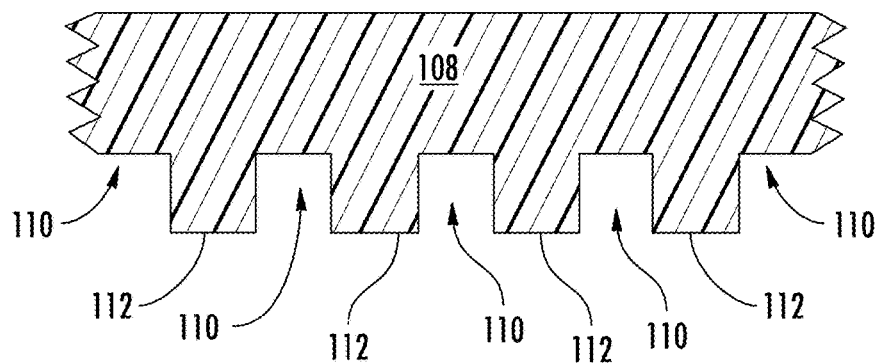

Referring now to FIGS. 1C and 1D, a force $F_r$ is applied to treated liquid material 108 to remove it from patterned master 100. As shown in FIGS. 1C and 1D, treated liquid material 108 includes a plurality of recesses 110, which are mirror images of the plurality of non-recessed surface areas 102 of patterned master 100. Continuing with FIGS. 1C and 1D, treated liquid material 108 includes a plurality of first patterned surface areas 112, which are mirror images of the plurality of recesses 104 of patterned master 100. Treated liquid material 108 can now be used as a patterned template for soft lithography and imprint lithography applications. Accordingly, treated liquid material 108 can be used as a patterned template for the formation of isolated micro- and nanoparticles. For the purposes of FIGS. 1A-1D, 2A-2E, and 3A-3F, the numbering scheme for like structures is retained throughout, where possible.

Figure 2A:
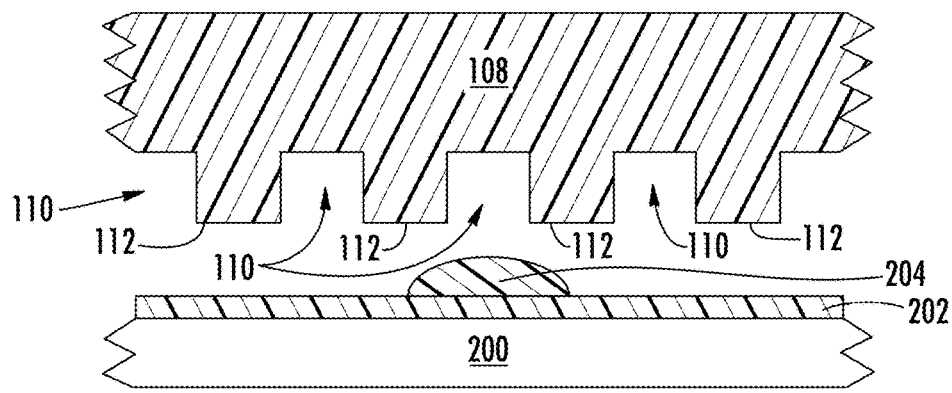
FIGS. 2A-2F are a schematic representation of the presently disclosed method for forming one or more micro- and/or nanoscale particles.

Referring now to FIG. 2A, in some embodiments, a substrate 200, for example, a silicon wafer, is treated or is coated with a non-wetting material 202. In some embodiments, non-wetting material 202 includes an elastomer (such a solvent resistant elastomer, including but not limited to a PFPE elastomer) that can be further exposed to UV light and cured to form a thin, non-wetting layer on the surface of substrate 200. Substrate 200 also can be made non-wetting by treating substrate 200 with non-wetting agent 202, for example a small molecule, such as an alkyl- or fluoroalkylsilane, or other surface treatment. Continuing with FIG. 2A, a droplet 204 of a curable resin, a monomer, or a solution from which the desired particles will be formed is then placed on the coated substrate 200.

Figure 2B:
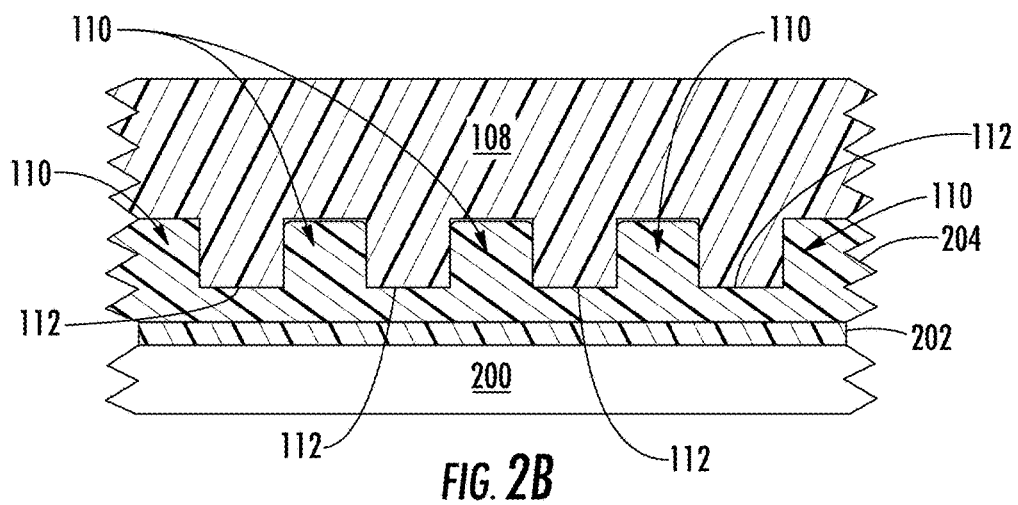

Referring now to FIG. 2A and FIG. 2B, patterned template 108 (as shown in FIG. 1D) is then contacted with droplet 204 of a particle precursor material so that droplet 204 fills the plurality of recessed areas 110 of patterned template 108.

Figure 2C:
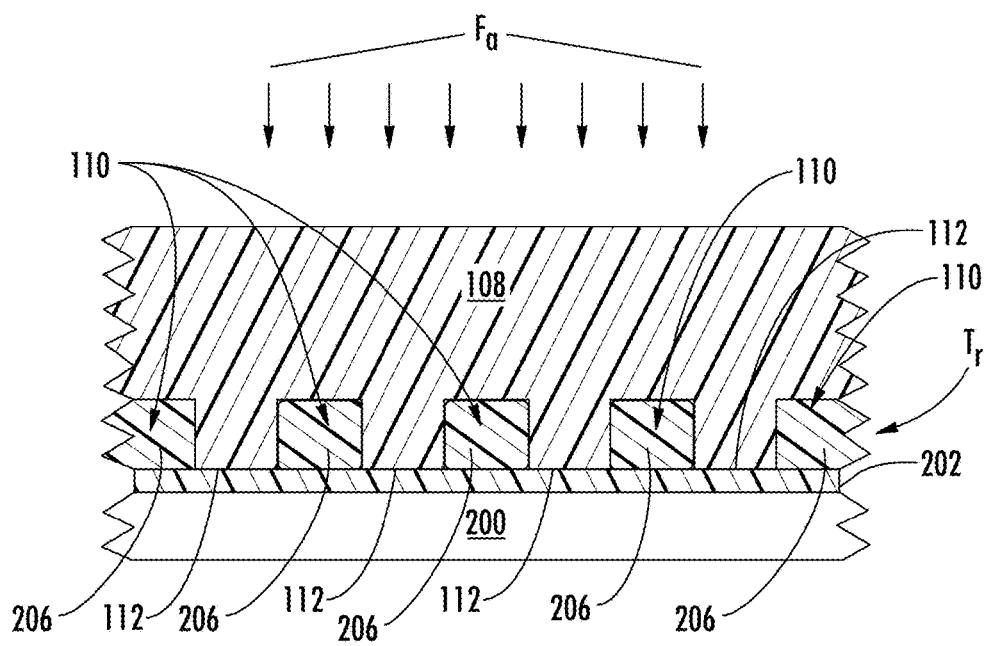
Figure 2D:
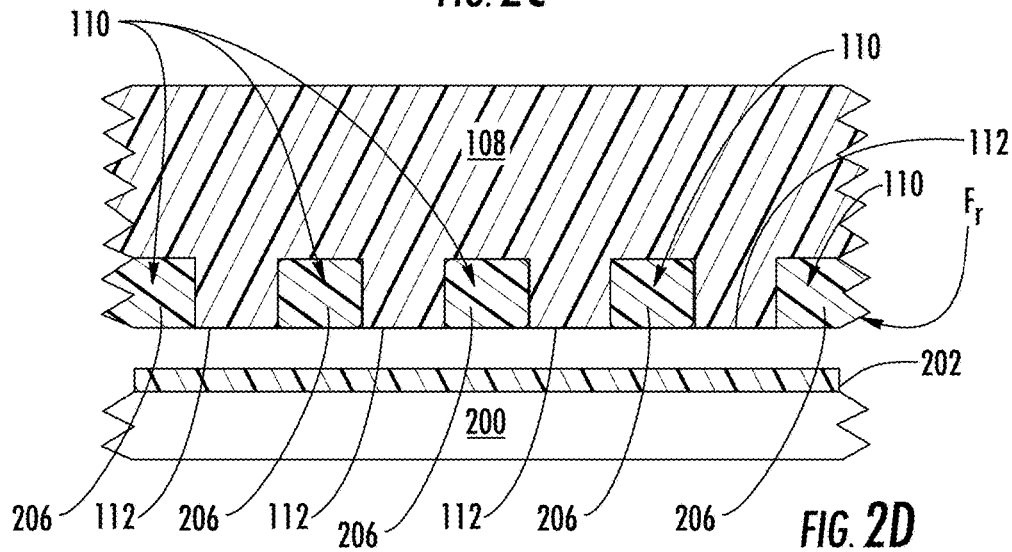

Referring now to FIGS. 2C and 2D, a force $F_a$ is applied to patterned template 108. While not wishing to be bound by any particular theory, once force $F_a$ is applied, the affinity of patterned template 108 for non-wetting coating or surface treatment 202 on substrate 200 in combination with the non-wetting behavior of patterned template 108 and surface treated or coated substrate 200 causes droplet 204 to be excluded from all areas except for recessed areas 110. Further, in embodiments essentially free of non-wetting or low wetting material 202 with which to sandwich droplet 204, a "scum" layer forms that interconnects the objects being stamped.

Continuing with FIGS. 2C and 2D, the particle precursor material filling recessed areas 110, e.g., a resin, monomer, solvent, combinations thereof, or the like, is then treated by a treating process $T_r$, e.g., photocured, UV-light treated, or actinic radiation treated, through patterned template 108 or thermally cured while under pressure, to form a plurality of micro- and/or nanoparticles 206. In some embodiments, a material, including but not limited to a polymer, an organic compound, or an inorganic compound, can be dissolved in a solvent, patterned using patterned template 108, and the solvent can be released.

Continuing with FIGS. 2C and 2D, once the material filling recessed areas 110 is treated, patterned template 108 is removed from substrate 200. Micro- and/or nanoparticles 206 are confined to recessed areas 110 of patterned template 108. In some embodiments, micro- and/or nanoparticles 206 can be retained on substrate 200 in defined regions once patterned template 108 is removed. This embodiment can be used in the manufacture of semiconductor devices where essentially scum-layer free features could be used as etch barriers or as conductive, semiconductive, or dielectric layers directly, mitigating or reducing the need to use traditional and expensive photolithographic processes.

Figure 2E:
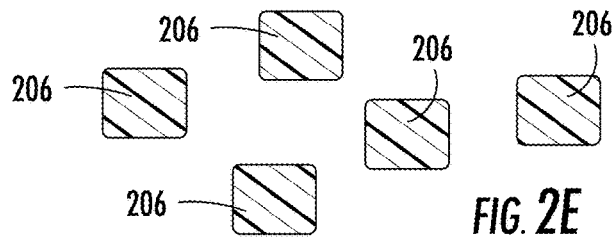

Referring now to FIGS. 2D and 2E, micro- and/or nanoparticles 206 can be removed from patterned template 108 to provide freestanding particles by a variety of methods, which include but are not limited to: (1) applying patterned template 108 to a surface that has an affinity for the particles 206; (2) deforming patterned template 108, or using other mechanical methods, including sonication, in such a manner that the particles 206 are naturally released from patterned template 108; (3) swelling patterned template 108 reversibly with supercritical carbon dioxide or another solvent that will extrude the particles 206; (4) washing patterned template 108 with a solvent that has an affinity for the particles 206 and will wash them out of patterned template 108; (5) applying patterned template 108 to a liquid that when hardened physically entraps particles 206; (6) applying patterned template 108 to a material that when hardened has a chemical and/or physical interaction with particles 206.

Figure 2F:
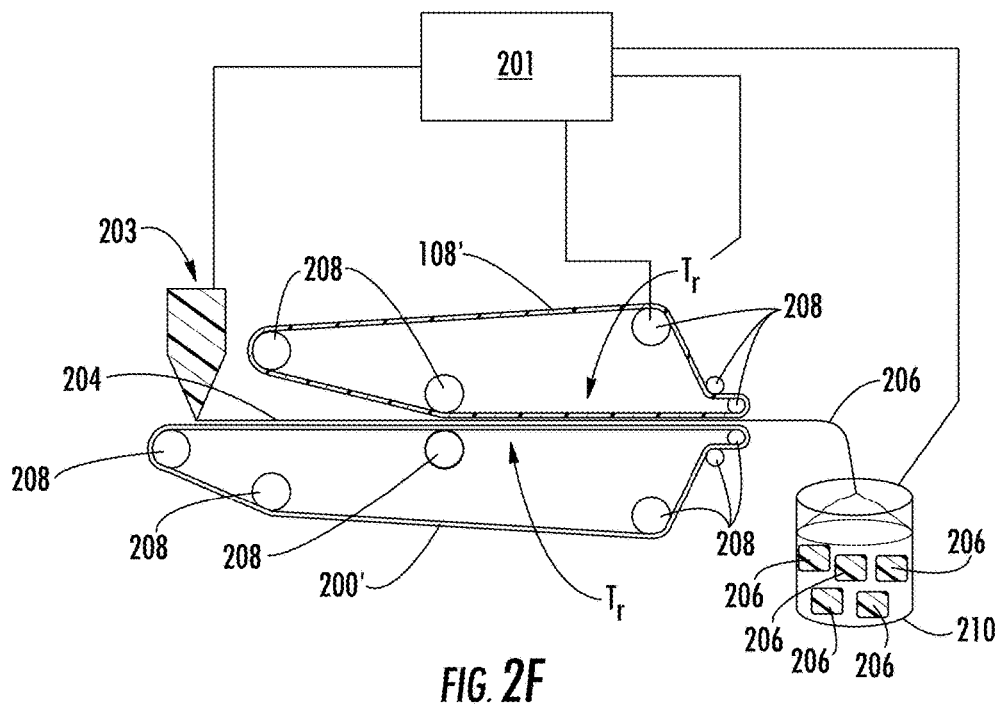

In some embodiments, the method of producing and harvesting particles includes a batch process. In some embodiments, the batch process is selected from one of a semi-batch process and a continuous batch process. Referring now to FIG. 2F, an embodiment of the presently disclosed subject matter wherein particles 206 are produced in a continuous process is schematically presented. An apparatus 199 is provided for carrying out the process. Indeed, while FIG. 2F schematically presents a continuous process for particles, apparatus 199 can be adapted for batch processes, and for providing a pattern on a substrate continuously or in batch, in accordance with the presently disclosed subject matter and based on a review of the presently disclosed subject matter by one of ordinary skill in the art.

Continuing, then, with FIG. 2F, droplet 204 of liquid material is applied to substrate 200' via reservoir 203. Substrate 200' can be coated or not coated with a non-wetting agent. Substrate 200' and pattern template 108' are placed in a spaced relationship with respect to each other and are also operably disposed with respect to each other to provide for the conveyance of droplet 204 between patterned template 108' and substrate 200'. Conveyance is facilitated through the provision of pulleys 208, which are in operative communication with controller 201. By way of representative non-limiting examples, controller 201 can include a computing system, appropriate software, a power source, a radiation source, and/or other suitable devices for controlling the functions of apparatus 199. Thus, controller 201 provides for power for and other control of the operation of pulleys 208 to provide for the conveyance of droplet 204 between patterned template 108' and substrate 200'. Particles 206 are formed and treated between substrate 200' and patterned template 108' by a treating process $T_R$, which is also controlled by controller 201. Particles 206 are collected in an inspecting device 210, which is also controlled by controller 201. Inspecting device 210 provides for one of inspecting, measuring, and both inspecting and measuring one or more characteristics of particles 206. Representative examples of inspecting devices 210 are disclosed elsewhere herein.

By way of further exemplifying embodiments of particle harvesting methods described herein, reference is made to FIGS. 37A-37F and FIGS. 38A-38G. In FIGS. 37A-37C and FIGS. 38A-38C particles which are produced in accordance with embodiments described herein remain in contact with an article 3700, 3800 having an affinity for particles 3705 and 3805 respectively. In one embodiment, article 3700 is a patterned template or mold as described herein. In one embodiment, article 3800 is a substrate as described herein.

Figure 37A:
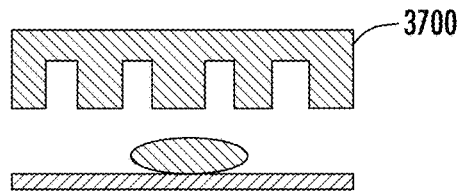
FIGS. 37A-37F are schematic representations of one embodiment of a method of the presently disclosed subject matter for harvesting particles from an article.
Figure 37B:
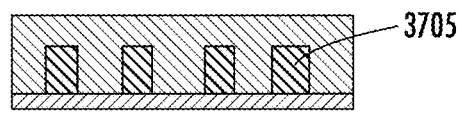
Figure 37C:
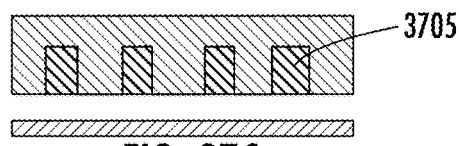
Figure 37D:
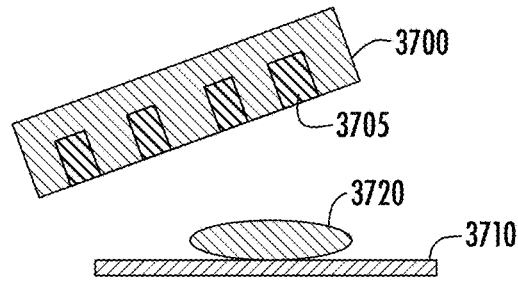
Figure 37E:
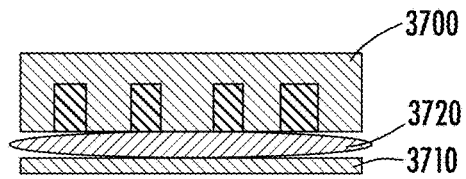
Figure 37F:
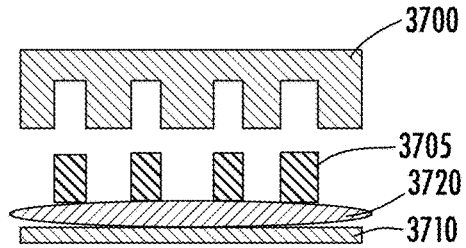
Figure 38A:
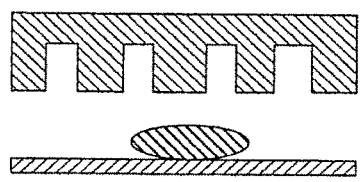
FIGS. 38A-38G are schematic representations of one embodiment of a method of the presently disclosed subject matter for harvesting particles from an article.
Figure 38B:
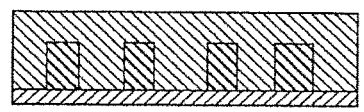
Figure 38C:
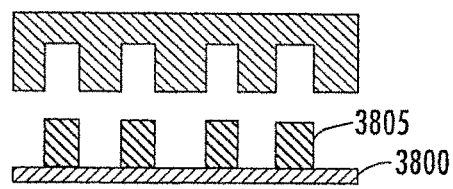
Figure 38D:
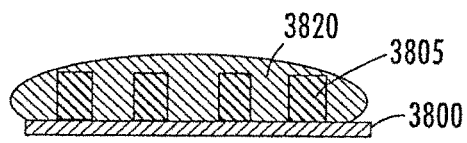
Figure 38E:
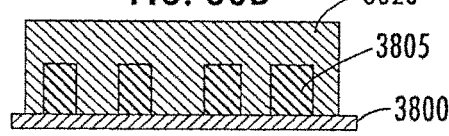
Figure 38F:
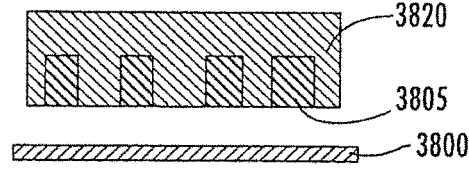
Figure 38G:
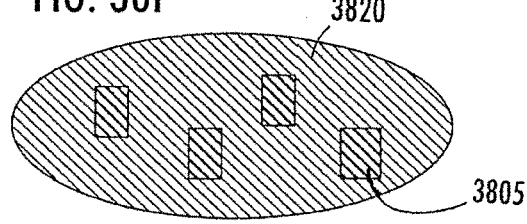

Referring now to FIGS. 37D-37F and FIGS. 38D-38G, material 3720, 3820 having an affinity for particles 3705, 3805 is put into contact with particles 3705, 3805 while particles 3705, 3805 remain in connection with articles 3700, 3800. In the embodiment of FIG. 37D, material 3720 is disposed on surface 3710. In the embodiment of FIG. 38D, material 3820 is applied directly to article 3800 having particles 3820. As illustrated in FIGS. 37E, 38D in some embodiments, article 3700, 3800 is put in engaging contact with material 3720, 3820. In one embodiment material 3720, 3820 is thereby dispersed to coat at least a portion of substantially all of particles 3705, 3805 while particles 3705, 3805 are attached to article 3700, 3800 (e.g., a patterned template). In one embodiment, illustrated in FIGS. 37F and 38F, articles 3700, 3800 are substantially disassociated with material 3720, 3820. In one embodiment, material 3720, 3820 has a higher affinity for particles 3705, 3805 than the affinity between article 3700, 3800 and particles 3705, 3805. In FIGS. 37F and 38F, the disassociation of article 3700, 3800 from material 3720, 3820 thereby releases particles 3705, 3805 from article 3700, 3800 leaving particles 3705, 3805 attached to material 3720, 3820.

In one embodiment material 3720, 3820 has an affinity for particles 3705 and 3805. For example, in some embodiments, material 3720, 3820 includes an adhesive or sticky surface when applied to article 3700, 3800. In other embodiments, material 3720, 3820 undergoes a transformation after it is brought into contact with article 3700, 3800. In some embodiments that transformation is an inherent characteristic of material 3705, 3805. In other embodiments, material 3705, 3805 is treated to induce the transformation. For example, in one embodiment material 3720, 3820 is an epoxy that hardens after it is brought into contact with article 3700, 3800. Thus when article 3700, 3800 is pealed away from the hardened epoxy, particles 3705, 3805 remain engaged with the epoxy and not article 3700, 3800. In other embodiments, material 3720, 3820 is water that is cooled to form ice. Thus, when article 3700, 3800 is stripped from the ice, particles 3705, 3805 remain in communication with the ice and not article 3700, 3800. In one embodiment, the particle-containing ice can be melted to create a liquid with a concentration of particles 3705, 3805. In some embodiments, material 3705, 3805 include, without limitation, one or more of a carbohydrate, an epoxy, a wax, polyvinyl alcohol, polyvinyl pyrrolidone, polybutyl acrylate, a polycyano acrylate and polymethyl methacrylate. In some embodiments, material 3720, 3820 includes, without limitation, one or more of liquids, solutions, powders, granulated materials, semi-solid materials, suspensions, combinations thereof, or the like.

Thus, in some embodiments, the method for forming and harvesting one or more particles includes:
(a) providing a patterned template and a substrate, wherein the patterned template includes a first patterned template surface having a plurality of recessed areas formed therein;
(b) disposing a volume of liquid material in or on at least one of:
  (i) the first patterned template surface;
  (ii) the plurality of recessed areas; and/or
  (iii) a substrate; and
(c) forming one or more particles by one of:
  (i) contacting the patterned template surface with the substrate and treating the liquid material; and
  (ii) treating the liquid material.

In some embodiments, the plurality of recessed areas includes a plurality of cavities. In some embodiments, the plurality of cavities includes a plurality of structural features. In some embodiments, the plurality of structural features have a dimension ranging from about 10 microns to about 1 nanometer in size. In some embodiments, the plurality of structural features have a dimension ranging from about 1 micron to about 100 nm in size. In some embodiments, the plurality of structural features have a dimension ranging from about 100 nm to about 1 nm in size. In some embodiments, the plurality of structural features have a dimension in both the horizontal and vertical plane.

According to yet another embodiment the particles are harvested on a fast dissolving substrate, sheet, or films. The film-forming agents can include, but are not limited to pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragacanth gum, guar gum, *acacia* gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein, combinations thereof, and the like. In some embodiments, pullulan is used as the primary filler. In still other embodiments, pullulan is included in amounts ranging from about 0.01 to about 99 wt %, preferably about 30 to about 80 wt %, more preferably from about 45 to about 70 wt %, and even more preferably from about 60 to about 65 wt % of the film.

The film can further include water, plasticizing agents, natural and/or artificial flavoring agents, sulfur precipitating agents, saliva stimulating agents, cooling agents, surfactants, stabilizing agents, emulsifying agents, thickening agents, binding agents, coloring agents, sweeteners, fragrances, combinations thereof, and the like.

Suitable sweeteners include both natural and artificial sweeteners. Examples of some sweeteners that can be used with the sheets of the presently disclosed subject matter include, but are not limited to: (a) water-soluble sweetening agents, such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin; (b) water-soluble artificial sweeteners, such as the soluble saccharin salts, sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like; (c) dipeptide based sweeteners, such as L-aspartic acid derived sweeteners, L-aspartyl-L-phenylalanine methyl ester (aspartame) and materials described in U.S. Pat. No. 3,492,131, which is incorporated herein by reference in its entirety, L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, and the like; (d) water-soluble sweeteners derived from naturally occurring water-soluble sweeteners, such as a chlorinated derivative of ordinary sugar (sucrose); and (e) protein based sweeteners, such as thaumatoccous danielli (Thaumatin I and II) and the like.

In general, an effective amount of auxiliary sweetener is utilized to provide the level of sweetness desired for a particular composition, and this amount will vary with the sweetener selected. The amount will normally be between about 0.01% to about 10% by weight of the composition when using an easily extractable sweetener. The water-soluble sweeteners described in category (a) above, are usually used in amounts of between about 0.01 to about 10 wt %, and preferably in amounts of between about 2 to about 5 wt %. The sweeteners described in categories (b)-(e) are generally used in amounts of between about 0.01 to about 10 wt %, with between about 2 to about 8 wt % being preferred and between about 3 to about 6 wt % being most preferred. These amounts can be used to achieve a desired level of sweetness independent from the flavor level achieved from any optional flavor oils used. Of course, sweeteners need not be added to films intended for non-oral administration.

The flavorings that can be used in the films include natural and artificial flavors. These flavorings can be chosen from synthetic flavor oils and flavoring aromatics, and/or oils, oleo resins and extracts derived from plants, leaves, flowers, fruits, combinations thereof, and the like. Representative flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors, such as vanilla, chocolate, coffee, cocoa and citrus oil, including lemon, orange, grape, lime and grapefruit, and fruit essences including apple, pear, peach, strawberry, raspberry, cherry, plum, pineapple, apricot and so forth. These flavorings can be used individually or in admixture. Flavorings such as aldehydes and esters including cinnamyl acetate, cinnamaldehyde, citral, diethylacetal, dihydrocarvyl acetate, eugenyl formate, p-methylanisole, and so forth also can be used. Generally, any flavoring or food additive can be used, such as those described in Chemicals Used in Food Processing, publication 1274 by the National Academy of Sciences, pages 63-258, which is incorporated herein by reference in its entirety. Further examples of aldehyde flavorings include, but are not limited to, acetaldehyde (apple); benzaldehyde (cherry, almond); cinnamic aldehyde (cinnamon); citral, i.e., alpha citral (lemon, lime); neral, i.e. beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal; decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl-5-heptenal, i.e. melonal (melon); 2-6-dimethyloctanal (green fruit); 2-dodecenal (citrus, mandarin); cherry; grape; mixtures thereof; and the like.

The amount of flavoring employed is normally a matter of preference subject to such factors as flavor type, individual flavor, strength desired, strength necessary to mask other less desirable flavors, and the like. Thus, the amount can be varied to obtain the result desired in the final product. In general, amounts of between about 0.1 to about 30 wt % are useable with amounts of about 2 to about 25 wt % being preferred and amounts from about 8 to about 10 wt % are more preferred.

The films also can contain coloring agents or colorants. The coloring agents are used in amounts effective to produce a desired color. The coloring agents useful in the presently disclosed subject matter, include pigments, such as titanium dioxide, which can be incorporated in amounts of up to about 5 wt %, and preferably less than about 1 wt %. Colorants can also include natural food colors and dyes suitable for food, drug and cosmetic applications. These colorants are known as FD&C dyes and lakes. The materials acceptable for the foregoing spectrum of use are preferably water-soluble, and include FD&C Blue No. 2, which is the disodium salt of 5,5-indigotindisulfonic acid. Similarly, the dye known as Green No. 3 comprises a triphenylmethane dye and is the monosodium salt of 4-[4-N-ethyl-p-sulfobenzylamino) diphenyl-methylene]-[1-N-ethyl-N-p-sulfonium benzyl)-2,5-cyclo-hexadienimine]. A full recitation of all FD&C and D&C dyes and their corresponding chemical structures can be found in the Kirk-Othmer Encyclopedia of Chemical Technology, Volume 5, Pages 857-884, which is incorporated herein by reference in its entirety. Furthermore, the materials and methods described in U.S. Pat. No. 6,923,981 and the references cited therein, all of which are incorporated herein by reference, disclose appropriate fast-dissolve films for use with the particles of the presently disclosed subject matter.

After the particles are harvested on such sugar sheets, for example, the fast dissolving sheet can act as the delivery device. According to such embodiments, the fast dissolve films can be placed on biological tissues and as the film is dissolved and/or absorbed, the particles contained therein are also dissolved or absorbed. The films can be configured for transdermal delivery, trans mucosal delivery, nasal delivery, anal delivery, vaginal delivery, combinations thereof, and the like.

In some embodiments of the method for forming one or more particles, the patterned template includes a solvent resistant, low surface energy polymeric material derived from casting low viscosity liquid materials onto a master template and then curing the low viscosity liquid materials to generate a patterned template. In some embodiments, the patterned template includes a solvent resistant elastomeric material.

In some embodiments, at least one of the patterned template and substrate includes a material selected from the group including a perfluoropolyether material, a fluoroolefin material, an acrylate material, a silicone material, a styrenic material, a fluorinated thermoplastic elastomer (TPE), a triazine fluoropolymer, a perfluorocyclobutyl material, a fluorinated epoxy resin, and a fluorinated monomer or fluorinated oligomer that can be polymerized or crosslinked by a metathesis polymerization reaction.

In some embodiments, the perfluoropolyether material includes a backbone structure selected from the group including:

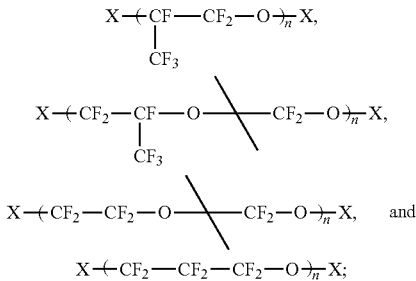

wherein X is present or absent, and when present includes an endcapping group.

In some embodiments, the fluoroolefin material is selected from the group including:

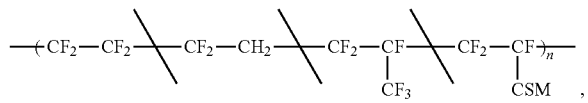

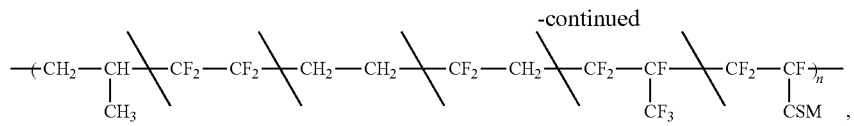

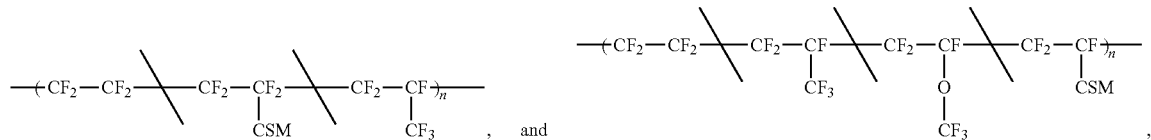

wherein CSM includes a cure site monomer.

In some embodiments, the fluoroolefin material is made from monomers which include tetrafluoroethylene, vinylidene fluoride, hexafluoropropylene, 2,2-bis(trifluoromethyl)-4,5-difluoro-1,3-dioxole, a functional fluoroolefin, functional acrylic monomer, and a functional methacrylic monomer.

In some embodiments, the silicone material includes a fluoroalkyl functionalized polydimethylsiloxane (PDMS) having the following structure:

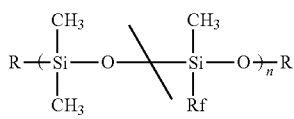

wherein:

R is selected from the group including an acrylate, a methacrylate, and a vinyl group; and Rf includes a fluoroalkyl chain.

In some embodiments, the styrenic material includes a fluorinated styrene monomer selected from the group including:

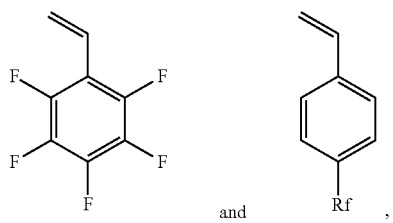

wherein Rf includes a fluoroalkyl chain.

In some embodiments, the acrylate material includes a fluorinated acrylate or a fluorinated methacrylate having the following structure:

$$\begin{array}{c} R \\ | \\ CH_2=C \\ | \\ C=O \\ | \\ O \\ | \\ Rf \end{array}$$

wherein:

R is selected from the group including H, alkyl, substituted alkyl, aryl, and substituted aryl; and Rf includes a fluoroalkyl chain.

In some embodiments, the triazine fluoropolymer includes a fluorinated monomer. In some embodiments, the fluorinated monomer or fluorinated oligomer that can be polymerized or crosslinked by a metathesis polymerization reaction includes a functionalized olefin. In some embodiments, the functionalized olefin includes a functionalized cyclic olefin.

In some embodiments, at least one of the patterned template and the substrate has a surface energy lower than 18 mN/m. In some embodiments, at least one of the patterned template and the substrate has a surface energy lower than 15 mN/m. According to a further embodiment the patterned template and/or the substrate has a surface energy between about 10 mN/m and about 20 mN/m. According to another, the patterned template and/or the substrate has a low surface energy of between about 12 mN/m and about 15 mN/m.

In some embodiments, the substrate is selected from the group including a polymer material, an inorganic material, a silicon material, a quartz material, a glass material, and surface treated variants thereof. In some embodiments, the substrate includes a patterned area.

According to an alternative embodiment, the PFPE material includes a urethane block as described and shown in the following structures:

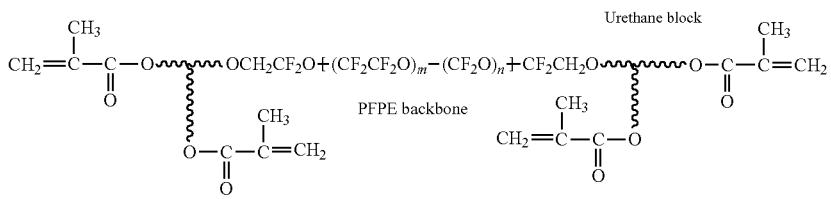

PFPE methacrylate

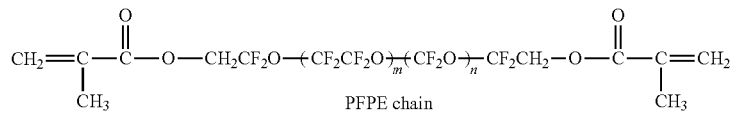

PFPE urethane acrylate

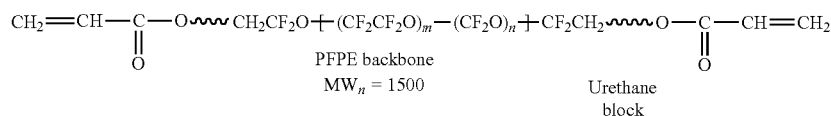

According to an embodiment of the presently disclosed subject matter, PFPE urethane tetrafunctional methacrylate materials, such as the above described material, can be used as the materials and methods of the presently disclosed subject matter or can be used in combination with other materials and methods described herein, as will be appreciated by one of ordinary skill in the art.

In some embodiments, the patterned template includes a patterned template formed by a replica molding process. In some embodiments, the replica molding process includes: providing a master template; contacting a liquid material with the master template; and curing the liquid material to form a patterned template.

In some embodiments, the master template includes, without limitation, one or more of a template formed from a lithography process, a naturally occurring template, combinations thereof, or the like. In some embodiments, the natural template is selected from one of a biological structure and a self-assembled structure. In some embodiments, the one of a biological structure and a self-assembled structure is selected from the group including a naturally occurring crystal, an enzyme, a virus, a protein, a micelle, and a tissue surface.

In some embodiments, the method includes modifying the patterned template surface by a surface modification step. In some embodiments, the surface modification step is selected from the group including a plasma treatment, a chemical treatment, and an adsorption process. In some embodiments, the adsorption process includes adsorbing molecules selected from the group including a polyelectrolyte, a poly(vinylalcohol), an alkylhalosilane, and a ligand.

In some embodiments, the method includes positioning the patterned template and the substrate in a spaced relationship to each other such that the patterned template surface and the substrate face each other in a predetermined alignment.

In some embodiments, the disposing of the volume of liquid material on one of the patterned template or the substrate is regulated by a spreading process. In some embodiments, the spreading process includes:
(a) disposing a first volume of liquid material on one of the patterned template and the substrate to form a layer of liquid material thereon; and
(b) drawing an implement across the layer of liquid material to:
    (i) remove a second volume of liquid material from the layer of liquid material on the one of the patterned template and the substrate; and
    (ii) leave a third volume of liquid material on the one of the patterned template and the substrate.

In some embodiments, an article is contacted with the layer of liquid material and a force is applied to the article to thereby remove the liquid material from the one of the patterned material and the substrate. In some embodiments, the article is selected from the group including a roller, a "squeegee" blade type device, a nonplanar polymeric pad, combinations thereof, or the like. In some embodiments, the liquid material is removed by some other mechanical apparatus.

In some embodiments, the contacting of the patterned template surface with the substrate forces essentially all of the disposed liquid material from between the patterned template surface and the substrate.

In some embodiments, the treating of the liquid material includes a process selected from the group including a thermal process, a phase change, an evaporative process, a photochemical process, and a chemical process.

In some embodiments as described in detail herein below, the method further includes:
(a) reducing the volume of the liquid material disposed in the plurality of recessed areas by one of:
    (i) applying a contact pressure to the patterned template surface; and
    (ii) allowing a second volume of the liquid to evaporate or permeate through the template;
(b) removing the contact pressure applied to the patterned template surface;
(c) introducing gas within the recessed areas of the patterned template surface;
(d) treating the liquid material to form one or more particles within the recessed areas of the patterned template surface; and
(e) releasing the one or more particles.

In some embodiments, the releasing of the one or more particles is performed by at least one of:
(a) applying the patterned template to a substrate, wherein the substrate has an affinity for the one or more particles;
(b) deforming the patterned template such that the one or more particles is released from the patterned template;
(c) swelling the patterned template with a first solvent to extrude the one or more particles;
(d) washing the patterned template with a second solvent, wherein the second solvent has an affinity for the one or more particles;
(e) applying a mechanical force to the one or more particles;
(f) applying the patterned template to a liquid that when hardened physically entraps particles; and
(g) applying the patterned template to a material that when hardened has a chemical and/or physical interaction with particles.

In some embodiments, the mechanical force is applied by contacting one of a Doctor blade and a brush with the one or more particles. In some embodiments, the mechanical force is applied by ultrasonics, megasonics, electrostatics, or magnetics means.

In some embodiments, the method includes harvesting or collecting the particles. In some embodiments, the harvesting or collecting of the particles includes a process selected from the group including scraping with a doctor blade, a brushing process, a dissolution process, an ultrasound process, a megasonics process, an electrostatic process, and a magnetic process. In some embodiments, the harvesting or collecting of the particles includes applying a material to at least a portion of a surface of the particle wherein the material has an affinity for the particles. In some embodiments, the material includes an adhesive or sticky surface. In some embodiments, the material includes, without limitation, one or more of a carbohydrate, an epoxy, a wax, polyvinyl alcohol, polyvinyl pyrrolidone, polybutyl acrylate, a polycyano acrylate, a polyacrylic acid and polymethyl methacrylate. In some embodiments, the harvesting or collecting of the particles includes cooling water to form ice (e.g., in contact with the particles). In some embodiments, the presently disclosed subject matter describes a particle or plurality of particles formed by the methods described herein. In some embodiments, the plurality of particles includes a plurality of monodisperse particles. In some embodiments, the particle or plurality of particles is selected from the group including a semiconductor device, a crystal, a drug delivery vector, a gene delivery vector, a disease detecting device, a disease locating device, a photovoltaic device, a porogen, a cosmetic, an electret, an additive, a catalyst, a sensor, a detoxifying agent, an abrasive, such as a CMP, a micro-electro-mechanical system (MEMS), a cellular scaffold, a taggart, a pharmaceutical agent, and a biomarker. In some embodiments, the particle or plurality of particles include a freestanding structure.

Further, in some embodiments, the presently disclosed subject matter describes a method of fabricating isolated liquid objects, the method including (a) contacting a liquid material with the surface of a first low surface energy material; (b) contacting the surface of a second low surface energy material with the liquid, wherein at least one of the surfaces of either the first or second low surface energy material is patterned; (c) sealing the surfaces of the first and the second low surface energy materials together; and (d) separating the two low surface energy materials to produce a replica pattern including liquid droplets.

In some embodiments, the liquid material includes poly(ethylene glycol)-diacrylate. In some embodiments, the low surface energy material includes perfluoropolyether-diacrylate. In some embodiments, a chemical process is used to seal the surfaces of the first and the second low surface energy materials. In some embodiments, a physical process is used to seal the surfaces of the first and the second low surface energy materials. In some embodiments, one of the surfaces of the low surface energy material is patterned. In some embodiments, one of the surfaces of the low surface energy material is not patterned.

In some embodiments, the method further includes using the replica pattern composed of liquid droplets to fabricate other objects. In some embodiments, the replica pattern of liquid droplets is formed on the surface of the low surface energy material that is not patterned. In some embodiments, the liquid droplets undergo direct or partial solidification. In some embodiments, the liquid droplets undergo a chemical transformation. In some embodiments, the solidification of the liquid droplets or the chemical transformation of the liquid droplets produce freestanding objects. In some embodiments, the freestanding objects are harvested. In some embodiments, the freestanding objects are bonded in place. In some embodiments, the freestanding objects are directly solidified, partially solidified, or chemically transformed.

In some embodiments, the liquid droplets are directly solidified, partially solidified, or chemically transformed on or in the patterned template to produce objects embedded in the recesses of the patterned template. In some embodiments, the embedded objects are harvested. In some embodiments, the embedded objects are bonded in place. In some embodiments, the embedded objects are used in other fabrication processes.

In some embodiments, the replica pattern of liquid droplets is transferred to other surfaces. In some embodiments, the transfer takes place before the solidification or chemical transformation process. In some embodiments, the transfer takes place after the solidification or chemical transformation process. In some embodiments, the surface to which the replica pattern of liquid droplets is transferred is selected from the group including a non-low surface energy surface, a low surface energy surface, a functionalized surface, and a sacrificial surface. In some embodiments, the method produces a pattern on a surface that is essentially free of one or more scum layers. In some embodiments, the method is used to fabricate semiconductors and other electronic and photonic devices or arrays. In some embodiments, the method is used to create freestanding objects. In some embodiments, the method is used to create three-dimensional objects using multiple patterning steps. In some embodiments, the isolated or patterned object includes materials selected from the group including organic, inorganic, polymeric, and biological materials. In some embodiments, a surface adhesive agent is used to anchor the isolated structures on a surface.

In some embodiments, the liquid droplet arrays or solid arrays on patterned or non-patterned surfaces are used as regiospecific delivery devices or reaction vessels for additional chemical processing steps. In some embodiments, the additional chemical processing steps are selected from the group including printing of organic, inorganic, polymeric, biological, and catalytic systems onto surfaces; synthesis of organic, inorganic, polymeric, biological materials; and other applications in which localized delivery of materials to surfaces is desired. Applications of the presently disclosed subject matter include, but are not limited to, micro and nanoscale patterning or printing of materials. In some embodiments, the materials to be patterned or printed are selected from the group including surface-binding molecules, inorganic compounds, organic compounds, polymers, biological molecules, nanoparticles, viruses, biological arrays, and the like.

In some embodiments, the applications of the presently disclosed subject matter include, but are not limited to, the synthesis of polymer brushes, catalyst patterning for CVD carbon nanotube growth, cell scaffold fabrication, the application of patterned sacrificial layers, such as etch resists, and the combinatorial fabrication of organic, inorganic, polymeric, and biological arrays.

In some embodiments, non-wetting imprint lithography, and related techniques, are combined with methods to control the location and orientation of chemical components within an individual object. In some embodiments, such methods improve the performance of an object by rationally structuring the object so that it is optimized for a particular application. In some embodiments, the method includes incorporating biological targeting agents into particles for drug delivery, vaccination, and other applications. In some embodiments, the method includes designing the particles to include a specific biological recognition motif. In some embodiments, the biological recognition motif includes biotin/avidin and/or other proteins.

In some embodiments, the method includes tailoring the chemical composition of these materials and controlling the reaction conditions, whereby it is then possible to organize the biorecognition motifs so that the efficacy of the particle is optimized. In some embodiments, the particles are designed and synthesized so that recognition elements are located on the surface of the particle in such a way to be accessible to cellular binding sites, wherein the core of the particle is preserved to contain bioactive agents, such as therapeutic molecules. In some embodiments, a non-wetting imprint lithography method is used to fabricate the objects, wherein the objects are optimized for a particular application by incorporating functional motifs, such as biorecognition agents, into the object composition. In some embodiments, the method further includes controlling the microscale and nanoscale structure of the object by using methods selected from the group including self-assembly, stepwise fabrication procedures, reaction conditions, chemical composition, crosslinking, branching, hydrogen bonding, ionic interactions, covalent interactions, and the like. In some embodiments, the method further includes controlling the microscale and nanoscale structure of the object by incorporating chemically organized precursors into the object. In some embodiments, the chemically organized precursors are selected from the group including block copolymers and core-shell structures.

In sum, the presently disclosed subject matter describes a non-wetting imprint lithography technique that is scalable and offers a simple, direct route to such particles without the use of self-assembled, difficult to fabricate block copolymers and other systems II.A. Micro and Nano Particles According to some embodiments of the presently disclosed subject matter, a particle is formed that has a solid geometric shape corresponding to a mold having a desired shape and is less than about 10 μm in a given dimension (e.g. minimum, intermediate, or maximum dimension). The particle can be of an organic material or an inorganic material and can be one uniform compound or component or a mixture of compounds or components.

In some embodiments, the particle includes a therapeutic or diagnostic agent coupled with the particle. The therapeutic or diagnostic agent can be physically coupled or chemically coupled with the particle, encompassed within the particle, at least partially encompassed within the particle, coupled to the exterior of the particle, combinations thereof, and the like. The therapeutic agent can be a drug, a biologic, a ligand, an oligopeptide, a cancer treating agent, a viral treating agent, a bacterial treating agent, a fungal treating agent, combinations thereof, or the like.

According to some embodiments, the particle is hydrophilic such that the particle avoids clearance by biological organism, such as a human.

According to other embodiments, the particle can be substantially coated. The coating, for example, can be a sugar based coating where the sugar is preferably glucose, sucrose, maltose, derivatives thereof, combinations thereof, or the like.

In yet other embodiments, the particle can include a functional location such that the particle can be used as an analytical material. According to such embodiments, a particle includes a functional molecular imprint. The functional molecular imprint can include functional monomers arranged as a negative image of a template. The template, for example, can be but is not limited to, an enzyme, a protein, an antibiotic, an antigen, a nucleotide sequence, an amino acid, a drug, a biologic, nucleic acid, combinations thereof, or the like. In other embodiments, the particle itself, for example, can be, but is not limited to, an artificial functional molecule. In one embodiment, the artificial functional molecule is a functionalized particle that has been molded from a molecular imprint. As such, a molecular imprint is generated in accordance with methods and materials of the presently disclosed subject matter and then a particle is formed from the molecular imprint, in accordance with further methods and materials of the presently disclosed subject matter. Such an artificial functional molecule includes substantially similar steric and chemical properties of a molecular imprint template. In one embodiment, the functional monomers of the functionalized particle are arranged substantially as a negative image of functional groups of the molecular imprint.

According to some embodiments, particles formed in the patterned templates described herein are less than about 10 μm in a dimension. In other embodiments, the particle is between about 10 μm and about 1 μm in dimension. In yet further embodiments, the particle is less than about 1 μm in dimension. According to some embodiments the particle is between about 1 nm and about 500 nm in a dimension. According to other embodiments, the particle is between about 10 nm and about 200 nm in a dimension. In still further embodiments, the particle is between about 80 nm and 120 nm in a dimension. According to still more embodiments the particle is between about 20 nm and about 120 nm in dimension. In further embodiments, the particle has a maximum cross-sectional dimension of less than about 1 micrometer. In some embodiments, the particle has a maximum cross-sectional dimension between about 5 nanometers and about 1 micrometer. In some embodiments, the particle has a maximum cross-sectional dimension between about 10 nanometers and about 1 micrometer. In some embodiments, the particle has a maximum cross-sectional dimension less than about 800 nanometers. In some embodiments, the particle has a maximum cross-sectional dimension less than about 750 nanometers. In some embodiments, the particle has a maximum cross-sectional dimension less than about 500 nanometers. In some embodiments, the particle has a maximum cross-sectional dimension less than about 300 nanometers. In some embodiments, the particle has a maximum cross-sectional dimension less than about 250 nanometers. In some embodiments, the particle has a maximum cross-sectional dimension less than about 200 nanometers. In some embodiments, the particle has a maximum cross-sectional dimension less than about 150 nanometers. In some embodiments, the particle has a maximum cross-sectional dimension less than about 100 nanometers. In some embodiments, particles are fabricated in an array of substantially congruent recesses thereby forming a plurality of substantially congruent particles. The dimension of the particle can be a predetermined dimension, a cross-sectional diameter, a circumferential dimension, or the like.

According to further embodiments, the particles include patterned features that are about 2 nm in a dimension. In still further embodiments, the patterned features are between about 2 nm and about 200 nm. In other embodiments, the particle is less than about 80 nm in a widest dimension.

According to other embodiments, the particles produced by the methods and materials of the presently disclosed subject matter have a poly dispersion index of between about 0.80 and about 1.20, between about 0.90 and about 1.10, between about 0.95 and about 1.05, between about 0.99 and about 1.01, between about 0.999 and about 1.001, combinations thereof, and the like. Furthermore, in other embodiments the particle has a monodispersity.

According to other embodiments, particles of many predetermined regular and irregular shape and size configurations can be made with the materials and methods of the presently disclosed subject matter. Examples of representative particle shapes that can be made using the materials and methods of the presently disclosed subject matter include, but are not limited to, non-spherical, spherical, viral shaped, bacteria shaped, cell shaped, rod shaped (e.g., where the rod is less than about 200 nm in diameter), chiral shaped, right triangle shaped, flat shaped (e.g., with a thickness of about 2 nm, disc shaped with a thickness of greater than about 2 nm, or the like), boomerang shaped, combinations thereof, and the like.

In some embodiments, the material from which the particles are formed includes, without limitation, one or more of a polymer, a liquid polymer, a solution, a monomer, a plurality of monomers, a polymerization initiator, a polymerization catalyst, an inorganic precursor, an organic material, a natural product, a metal precursor, a pharmaceutical agent, a tag, a magnetic material, a paramagnetic material, a ligand, a cell penetrating peptide, a porogen, a surfactant, a plurality of immiscible liquids, a solvent, a charged species, combinations thereof, or the like. In further embodiments, the materials included in the particles or from which the particles can be formed includes compositions, monomers, polymers, and materials found in Polymer Handbook, Grulke, Eric A., et al., John Wiley & Sons; 4th edition (May 29, 2003) which is incorporated herein by reference in its entirety.

In some embodiments, the monomer includes butadienes, styrenes, propene, acrylates, methacrylates, vinyl ketones, vinyl esters, vinyl acetates, vinyl chlorides, vinyl fluorides, vinyl ethers, acrylonitrile, methacrylnitrile, acrylamide, methacrylamide allyl acetates, fumarates, maleates, ethylenes, propylenes, tetrafluoroethylene, ethers, isobutylene, fumaronitrile, vinyl alcohols, acrylic acids, amides, carbohydrates, esters, urethanes, siloxanes, formaldehyde, phenol, urea, melamine, isoprene, isocyanates, epoxides, bisphenol A, alcohols, chlorosilanes, dihalides, dienes, alkyl olefins, ketones, aldehydes, vinylidene chloride, anhydrides, saccharide, acetylenes, naphthalenes, pyridines, lactams, lactones, acetals, thiiranes, episulfide, peptides, derivatives thereof, and combinations thereof.

In yet other embodiments, the polymer includes polyamides, proteins, polyesters, polystyrene, polyethers, polyketones, polysulfones, polyurethanes, polysiloxanes, polysilanes, cellulose, amylose, polyacetals, polyethylene, glycols, poly(acrylate)s, poly(methacrylate)s, poly(vinyl alcohol), poly(vinylidene chloride), poly(vinyl acetate), poly(ethylene glycol), polystyrene, polyisoprene, polyisobutylenes, poly(vinyl chloride), poly(propylene), poly(lactic acid), polyisocyanates, polycarbonates, alkyds, phenolics, epoxy resins, polysulfides, polyimides, liquid crystal polymers, heterocyclic polymers, polypeptides, conducting polymers including polyacetylene, polyquinoline, polyaniline, polypyrrole, polythiophene, and poly(p-phenylene), dendimers, fluoropolymers, derivatives thereof, combinations thereof, and the like.

In still further embodiments, the material from which the particles are formed includes a non-wetting agent. According to another embodiment, the material is a liquid material in a single phase. In other embodiments, the liquid material includes a plurality of phases. In some embodiments, the liquid material includes, without limitation, one or more of multiple liquids, multiple immiscible liquids, surfactants, dispersions, emulsions, microemulsions, micelles, particulates, colloids, porogens, active ingredients, combinations thereof, or the like.

In some embodiments, additional components are included with the material of the particle to functionalize the particle. According to these embodiments the additional components can be encased within the isolated structures, partially encased within the isolated structures, on the exterior surface of the isolated structures, combinations thereof, or the like. Additional components can include, but are not limited to, drugs, biologics, more than one drug, more than one biologic, combinations thereof, and the like.

In some embodiments, the drug is a psychotherapeutic agent. In other embodiments, the psychotherapeutic agent is used to treat depression and can include, for example, sertraline, venlafaxine hydrochloride, paroxetine, bupropion, citalopram, fluoxetine, mirtazapine, escitalopram, and the like. In some embodiments, the psychotherapeutic agent is used to treat schizophrenia and can include, for example, olanazapine, risperidone, quetiapine, aripiprazole, ziprasidone, and the like. According to other embodiments, the psychotherapeutic agent is used to treat attention deficit disorder (ADD) or attention deficit hyperactivity disorder (ADHD), and can include, for example, methylphenidate, atomoxetine, amphetamine, dextroamphetamine, and the like. In some other embodiments, the drug is a cholesterol drug and can include, for example, atorvastatin, simvastatin, pravastatin, ezetimibe, rosuvastatin, fenofibrate fluvastatin, and the like. In yet some other embodiments, the drug is a cardiovascular drug and can include, for example, amlodipine, valsartan, losartan, hydrochlorothiazide, metoprolol, candesartan, ramipril, irbesartan, amlodipine, benazepril, nifedipine, carvedilol, enalapril, telmisartan, quinapril, doxazosin mesylate, felodipine, lisinopril, and the like. In some embodiments, the drug is a blood modifier and can include, for example, epoetin alfa, darbepoetin alfa, epoetin beta, clopidogrel, pegfilgrastim, filgrastim, enoxaparin, Factor VIIA, antihemophilic factor, immune globulin, and the like. According to a further embodiment, the drug can include a combination of the above listed drugs.

In some embodiments, the additional components included with the particles of the presently disclosed subject matter can include, but are not limited, to anti-infective agents. In some embodiments, the anti-infective agent is used to treat bacterial infections and can include, for example, azithromycin, amoxicillin, clavulanic acid, levofloxacin, clarithromycin, ceftriaxone, ciprofloxacin, piperacillin, tazobactam sodium, imipenem, cilastatin, linezolid, meropenem, cefuroxime, moxifloxacin, and the like. In some embodiments the anti-infective agent is used to treat viral infections and can include, for example, lamivudine, zidovudine, valacyclovir, peginterferon, lopinavir, ritonavir, tenofovir, efavirenz, abacavir, lamivudine, zidovudine, atazanavir, and the like. In other embodiments, the anti-infective agent is used to treat fungal infections and can include, for example, terbinafine, fluconazole, itraconazole, caspofungin acetate, and the like. In some embodiments, the drug is a gastrointestinal drug and can include, for example, esomeprazole, lansoprazole, omeprazole, pantoprazole, rabeprazole, ranitidine, ondansetron, and the like. According to yet other embodiments, the drug is a respiratory drug and can include, for example, fluticasone, salmeterol, montelukast, budesonide, formoterol, fexofenadine, cetirizine, desloratadine, mometasone furoate, tiotropium, albuterol, ipratropium, palivizumab, and the like. In yet other embodiments, the drug is an antiarthritic drug and can include, for example, celecoxib, infliximab, etanercept, rofecoxib, valdecoxib, adalimumab, meloxicam, diclofenac, fentanyl, and the like. According to a further embodiment, the drug can include a combination of the above listed drugs.

According to alternative embodiments, the additional components included with the particles of the presently disclosed subject matter can include, but are not limited to an anticancer agent and can include, for example, nitrogen mustard, cisplatin, doxorubicin, docetaxel, anastrozole, trastuzumab, capecitabine, letrozole, leuprolide, bicalutamide, goserelin, rituximab, oxaliplatin, bevacizumab, irinotecan, paclitaxel, carboplatin, imatinib, gemcitabine, temozolomide, gefitinib, and the like. In some embodiments, the drug is a diabetes drug and can include, for example, rosiglitazone, pioglitazone, insulin, glimepiride, voglibose, and the like. In other embodiments, the drug is an anticonvulsant and can include, for example, gabapentin, topiramate, oxcarbazepine, carbamazepine, lamotrigine, divalproex, levetiracetam, and the like. In some embodiments, the drug is a bone metabolism regulator and can include, for example, alendronate, raloxifene, risedronate, zoledronic, and the like. In some embodiments, the drug is a multiple sclerosis drug and can include, for example, interferon, glatiramer, copolymer-1, and the like. In other embodiments, the drug is a hormone and can include, for example, somatropin, norelgestromin, norethindrone, desogestrel, progestin, estrogen, octreotide, levothyroxine, and the like. In yet other embodiments, the drug is a urinary tract agent, and can include, for example, tamsulosin, finasteride, tolterodine, and the like. In some embodiments, the drug is an immunosuppressant and can include, for example, mycophenolate mofetil, cyclosporine, tacrolimus, and the like. In some embodiments, the drug is an ophthalmic product and can include, for example, latanoprost, dorzolamide, botulinum, verteporfin, and the like. In some embodiments, the drug is a vaccine and can include, for example, pneumococcal, hepatitis, influenza, diphtheria, and the like. In other embodiments, the drug is a sedative and can include, for example, zolpidem, zaleplon, eszopiclone, and the like. In some embodiments, the drug is an Alzheimer disease therapy and can include, for example, donepexil, rivastigmine, tacrine, and the like. In some embodiments, the drug is a sexual dysfunction therapy and can include, for example, sildenafil, tadalafil, alprostadil, levothyroxine, and the like. In an alternative embodiment, the drug is an anesthetic and can include, for example, sevoflurane, propofol, mepivacaine, bupivacaine, ropivacaine, lidocaine, nesacaine, etidocaine, and the like. In some embodiments, the drug is a migraine drug and can include, for example, sumatriptan, almotriptan, rizatriptan, naratriptan, and the like. In some embodiments, the drug is an infertility agent and can include, for example, follitropin, choriogonadotropin, menotropin, follicle stimulating hormone (FSH), and the like. In some embodiments, the drug is a weight control product and can include, for example, orlistat, dexfenfluramine, sibutramine, and the like. According to a further embodiment, the drug can include a combination of the above listed drugs.

In some embodiments, one or more additional components are included with the particles. The additional components can include: targeting ligands such as cell-targeting peptides, cell-penetrating peptides, integrin receptor peptide (GRGDSP), melanocyte stimulating hormone, vasoactive intestional peptide, anti-Her2 mouse antibodies, and the like; vitamins; viruses; polysaccharides; cyclodextrins; liposomes; proteins; optical nanoparticles such as CdSe for optical applications; borate nanoparticles to aid in boron neutron capture therapy (BNCT) targets; combinations thereof; and the like.

In some embodiments, imaging agents are included with the particles. In some embodiments, the imaging agent is an x-ray agent and can include, for example, barium sulfate, ioxaglate meglumine, ioxaglate sodium, diatrizoate meglumine, diatrizoate sodium, ioversol, iothalamate meglumine, iothalamate sodium, iodixanol, iohexol, iopentol, iomeprol, iopamidol, iotroxate meglumine, iopromide, iotrolan, sodium amidotrizoate, meglumine amidotrizoate, and the like. In some embodiments, the imaging agent is a MRI agent and can include, for example, gadopentetate dimeglumine, ferucarbotran, gadoxetic acid disodium, gadobutrol, gadoteridol, gadobenate dimeglumine, ferumoxsil, gadoversetamide, gadolinium complexes, gadodiamide, mangafodipir, and the like. In some embodiments, the imaging agent is an ultrasound agent and can include, for example, galactose, palmitic acid, $SF_6$, and the like. In some embodiments, the imaging agent is a nuclear agent and can include, for example, technetium (Tc99m) tetrofosmin, ioflupane, technetium (Tc99m) depreotide, technetium (Tc99m) exametazime, fluorodeoxyglucose (FDG), samarium (Sm153) lexidronam, technetium (Tc99m) mebrofenin, sodium iodide (I125 and I131), technetium (Tc99m) medronate, technetium (Tc99m) tetrofosmin, technetium (Tc99m) fanolesomab, technetium (Tc99m) mertiatide, technetium (Tc99m) oxidronate, technetium (Tc99m) pentetate, technetium (Tc99m) gluceptate, technetium (Tc99m) albumin, technetium (Tc99m) pyrophosphate, thallous (TI201) chloride, sodium chromate (Cr51), gallium (Ga67) citrate, indium (In111) pentetreotide, iodinated (I125) albumin, chromic phosphate (P32), sodium phosphate (P32), and the like. According to a further embodiment, the agent can include a combination of the above listed agents, drugs, biologics, and the like.

According to other embodiments, one or more other drugs can be included with the particles of the presently disclosed subject matter and can be found in Physician's Desk Reference, Thomson Healthcare, 59th Bk&Cr edition (2004), which is incorporated herein by reference in its entirety.

In some embodiments, the particles are coated with a patient appealing substance to facilitate and encourage consumption of the particles as oral drug delivery vehicles. The particles can be coated or substantially coated with a substance (e.g., a food substance) that can mask any taste the particle and/or drug combination might have. According to some embodiments, the particle is coated with a sugar based substance to impart to the particle an appealing sweet taste. According to other embodiments, the particles can be coated with materials described in relation to the fast-dissolve embodiments described herein above.

Figure 45:
FIG. 45 shows a labeled particle associated with a cell according to an embodiment of the presently disclosed subject matter.
Figure 46:
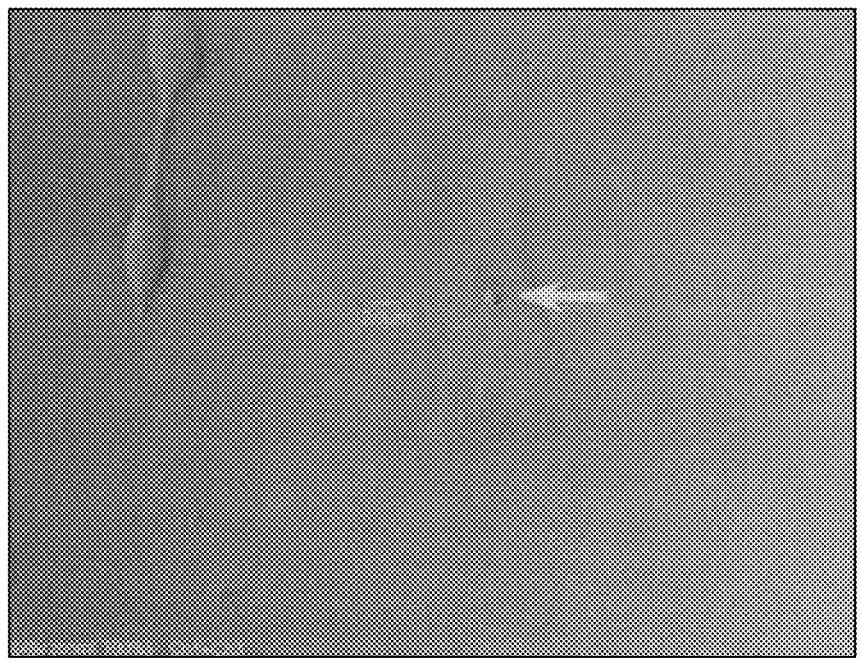
FIG. 46 shows a labeled particle associated with a cell according to an embodiment of the presently disclosed subject matter.

According to some embodiments, radiotracers and/or radiopharmaceuticals are included with the particles. Examples of radiotracers and/or radiopharmaceuticals that can be combined with the isolated structures of the presently disclosed subject matter include, but are not limited to, [$^{15}$O]oxygen, [$^{15}$O]carbon monoxide, [$^{15}$O]carbon dioxide, [$^{15}$O]water, [$^{13}$N]ammonia, [$^{18}$F]FDG, [$^{18}$F]FMISO, [$^{18}$F]MPPF, [$^{18}$F]A85380, [$^{18}$F]FLT, [$^{11}$C]SCH23390, [$^{11}$C]flumazenil, [$^{11}$C]PK11195, [$^{11}$C]PIB, [$^{11}$C]AG1478, [$^{11}$C]choline, [$^{11}$C]AG957, [$^{18}$F]nitroisatin, [$^{18}$F]mustard, combinations thereof, and the like. In some embodiments elemental isotopes are included with the particles. In some embodiments, the isotopes include $^{11}C$, $^{13}N$, $^{15}O$, $^{18}F$, $^{32}P$, $^{51}Cr$, $^{57}Co$, $^{67}Ga$, $^{81}Kr$, $^{82}Rb$, $^{89}Sr$, $^{99}Tc$, $^{111}In$, $^{123}I$, $^{125}I$, $^{131}I$, $^{133}Xe$, $^{153}Sm$, $^{201}Tl$, or the like. According to a further embodiment, the isotope can include a combination of the above listed isotopes, and the like. Likewise, the particles can include a fluorescent label such that the particle can be identified. Examples of fluorescent labeled particles are shown in FIGS. 45 and 46. FIG. 45 shows a particle that has been fluorescently labeled and is associated with a cell membrane and the particle shown in FIG. 46 is within the cell.

According to still further embodiments, contrast agents can be included with the material from which the particles are formed. Adding contrast agents enhances diagnostic imaging of physiologic structures for clinical evaluations and other testing. For example, ultrasound imaging techniques often involve the use of contrast agents, as contrast agents can serve to improve the quality and usefulness of images which are obtained with ultrasound. The viability of currently available ultrasound contrast agents and methods involving their use is highly dependent on a variety of factors, including the particular region being imaged. For example, difficulty is encountered in obtaining useful diagnostic images of heart tissue and the surrounding vasculature due, at least in part, to the large volume of blood which flows through the chambers of the heart relative to the volume of blood which flows in the blood vessels of the heart tissue itself. The high volume of blood flowing through the chambers of the heart can result in insufficient contrast in ultrasound images of the heart region, especially the heart tissue. The high volume of blood flowing through the chambers of the heart also can produce diagnostic artifacts including, for example, shadowing or darkening, in ultrasound images of the heart. Diagnostic artifacts can be highly undesirable since they can hamper or even prevent visualization of a region of interest. Thus, in certain circumstances, diagnostic artifacts can render a diagnostic image substantially unusable.

In addition to ultrasound, computed tomography (CT) is a valuable diagnostic imaging technique for studying various areas of the body. Like ultrasound, CT imaging is greatly enhanced with the aid of contrast agents. In CT, the radiodensity (electron density) of matter is measured. Because of the similarity in the measured densities of various tissues in the body, it has been necessary to use contrast agents which can change the relative densities of different tissues. This characteristic has resulted in an overall improvement in the diagnostic efficacy of CT. Barium and iodine compounds, for example, have been developed for this purpose and can be included with the particles of the presently disclosed subject matter in some embodiments. Accordingly, in other embodiments, contrast agents that can be used with the materials of the presently disclosed subject matter, include for example, but are not limited to, barium sulfate, Iodinated water-soluble contrast media, combinations thereof, and the like.

Magnetic resonance imaging (MRI) is another diagnostic imaging technique that is used for producing cross-sectional images of a tissue in a variety of scanning planes. Like ultrasound and CT, MRI also benefits from the use of contrast agents. In some embodiments of the presently disclosed subject matter, contrast agents for MRI are used with the materials of the presently disclosed subject matter to enhance MRI imaging. Contrast agents for MRI imaging that can be useful with the materials of the presently disclosed subject matter include, but are not limited to, paramagnetic contrast agents, metal ions, transition metal ions, metal ions that are chelated with ligands, metal oxides, iron oxides, nitroxides, stable free radicals, stable nitroxides, lanthanide and actinide elements, lipophilic derivatives, proteinaceous macromolecules, alkylated, nitroxides 2,2,5, 5-tetramethyl-1-pyrrolidinyloxy, free radical, 2,2,6,6-tetramethyl-1-piperidinyloxy, free radical, combinations thereof, and the like.

According to yet other embodiments contrast agents that can be used with the materials of the presently disclosed subject matter include, but are not limited to, superparamagnetic contrast agents, ferro- or ferrimagnetic compounds such as pure iron, magnetic iron oxide, such as magnetite, $\gamma$-$Fe_2O_3$, $Fe_3O_4$, manganese ferrite, cobalt ferrite, nickel ferrite; paramagnetic gases such as oxygen 17 gas, hyperpolarized xenon, neon, helium gas, combinations thereof, and the like. If desired, the paramagnetic or superparamagnetic contrast agents used with the materials of the presently disclosed include, but are not limited to, paramagnetic or superparamagetic agents that are delivered as alkylated or having other derivatives incorporated into the compositions, combinations thereof, and the like.

In yet another embodiment, contrast agents for X-ray techniques useful for combination with the particles of the presently disclosed subject matter include, but are not limited to, carboxylic acid and non-ionic amide contrast agents typically containing at least one 2,4,6-triiodophenyl group having substituents such as carboxyl, carbamoyl, N-alkylcarbamoyl, N-hydroxyalkylcarbamoyl, acylamino, N-alkylacylamino or acylaminomethyl at the 3- and/or 5-positions, as in metrizoic acid, diatrizoic acid, iothalamic acid, ioxaglic acid, iohexol, iopentol, iopamidol, iodixanol, iopromide, metrizamide, iodipamide, meglumine iodipamide, meglumine acetrizoate, meglumine diatrizoate, combinations thereof, and the like.

Still other contrast agents that can be included with the particle materials of the presently disclosed subject matter include, but are not limited to, barium sulfate, a barium sulfate suspension, sodium bicarbonate and tartaric acid mixtures, lothalamate meglumine, lothalamate sodium, hydroxypropyl methylcellulose, ferumoxsil, ioxaglate meglumine, ioxaglate sodium, diatrizoate meglumine, diatrizoate sodium, gadoversetamide, ioversol, organically bound iodine, methiodal sodium, ioxitalamate meglumine, iocarmate meglumine, metrizamide, iohexal, iopamidol, combinations thereof, and the like.

U.S. Pat. Nos. 6,884,407 and 6,331,289, along with the references cited therein, disclose contrasts that are useful with the particles of the presently disclosed subject matter, these references are incorporated by reference herein along with the references cited therein.

According to further embodiments the particle can include or can be formed into and used as a tag or a taggant. A taggant that can be included in the particle or can be the particle includes, but is not limited to, a fluorescent, radio-labeled, magnetic, biologic, shape specific, size specific, combinations thereof, or the like.

In some embodiments, a therapeutic agent for combination with the particles of the presently disclosed subject matter is selected from one of a drug and genetic material. In some embodiments, the genetic material includes, without limitation, one or more of a non-viral gene vector, DNA, RNA, RNAi, a viral particle, agents described elsewhere herein, combinations thereof, or the like.

In some embodiments, the particle includes a biodegradable polymer. In other embodiments, the polymer is modified to be a biodegradable polymer (e.g., a poly(ethylene glycol) that is functionalized with a disulfide group). In some embodiments, the biodegradable polymer includes, without limitation, one or more of a polyester, a polyanhydride, a polyamide, a phosphorous-based polymer, a poly(cyanoacrylate), a polyurethane, a polyorthoester, a polydihydropyran, a polyacetal, combinations thereof, or the like.

In some embodiments, the polyester includes, without limitation, one or more of polylactic acid, polyglycolic acid, poly(hydroxybutyrate), poly(ε-caprolactone), poly(β-malic acid), poly(dioxanones), combinations thereof, or the like. In some embodiments, the polyanhydride includes, without limitation, one or more of poly(sebacic acid), poly(adipic acid), poly(terpthalic acid), combinations thereof, or the like. In yet other embodiments, the polyamide includes, without limitation, one or more of poly(imino carbonates), polyaminoacids, combinations thereof, or the like.

According to some embodiments, the phosphorous-based polymer includes, without limitation, one or more of a polyphosphate, a polyphosphonate, a polyphosphazene, combinations thereof, or the like. Further, in some embodiments, the biodegradable polymer further includes a polymer that is responsive to a stimulus. In some embodiments, the stimulus includes, without limitation, one or more of pH, radiation, ionic strength, oxidation, reduction, temperature, an alternating magnetic field, an alternating electric field, combinations thereof, or the like. In some embodiments, the stimulus includes an alternating magnetic field.

In some embodiments, a pharmaceutical agent can be combined with the particle material. The pharmaceutical agent can be, but is not limited to, a drug, a peptide, RNAi, DNA, combinations thereof, or the like. In other embodiments, the tag is selected from the group including a fluorescence tag, a radiolabeled tag, a contrast agent, combinations thereof, or the like. In some embodiments, the ligand includes a cell targeting peptide, or the like.

In use, the particles of the presently disclosed subject matter can be used as treatment devices. In such uses, the particle is administered in a therapeutically effective amount to a patient. According to yet other uses, the particle can be utilized as a physical tag. In such uses, a particle of a predetermined shape having a diameter of less than about 1 μm in a dimension is used as a taggant to identify products or the origin of a product. The particle as a taggant can be either identifiable to a particular shape or a particular chemical composition.

Further uses of the micro and/or nano particles include medical treatments such as orthopedic, oral, maxillofacial, and the like. For example, the particles described above that are or include pharmaceutical agents can be used in combination with traditional hygiene and/or surgical procedures. According to such an application, the particles can be used to directly and locally deliver pharmaceutical agents, or the like to an area of surgical interest. In some embodiments, medications used in oral medicine can fight oral diseases, prevent or treat infections, control pain, relieve anxiety, assist in the regeneration of damaged tissue, combinations thereof, and the like. For example, during oral or maxillofacial treatments, bleeding often occurs. As a result, bacteria from the mouth can directly enter the bloodstream and easily reach the heart. This occurrence presents a risk for some persons with cardiac abnormalities because the bacteria can cause bacterial endocarditis, a serious inflammation of the heart valves or tissues. Antibiotics reduce this risk. Traditional antibiotic delivery techniques, however, can be slow to reach the bloodstream, thus giving the bacterial a head start. To the contrary, applying particles of the presently disclosed subject matter, made from or including appropriate antibiotics, directly to the site of oral or maxillofacial treatment can greatly reduce the probability of a serious bacterial infection. Such procedures aided by the particles can include professional teeth cleaning, incision and drainage of infected oral tissue, oral injections, extractions, surgeries that involve the maxillary sinus, combinations thereof, and the like.

According to further embodiments, compositions can be formulated and made into particles according to materials and methods of the presently disclosed subject matter that are designed to be applied to defective teeth and gums for preventing diseases, such as carious tooth, pyorrhea alveolaris, or the like.

Further embodiments include particles having a composition for the repair and healing of tissue, bone defects and bone voids, resins for artificial teeth, resins for tooth bed, and other tooth fillers. For example, particles can be constructed from calcium based component, such as, but not limited to, calcium phosphates, calcium sulfates, calcium carbonates, calcium bone cements, amorphous calcium phosphate, crystalline calcium phosphate, combinations thereof, and the like. In use, such particles can be locally applied to a site of orthopedic treatment to facilitate recovery of the natural bone material. Furthermore, because of the small size of the particles and the ability to form the particles in practically any shape and configuration desirable, the particles can be administered to a site of orthopedic interest and interact with the site on a scale of the particle size. That is, the particles can integrate into very small spaces, cracks, gaps, and the like within the bone, such as a bone fracture, or between the bone and an implant. Thus, the particles can deliver pharmaceutical, regenerative, or the like materials to the orthopedic treatment site and integrate these materials where they were not previously applyable. Still further, the particles can increase the mechanical strength and integrity of fixation of a bone implant, such as an artificial joint fixation, because, due to control over the size and shape of the particles, they can neatly and orderly fill small voids between the implant and the natural bone tissue.

In other embodiments, medications to control pain and anxiety that are commonly used in oral, maxillofacial, orthopedic, and other procedures can be included in the particles. Such agents that can be incorporated with the particle include, but are not limited to, anti-inflammatory medications that are used to relieve the discomfort of mouth and gum problems, and can include corticosteroids, opioids, carprofen, meloxicam, etodolac, diclofenac, flurbiprofen, ibuprofen, ketorolac, nabumetone, naproxen, naproxen sodium, and oxaprozin. Oral anesthetics are used to relieve pain or irritation caused by many conditions, including toothaches, teething, sores, or dental appliances, and can include articaine, epinephrine, ravocaine, novocain, levophed, propoxycaine, procaine, norepinephrine bitartrate, marcaine, lidocaine, carbocaine, neocobefrin, mepivacaine, levonordefrin, etidocaine, dyclonine, and the like. Antibiotics are commonly used to control plaque and gingivitis in the mouth, treat periodontal disease, as well as reduce the risk of bacteria from the mouth entering the bloodstream. Oral antibiotics can include chlorhexidine, doxycycline, demeclocycline, minocycline, oxytetracycline, tetracycline, triclosan, clindamycin, ofloxacin, metronidazole, tinidazole, and ketoconazole. Fluoride also can be or be included in the particles of the presently disclosed subject matter and is used to prevent tooth decay. Fluoride is absorbed by teeth and helps strengthen teeth to resist acid and block the cavity-forming action of bacteria. As a varnish or a mouth rinse, fluoride helps reduce tooth sensitivity.

Other useful agents for dental applications are substances such as flavonoids, benzenecarboxylic acids, benzopyrones, steroids, pilocarpine, terpenes, and the like. Still further agents used within the particles include anethole, anisaldehyde, anisic acid, cinnamic acid, asarone, furfuryl alcohol, furfural, cholic acid, oleanolic acid, ursolic acid, sitosterol, cineol, curcumine, alanine, arginine, homocerine, mannitol, berterine, bergapten, santonin, caryophyllene, caryophyllene oxide, terpinene, chymol, terpinol, carvacrol, carvone, sabinene, inulin, lawsone, hesperedin, naringenin, flavone, flavonol, quercetin, apigenin, formonoretin, coumarin, acetyl coumarin, magnolol, honokiol, cappilarin, aloetin, and the like. Still further oral and maxillofacial treatment compounds include sustained release biodegradable compounds, such as, for example (meth)acrylate type monomers and/or polymers. Other compounds useful for the particles of the presently disclosed subject matter can be found in U.S. Pat. No. 5,006,340, which is incorporated herein by reference in its entirety.

III. Formation of Rounded Particles Through "Liquid Reduction"

Referring now to FIGS. 3A through 3F, the presently disclosed subject matter provides a "liquid reduction" process for forming particles that have shapes that do not conform to the shape of the template, including but not limited to spherical and non-spherical, regular and non-regular micro- and nanoparticles. For example, a "cube-shaped" template can allow for spherical particles to be made, whereas a "Block arrow-shaped" template can allow for "lolli-pop" shaped particles or objects to be made wherein the introduction of a gas allows surface tension forces to reshape the resident liquid prior to treating it. While not wishing to be bound by any particular theory, the non-wetting characteristics that can be provided in some embodiments of the presently disclosed patterned template and/or treated or coated substrate allows for the generation of rounded, e.g., spherical, particles.

Figure 3A:
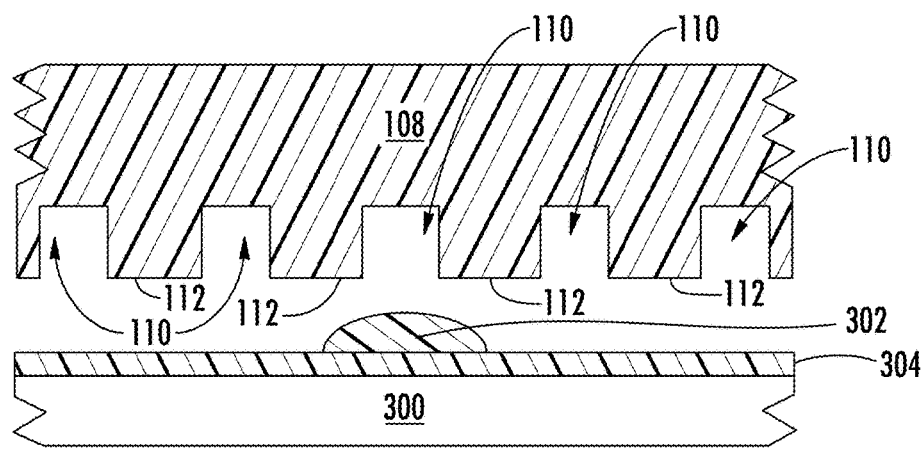
FIGS. 3A-3F are a schematic representation of the presently disclosed method for preparing one or more spherical particles.

Referring now to FIG. 3A, droplet 302 of a liquid material is disposed on substrate 300, which in some embodiments is coated or treated with a non-wetting material 304. A patterned template 108, which includes a plurality of recessed areas 110 and patterned surface areas 112, also is provided.

Figure 3B:
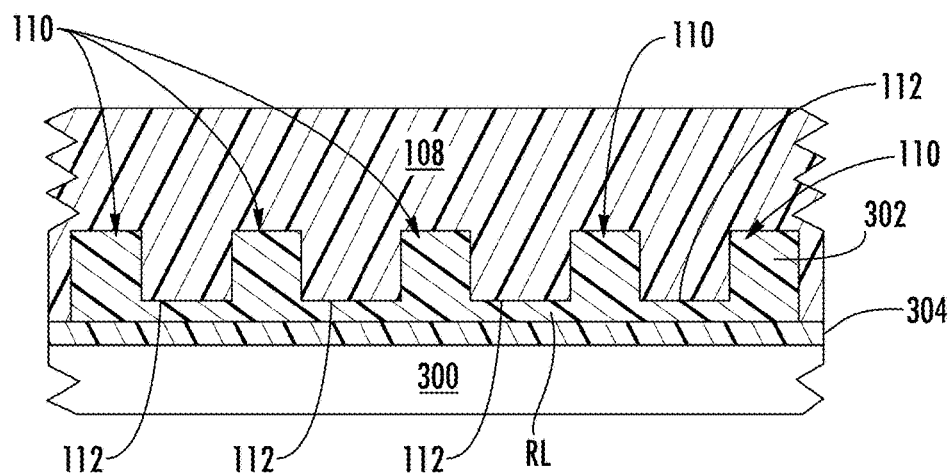

Referring now to FIG. 3B, patterned template 108 is contacted with droplet 302. The liquid material including droplet 302 then enters recessed areas 110 of patterned template 108. In some embodiments, a residual, or "scum," layer RL of the liquid material including droplet 302 remains between the patterned template 108 and substrate 300.

Figure 3C:
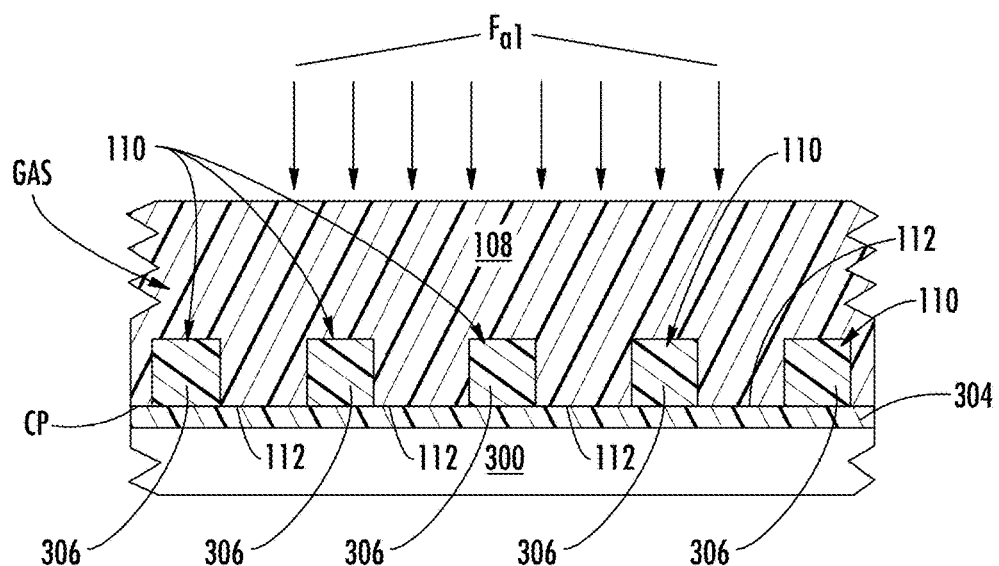

Referring now to FIG. 3C, a first force $F_{a1}$ is applied to patterned template 108. A contact point CP is formed between the patterned template 108 and the substrate and displacing residual layer RL. Particles 306 are formed in the recessed areas 110 of patterned template 108.

Figure 3D:
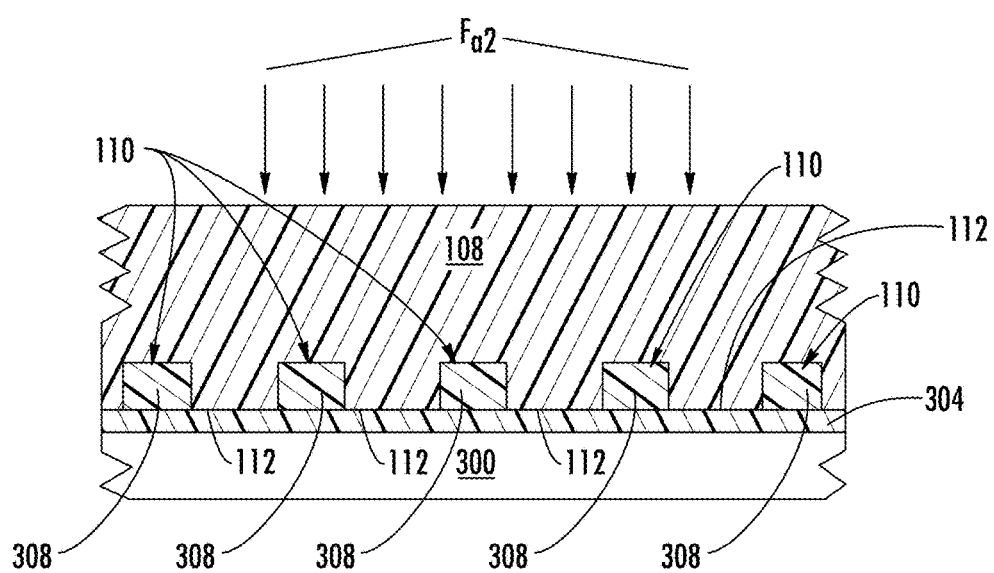

Referring now to FIG. 3D, a second force $F_{a2}$, wherein the force applied by $F_{a2}$ is greater than the force applied by $F_{a1}$, is then applied to patterned template 108, thereby forming smaller liquid particles 308 inside recessed areas 112 and forcing a portion of the liquid material including droplet 302 out of recessed areas 112.

Figure 3E:
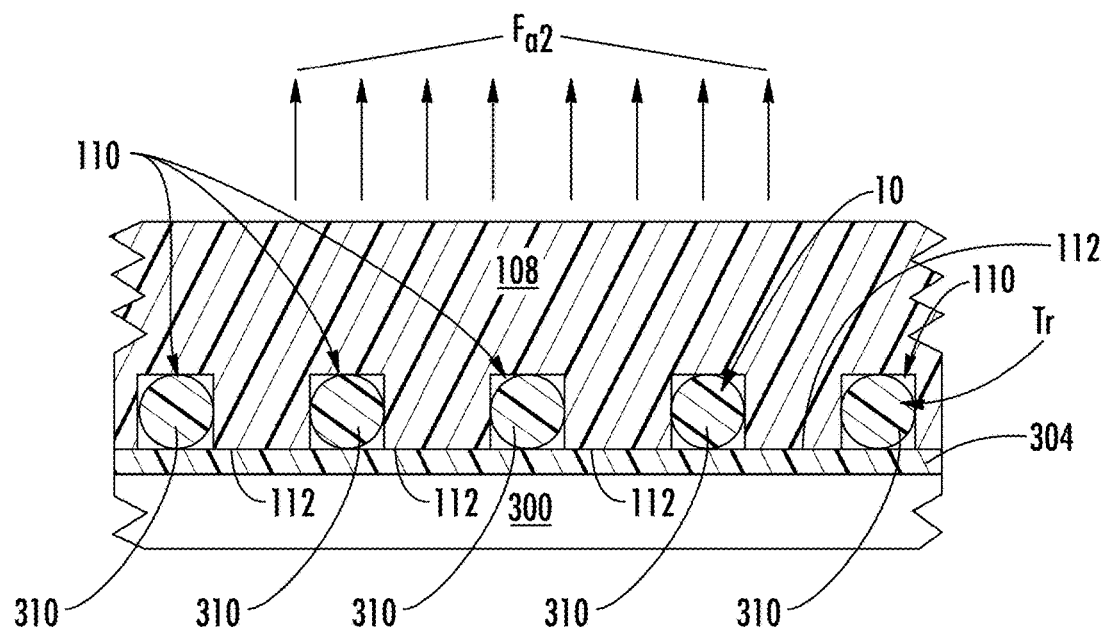

Referring now to FIG. 3E, the second force $F_{a2}$ is released, thereby returning the contact pressure to the original contact pressure applied by first force $F_{a1}$. In some embodiments, patterned template 108 includes a gas permeable material, which allows a portion of space with recessed areas 112 to be filled with a gas, such as nitrogen, thereby forming a plurality of liquid spherical droplets 310. Once this liquid reduction is achieved, the plurality of liquid spherical droplets 310 are treated by a treating process $T_r$.

Figure 3F:
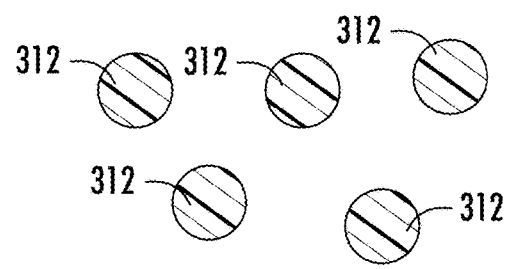

Referring now to FIG. 3F, treated liquid spherical droplets 310 are released from patterned template 108 to provide a plurality of freestanding spherical particles 312.

IIIA. Formation of Small Particles Through Evaporation

Referring now to FIGS. 41A through 41E, an embodiment of the presently disclosed subject matter includes a process for forming particles through evaporation. In one embodiment, the process produces a particle having a shape that does not necessarily conform to the shape of the template. The shape can include, but is not limited to, any three dimensional shape. According to some embodiments, the particle forms a spherical or non-spherical and regular or non-regular shaped micro- and nanoparticle. While not wishing to be bound by any particular theory, an example of producing a spherical or substantially spherical particle includes using a patterned template and/or substrate of a non-wetting material or treating the surfaces of the patterned template and substrate particle forming recesses with a non-wetting agent such that the material from which the particle will be formed does not wet the surfaces of the recess. Because the material from which the particle will be formed cannot wet the surfaces of the patterned template and/or substrate the particle material has a greater affinity for itself than the surfaces of the recesses and thereby forms a rounded, curved, or substantially spherical shape.

A non-wetting substance can be defined through the concept of the contact angle (Θ), which can be used quantitatively to measure interaction between any liquid and solid surface. When the contact angle between a drop of liquid on the surface is 90<Θ<180, the surface is considered non-wetting. In general, fluorinated surfaces are non-wetting to aqueous and organic liquids. Fluorinated surfaces can include a fluoropolyether material, a fluoroolefin material, an acrylate material, a silicone material, a styrenic material, a fluorinated thermoplastic elastomer (TPE), a triazine fluoropolymer, a perfluorocyclobutyl material, a fluorinated epoxy resin, and/or a fluorinated monomer or fluorinated oligomer that can be polymerized or crosslinked by a metathesis polymerization reaction, surfaces created by treating a silicon or glass surface with a fluorinated silane, or coating a surface with a fluorinated polymer. Further, surfaces of materials that are typically wettable materials can be made non-wettable by surface treatments. Materials that can be made substantially non-wetting by surface treatments include, but are not limited to, a typical wettable polymer material, an inorganic material, a silicon material, a quartz material, a glass material, combinations thereof, and the like. Surface treatments to make these types of materials non-wetting include, for example, layering the wettable material with a surface layer of the above described non-wetting materials, and techniques of the like that will be appreciated by one of ordinary skill in the art.

Figure 41A:
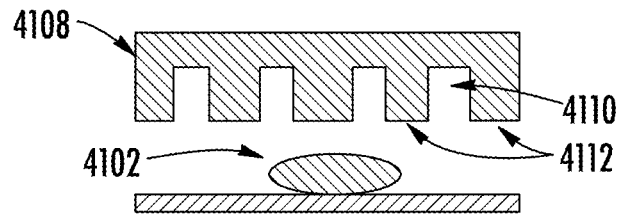
FIGS. 41A-41E show a sequence of forming small particles through evaporation according to an embodiment of the presently disclosed subject matter.

Referring now to FIG. 41A, droplet 4102 of a liquid material of the presently disclosed subject matter that is to become the particle is disposed on non-wetting substrate 4100, which in some embodiments is a material or a surface coated or treated with a non-wetting material, as described herein above. A patterned template 4108, which includes a plurality of recessed areas 4110 and patterned surface areas 4112, also is provided.

Figure 41B:
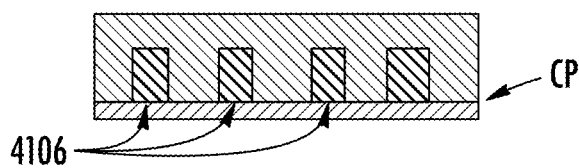

Referring now to FIG. 41B, patterned template 4108 is contacted with droplet 4102. The liquid material including droplet 4102 then enters recessed areas 4110 of patterned template 4108. According to some embodiments, mechanical or physical manipulation of droplet 4102 and patterned template 4108 is provided to facilitate the droplet 4102 in substantially filling and conforming to recessed areas 4110. Such mechanical and/or physical manipulation can include, but is not limited to, vibration, rotation, centrifugation, pressure differences, a vacuum environment, combinations thereof, or the like. A contact point CP is formed between the patterned surface areas 4112 and the substrate 4100. Particles 4106 are formed in the recessed areas 4110 of patterned template 4108.

Figure 41C:
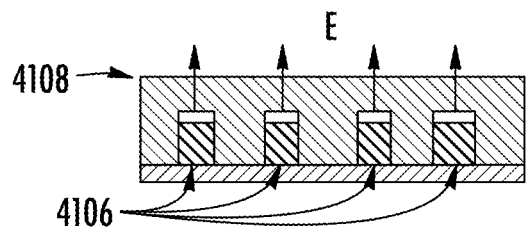

Referring now to FIG. 41C, an evaporative process, E, is performed, thereby reducing the volume of liquid particles 4106 inside recessed areas 4110. Examples of an evaporative process E that can be used with the present embodiments include forming patterned template 4108 from a gas permeable material, which allows volatile components of the material to become the particles to pass through the template, thereby reducing the volume of the material to become the particles in the recesses. According to another embodiment, an evaporative process E suitable for use with the presently disclosed subject matter includes providing a portion of the recessed areas 4110 filled with a gas, such as nitrogen, which thereby increases the evaporation rate of the material to become the particles. According to further embodiments, after the recesses are filled with material to become the particles, a space can be left between the patterned template and substrate such that evaporation is enhanced. In yet another embodiment, the combination of the patterned template, substrate, and material to become the particle can be heated or otherwise treated to enhance evaporation of the material to become the particle. Combinations of the above described evaporation processes are encompassed by the presently disclosed subject matter.

Figure 41D:
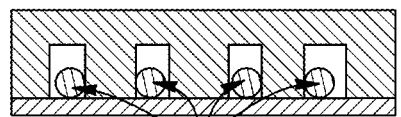

Referring now to FIG. 41D, once liquid reduction is achieved, the plurality of liquid droplets 4114 are treated by a treating process $T_r$. Treating process $T_r$ can be photo curing, thermal curing, phase change, solvent evaporation, crystallization, oxidative/reductive processes, combinations thereof, or the like to solidify the material of droplet 4102.

Figure 41E:
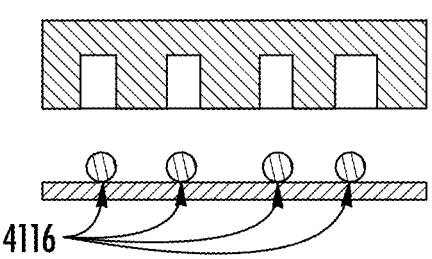

Referring now to FIG. 41E, patterned template 4108 is separated from substrate 4100 according to methods and techniques described herein. After separation of patterned template 4108 from substrate 4100, treated liquid spherical droplets 4114 are released from patterned template 4108 to provide a plurality of freestanding spherical particles 4116. In some embodiments release of the particles 4116 is facilitated by a solvent, applying a substance to the particles with an affinity for the particles, subjecting the particles to gravitational forces, combinations thereof, and the like.

According to some embodiments the particles are less than about 200 nm in diameter. According to some embodiments the particles are between about 80 nm and 200 nm in diameter. According to some embodiments the particles are between about 100 nm and about 200 nm in diameter.

IV. Formation of Polymeric Nano- to Micro-Electrets

Figure 4A:
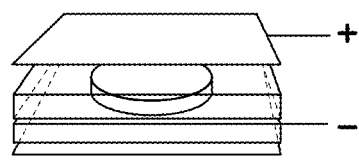
FIGS. 4A-4D are a schematic representation of the presently disclosed method for fabricating charged polymeric particles.
Figure 4B:
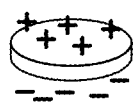
Figure 4C:
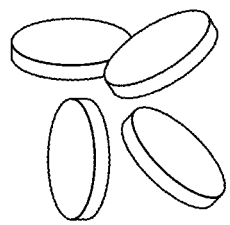
Figure 4D:
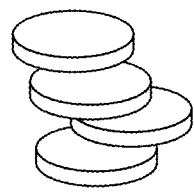

Referring now to FIGS. 4A and 4B, in some embodiments, the presently disclosed subject matter describes a method for preparing polymeric nano- to micro-electrets by applying an electric field during the polymerization and/or crystallization step during molding (FIG. 4A) to yield a charged polymeric particle (FIG. 4B). In some embodiments, the charged polymeric particles spontaneously aggregate into chain-like structures (FIG. 4D) instead of the random configurations shown in FIG. 4C.

In some embodiments, the charged polymeric particle includes a polymeric electret. In some embodiments, the polymeric electret includes a polymeric nano-electret. In some embodiments, the charged polymeric particles aggregate into chain-like structures. In some embodiments, the charged polymeric particles include an additive for an electro-rheological device. In some embodiments, the electro-rheological device is selected from the group including clutches and active dampening devices. In some embodiments, the charged polymeric particles include nano-piezoelectric devices. In some embodiments, the nano-piezoelectric devices are selected from the group including actuators, switches, and mechanical sensors.

V. Formation of Multilayer Structures

In some embodiments, the presently disclosed subject matter provides a method for forming multilayer structures, including multilayer particles. In some embodiments, the multilayer structures, including multilayer particles, include nanoscale multilayer structures. In some embodiments, multilayer structures are formed by depositing multiple thin layers of immiscible liquids and/or solutions onto a substrate and forming particles as described by any of the methods hereinabove. The immiscibility of the liquid can be based on any physical characteristic, including but not limited to density, polarity, and volatility. Examples of possible morphologies of the presently disclosed subject matter are illustrated in FIGS. 5A-5C and include, but are not limited to, multi-phase sandwich structures, core-shell particles, and internal emulsions, microemulsions and/or nano-sized emulsions.

Figure 5A:
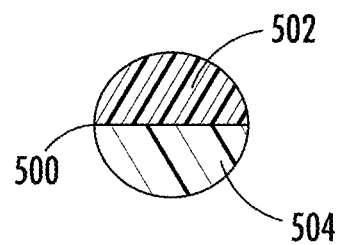
FIGS. 5A-5C are a schematic illustration of multilayer particles that can be formed using the presently disclosed soft lithography method.

Referring now to FIG. 5A, a multi-phase sandwich structure 500 of the presently disclosed subject matter is shown, which by way of example, includes a first liquid material 502 and a second liquid material 504.

Figure 5B:
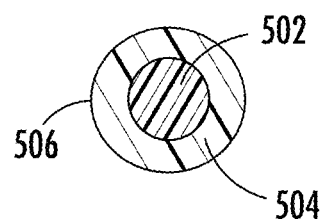

Referring now to FIG. 5B, a core-shell particle 506 of the presently disclosed subject matter is shown, which by way of example, includes a first liquid material 502 and a second liquid material 504.

Figure 5C:
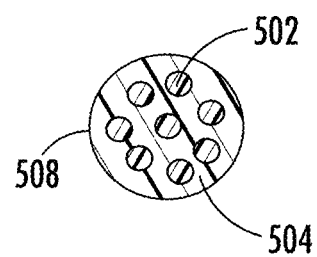

Referring now to FIG. 5C, an internal emulsion particle 508 of the presently disclosed subject matter is shown, which by way of example, includes a first liquid material 502 and a second liquid material 504.

More particularly, in some embodiments, the method includes disposing a plurality of immiscible liquids between the patterned template and substrate to form a multilayer structure, e.g., a multilayer nanostructure. In some embodiments, the multilayer structure includes a multilayer particle. In some embodiments, the multilayer structure includes a structure selected from the group including multi-phase sandwich structures, core-shell particles, internal emulsions, microemulsions, and nanosized emulsions.

VI. Fabrication of Complex Multi-Dimensional Structures

In some embodiments, the currently disclosed subject matter provides a process for fabricating complex, multi-dimensional structures. In some embodiments, complex multi-dimensional structures can be formed by performing the steps illustrated in FIGS. 2A-2E. In some embodiments, the method includes imprinting onto a patterned template that is aligned with a second patterned template (instead of imprinting onto a smooth substrate) to generate isolated multi-dimensional structures that are cured and released as described herein. A schematic illustration of an embodiment of a process for forming complex multi-dimensional structures and examples of such structures are provided in FIGS. 6A-6C.

Figure 6A:
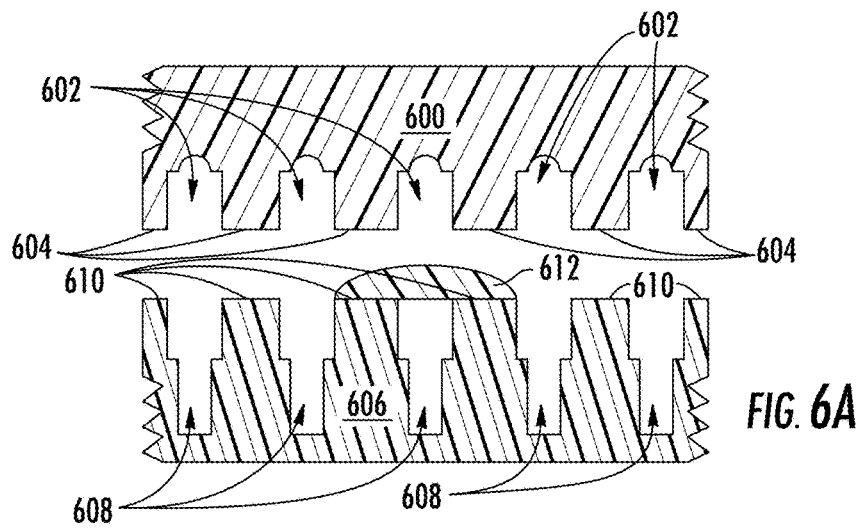
FIGS. 6A-6C are a schematic representation of the presently disclosed method for making three-dimensional nanostructures using a soft lithography technique.

Referring now to FIG. 6A, a first patterned template 600 is provided. First patterned template 600 includes a plurality of recessed areas 602 and a plurality of non-recessed surfaces 604. Also provided is a second patterned template 606. Second patterned template 606 includes a plurality of recessed areas 608 and a plurality of non-recessed surfaces

610. As shown in FIG. 6A, first patterned template 600 and second patterned template 606 are aligned in a predetermined spaced relationship. A droplet of liquid material 612 is disposed between first patterned template 600 and second patterned template 606.

Figure 6B:
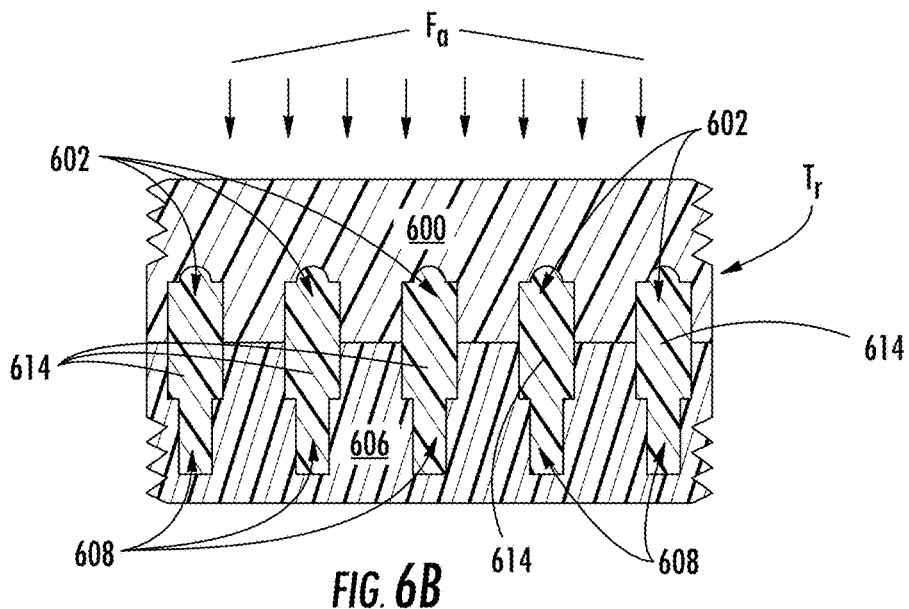

Referring now to FIG. 6B, patterned template 600 is contacted with patterned template 606. A force $F_a$ is applied to patterned template 600 causing the liquid material including droplet 612 to migrate to the plurality of recessed areas 602 and 608. The liquid material including droplet 612 is then treated by treating process $T_r$ to form a patterned, treated liquid material 614.

Figure 6C:
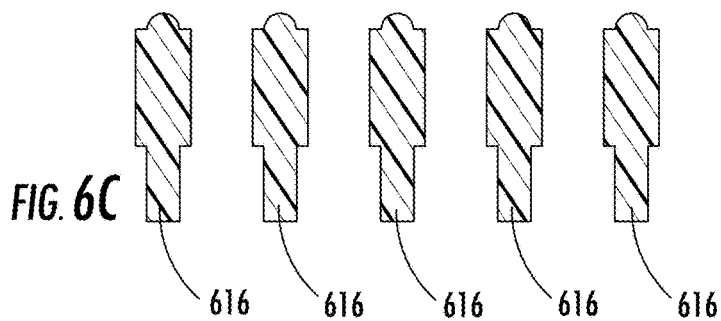

Referring now to FIG. 6C, the patterned, treated liquid material 614 of FIG. 6B is released by any of the releasing methods described herein to provide a plurality of multi-dimensional patterned structures 616.

In some embodiments, patterned structure 616 includes a nanoscale-patterned structure. In some embodiments, patterned structure 616 includes a multi-dimensional structure. In some embodiments, the multi-dimensional structure includes a nanoscale multi-dimensional structure. In some embodiments, the multi-dimensional structure includes a plurality of structural features. In some embodiments, the structural features include a plurality of heights.

In some embodiments, a microelectronic device including patterned structure 616 is provided. Indeed, patterned structure 616 can be any structure imaginable, including "dual damscene" structures for microelectronics. In some embodiments, the microelectronic device is selected from the group including integrated circuits, semiconductor particles, quantum dots, and dual damascene structures. In some embodiments, the microelectronic device exhibits certain physical properties selected from the group including etch resistance, low dielectric constant, high dielectric constant, conducting, semiconducting, insulating, porosity, and non-porosity.

In some embodiments, the presently disclosed subject matter discloses a method of preparing a multidimensional, complex structure. Referring now to FIGS. 7A-7F, in some embodiments, a first patterned template 700 is provided. First patterned template 700 includes a plurality of non-recessed surface areas 702 and a plurality of recessed surface areas 704. Continuing particularly with FIG. 7A, also provided is a substrate 706. In some embodiments, substrate 706 is coated with a non-wetting agent 708. A droplet of a first liquid material 710 is disposed on substrate 706.

Figure 7A:
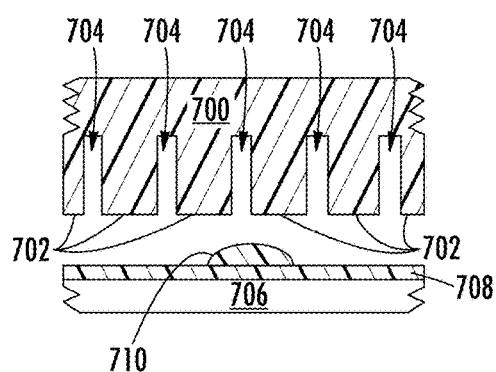
FIGS. 7A-7F are a schematic representation of an embodiment of the presently disclosed method for preparing a multi-dimensional complex structure.
Figure 7B:
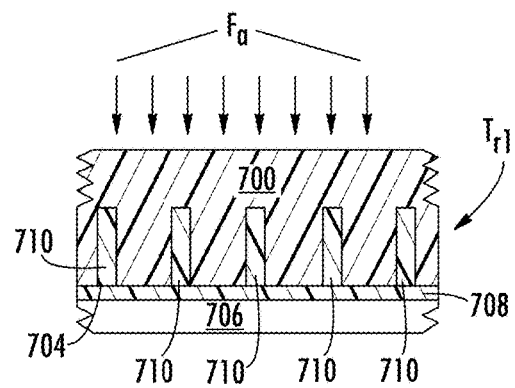
Figure 7C:
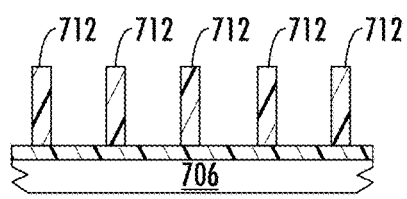

Referring now to FIGS. 7B and 7C, first patterned template 700 is contacted with substrate 706. A force $F_a$ is applied to first patterned template 700 such that the droplet of the first liquid material 710 is forced into recesses 704. The liquid material including the droplet of first liquid material 710 is treated by a first treating process $T_{r1}$ to form a treated first liquid material within the plurality of recesses 704. In some embodiments, first treating process $T_{r1}$ includes a partial curing process causing the treated first liquid material to adhere to substrate 706. Referring particularly to FIG. 7C, first patterned template 700 is removed to provide a plurality of structural features 712 on substrate 706.

Figure 7D:
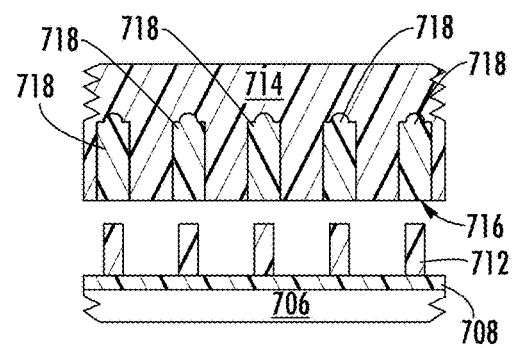
Figure 7E:
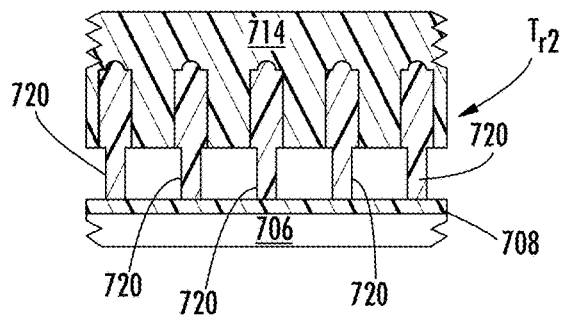
Figure 7F:
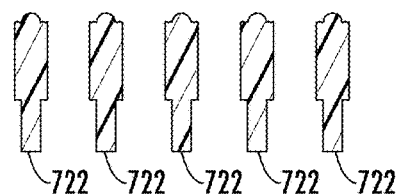

Referring now to FIGS. 7D-7F, a second patterned template 714 is provided. Second patterned substrate 714 includes a plurality of recesses 716, which are filled with a second liquid material 718. The filling of recesses 716 can be accomplished in a manner similar to that described in FIGS. 7A and 7B with respect to recesses 704. Referring particularly to FIG. 7E, second patterned template 714 is contacted with structural features 712. Second liquid material 718 is treated with a second treating process $T_{r2}$ such that the second liquid material 718 adheres to the plurality of structural feature 712, thereby forming a multidimensional structure 720. Referring particularly to FIG. 7F, second patterned template 714 and substrate 706 are removed, providing a plurality of free standing multidimensional structures 722. In some embodiments, the process schematically presented in FIGS. 7A-7F can be carried out multiple times as desired to form intricate nanostructures.

Accordingly, in some embodiments, a method for forming multidimensional structures is provided, the method including:

(a) providing a particle prepared by the process described in the figures;

(b) providing a second patterned template;

(c) disposing a second liquid material in the second patterned template;

(d) contacting the second patterned template with the particle of step (a); and (e) treating the second liquid material to form a multidimensional structure.

VII. Functionalization of Particles

Figure 36A:
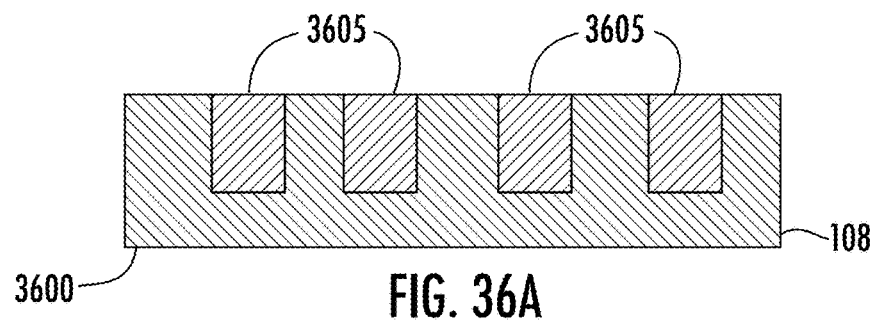
FIGS. 36A-36D are schematic representations of one embodiment of a method for functionalizing particles of the presently disclosed subject matter.
Figure 36B:
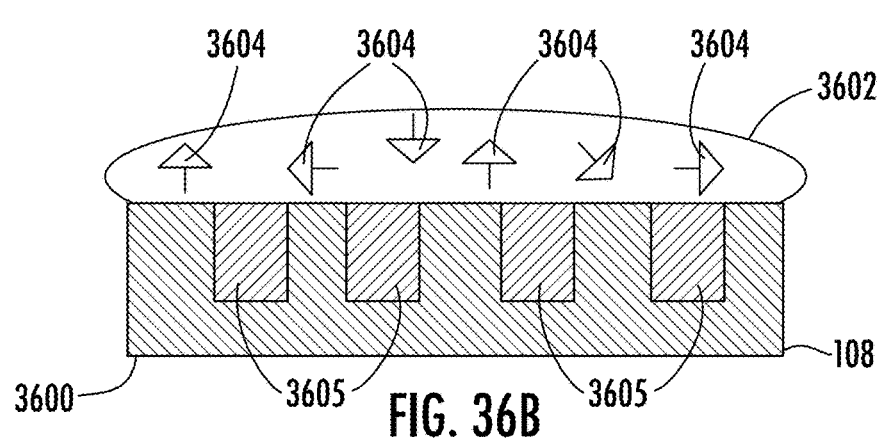
Figure 40A:
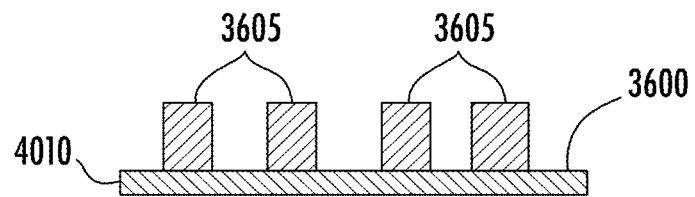
FIGS. 40A-40D schematic representations of one embodiment of one process of the presently disclosed subject matter for harvesting particles from an article.
Figure 40B:
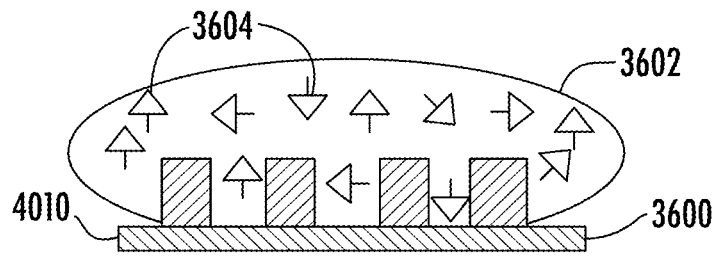

In some embodiments, the presently disclosed subject matter provides a method for functionalizing isolated micro- and/or nanoparticles. In one embodiment, the functionalization includes introducing chemical functional groups to a surface either physically or chemically. In some embodiments, the method of functionalization includes introducing at least one chemical functional group to at least a portion of microparticles and/or nanoparticles. In some embodiments, particles 3605 are at least partially functionalized while particles 3605 are in contact with an article 3600. In one embodiment, the particles 3605 to be functionalized are located within a mold or patterned template 108 (FIGS. 35A-36D). In some embodiments, particles 3605 to be functionalized are attached to a substrate (e.g., substrate 4010 of FIGS. 40A-40D). In some embodiments, at least a portion of the exterior of the particles 3605 can be chemically modified by performing the steps illustrated in FIGS. 36A-36D. In one embodiment, the particles 3605 to be functionalized are located within article 3600 as illustrated in FIGS. 36A and 40A. As illustrated in FIGS. 36A-36D and 40A-40D, some embodiments include contacting an article 3600 containing particles 3605 with a solution 3602 containing a modifying agent 3604.

Figure 36C:
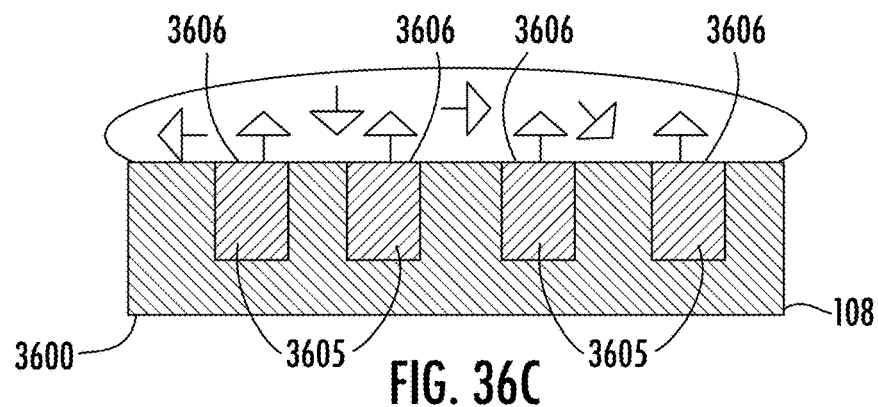
Figure 40C:
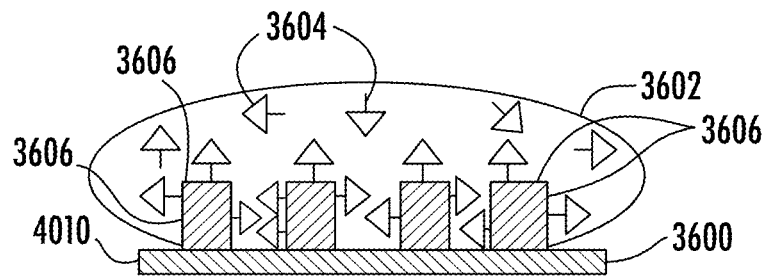

In one embodiment, illustrated in FIGS. 36C and 40C, modifying agent 3604 attaches (e.g., chemically) to exposed particle surface 3606 by chemically reacting with or physically adsorbing to a linker group on particle surface 3606. In one embodiment, the linker group on particle 3606 is a chemical functional group that can attach to other species via chemical bond formation or physical affinity. In some embodiments, the linker group includes a functional group that includes, without limitation, sulfides, amines, carboxylic acids, acid chlorides, alcohols, alkenes, alkyl halides, isocyanates, compounds disclosed elsewhere herein, combinations thereof, or the like.

Figure 36D:
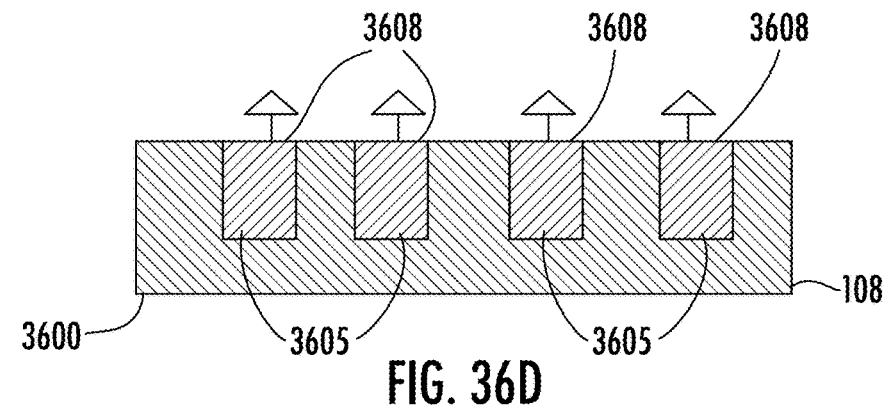
Figure 40D:
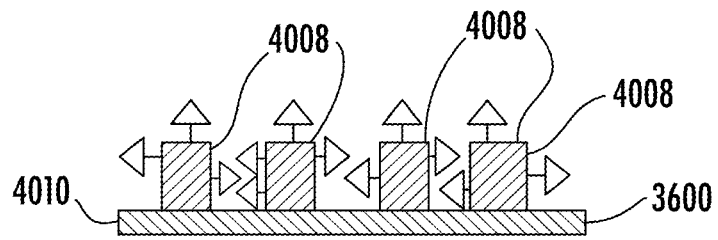

In one embodiment, illustrated in FIGS. 36D and 40D, excess solution is removed from article 3600 while particle 3605 remains in contact with article 3600. In some embodiments, excess solution is removed from the surface containing the particles. In some embodiments, excess solution is removed by rinsing with or soaking in a liquid, by applying an air stream, or by physically shaking or scraping the surface. In some embodiments, the modifying agent includes an agent selected from the group including dyes, fluorescent tags, radiolabeled tags, contrast agents, ligands, peptides, pharmaceutical agents, proteins, DNA, RNA, siRNA, compounds and materials disclosed elsewhere herein, combinations thereof, and the like.

In one embodiment, functionalized particles 3608, 4008 are harvested from article 3600 using, for example, methods described herein. In some embodiments, functionalizing and subsequently harvesting particles that reside on an article (e.g., a substrate, a mold or patterned template) have advantages over other methods (e.g., methods in which the particles must be functionalized while in solution). In one embodiment of the presently disclosed subject matter, fewer particles are lost in the process, giving a high product yield. In one embodiment of the presently disclosed subject matter, a more concentrated solution of the modifying agent can be applied in lower volumes. In one embodiment of the presently disclosed subject matter, where particles are functionalized while they remain associated with article 3600 functionalization does not need to occur in a dilute solution. In one embodiment, the use of more concentrated solution facilitates, for example, the use of lower volumes of modifying agent and/or lower times to functionalize. In one embodiment, particles in a tight, 2-dimensional array, but not touching, are susceptible to application of thin, concentrated solutions for faster functionalization. In some embodiments, lower volume/higher concentration modifying agent solutions are useful, for example, in connection with modifying agents that are difficult and expensive to make and handle (e.g., biological agents such as peptides, DNA, or RNA). In some embodiments, functionalizing particles that remain connected to article 3600 eliminates difficult and/or time-consuming steps to remove excess unreacted material (e.g., dialysis, extraction, filtration and column separation). In one embodiment of the presently disclosed subject matter, highly pure functionalized product can be produced at a reduced effort and cost.

VIII. Imprint Lithography

Referring now to FIGS. 8A-8D, a method for forming a pattern on a substrate is illustrated. In the embodiment illustrated in FIG. 8, an imprint lithography technique is used to form a pattern on a substrate.

Figure 8A:
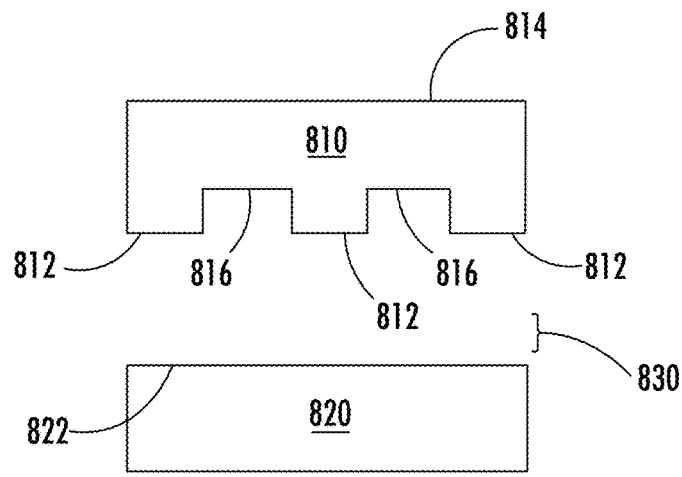
FIGS. 8A-8E are a schematic representation of the presently disclosed imprint lithography process resulting in a "scum layer"

Referring now to FIG. 8A, a patterned template 810 is provided. In some embodiments, patterned template 810 includes a solvent resistant, low surface energy polymeric material, derived from casting low viscosity liquid materials onto a master template and then curing the low viscosity liquid materials to generate a patterned template as defined hereinabove. Patterned template 810 further includes a first patterned template surface 812 and a second template surface 814. The first patterned template surface 812 further includes a plurality of recesses 816. The patterned template derived from a solvent resistant, low surface energy polymeric material could be mounted on another material to facilitate alignment of the patterned template or to facilitate continuous processing such as a conveyor belt. This might be particularly useful in the fabrication of precisely placed structures on a surface, such as in the fabrication of a complex devices or a semiconductor, electronic or photonic devices.

Referring again to FIG. 8A, a substrate 820 is provided. Substrate 820 includes a substrate surface 822. In some embodiments, substrate 820 is selected from the group including a polymer material, an inorganic material, a silicon material, a quartz material, a glass material, and surface treated variants thereof. In some embodiments, at least one of patterned template 810 and substrate 820 has a surface energy lower than 18 mN/m. In some embodiments, at least one of patterned template 810 and substrate 820 has a surface energy lower than 15 mN/m. According to a further embodiment the patterned template 810 and/or the substrate 820 has a surface energy between about 10 mN/m and about 20 mN/m. According to some embodiments, the patterned template 810 and/or the substrate 820 has a low surface energy of between about 12 mN/m and about 15 mN/m.

In some embodiments, as illustrated in FIG. 8A, patterned template 810 and substrate 820 are positioned in a spaced relationship to each other such that first patterned template surface 812 faces substrate surface 822 and a gap 830 is created between first patterned template surface 812 and substrate surface 822. This is an example of a predetermined relationship.

Figure 8B:
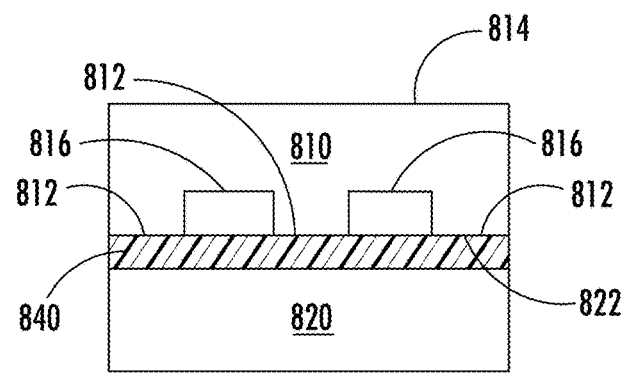

Referring now to FIG. 8B, a volume of liquid material 840 is disposed in gap 830 between first patterned template surface 812 and substrate surface 822. In some embodiments, the volume of liquid material 840 is disposed directed on a non-wetting agent (not shown), which is disposed on first patterned template surface 812.

Figure 8C:
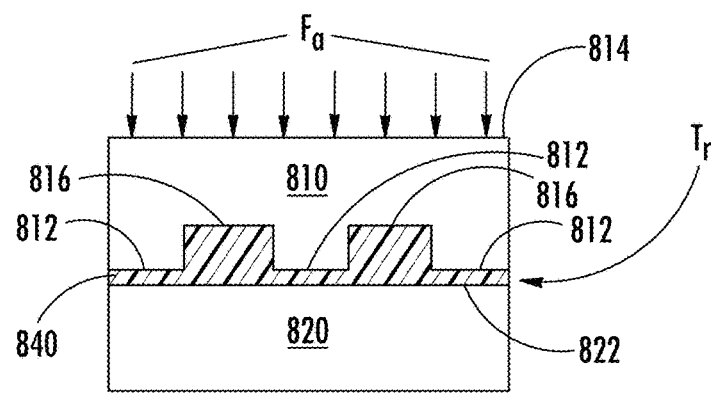

Referring now to FIG. 8C, in some embodiments, first patterned template 812 is contacted with the volume of liquid material 840. A force $F_a$ is applied to second template surface 814 thereby forcing the volume of liquid material 840 into the plurality of recesses 816. In some embodiments, as illustrated in FIG. 8C, a portion of the volume of liquid material 840 remains between first patterned template surface 812 and substrate surface 820 after force $F_a$ is applied.

Referring again to FIG. 8C, in some embodiments, the volume of liquid material 840 is treated by a treating process $T_r$ while force $F_a$ is being applied to form a treated liquid material 842. In some embodiments, treating process $T_r$ includes a process selected from the group including a thermal process, a photochemical process, and a chemical process.

Figure 8D:
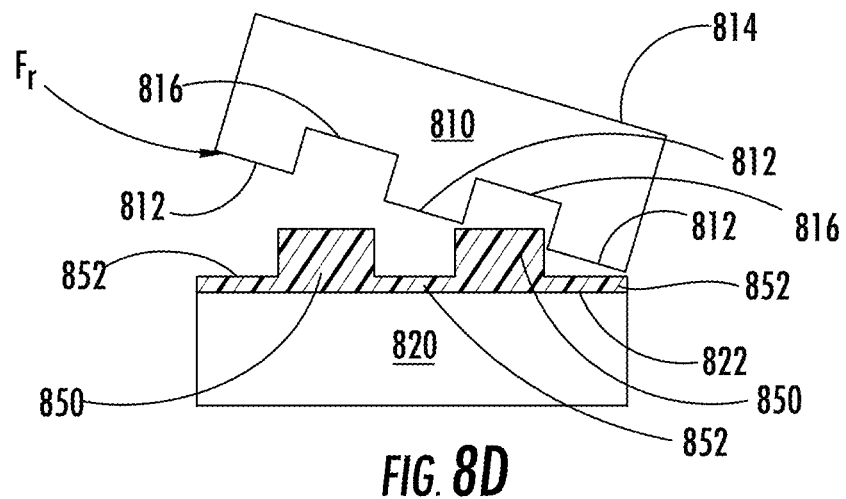
Figure 8E:
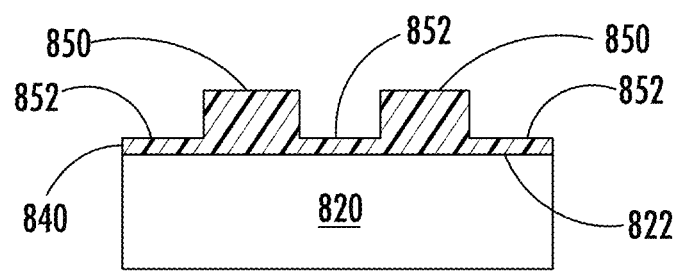

Referring now to FIG. 8D, a force $F_r$ is applied to patterned template 810 to remove patterned template 810 from treated liquid material 842 to reveal a pattern 850 on substrate 820 as shown in FIG. 8E. In some embodiments, a residual, or "scum," layer 852 of treated liquid material 842 remains on substrate 820.

More particularly, the method for forming a pattern on a substrate includes:
  (a) providing patterned template and a substrate, wherein the patterned template includes a patterned template surface having a plurality of recessed areas formed therein;
  (b) disposing a volume of liquid material in or on at least one of:
    (i) the patterned template surface;
    (ii) the plurality of recessed areas; and
    (iii) the substrate;
  (c) contacting the patterned template surface with the substrate; and
  (d) treating the liquid material to form a pattern on the substrate.

In some embodiments, the patterned template includes a solvent resistant, low surface energy polymeric material derived from casting low viscosity liquid materials onto a master template and then curing the low viscosity liquid materials to generate a patterned template. In some embodiments, the patterned template includes a solvent resistant elastomeric material.

In some embodiments, at least one of the patterned template and substrate includes a material selected from the group including a perfluoropolyether material, a fluoroolefin material, an acrylate material, a silicone material, a styrenic material, a fluorinated thermoplastic elastomer (TPE), a triazine fluoropolymer, a perfluorocyclobutyl material, a fluorinated epoxy resin, and a fluorinated monomer or fluorinated oligomer that can be polymerized or crosslinked by a metathesis polymerization reaction.

In some embodiments, the perfluoropolyether material includes a backbone structure selected from the group including:

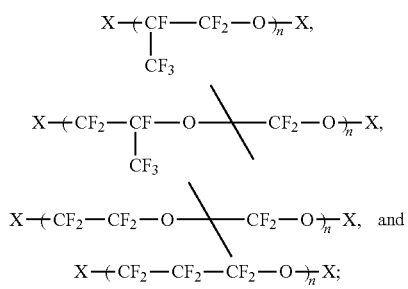

wherein X is present or absent, and when present includes an endcapping group.

In some embodiments, the fluoroolefin material is selected from the group including:

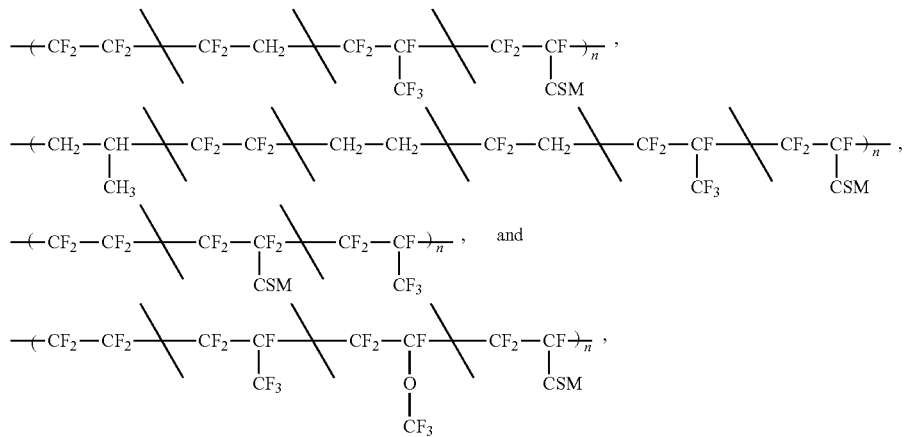

wherein CSM includes a cure site monomer.

In some embodiments, the fluoroolefin material is made from monomers which include tetrafluoroethylene, vinylidene fluoride, hexafluoropropylene, 2,2-bis(trifluoromethyl)-4,5-difluoro-1,3-dioxole, a functional fluoroolefin, functional acrylic monomer, and a functional methacrylic monomer.

In some embodiments, the silicone material includes a fluoroalkyl functionalized polydimethylsiloxane (PDMS) having the following structure:

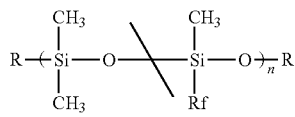

wherein:

R is selected from the group including an acrylate, a methacrylate, and a vinyl group; and Rf includes a fluoroalkyl chain.

In some embodiments, the styrenic material includes a fluorinated styrene monomer selected from the group including:

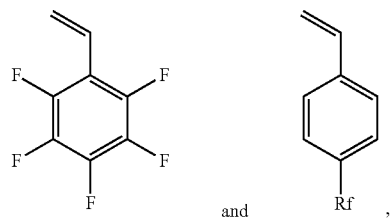

wherein Rf includes a fluoroalkyl chain.

In some embodiments, the acrylate material includes a fluorinated acrylate or a fluorinated methacrylate having the following structure:

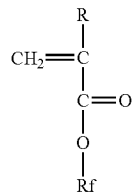

wherein:
R is selected from the group including H, alkyl, substituted alkyl, aryl, and substituted aryl; and
Rf includes a fluoroalkyl chain.

In some embodiments, the triazine fluoropolymer includes a fluorinated monomer.

In some embodiments, the fluorinated monomer or fluorinated oligomer that can be polymerized or crosslinked by a metathesis polymerization reaction includes a functionalized olefin. In some embodiments, the functionalized olefin includes a functionalized cyclic olefin.

In some embodiments, at least one of the patterned template and the substrate has a surface energy lower than 18 mN/m. In some embodiments, at least one of the patterned template and the substrate has a surface energy lower than 15 mN/m. According to a further embodiment the patterned template and/or the substrate has a surface energy between about 10 mN/m and about 20 mN/m. According to some embodiments, the patterned template and/or the substrate has a low surface energy of between about 12 mN/m and about 15 mN/m.

In some embodiments, the substrate is selected from the group including a polymer material, an inorganic material, a silicon material, a quartz material, a glass material, and surface treated variants thereof. In some embodiments, the substrate is selected from one of an electronic device in the process of being manufactured and a photonic device in the process of being manufactured. In some embodiments, the substrate includes a patterned area.

In some embodiments, the plurality of recessed areas includes a plurality of cavities. In some embodiments, the plurality of cavities include a plurality of structural features. In some embodiments, the plurality of structural features has a dimension ranging from about 10 microns to about 1 nanometer in size. In some embodiments, the plurality of structural features has a dimension ranging from about 10 microns to about 1 micron in size. In some embodiments, the plurality of structural features has a dimension ranging from about 1 micron to about 100 nm in size. In some embodiments, the plurality of structural features has a dimension ranging from about 100 nm to about 1 nm in size. In some embodiments, the plurality of structural features has a dimension in both the horizontal and vertical plane.

Referring now to FIGS. 39A-39F, one embodiment of a method for forming a complex pattern on a substrate is illustrated. In the embodiment illustrated in FIG. 39, an imprint lithography technique is used to form a pattern on a substrate.

Referring now to FIG. 39A, a patterned master 3900 is provided. Patterned master 3900 includes a plurality of non-recessed surface 3920 areas and a plurality of recesses 3930. In some embodiments, recesses 3930 include one or more sub-recesses 3932. In some embodiments, recesses 3930 include a multiplicity of sub-recesses 3932. In some embodiments, patterned master 3900 includes an etched substrate, such as a silicon wafer, which is etched in the desired pattern to form patterned master 3900.

Referring now to FIG. 39B, a flowable material 3901, for example, a liquid fluoropolymer composition, such as a PFPE-based precursor, is poured onto patterned master 3900. In some embodiments, flowable material 3901 is treated by a treating process, for example exposure to UV light, thereby forming a treated material mold 3910 in the desired pattern.

In one embodiment, illustrated in FIG. 39C, mold 3910 is removed from patterned master 3900. In one embodiment, treated material mold 3910 is a cross-linked polymer. In one embodiment, treated material mold 3910 is an elastomer. In one embodiment, a force is applied to one or more of mold 3910 or patterned master 3900 to separate mold 3910 from patterned master 3900. FIG. 39C illustrates one embodiment of mold 3910 and patterned master 3900 wherein mold 3910 includes a plurality of recesses and sub-recesses which are mirror images of the plurality of non-recessed surface areas of patterned master 3900. In one embodiment of mold 3910 the plurality of non-recessed areas elastically deform to facilitate removal of mold 3910 from master 3900. Mold 3910, in one embodiment, is a useful patterned template for soft lithography and imprint lithography applications.

Referring now to FIG. 39D, a mold 3910 is provided. In some embodiments, mold 3910 includes a solvent resistant, low surface energy polymeric material, derived from casting low viscosity liquid materials onto a master template and then curing the low viscosity liquid materials to generate a patterned template as defined hereinabove. Mold 3910 further includes a first patterned template surface 812 and a second template surface 814. The first patterned template surface 812 further includes a plurality of recesses 816 and subrecesses 3942. In one embodiment, multiple layers of subrecesses 3942 form sub-sub-recesses and so on. In some embodiments, mold 3910 is derived from a solvent resistant, low surface energy polymeric material and is mounted on another material to facilitate alignment of the mold or to facilitate continuous processing, such as a continuous process using a conveyor belt. In one embodiment, such continuous processing is useful in the fabrication of precisely placed structures on a surface, such as in the fabrication of a complex device or a semiconductor, electronic or photonic device.

Referring again to FIG. 39D, a substrate 3903 is provided. In some embodiments, substrate 3903 includes, without limitation, one or more of a polymer material, an inorganic material, a silicon material, a quartz material, a glass material, and surface treated variants thereof. In some embodiments, at least one of mold 3910 and substrate 3903 has a surface energy lower than 18 mN/m. In some embodiments, at least one of mold 3910 and substrate 3903 has a surface energy lower than 15 mN/m. According to a further embodiment the mold 3910 and/or the substrate 3903 has a surface energy between about 10 mN/m and about 20 mN/m. According to some embodiments, the mold 3910 and/or the substrate 3903 has a low surface energy of between about 12 mN/m and about 15 mN/m.

In some embodiments, as illustrated in FIG. 39D, mold 3910 and substrate 3903 are positioned in a spaced relationship to each other such that first patterned template surface 812 faces substrate surface 822 and a gap 830 is created between first patterned template surface 812 and the substrate surface 822. This is merely one example of a predetermined relationship.

Referring again to FIG. 39D, a volume of liquid material 3902 is disposed in the gap between first patterned template surface 812 and substrate surface 822. In some embodiments, the volume of liquid material 3902 is disposed directly on a non-wetting agent (not shown), which is disposed on first patterned template surface 812.

Referring now to FIG. 39E, in some embodiments, mold 3910 is contacted with the volume of liquid material 3902 (not shown in FIG. 39E). A force F is applied to the mold 3910 thereby forcing the volume of liquid material 3902 into the plurality of recesses 816 and sub-recesses. In some embodiments, such as was illustrated in FIG. 8C, a portion of the volume of liquid material 3902 remains between mold 3910 and substrate 3903 surface after force F is applied.

Referring again to FIG. 39E, in some embodiments, the volume of liquid material 3902 is treated by a treating process while force F is being applied to form a product 3904. In some embodiments, the treating process includes, without limitation, one or more of a photochemical process, a chemical process, combinations thereof, or the like.

Referring now to FIG. 39F, mold 3910 is removed from product 3904 to reveal a patterned product on substrate 3903 as shown in FIG. 39F. In some embodiments, a residual, or "scum," layer (not shown) of treated liquid material remains on substrate 3903.

In some embodiments, the liquid material from which the particles will be formed is selected from the group including a polymer, a solution, a monomer, a plurality of monomers, a polymerization initiator, a polymerization catalyst, an inorganic precursor, an organic material, a natural product, a metal precursor, a pharmaceutical agent, a tag, a magnetic material, a paramagnetic material, a superparamagnetic material, a ligand, a cell penetrating peptide, a porogen, a surfactant, a plurality of immiscible liquids, a solvent, a pharmaceutical agent with a binder, and a charged species. In some embodiments, the pharmaceutical agent is selected from the group including a drug, a peptide, RNAi, and DNA. In some embodiments, the tag is selected from the group including a fluorescence tag, a radiolabeled tag, and a contrast agent. In some embodiments, the ligand includes a cell targeting peptide.

Representative superparamagnetic or paramagnetic materials include but are not limited to $Fe_2O_3$, $Fe_3O_4$, FePt, Co, $MnFe_2O_4$, $CoFe_2O_4$, $CuFe_2O_4$, $NiFe_2O_4$ and ZnS doped with Mn for magneto-optical applications, CdSe for optical applications, and borates for boron neutron capture treatment.

In some embodiments, the liquid material is selected from one of a resist polymer and a low-k dielectric. In some embodiments, the liquid material includes a non-wetting agent.

In some embodiments, the disposing of the volume of liquid material is regulated by a spreading process. In some embodiments, the spreading process includes:

(a) disposing a first volume of liquid material on the patterned template to form a layer of liquid material on the patterned template; and
(b) drawing an implement across the layer of liquid material to:
   (i) remove a second volume of liquid material from the layer of liquid material on the patterned template; and
   (ii) leave a third volume of liquid material on the patterned template.

In some embodiments, the contacting of the first template surface with the substrate eliminates essentially all of the disposed volume of liquid material.

In some embodiments, the treating of the liquid includes, without limitation, one or more of a thermal process, a photochemical process, a chemical process, an evaporative process, a phase change, an oxidative process, a reductive process, combinations thereof, or the like.

In some embodiments, the method includes a batch process. In some embodiments, the batch process is selected from one of a semi-batch process and a continuous batch process.

In some embodiments, the presently disclosed subject matter describes a patterned substrate formed by the presently disclosed methods.

IX. Imprint Lithography Free of a Residual "Scum Layer"

A characteristic of imprint lithography that has restrained its full potential is the formation of a "scum layer" once the liquid material, e.g., a resin, is patterned. The "scum layer" includes residual liquid material that remains between the stamp and the substrate. In some embodiments, the presently disclosed subject matter provides a process for generating patterns essentially free of a scum layer.

Figure 9A:
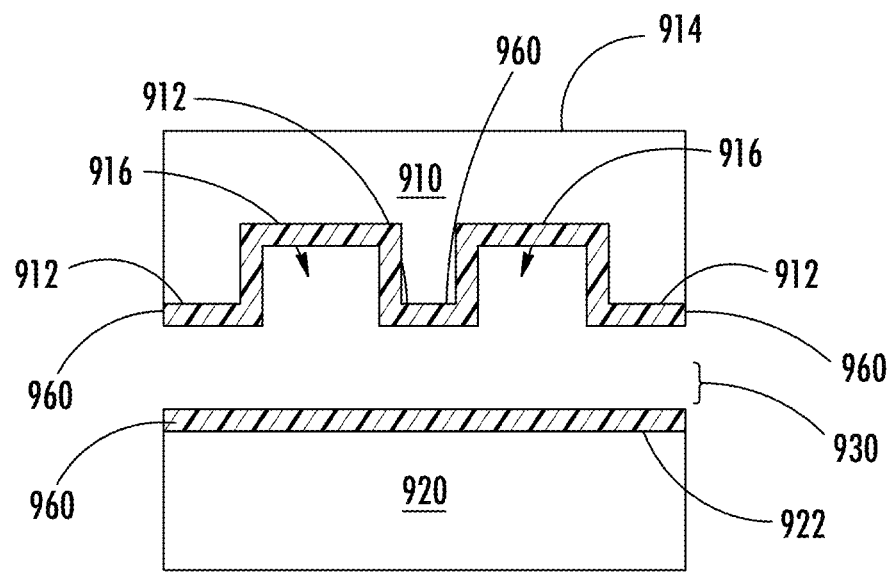
FIGS. 9A-9E are a schematic representation of the presently disclosed imprint lithography method, which eliminates the "scum layer" by using a functionalized, non-wetting patterned template and a non-wetting substrate.

Referring now to FIGS. 9A-9E, in some embodiments, a method for forming a pattern on a substrate is provided, wherein the pattern is essentially free of a scum layer. Referring now to FIG. 9A, a patterned template 910 is provided. Patterned template 910 further includes a first patterned template surface 912 and a second template surface 914. The first patterned template surface 912 further includes a plurality of recesses 916. In some embodiments, a non-wetting agent 960 is disposed on the first patterned template surface 912.

Referring again to FIG. 9A, a substrate 920 is provided. Substrate 920 includes a substrate surface 922. In some embodiments, a non-wetting agent 960 is disposed on substrate surface 920.

In some embodiments, as illustrated in FIG. 9A, patterned template 910 and substrate 920 are positioned in a spaced relationship to each other such that first patterned template surface 912 faces substrate surface 922 and a gap 930 is created between first patterned template surface 912 and substrate surface 922.

Figure 9B:
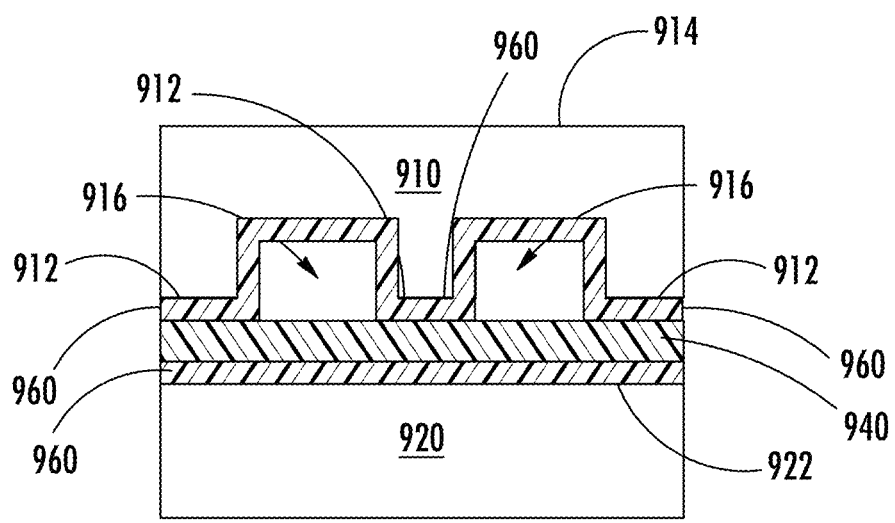

Referring now to FIG. 9B, a volume of liquid material 940 is disposed in the gap 930 between first patterned template surface 912 and substrate surface 922. In some embodiments, the volume of liquid material 940 is disposed directly on first patterned template surface 912. In some embodiments, the volume of liquid material 940 is disposed directly on non-wetting agent 960, which is disposed on first patterned template surface 912. In some embodiments, the volume of liquid material 940 is disposed directly on substrate surface 920. In some embodiments, the volume of liquid material 940 is disposed directly on non-wetting agent 960, which is disposed on substrate surface 920.

Figure 9C:
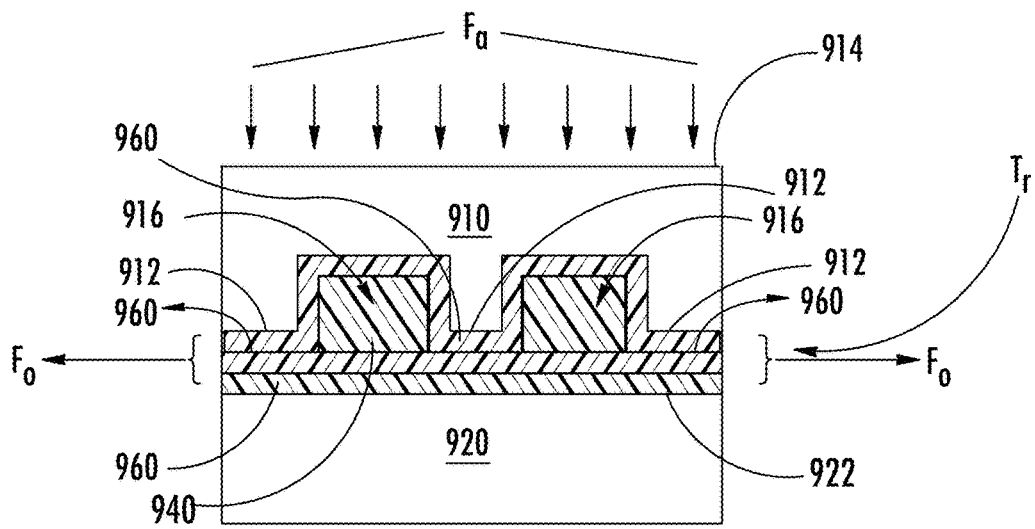

Referring now to FIG. 9C, in some embodiments, first patterned template surface 912 is contacted with the volume of liquid material 940. A force $F_a$ is applied to second template surface 914 thereby forcing the volume of liquid material 940 into the plurality of recesses 916. In contrast with the embodiment illustrated in FIG. 8, a portion of the volume of liquid material 940 is forced out of gap 930 by force $F_o$ when force $F_a$ is applied.

Referring again to FIG. 9C, in some embodiments, the volume of liquid material 940 is treated by a treating process $T_r$ while force $F_a$ is being applied to form a treated liquid material 942.

Figure 9D:
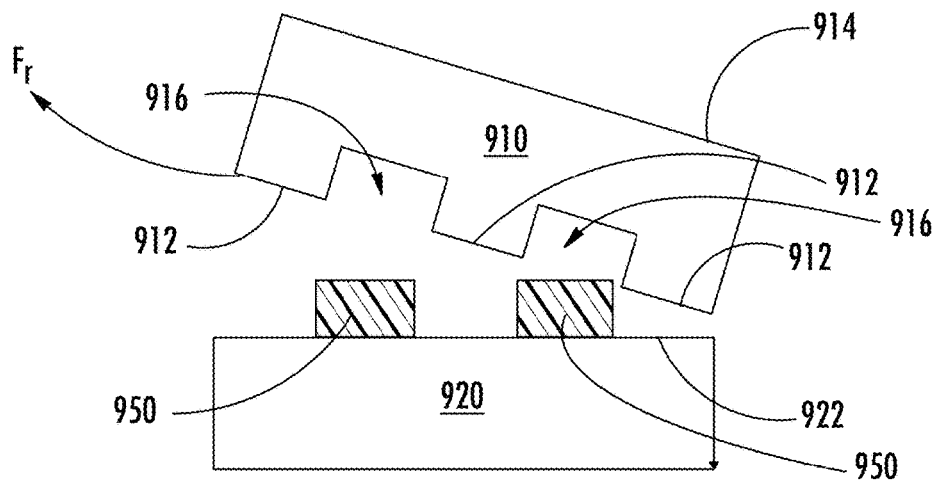
Figure 9E:
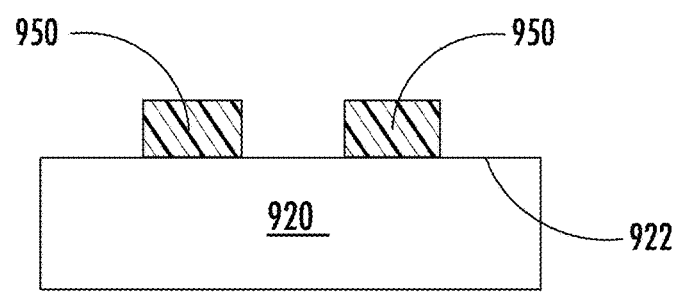

Referring now to FIG. 9D, a force $F_r$ is applied to patterned template 910 to remove patterned template 910 from treated liquid material 942 to reveal a pattern 950 on substrate 920 as shown in FIG. 9E. In this embodiment, substrate 920 is essentially free of a residual, or "scum," layer of treated liquid material 942.

In some embodiments, at least one of the template surface and substrate includes a functionalized surface element. In some embodiments, the functionalized surface element is functionalized with a non-wetting material. In some embodiments, the non-wetting material includes functional groups that bind to the liquid material. In some embodiments, the non-wetting material is a trichloro silane, a trialkoxy silane, a trichloro silane including non-wetting and reactive functional groups, a trialkoxy silane including non-wetting and reactive functional groups, and/or mixtures thereof.

In some embodiments, the point of contact between the two surface elements is free of liquid material. In some embodiments, the point of contact between the two surface elements includes residual liquid material. In some embodiments, the height of the residual liquid material is less than 30% of the height of the structure. In some embodiments, the height of the residual liquid material is less than 20% of the height of the structure. In some embodiments, the height of the residual liquid material is less than 10% of the height of the structure. In some embodiments, the height of the residual liquid material is less than 5% of the height of the structure. In some embodiments, the volume of liquid material is less than the volume of the patterned template. In some embodiments, substantially all of the volume of liquid material is confined to the patterned template of at least one of the surface elements. In some embodiments, having the point of contact between the two surface elements free of liquid material retards slippage between the two surface elements.

X. Solvent-Assisted Micro-Molding (SAMIM)

In some embodiments, the presently disclosed subject matter describes a solvent-assisted micro-molding (SAMIM) method for forming a pattern on a substrate.

Figure 10A:
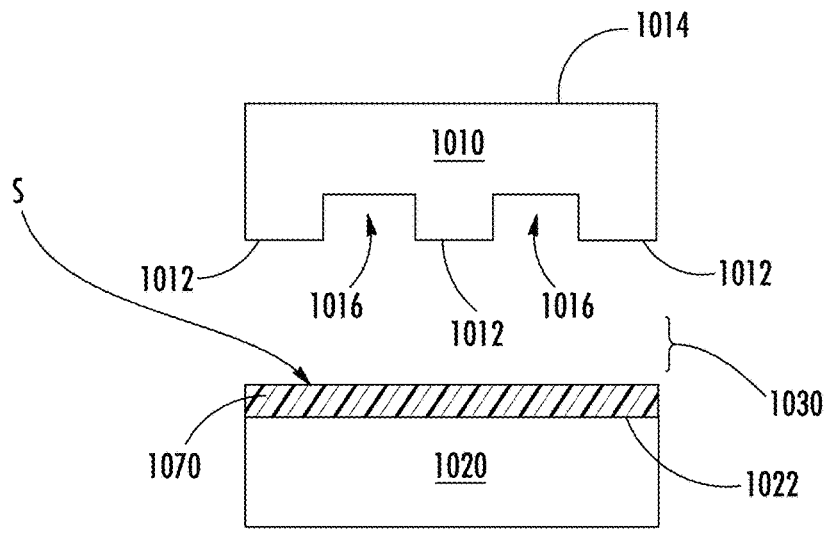
FIGS. 10A-10E are a schematic representation of the presently disclosed solvent-assisted micro-molding (SAMIM) method for forming a pattern on a substrate.

Referring now to FIG. 10A, a patterned template 1010 is provided. Patterned template 1010 further includes a first patterned template surface 1012 and a second template surface 1014. The first patterned template surface 1012 further includes a plurality of recesses 1016.

Referring again to FIG. 10A, a substrate 1020 is provided. Substrate 1020 includes a substrate surface 1022. In some embodiments, a polymeric material 1070 is disposed on substrate surface 1022. In some embodiments, polymeric material 1070 includes a resist polymer.

Referring again to FIG. 10A, patterned template 1010 and substrate 1020 are positioned in a spaced relationship to each other such that first patterned template surface 1012 faces substrate surface 1022 and a gap 1030 is created between first patterned template surface 1012 and substrate surface 1022. As shown in FIG. 10A, a solvent S is disposed within gap 1030, such that solvent S contacts polymeric material 1070 forming a swollen polymeric material 1072.

Figure 10B:
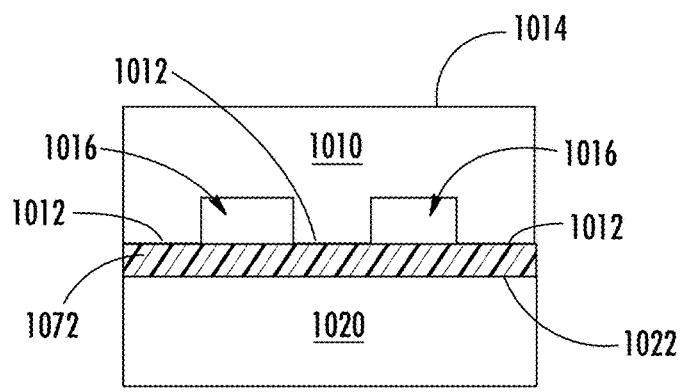
Figure 10C:
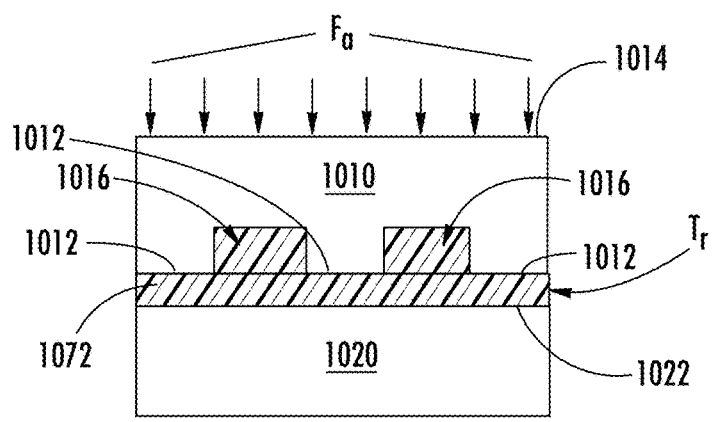

Referring now to FIGS. 10B and 10C, first patterned template surface 1012 is contacted with swollen polymeric material 1072. A force $F_a$ is applied to second template surface 1014 thereby forcing a portion of swollen polymeric material 1072 into the plurality of recesses 1016 and leaving a portion of swollen polymeric material 1072 between first patterned template surface 1012 and substrate surface 1020. The swollen polymeric material 1072 is then treated by a treating process $T_r$, while under pressure.

Figure 10D:
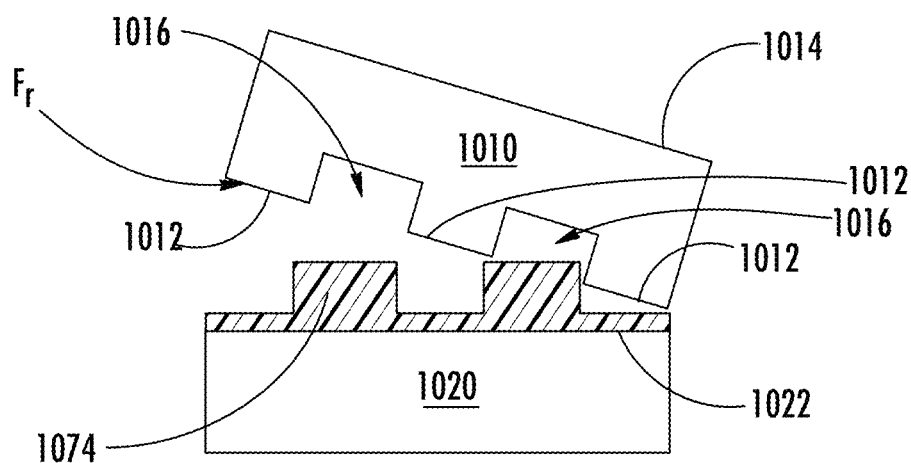
Figure 10E:
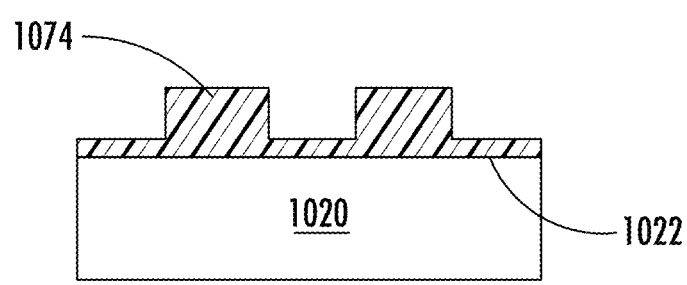

Referring now to FIG. 10D, a force $F_r$ is applied to patterned template 1010 to remove patterned template 1010 from treated swollen polymeric material 1072 to reveal a polymeric pattern 1074 on substrate 1020 as shown in FIG. 10E.

XI. Removing the Patterned Structure from the Patterned Template and/or Substrate In some embodiments, the patterned structure (e.g., a patterned micro- or nanostructure) is removed from at least one of the patterned template and/or the substrate. This can be accomplished by a number of approaches, including but not limited to applying the surface element containing the patterned structure to a surface that has an affinity for the patterned structure; applying the surface element containing the patterned structure to a material that when hardened has a chemical and/or physical interaction with the patterned structure; deforming the surface element containing the patterned structure such that the patterned structure is released from the surface element; swelling the surface element containing the patterned structure with a first solvent to extrude the patterned structure; and washing the surface element containing the patterned structure with a second solvent that has an affinity for the patterned structure.

In some embodiments, the surface that has an affinity for the particles includes an adhesive or sticky surface (e.g. carbohydrates, epoxies, waxes, polyvinyl alcohol, polyvinyl pyrrolidone, polybutyl acrylate, polycyano acrylates, polymethyl methacrylate). In some embodiments, the liquid is water that is cooled to form ice. In some embodiments, the water is cooled to a temperature below the Tm of water but above the Tg of the particle. In some embodiments the water is cooled to a temperature below the Tg of the particles but above the Tg of the mold or substrate. In some embodiments, the water is cooled to a temperature below the Tg of the mold or substrate.

In some embodiments, the first solvent includes super-critical fluid carbon dioxide. In some embodiments, the first solvent includes water. In some embodiments, the first solvent includes an aqueous solution including water and a detergent. In embodiments, the deforming the surface element is performed by applying a mechanical force to the surface element. In some embodiments, the method of removing the patterned structure further includes a sonication method.

XII. Method of Fabricating Molecules and for Delivering a Therapeutic Agent to a Target In some embodiments, the presently disclosed subject matter describes methods, processes, and products by processes, for fabricating delivery molecules, for use in drug discovery and drug therapies. In some embodiments, the method or process for fabricating a delivery molecule includes a combinatorial method or process. In some embodiments, the method for fabricating molecules includes a non-wetting imprint lithography method.

XII.A. Method of Fabricating Molecules

In some embodiments, the non-wetting imprint lithography method of the presently disclosed subject matter is used to generate a surface derived from or including a solvent resistant, low surface energy polymeric material. The surface is derived from casting low viscosity liquid materials onto a master template and then curing the low viscosity liquid materials to generate a patterned template, as described herein. In some embodiments, the surface includes a solvent resistant elastomeric material.

In some embodiments, the non-wetting imprint lithography method is used to generate isolated structures. In some embodiments, the isolated structures include isolated micro-structures. In some embodiments, the isolated structures include isolated nano-structures. In some embodiments, the isolated structures include a biodegradable material. In some embodiments, the isolated structures include a hydrophilic material. In some embodiments, the isolated structures include a hydrophobic material. In some embodiments, the isolated structures include a particular shape. In another embodiment, the isolated structures include or are configured to hold include "cargo." According to one embodiment, the cargo held by the isolated structure can include an element, a molecule, a chemical substance, an agent, a drug, a biologic, a protein, DNA, RNA, a diagnostic, a therapeutic, a cancer treatment, a viral treatment, a bacterial treatment, a fungal treatment, an auto-immune treatment, combinations thereof, or the like. According to an alternative embodiment, the cargo protrudes from the surface of the isolated structure, thereby functionalizing the isolated structure. According to yet another embodiment, the cargo is completely contained within the isolated particle such that the cargo is stealthed or sheltered from an environment to which the isolated structure can be subjected. According to yet another embodiment, the cargo is contained substantially on the surface of the isolated structure. In a further embodiment, the cargo is associated with the isolated structure in a combination of one of the above techniques, or the like.

According to another embodiment, the cargo is attached to the isolated structure by chemical binding or physical constraint. In some embodiments, the chemical binding includes, but is not limited to, covalent binding, ionic bonding, other intra- and inter-molecular forces, hydrogen bonding, van der Waals forces, combinations thereof, and the like.

In some embodiments, the non-wetting imprint lithography method further includes adding molecular modules, fragments, or domains to the solution to be molded. In some embodiments, the molecular modules, fragments, or domains impart functionality to the isolated structures. In some embodiments, the functionality imparted to the isolated structure includes a therapeutic functionality.

In some embodiments, a therapeutic agent, such as a drug, a biologic, combinations thereof, and the like, is incorporated into the isolated structure. In some embodiments, the physiologically active drug is tethered to a linker to facilitate its incorporation into the isolated structure. In some embodiments, the domain of an enzyme or a catalyst is added to the isolated structure. In some embodiments, a ligand or an oligopeptide is added to the isolated structure. In some embodiments, the oligopeptide is functional. In some embodiments, the functional oligopeptide includes a cell targeting peptide. In some embodiments, the functional oligopeptide includes a cell penetrating peptide. In some embodiments an antibody or functional fragment thereof is added to the isolated structure.

In some embodiments, a binder is added to the isolated structure. In some embodiments, the isolated structure including the binder is used to fabricate identical structures. In some embodiments, the isolated structure including the binder is used to fabricate structures of a varying structure. In some embodiments, the structures of a varying structure are used to explore the efficacy of a molecule as a therapeutic agent. In some embodiments, the shape of the isolated structure mimics a biological agent. In some embodiments, the method further includes a method for drug discovery.

XII.B. Method of Delivering a Therapeutic Agent to a Target

In some embodiments, a method of delivering a therapeutic agent to a target is disclosed, the method including: providing a particle produced as described herein; admixing the therapeutic agent with the particle; and delivering the particle including the therapeutic agent to the target.

In some embodiments, the therapeutic agent includes a drug. In some embodiments, the therapeutic agent includes genetic material. In some embodiments, the genetic material includes, without limitation, one or more of a non-viral gene vector, DNA, RNA, RNAi, a viral particle, combinations thereof, or the like.

In some embodiments, the particle has a diameter of less than 100 microns. In some embodiments, the particle has a diameter of less than 10 microns. In some embodiments, the particle has a diameter of less than 1 micron. In some embodiments, the particle has a diameter of less than 100 nm. In some embodiments, the particle has a diameter of less than 10 nm.

In some embodiments, the particle includes a biodegradable polymer. A biodegradable polymer is defined as a polymer that undergoes a reduction in molecular weight upon either a change in biological condition or exposure to a biological agent. In some embodiments, the biodegradable polymer includes, without limitation, one or more of a polyester, a polyanhydride, a polyamide, a phosphorous-based polymer, a poly(cyanoacrylate), a polyurethane, a polyorthoester, a polydihydropyran, a polyacetal, combinations thereof, or the like. In some embodiments, the polymer is modified to be a biodegradable polymer (e.g. a poly (ethylene glycol) that is functionalized with a disulfide group). In some embodiments, the polyester includes, without limitation, one or more of polylactic acid, polyglycolic acid, poly(hydroxybutyrate), poly($\epsilon$-caprolactone), poly($\beta$-malic acid), poly(dioxanones), combinations thereof, or the like. In some embodiments, the polyanhydride includes, without limitation, one or more of poly(sebacic acid), poly (adipic acid), poly(terpthalic acid), combinations thereof, or the like. In some embodiments, the polyamide includes, without limitation, one or more of a poly(imino carbonate), a polyaminoacid, combinations thereof, or the like. In some embodiments, the phosphorous-based polymer includes, without limitation, one or more of polyphosphates, polyphosphonates, polyphosphazenes, combinations thereof, or the like. In some embodiments, the polymer is responsive to stimuli, such as pH, radiation, oxidation, reduction, ionic strength, temperature, and alternating magnetic or electric fields.

Responses to such stimuli can include swelling, bond cleavage, heating, combinations thereof, or the like, which can facilitate release of the isolated structures cargo, degradation of the isolated structure itself, combinations thereof, and the like.

In some embodiments, the presently disclosed subject matter describes magneto containing particles for applications in hyperthermia therapy, cancer and gene therapy, drug delivery, magnetic resonance imaging contrast agents, vaccine adjuvants, memory devices, spintronics, combinations thereof, and the like.

Without being bound to any one particular theory, the magneto containing particles, e.g., a magnetic nanoparticle, produce heat by the process of hyperthermia (between 41 and 46° C.) or thermo ablation (greater than 46° C.), i.e., the controlled heating of the nanoparticles upon exposure to an AC-magnetic field. The heat is used to (i) induce a phase change in the polymer component (for example melt and release an encapsulated material) and/or (ii) hyperthermia treatment of specific cells and/or (iii) increase the effectiveness of the encapsulated material. The triggering mechanism of the magnetic nanoparticles via electromagnetic heating enhance the (iv) degradation rate of the particulate; (v) can induce swelling; and/or (vi) induce dissolution/phase change that can lead to a greater surface area, which can be beneficial when treating a variety of diseases.

In some embodiments, the presently disclosed subject matter describes an alternative therapeutic agent delivery method, which utilizes "non-wetting" imprint lithography to fabricate monodisperse magnetic nanoparticles for use in a drug delivery system. Such particles can be used for: (1) hyperthermia treatment of cancer cells; (2) MRI contrast agents; (3) guided delivery of the particle; and (4) triggered degradation of the drug delivery vector.

In some embodiments, the therapeutic agent delivery system includes a biocompatible material and a magnetic nanoparticle. In some embodiments, the biocompatible material has a melting point below 100° C. In some embodiments, the biocompatible material includes, without limitation, one or more of a polylactide, a polyglycolide, a hydroxypropylcellulose, a wax, combinations thereof, or the like.

In some embodiments, once the magnetic nanoparticle is delivered to the target or is in close proximity to the target, the magnetic nanoparticle is exposed to an AC-magnetic field. The exposure to the AC-magnetic field causes the magnetic nanoparticle to undergo a controlled heating. Without being bound to any one particular theory, the controlled heating is a result of a thermo ablation process. In some embodiments, the heat is used to induce a phase change in the polymer component of the nanoparticle. In some embodiments, the phase change includes a melting process. In some embodiments, the phase change results in the release of an encapsulated material. In some embodiments, the release of an encapsulated material includes a controlled release. In some embodiments, the controlled release of the encapsulated material results in a concentrated dosing of the therapeutic agent. In some embodiments, the heating results in the hyperthermic treatment of the target, e.g., specific cells. In some embodiments, the heating results in an increase in the effectiveness of the encapsulated material. In some embodiments, the triggering mechanism of the magnetic nanoparticles induced by the electromagnetic heating enhances the degradation rate of the particle and can induce swelling and/or a dissolution/phase change that can lead to a greater surface area which can be beneficial when treating a variety of diseases.

The presently described magnetic containing materials also lend themselves to other applications. The magnetoparticles can be assembled into well-defined arrays driven by their shape, functionalization of the surface and/or exposure to a magnetic field for investigations of and not limited to magnetic assay devices, memory devices, spintronic applications, and separations of solutions.

Thus, the presently disclosed subject matter provides a method for delivering a therapeutic agent to a target, the method including:
(a) providing a particle prepared by the presently disclosed methods;
(b) admixing the therapeutic agent with the particle; and
(c) delivering the particle including the therapeutic agent to the target.

In some embodiments, the method includes exposing the particle to an alternating magnetic field once the particle is delivered to the target. In some embodiments, the exposing of the particle to an alternating magnetic field causes the particle to produce heat through one of a hypothermia process, a thermo ablation process, combinations thereof, or the like.

In some embodiments, the heat produced by the particle induces one of a phase change in the polymer component of the particle and a hyperthermic treatment of the target. In some embodiments, the phase change in the polymer component of the particle includes a change from a solid phase to a liquid phase. In some embodiments, the phase change from a solid phase to a liquid phase causes the therapeutic agent to be released from the particle. In some embodiments, the release of the therapeutic agent from the particle includes a controlled release.

In some embodiments, the target includes, without limitation, one or more of a cell-targeting peptide, a cell-penetrating peptide, an integrin receptor peptide (GRGDSP), a melanocyte stimulating hormone, a vasoactive intestional peptide, an anti-Her2 mouse antibody, a vitamin, combinations thereof, or the like.

In one embodiment, the presently disclosed subject matter provides a method for modifying a particle surface. In one embodiment the method of modifying a particle surface includes: (a) providing particles in or on at least one of: (i) a patterned template; and (ii) a substrate; (b) disposing a solution containing a modifying group in or on at least one of: (i) the patterned template; and (ii) the substrate; and (c) removing excess unreacted modifying groups.

In one embodiment of the method for modifying a particle, the modifying group chemically attaches to the particle through a linking group. In another embodiment of the method for modifying a particle, the linker group includes, without limitation, one or more of sulfides, amines, carboxylic acids, acid chlorides, alcohols, alkenes, alkyl halides, isocyanates, combinations thereof, or the like. In another embodiment, the method of modifying the particles includes a modifying agent that includes, without limitation, one or more of dyes, fluorescence tags, radiolabeled tags, contrast agents, ligands, peptides, pharmaceutical agents, proteins, DNA, RNA, siRNA, combinations thereof, or the like.

With respect to the methods of the presently disclosed subject matter, any animal subject can be treated. The term "subject" as used herein refers to any vertebrate species. The methods of the presently claimed subject matter are particularly useful in the diagnosis of warm-blooded vertebrates. Thus, the presently claimed subject matter concerns mammals. In some embodiments provided is the diagnosis and/or treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the diagnosis and/or treatment of livestock, including, but not limited to domesticated swine (pigs and hogs), ruminants, horses, poultry, and the like.

The following references are incorporated herein by reference in their entirety. Published International PCT Application No. WO2004081666 to DeSimone et al.; U.S. Pat. No. 6,528,080 to Dunn et al.; U.S. Pat. No. 6,592,579 to Arndt et al., Published International PCT Application No. WO00066192 to Jordan; Hilger, I. et al., *Radiology* 570-575 (2001); Mornet, S. et al., *J. Mat. Chem.*, 2161-2175 (2004); Berry, C. C. et al., *J. Phys. D: Applied Physics* 36, R198-R206 (2003); Babincova, M. et al., *Bioelectrochemistry* 55, 17-19 (2002); Wolf, S. A. et al., *Science* 16, 1488-1495 (2001); and Sun, S. et al., *Science* 287, 1989-1992 (2000); U.S. Pat. No. 6,159,443 to Hallahan; and Published PCT Application No. WO 03/066066 to Hallahan et al.

XIII. Method of Patterning Natural and Synthetic Structures

In some embodiments, the presently disclosed subject matter describes methods and processes, and products by processes, for generating surfaces and molds from natural structures, single molecules, or self-assembled structures. Accordingly, in some embodiments, the presently disclosed subject matter describes a method of patterning a natural structure, single molecule, and/or a self-assembled structure. In some embodiments, the method further includes replicating the natural structure, single molecule, and/or a self-assembled structure. In some embodiments, the method further includes replicating the functionality of the natural structure, single molecule, and/or a self-assembled structure.

More particularly, in some embodiments, the method further includes taking the impression or mold of a natural structure, single molecule, and/or a self-assembled structure. In some embodiments, the impression or mold is taken with a low surface energy polymeric precursor. In some embodiments, the low surface energy polymeric precursor includes a perfluoropolyether (PFPE) functionally terminated diacrylate. In some embodiments, the natural structure, single molecule, and/or self-assembled structure includes, without limitation, one or more of enzymes, viruses, antibodies, micelles, tissue surfaces, combinations thereof, or the like.

In some embodiments, the impression or mold is used to replicate the features of the natural structure, single molecule, and/or a self-assembled structure into an isolated object or a surface. In some embodiments, a non-wetting imprint lithography method is used to impart the features into a molded part or surface. In some embodiments, the molded part or surface produced by this process can be used in many applications, including, but not limited to, drug delivery, medical devices, coatings, catalysts, or mimics of the natural structures from which they are derived. In some embodiments, the natural structure includes biological tissue. In some embodiments, the biological tissue includes tissue from a bodily organ, such as a heart. In some embodiments, the biological tissue includes vessels and bone. In some embodiments, the biological tissue includes tendon or cartilage. For example, in some embodiments, the presently disclosed subject matter can be used to pattern surfaces for tendon and cartilage repair. Such repair typically requires the use of collagen tissue, which comes from cadavers and must be machined for use as replacements. Most of these replacements fail because one cannot lay down the primary pattern that is required for replacement. The soft lithographic methods described herein alleviate this problem.

In some embodiments, the presently disclosed subject matter can be applied to tissue regeneration using stem cells. Almost all stem cell approaches known in the art require molecular patterns for the cells to seed and then grow, thereby taking the shape of an organ, such as a liver, a kidney, or the like. In some embodiments, the molecular scaffold is cast and used as crystals to seed an organ in a form of transplant therapy. In some embodiments, the stem cell and nano-substrate is seeded into a dying tissue, e.g., liver tissue, to promote growth and tissue regeneration. In some embodiments, the material to be replicated in the mold includes a material that is similar to or the same as the material that was originally molded. In some embodiments, the material to be replicated in the mold includes a material that is different from and/or has different properties than the material that was originally molded. This approach could play an important role in addressing the organ transplant shortage.

In some embodiments, the presently disclosed subject matter is used to take the impression of one of an enzyme, a bacterium, and a virus. In some embodiments, the enzyme, bacterium, or virus is then replicated into a discrete object or onto a surface that has the shape reminiscent of that particular enzyme, bacterium, or virus replicated into it. In some embodiments, the mold itself is replicated on a surface, wherein the surface-attached replicated mold acts as a receptor site for an enzyme, bacterium, or virus particle. In some embodiments, the replicated mold is useful as a catalyst, a diagnostic sensor, a therapeutic agent, a vaccine, combinations thereof, and the like. In some embodiments, the surface-attached replicated mold is used to facilitate the discovery of new therapeutic agents.

In some embodiments, the macromolecular, e.g., enzyme, bacterial, or viral, molded "mimics" serve as non-self-replicating entities that have the same surface topography as the original macromolecule, bacterium, or virus. In some embodiments, the molded mimics are used to create biological responses, e.g., an allergic response, to their presence, thereby creating antibodies or activating receptors. In some embodiments, the molded mimics function as a vaccine. In some embodiments, the efficacy of the biologically-active shape of the molded mimics is enhanced by a surface modification technique.

XIII.A. Molecular Imprinting

According to some embodiments, the materials and methods of the presently disclosed subject matter can be used with molecular imprinting techniques to form polymers with recognition cites. Drug research and development often requires the analysis of highly specific and sensitive chemical and/or biologic agents collectively called "recognition agents." Natural recognition agents, such as for example, enzymes, proteins, drug candidates, biomolecules, herbicides, amino acids, derivatives of amino acids, peptides, nucleotides, nucleotide bases, combinations thereof, and the like, tend to be very specific and sensitive as well as being labile and have a low density of binding sites. Because of the delicacy of natural recognition agents, artificial recognition agents are more stable and have become popular research tools. Molecular imprinting has emerged in recent years as a highly accepted tool for the development of artificial recognition agents.

Imprinting of molecules occurs by the polymerization of functional and cross-linking monomers in the presence of a template molecule. First, a template molecule, such as, by way of example but not limitation, an enzyme, a protein, a drug candidate, a biomolecule, a herbicide, an amino acid, a derivative of an amino acid, a peptide, nucleotides, nucleotide bases, a virus, combinations thereof, and the like is introduced to a liquid polymer solution. In some embodiments, the liquid polymer solution is a liquid polymer of the presently disclosed subject matter and includes functional and cross-linked monomers. The functional and cross-linked monomers are allowed to establish bond formations and other chemical and physical associations and orientations with the template in the polymer. In some embodiments, a functional monomer includes two functional groups. At one end of the monomer the monomer is configured to interact with the template, for example through noncovalent interactions (i.e., hydrogen bonding, van der Waals forces, or hydrophobic interactions). The other end of the monomer, i.e., the end that is not interacting with the template, includes a group that is able to bind with the polymer. During polymerization, the monomers are locked in position around the template, for example with covalent binding, and remain in such a position after the template is removed.

After polymerization or curing the template is removed from the polymer. The template can be removed by dissolving the template in a solvent in some embodiments. The resultant imprint of the template has a steric (size and shape) and chemical (spatial arrangements or complementary functionality) memory of the template. After polymerization and removal of the template, the functional groups of the polymers molecular imprint can then bind a target provided that the binding sites of the imprint and the target molecule complement each other in size, shape, and chemical functionality. This process provides a material with a high stability against physicochemical perturbations that has specificity toward a target molecule and, as such, the material can be used in high throughput assays and in conjunction with physical and chemical parameters that a natural recognition agent cannot withstand.

According to some embodiments, applications of molecular imprinting include, but are not limited to, purification, separation, screening of bioactive molecules, sensors, catalysis, chromatographic separation, drug screening, chemosensors, catalysis, biodefense, immunoassays, combinations thereof, and the like.

Useful applications and experimentations of molecular imprinting that can be used in combination with the materials and methods of the presently disclosed subject matter can be found in: Vivek Babu Kandimalla, Hunagxian Ju, *Molecular Imprinting: A Dynamic Technique for Diverse Applications in Analytical Chemistry*, Anal. Bioanal. Chem. (2004) 380: 587-605, and the references cited therein, which are all hereby incorporated by reference in their entirety herein.

XIII.B. Artificial Functional Molecules

According to some embodiments of the presently disclosed subject matter, following the formation of a molecular imprint of a template molecule, as described herein, the molecular imprint can then be used as a mold and receive the materials and methods of the presently disclosed subject matter to form, for example, an artificial functional molecule. After forming the functionalized molecular imprint mold in the polymer material, a polymer precursor solution including, but not limited to, functional and cross-linked monomers, can be applied to the functionalized imprint mold in accord with the materials and methods disclosed herein to form an artificial functional molecule. During molding of the artificial functional molecule, the functionalized monomers in the polymer precursor will align with the functionalized parts of the imprint mold such that the artificial functional molecule will posses a steric (size and shape) and chemical (spatial arrangements or complementary functionality) memory of the imprint mold. The artificial functional molecule, which is the steric and chemical memory of the imprint mold, has similar chemical and physical properties to the original template molecule and can trigger membrane channels; bind to receptors; enter cells; interact with proteins and enzymes; trigger immune responses; trigger physiological responses; trigger release of bioregulatory agents such as, for example, hormones, "feel good" molecules, neurotransmitters, and the like; inhibit responses; trigger regulatory functions; combinations thereof; and the like.

According to other embodiments, molecular imprints and artificial functional molecules of the presently disclosed subject matter can be used in conjunction with particles of the presently disclosed subject matter, as disclosed herein, that have drugs, biologics, or other agents for analysis associated with the particle. Accordingly, the particles with drugs, biologics, or other agents can be analyzed for interaction and/or binding with the artificial functional molecule particles and/or molecular imprint, thereby, making a complete analysis system having high stability against physicochemical perturbations and, as such, the materials can be used in high throughput assays and in conjunction with physical and chemical parameters that natural recognition agents can not withstand. Further, the presently disclosed analysis systems made of the materials and methods of the presently disclosed subject matter are economical to manufacture, increase throughput of drug and biomolecule research and development, and the like.

Figure 44A:
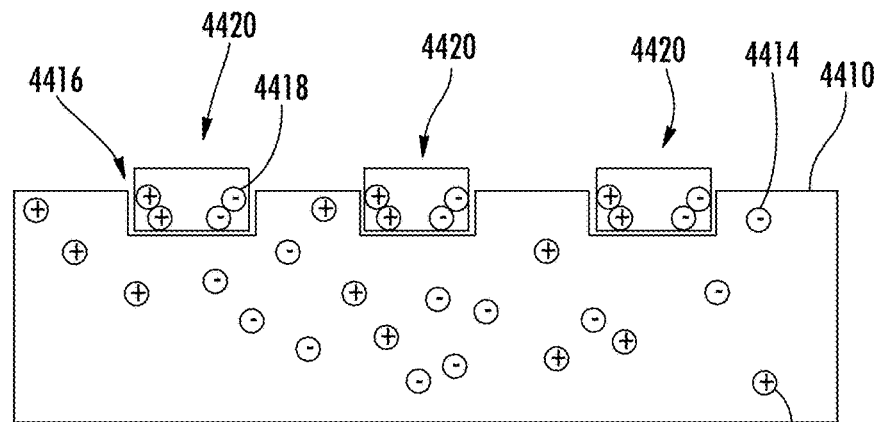
FIG. 44A-C show sequence of molecular imprinting according to an embodiment of the presently disclosed subject matter.
Figure 44B:
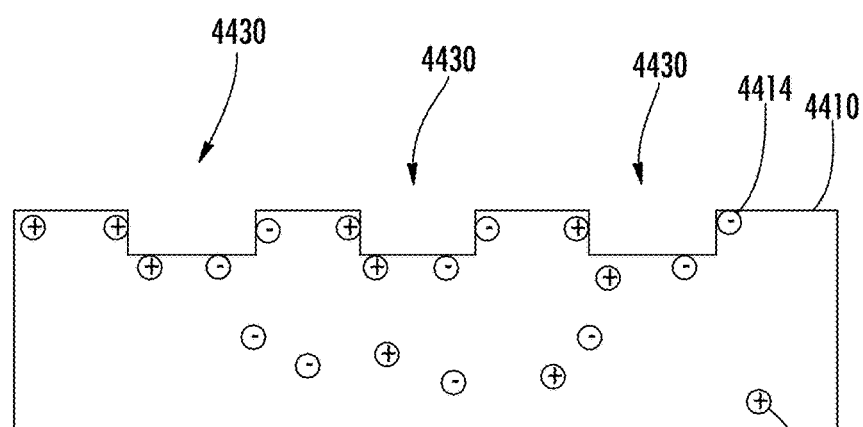
Figure 44C:
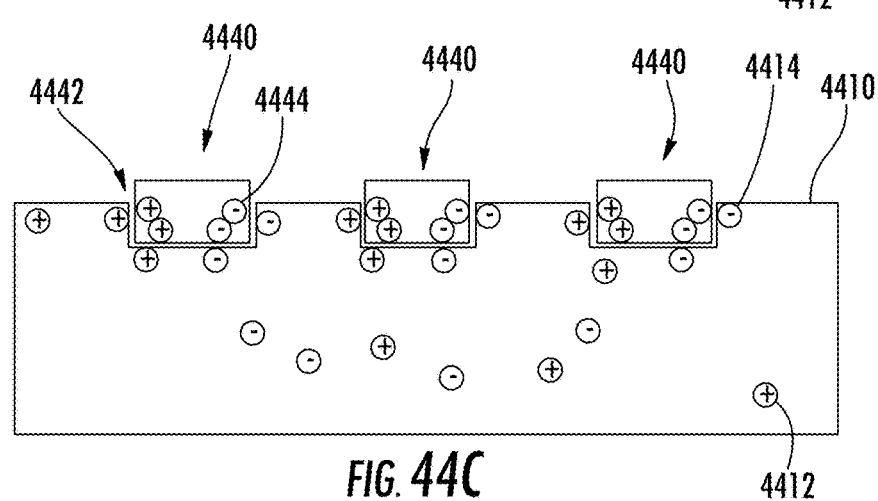

Referring now to FIG. 44, an embodiment of forming an artificial functional molecule includes creating a molecular imprinting such as shown in FIG. 44A. A substrate material 4410, such as liquid perfluoropolyether, contains functional monomers 4412 and 4414. Substrate material 4410 is imprinted with template molecules 4420 having specific steric and chemical groupings 4418 associated therewith. Template molecules 4420 form imprint wells 4416 in substrate material 4410. Substrate material 4410 is then cured, for example by photocuring, thermal curing, combinations thereof, or the like as described herein.

Next, in FIG. 44B, template molecules 4420 are removed, dissociated, or dissolved from association with substrate material 4410. Before curing of substrate material 4410, however, functional monomers 4412 and 4414 of substrate material 4410 associate with their negative or mirror image in template molecules 4420 and during polymerization the functional monomers become locked in position. Thereby, a molecular imprint 4430 that is the steric and chemical mirror image of the template molecule 4420 is formed in the substrate material.

Next, an artificial functional molecule 4440 is formed in molecular imprint 4430. According to an embodiment, the materials and methods of the presently disclosed subject matter are utilized, as described elsewhere herein, to make particles that mimic, both stericly and chemically template molecule 4420 that made imprint 4430. According to one embodiment, liquid PFPE is prepared and mixed with functional monomers 4444 and the mixture is introduced into molecular imprint cavity 4442 in substrate 4410. Functional monomers 4444 in the PFPE associate with their mirror image functional monomer 4412 and 4414 lock into place in substrate material 4410. The PFPE mixture is then cured such that artificial functional molecules 4440 are formed in imprint cavity 4442 and mimic template molecule 4420 both stericly and chemically. Artificial functional molecules 4444 are then removed from the substrate 4410 as described herein.

XIV. Method of Modifying the Surface of an Imprint Lithography Mold to Impart Surface Characteristics to Molded Products In some embodiments, the presently disclosed subject matter describes a method of modifying the surface of an imprint lithography mold. In some embodiments, the method further includes imparting surface characteristics to a molded product. In some embodiments, the molded product includes an isolated molded product. In some embodiments, the isolate molded product is formed using a non-wetting imprint lithography technique. In some embodiments, the molded product includes a contact lens, a medical device, and the like.

More particularly, the surface of a solvent resistant, low surface energy polymeric material, or more particularly a PFPE mold is modified by a surface modification step, wherein the surface modification step includes, without limitation, one or more of plasma treatment, chemical treatment, the adsorption of molecules, combinations thereof, or the like. In some embodiments, the molecules adsorbed during the surface modification step include, without limitation, one or more of polyelectrolytes, poly(vinylalcohol), alkylhalosilanes, ligands, combinations thereof, or the like. In some embodiments, the structures, particles, or objects obtained from the surface-treated molds can be modified by the surface treatments in the mold. In some embodiments, the modification includes the pre-orientation of molecules or moieties with the molecules including the molded products. In some embodiments, the pre-orientation of the molecules or moieties imparts certain properties to the molded products, including catalytic, wettable, adhesive, non-stick, interactive, or not interactive, when the molded product is placed in another environment. In some embodiments, such properties are used to facilitate interactions with biological tissue or to prevent interaction with biological tissues. Applications of the presently disclosed subject matter include sensors, arrays, medical implants, medical diagnostics, disease detection, and separation media.

XV. Methods for Selectively Exposing the Surface of an Article to an Agent

Also disclosed herein is a method for selectively exposing the surface of an article to an agent. In some embodiments the method includes:

(a) shielding a first portion of the surface of the article with a masking system, wherein the masking system includes a elastomeric mask in conformal contact with the surface of the article; and (b) applying an agent to be patterned within the masking system to a second portion of the surface of the article, while preventing application of the agent to the first portion shielded by the masking system.

In some embodiments, the elastomeric mask includes a plurality of channels. In some embodiments, each of the channels has a cross-sectional dimension of less than about 1 millimeter. In some embodiments, each of the channels has a cross-sectional dimension of less than about 1 micron. In some embodiments, each of the channels has a cross-sectional dimension of less than about 100 nm. In some embodiments, each of the channels has a cross-sectional dimension of about 1 nm. In some embodiments, the agent swells the elastomeric mask less than 25%.

In some embodiments, the agent includes an organic electroluminescent material or a precursor thereof. In some embodiments, the method further including allowing the organic electroluminescent material to form from the agent at the second portion of the surface, and establishing electrical communication between the organic electroluminescent material and an electrical circuit.

In some embodiments, the agent includes a liquid or is carried in a liquid. In some embodiments, the agent includes the product of chemical vapor deposition. In some embodiments, the agent includes a product of deposition from a gas phase. In some embodiments, the agent includes a product of e-beam deposition, evaporation, or sputtering. In some embodiments, the agent includes a product of electrochemical deposition. In some embodiments, the agent includes a product of electroless deposition. In some embodiments, the agent is applied from a fluid precursor. In some embodiments, includes a solution or suspension of an inorganic compound. In some embodiments, the inorganic compound hardens on the second portion of the article surface.

In some embodiments, the fluid precursor includes a suspension of particles in a fluid carrier. In some embodiments, the method further includes allowing the fluid carrier to dissipate thereby depositing the particles at the first region of the article surface. In some embodiments, the fluid precursor includes a chemically active agent in a fluid carrier. In some embodiments, the method further includes allowing the fluid carrier to dissipate thereby depositing the chemically active agent at the first region of the article surface.

In some embodiments, the chemically active agent includes a polymer precursor. In some embodiments, the method further includes forming a polymeric article from the polymer precursor. In some embodiments, the chemically active agent includes an agent capable of promoting deposition of a material. In some embodiments, the chemically active agent includes an etchant. In some embodiments, the method further includes allowing the second portion of the surface of the article to be etched. In some embodiments, the method further includes removing the elastomeric mask of the masking system from the first portion of the article surface while leaving the agent adhered to the second portion of the article surface.

XVI. Methods for Forming Engineered Membranes

The presently disclosed subject matter also describes a method for forming an engineered membrane. In some embodiments, a patterned non-wetting template is formed by contacting a first liquid material, such as a PFPE material, with a patterned substrate and treating the first liquid material, for example, by curing through exposure to UV light to form a patterned non-wetting template. The patterned substrate includes a plurality of recesses or cavities configured in a specific shape such that the patterned non-wetting template includes a plurality of extruding features. The patterned non-wetting template is contacted with a second liquid material, for example, a photocurable resin. A force is then applied to the patterned non-wetting template to displace an excess amount of second liquid material or "scum layer." The second liquid material is then treated, for example, by curing through exposure to UV light to form an interconnected structure including a plurality of shape and size specific holes. The interconnected structure is then removed from the non-wetting template. In some embodiments, the interconnected structure is used as a membrane for separations.

XVII. Methods for Inspecting Processes and Products by Processes

It will be important to inspect the objects/structures/particles described herein for accuracy of shape, placement and utility. Such inspection can allow for corrective actions to be taken or for defects to be removed or mitigated. The range of approaches and monitoring devices useful for such inspections include: air gages, which use pneumatic pressure and flow to measure or sort dimensional attributes; balancing machines and systems, which dynamically measure and/or correct machine or component balance; biological microscopes, which typically are used to study organisms and their vital processes; bore and ID gages, which are designed for internal diameter dimensional measurement or assessment; boroscopes, which are inspection tools with rigid or flexible optical tubes for interior inspection of holes, bores, cavities, and the like; calipers, which typically use a precise slide movement for inside, outside, depth or step measurements, some of which are used for comparing or transferring dimensions; CMM probes, which are transducers that convert physical measurements into electrical signals, using various measuring systems within the probe structure; color and appearance instruments, which, for example, typically are used to measure the properties of paints and coatings including color, gloss, haze and transparency; color sensors, which register items by contrast, true color, or translucent index, and are based on one of the color models, most commonly the RGB model (red, green, blue); coordinate measuring machines, which are mechanical systems designed to move a measuring probe to determine the coordinates of points on a work piece surface; depth gages, which are used to measure of the depth of holes, cavities or other component features; digital/video microscopes, which use digital technology to display the magnified image; digital readouts, which are specialized displays for position and dimension readings from inspection gages and linear scales, or rotary encoders on machine tools; dimensional gages and instruments, which provide quantitative measurements of a product's or component's dimensional and form attributes such as wall thickness, depth, height, length, I.D., O.D., taper or bore; dimensional and profile scanners, which gather two-dimensional or three-dimensional information about an object and are available in a wide variety of configurations and technologies; electron microscopes, which use a focused beam of electrons instead of light to "image" the specimen and gain information as to its structure and composition; fiberscopes, which are inspection tools with flexible optical tubes for interior inspection of holes, bores, and cavities; fixed gages, which are designed to access a specific attribute based on comparative gaging, and include Angle Gages, Ball Gages, Center Gages, Drill Size Gages, Feeler Gages, Fillet Gages, Gear Tooth Gages, Gage or Shim Stock, Pipe Gages, Radius Gages, Screw or Thread Pitch Gages, Taper Gages, Tube Gages, U.S. Standard Gages (Sheet/Plate), Weld Gages and Wire Gages; specialty/form gages, which are used to inspect parameters such as roundness, angularity, squareness, straightness, flatness, runout, taper and concentricity; gage blocks, which are manufactured to precise gagemaker tolerance grades for calibrating, checking, and setting fixed and comparative gages; height gages, which are used for measuring the height of components or product features; indicators and comparators, which measure where the linear movement of a precision spindle or probe is amplified; inspection and gaging accessories, such as layout and marking tolls, including hand tools, supplies and accessories for dimensional measurement, marking, layout or other machine shop applications such as scribes, transfer punches, dividers, and layout fluid; interferometers, which are used to measure distance in terms of wavelength and to determine wavelengths of particular light sources; laser micrometers, which measure extremely small distances using laser technology; levels, which are mechanical or electronic tools that measure the inclination of a surface relative to the earth's surface; machine alignment equipment, which is used to align rotating or moving parts and machine components; magnifiers, which are inspection instruments that are used to magnify a product or part detail via a lens system; master and setting gages, which provide dimensional standards for calibrating other gages; measuring microscopes, which are used by toolmakers for measuring the properties of tools, and often are used for dimensional measurement with lower magnifying powers to allow for brighter, sharper images combined with a wide field of view; metallurgical microscopes, which are used for metallurgical inspection; micrometers, which are instruments for precision dimensional gaging including a ground spindle and anvil mounted in a C-shaped steel frame. Noncontact laser micrometers are also available; microscopes (all types), which are instruments that are capable of producing a magnified image of a small object; optical/light microscopes, which use the visible or near-visible portion of the electromagnetic spectrum; optical comparators, which are instruments that project a magnified image or profile of a part onto a screen for comparison to a standard overlay profile or scale; plug/pin gages, which are used for a "go/no-go" assessment of hole and slot dimensions or locations compared to specified tolerances; protractors and angle gages, which measure the angle between two surfaces of a part or assembly; ring gages, which are used for "go/no-go" assessment compared to the specified dimensional tolerances or attributes of pins, shafts, or threaded studs; rules and scales, which are flat, graduated scales used for length measurement, and which for OEM applications, digital or electronic linear scales are often used; snap gages, which are used in production settings where specific diametrical or thickness measurements must be repeated frequently with precision and accuracy; specialty microscopes, which are used for specialized applications including metallurgy, gemology, or use specialized techniques like acoustics or microwaves to perform their function; squares, which are used to indicate if two surfaces of a part or assembly are perpendicular; styli, probes, and cantilevers, which are slender rod-shaped stems and contact tips or points used to probe surfaces in conjunction with profilometers, SPMs, CMMs, gages and dimensional scanners; surface profilometers, which measure surface profiles, roughness, waviness and other finish parameters by scanning a mechanical stylus across the sample or through noncontact methods; thread gages, which are dimensional instruments for measuring thread size, pitch or other parameters; and videoscopes, which are inspection tools that capture images from inside holes, bores or cavities.

XVIII. Open Molding Techniques

According to some embodiments, the particles described herein are formed in an open mold. Open molding can reduce the number of steps and sequences of events required during molding of particles and can improve the evaporation rate of solvent from the particle precursor material, thereby, increasing the efficiency and rate of particle production.

Figure 47:
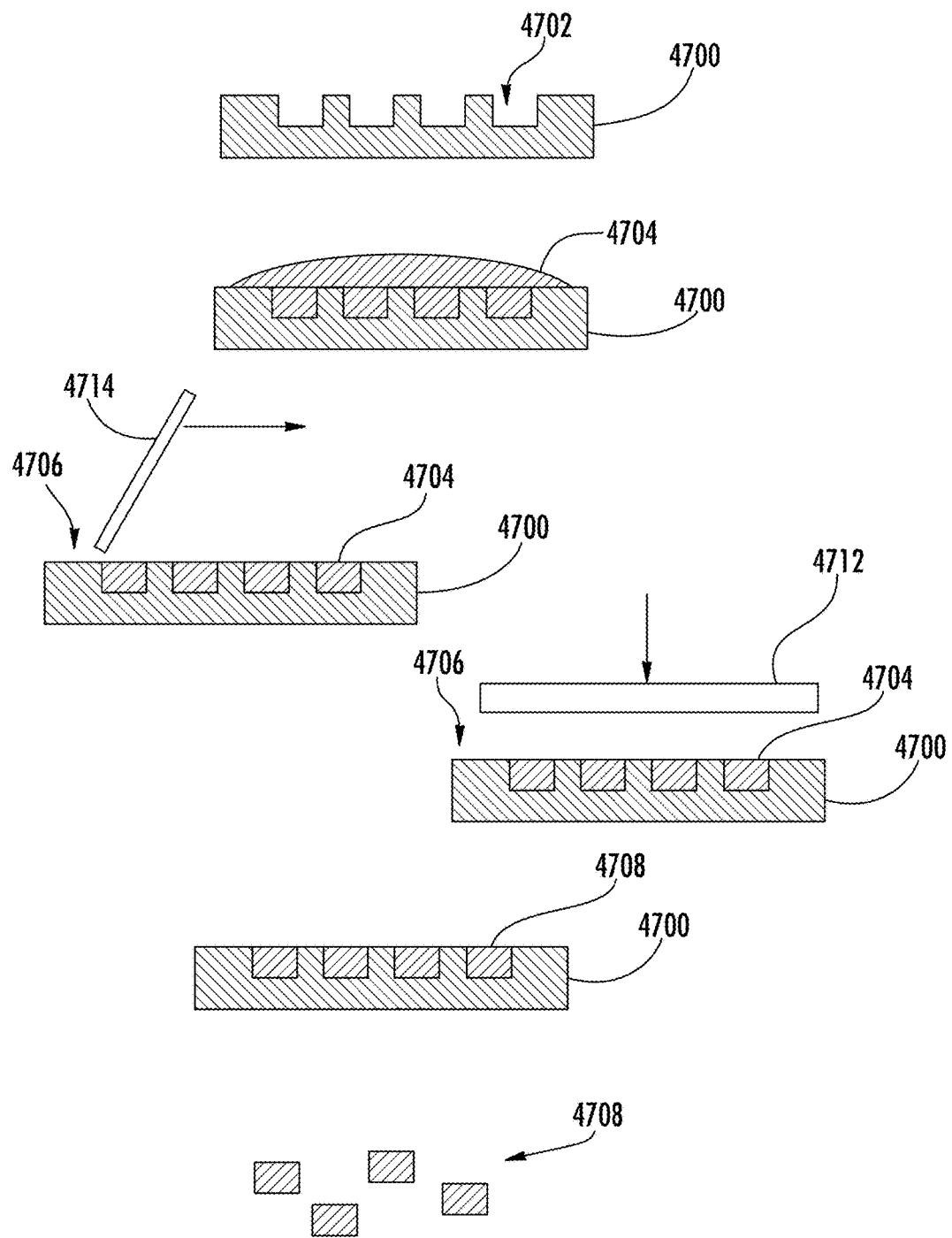
FIG. 47 shows particles fabricated through an open molding technique according to some embodiments of the present invention.

Referring to FIG. 47, surface or template 4700 includes cavities or recesses 4702 formed therein. A substance 4704, which can be, but is not limited to a liquid, a powder, a paste, a gel, a liquified solid, combinations thereof, and the like, is then deposited on surface 4700. The substance 4704 is introduced into recesses 4702 of surface 4700 and excess substance remaining on surface 4700 is removed 4706. Excess substance 4704 can be removed from the surface by, but is not limited to, doctor blading, applying pressure with a substrate, electrostatics, magnetics, gravitational forces, air pressure, combinations thereof, and the like. Next, substance 4704 remaining in recesses 4702 is hardened into particles 4708 by, but is not limited to, photocuring, thermal curing, solvent evaporation, oxidation or reductive polymerization, change of temperature, combinations thereof, and the like. After substance 4704 is hardened, the particles 4708 are harvested from recesses 4702.

According to some embodiments, surface 4700 is configured such that particle fabrication is accomplished in high throughput. In some embodiments, the surface is configured, for example, planer, cylindrical, spherical, curved, linear, a convery belt type arrangement, a gravure printing type arrangement (such as described in U.S. Pat. Nos. 4,557,195 and 4,905,594, all of which are incorporated herein by reference in their entirety), in large sheet arrangements, in multi-layered sheet arrangements, combinations thereof, and the like. According to such embodiments some recesses in the surface can be in a stage of being filled with substance while at another station of the surface excess substance is being removed. Meanwhile, yet another station of the surface can be hardening the substance and still another station being responsible for harvesting the particles from the recesses. In such embodiments, particles are fabricated efficiently and effectively in high throughput. In some embodiments the method and system are continuous, in other embodiments the method and system are batch, and in some embodiments the method and system are a combination of continuous and batch.

The composition of surface 4700 itself can be fabricated from any material that is chemically, physically, and commercially viable for a particular process to be carried out. According to some embodiments, the material for fabrication of surface 4700 is any of the materials described herein. More particularly, the material of surface 4700 is any material that has a low surface energy, is non-wettable, highly chemically inert, a solvent resistant low surface energy polymeric material, a solvent resistant elastomeric material, combinations thereof, and the like. Even more particularly, the material from which surface 4700 is fabricated is a perfluoropolyether material, a silicone material, a fluoroolefin material, an acrylate material, a silicone material, a styrenic material, a fluorinated thermoplastic elastomer (TPE), a triazine fluoropolymer, a perfluorocyclobutyl material, a fluorinated epoxy resin, a fluorinated monomer or fluorinated oligomer that can be polymerized or crosslinked by a metathesis polymerization reaction, combinations thereof, and the like.

According to some embodiments, recesses 4702 in surface 4700 are recesses of particular shapes and sizes. Recesses 4702 can be, but are not limited to, regular shaped, irregular shaped, variable shaped, and the like. In some embodiments, recesses 4702 are, but are not limited to, arched recesses, recesses with right angles, tapered recesses, diamond shaped, spherical, rectangle, triangle, polymorphic, molecular shaped, protein shaped, combinations thereof, and the like. In some embodiments, recesses 4702 can be electrically and/or chemically charged such that functional monomers within substance 4704 are attracted and/or repelled, thereby resulting in a functional particle as described elsewhere herein. According to some embodiments, recess 4704 is less than about 1 mm in a dimension. According to some embodiments, the recess is less than about 1 mm in its largest cross-sectional dimension. In other embodiments the recess includes a dimension that is between about 20 nm and about 1 mm. In other embodiments, the recess is between about 20 nm and about 500 micron in a dimension and/or in a largest dimension. More particularly, the recess is between about 50 nm and about 250 micron in a dimension and/or in a largest dimension.

According to embodiments of the present invention, any of the substances disclosed herein, for example, a drug, DNA, RNA, a biological molecule, a super absorptive material, combinations thereof, and the like can be substance 4704 that is deposited into recesses 4702 and molded into a particle. According to still further embodiments, substance 4704 to be molded is, but is not limited to, a polymer, a solution, a monomer, a plurality of monomers, a polymerization initiator, a polymerization catalyst, an inorganic precursor, a metal precursor, a pharmaceutical agent, a tag, a magnetic material, a paramagnetic material, a ligand, a cell penetrating peptide, a porogen, a surfactant, a plurality of immiscible liquids, a solvent, a charged species, combinations thereof, and the like. In still further embodiments, particle 4708 is, but is not limited to, organic polymers, charged particles, polymer electrets (poly(vinylidene fluoride), Teflon-fluorinated ethylene propylene, polytetrafluoroethylene), therapeutic agents, drugs, non-viral gene vectors, RNAi, viral particles, polymorphs, combinations thereof, and the like.

According to embodiments of the invention, substance 4704 to be molded into particles 4708 is deposited onto template surface 4700. In some embodiments substance 4704 is in a liquid form and therefore flows into recesses 4702 of surface 4700. According to other embodiments, substance 4704 takes on another physical form, such as for example, a powder, a gel, a paste, or the like, such that a force can be required to ensure substance 4704 becomes introduced into recesses 4702. Such a force that can be useful in introducing substance 4704 into recesses 4702 can be, but is not limited to, vibration, centrifugal, electrostatic, magnetic, electromagnetic, gravity, compression, combinations thereof, and the like. The force can also be utilized in embodiments where substance 4704 is a liquid to further ensure substance 4704 enters into recesses 4702.

Following introduction of substance 4704 onto template surface 4700 and recesses 4702 thereof, excess substance is removed from surface 4700 in some embodiments. Removal of excess substance 4704 can be accomplished by engaging surface 4700 with a second surface 4712 such that the excess substance is squeezed out. Second surface 4712 can be, but is not limited to, a flat surface, an arched surface, and the like. In some embodiments second surface 4712 is brought into contact with template surface 4700. According to other embodiments second surface 4712 is brought within a predetermine distance of template surface 4700. According to some embodiments, second surface 4712 is positioned with respect to template surface 4700 normal to the plane of template surface 4700. According to other embodiments second surface 4712 engages template surface 4700 with a predetermined contact angle. According to still further embodiments, second surface 4712 can be an arched surface, such as a cylinder, and can be rolled with respect to template surface 4700 to remove excess substance. According to yet further embodiments, second surface 4712 is composed of a composition that repels or attracts the excess substance, such as for example, a non-wetting substance, a hydrophobic surface repelling a hydrophilic substance, and the like.

According to other embodiments, excess substance 4704 can be removed from template surface 4700 by doctor blading, or otherwise passing a blade across template surface 4700. According to some embodiments, blade 4714 is composed of a metal, rubber, polymer, silicon based material, glass, hydrophobic substance, hydrophilic substance, combinations thereof, and the like. In some embodiments blade 4714 is positioned to contact surface 4700 and wipe away excess substance. In other embodiments, blade 4714 is positioned a predetermined distance from surface 4700 and drawn across surface 4700 to remove excess substance from template surface 4700. The distance blade 4714 is positioned from surface 4700 and the rate at which blade 4714 is drawn across surface 4700 are variable and determined by the material properties of blade 4714, template surface 4700, substance 4704 to be molded, combinations thereof, and the like. Doctor blading and similar techniques are disclosed in Lee et al., Two-Polymer Microtransfer Molding for Highly Layered Microstructures, Adv. Mater. 2005, 17, 2481-2485, which is incorporated herein by reference in its entirety.

Substance 4704 in recesses 4702 is then hardened to form particles 4708. The hardening of substance 4704 can be achieved by any of the methods and by utilizing any of the materials described herein. According to some embodiments the hardening is accomplished by, but is not limited to, solvent evaporation, photo curing, thermal curing, cooling, combinations thereof, and the like.

After substance 4704 has been hardened, particles 4708 are harvested from recesses 4702. According to some embodiments particle 4708 is harvested by contacting particle 4708 with an article that has affinity for particles 4708 that is greater than the affinity between particle 4708 and recess 4702. By way of example, but not limitation, particle 4708 is harvested by contacting particle 4708 with an adhesive substance that adheres to particle 4708 with greater affinity than affinity between particle 4708 and template recess 4702. According to some embodiments, the harvesting substance is, but is not limited to, water, organic solvents, carbohydrates, epoxies, waxes, polyvinyl alcohol, polyvinyl pyrrolidone, polybutyl acrylate, polycyano acrylates, polymethyl methacrylate, combinations thereof, and the like. According to still further embodiments substance 4704 in recesses 4702 forms a porous particle by solvent casting.

According to other embodiments, particles 4708 are harvested by subjecting the particle/recess combination and/or template surface to a physical force or energy such that particles 4708 are released from the recess 4702. In some embodiments the force is, but is not limited to, centrifugation, dissolution, vibration, ultrasonics, megasonics, gravity, flexure of the template, suction, electrostatic attraction, electrostatic repulsion, magnetism, physical template manipulation, combinations thereof, and the like.

According to some embodiments, particles 4708 are purified after being harvested. In some embodiments particles 4708 are purified from the harvesting substance. The harvesting can be, but is not limited to, centrifugation, separation, vibration, gravity, dialysis, filtering, sieving, electrophoresis, gas stream, magnetism, electrostatic separation, combinations thereof, and the like.

XVIII.A. Particles Formed from Open Molding

According to some embodiments, recesses 4702 are sized and shaped such that particles formed therefrom will make polymorphs of drugs. Forming a drug from particles 4708 of specific sizes and shapes can increase the efficacy, efficiency, potency, and the like, of a drug substance. For more on polymorphs, see Lee et al., Crystallization on Confined Engineered Surfaces: A Method to Control Crystal Size and Generate Different Polymorphs, J. Am. Chem. Soc., 127 (43), 14982-14983, 2005, which is incorporated herein by reference in its entirety.

According to some embodiments, particles 4708 form super absorbent polymer particles. Examples of super absorbent polymer materials that can be made into particles 4708 according to the present invention, include, but are not limited to, polyacrylates, polyacrylic acid, polyacrylamide, cellulose ethers, poly (ethylene oxide), poly (vinyl alcohol), polysuccinimides, polyacrylonitrile polymers, combinations thereof, and the like. According to further embodiments, these super absorbent polymers can be blended or cross-linked with other polymers, or their monomers can be co-polymerized with other monomers, or the like. According to still further embodiments, a starch is grafted onto these polymers.

According to further embodiments, particle 4708 formed from the methods and materials of the present invention include, but are not limited to, particles between 20 nm and 10 microns of a drug, a charged particle, a polymer electret, a therapeutic agent, a viral particle, a polymorph, a super absorbent particle, combinations thereof, and the like.

XIV. Seed Coating

According to some embodiments of the present invention, the materials and methods disclosed herein are used to coat seeds. Referring now to FIG. 48, to coat seeds, the seeds are suspended in a liquid solution 4808. The liquid solution containing the seeds 4808 is deposited onto a template 4802, where the template includes a recess 4812. The liquid solution containing the seed 4808 is brought into the recesses 4812 and the liquid is hardened such that the seed becomes coated. The coated seeds are then harvested from the recesses 4810. Harvesting of the coated seeds can be accomplished by any of the harvesting methods described herein.

According to some embodiments, template 4802 is generated by introducing a liquid template precursor to a scaffolding 4800 which contains a pattern that template 4802 will mask. The liquid template precursor is then hardened to form template 4802. The liquid template precursor can be any of the materials disclosed herein and can be hardened by any of the methods and materials disclosed herein. For example, the liquid template precursor can be a liquid PFPE precursor and contain a curable component (e.g., UV, photo, thermal, combinations thereof, and the like). According to this example, the liquid PFPE precursor is introduced to scaffolding 4800 and treated with UV radiation to cure the liquid PFPE into solid form.

According to further embodiments, liquid solution containing the seed 4808 is deposited onto a platform 4804 which is configured to sandwich liquid solution 4808 with template 4802. When liquid solution 4808 has been sandwiched into recesses 4812 of template 4802, liquid solution containing the seed 4808 is hardened such that the seed is coated in a solidified material 4810. Hardening can be by any of the methods and systems described herein, including, but not limited to, photo curing, thermal curing, evaporation, and the like. Following hardening of liquid solution 4808, platform 4804 and template 4802 are removed from each other and solidified coated seeds 4810 are harvested from template 4802 and/or the surface of platform 4804. Harvesting can be any of the harvesting methods described herein.

The coating of seeds with the materials and methods disclosed herein can, but is not limited to, preparing the seed for packaging, preparing coated seeds of a uniform size, preparing seeds with a uniform coating, preparing seeds with a uniform coated shape, eliminating surfactants, combinations thereof, and the like. Seed coating techniques compatible with the present invention are disclosed in U.S. Pat. No. 4,245,432, which is incorporated herein by reference in its entirety.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Representative Procedure for Synthesis and Curing Photocurable Perfluoropolyethers In some embodiments, the synthesis and curing of PFPE materials of the presently disclosed subject matter is performed by using the method described by Rolland, J. P., et al., *J. Am. Chem. Soc.*, 2004, 126, 2322-2323. Briefly, this method involves the methacrylate-functionalization of a commercially available PFPE diol ($M_n$=3800 g/mol) with isocyanatoethyl methacrylate. Subsequent photocuring of the material is accomplished through blending with 1 wt % of 2,2-dimethoxy-2-phenylacetophenone and exposure to UV radiation ($\lambda$=365 nm).

More particularly, in a typical preparation of perfluoropolyether dimethacrylate (PFPE DMA), poly(tetrafluoroethylene oxide-co-difluoromethylene oxide)$\alpha,\omega$ diol (ZDOL, average $M_n$ ca. 3,800 g/mol, 95%, Aldrich Chemical Company, Milwaukee, Wis., United States of America) (5.7227 g, 1.5 mmol) was added to a dry 50 mL round bottom flask and purged with argon for 15 minutes. 2-isocyanatoethyl methacrylate (EIM, 99%, Aldrich) (0.43 mL, 3.0 mmol) was then added via syringe along with 1,1,2-trichlorotrifluoroethane (Freon 113 99%, Aldrich) (2 mL), and dibutyltin diacetate (DBTDA, 99%, Aldrich) (50 µL). The solution was immersed in an oil bath and allowed to stir at 50° C. for 24 h. The solution was then passed through a chromatographic column (alumina, Freon 113, 2×5 cm). Evaporation of the solvent yielded a clear, colorless, viscous oil, which was further purified by passage through a 0.22-µm polyethersulfone filter.

In a representative curing procedure for PFPE DMA, 1 wt % of 2,2-dimethoxy-2-phenyl acetophenone (DMPA, 99% Aldrich), (0.05 g, 2.0 mmol) was added to PFPE DMA (5 g, 1.2 mmol) along with 2 mL Freon 113 until a clear solution was formed. After removal of the solvent, the cloudy viscous oil was passed through a 0.22-µm polyethersulfone filter to remove any DMPA that did not disperse into the PFPE DMA. The filtered PFPE DMA was then irradiated with a UV source (Electro-Lite Corporation, Danbury, Conn., United States of America, UV curing chamber model no. 81432-ELC-500, $\lambda$=365 nm) while under a nitrogen purge for 10 min. This resulted in a clear, slightly yellow, rubbery material.

Example 2

Representative Fabrication of a PFPE DMA Device

In some embodiments, a PFPE DMA device, such as a stamp, was fabricated according to the method described by Rolland, J. P., et al., *J. Am. Chem. Soc.*, 2004, 126, 2322-2323. Briefly, the PFPE DMA containing a photoinitiator, such as DMPA, was spin coated (800 rpm) to a thickness of 20 µm onto a Si wafer containing the desired photoresist pattern. This coated wafer was then placed into the UV curing chamber and irradiated for 6 seconds. Separately, a thick layer (about 5 mm) of the material was produced by pouring the PFPE DMA containing photoinitiator into a mold surrounding the Si wafer containing the desired photoresist pattern. This wafer was irradiated with UV light for one minute. Following this, the thick layer was removed. The thick layer was then placed on top of the thin layer such that the patterns in the two layers were precisely aligned, and then the entire device was irradiated for 10 minutes. Once complete, the entire device was peeled from the Si wafer with both layers adhered together.

Example 3

Figure 13:
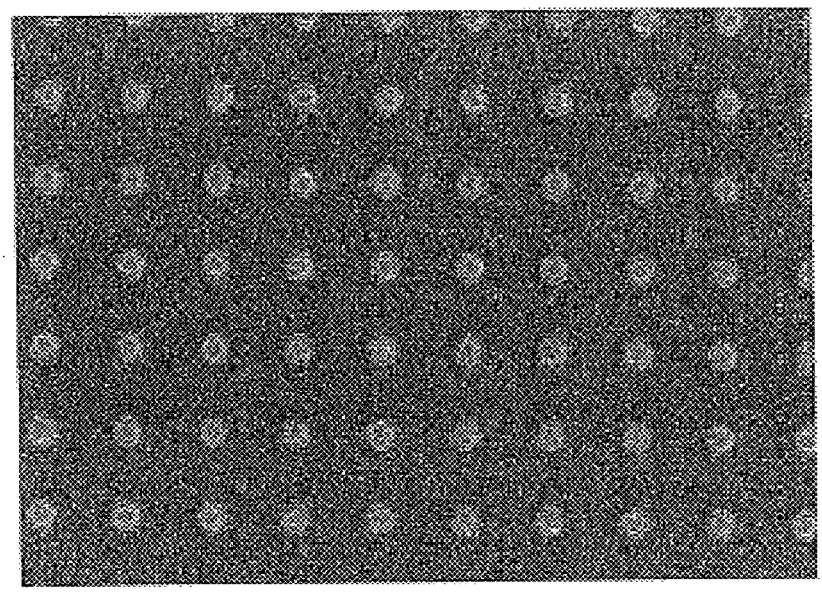
FIG. 13 is a scanning electron micrograph of a silicon master including 200 nm trapezoidal patterns.
Figure 14:
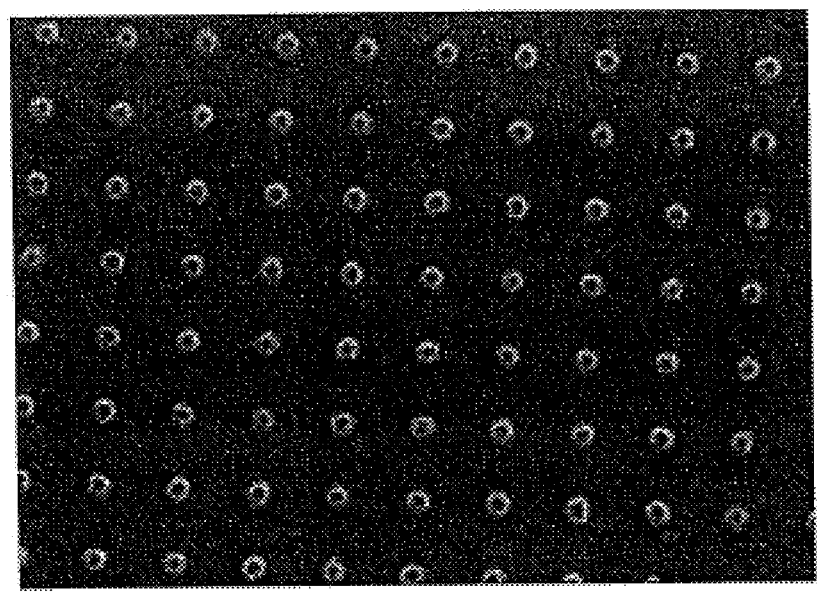
FIG. 14 is a scanning electron micrograph of 200-nm isolated trapezoidal particles of poly(ethylene glycol) (PEG) diacrylate.

Fabrication of Isolated Particles Using Non-Wetting Imprint Lithography 3.1 Fabrication of 200-nm Trapezoidal PEG Particles A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (See FIG. 13). A poly(dimethylsiloxane) mold is used to confine the liquid PFPE-DMA to the desired area. The apparatus was then subjected to UV light ($\lambda$=365 nm) for 10 minutes while under a nitrogen purge. The fully cured PFPE-DMA mold was then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Following this, 50 µL of PEG diacrylate is then placed on the treated silicon wafer and the patterned PFPE mold placed on top of it. The substrate is then placed in a molding apparatus and a small pressure is applied to push out excess PEG-diacrylate. The pressure used was at least about 100 N/cm². The entire apparatus was then subjected to UV light ($\lambda$=365 nm) for ten minutes while under a nitrogen purge. Particles are observed after separation of the PFPE mold and the treated silicon wafer using scanning electron microscopy (SEM) (see FIG. 14).

3.2 Fabrication of 500-nm Conical PEG Particles

Figure 12:
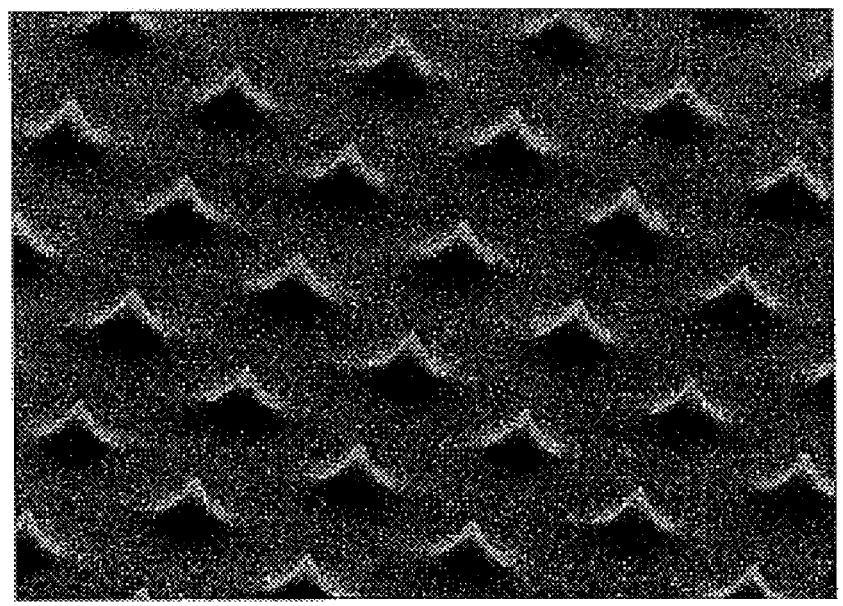
FIG. 12 is a scanning electron micrograph of a silicon master including 500 nm conical patterns that are <50 nm at the tip.
Figure 15:
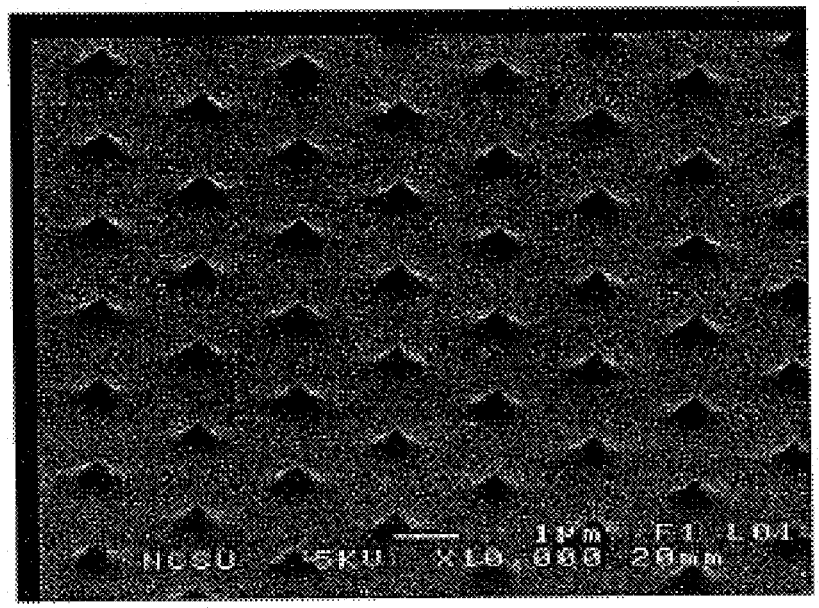
FIG. 15 is a scanning electron micrograph of 500-nm isolated conical particles of PEG diacrylate.

A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 12). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Following this, 50 µL of PEG diacrylate is then placed on the treated silicon wafer and the patterned PFPE mold placed on top of it. The substrate is then placed in a molding apparatus and a small pressure is applied to push out excess PEG-diacrylate. The entire apparatus is then subjected to UV light ($\lambda$=365 nm) for ten minutes while under a nitrogen purge. Particles are observed after separation of the PFPE mold and the treated silicon wafer using scanning electron microscopy (SEM) (see FIG. 15).

3.3 Fabrication of 3-µm Arrow-Shaped PEG Particles

Figure 11:
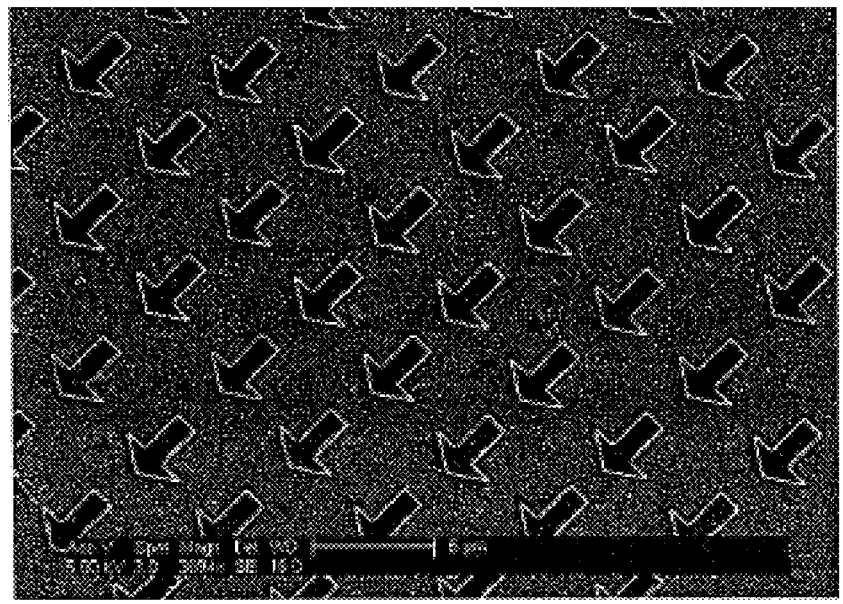
FIG. 11 is a scanning electron micrograph of a silicon master including 3-μm arrow-shaped patterns.
Figure 16:
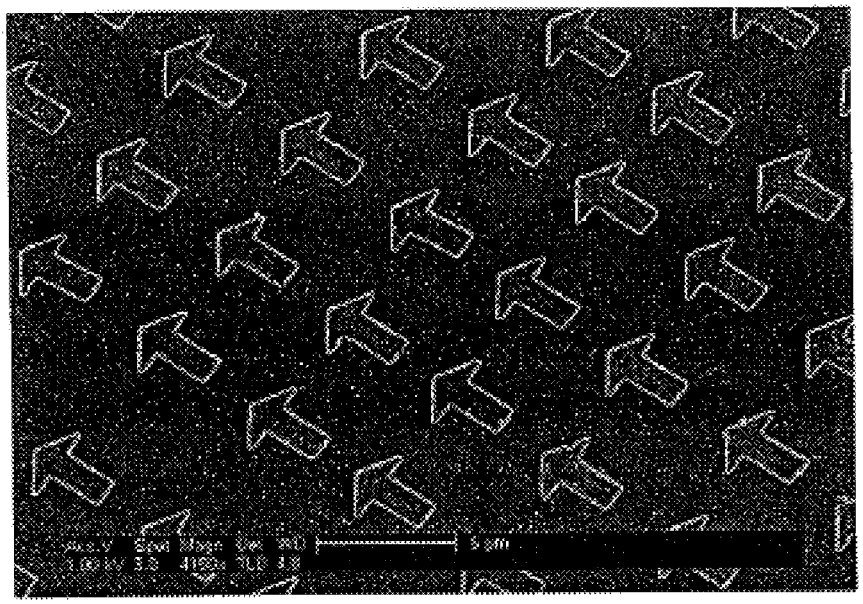
FIG. 16 is a scanning electron micrograph of 3-μm isolated arrow-shaped particles of PEG diacrylate.

A patterned perfluoropolyether (PFPE) mold is generated by pouring a PFPE-dimethacrylate (PFPE-DMA) containing 1-hydroxycyclohexyl phenyl ketone over a silicon substrate patterned with 3-µm arrow shapes (see FIG. 11). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Following this, 50 µL of PEG diacrylate is then placed on the treated silicon wafer and the patterned PFPE mold placed on top of it. The substrate is then placed in a molding apparatus and a small pressure is applied to push out excess PEG-diacrylate. The entire apparatus is then subjected to UV light ($\lambda$=365 nm) for ten minutes while under a nitrogen purge. Particles are observed after separation of the PFPE mold and the treated silicon wafer using scanning electron microscopy (SEM) (see FIG. 16).

3.4 Fabrication of 200-nm×750-nm×250-nm Rectangular PEG Particles

Figure 17:
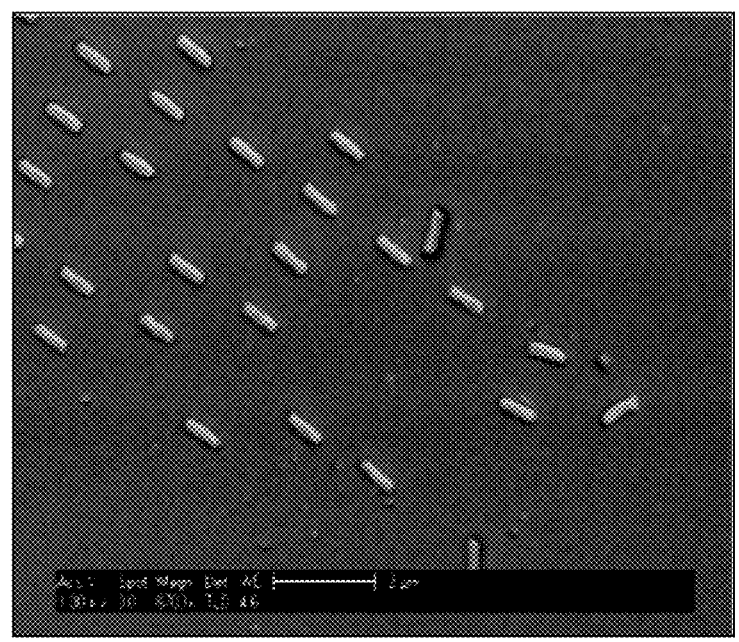
FIG. 17 is a scanning electron micrograph of 200-nm×750-nm×250-nm rectangular shaped particles of PEG diacrylate.

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm×750-nm×250-nm rectangular shapes. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly (ethylene glycol) (PEG) diacrylate (n=9) is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Following this, 50 µL of PEG diacrylate is then placed on the treated silicon wafer and the patterned PFPE mold placed on top of it. The substrate is then placed in a molding apparatus and a small pressure is applied to push out excess PEG-diacrylate. The entire apparatus is then subjected to UV light ($\lambda$=365 nm) for ten minutes while under a nitrogen purge. Particles are observed after separation of the PFPE mold and the treated silicon wafer using scanning electron microscopy (SEM) (see FIG. 17).

Figure 18:
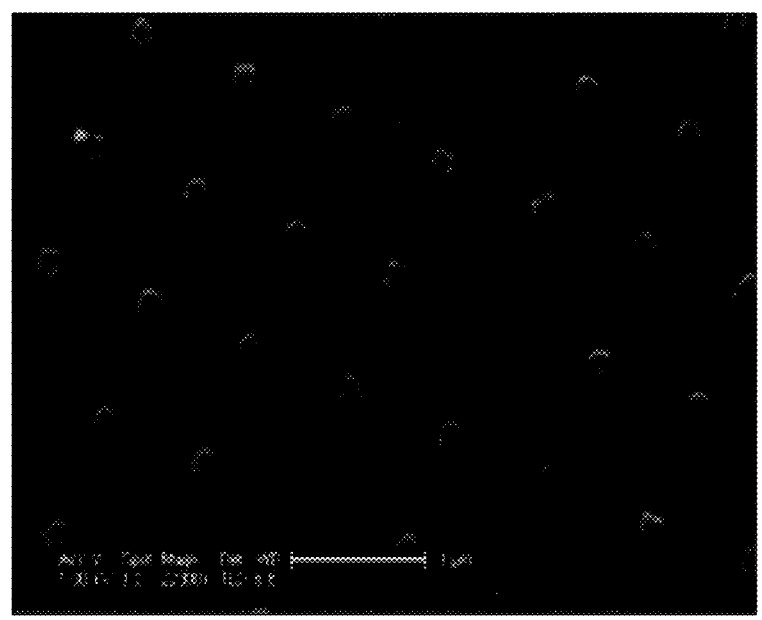
FIG. 18 is a scanning electron micrograph of 200-nm isolated trapezoidal particles of trimethylolpropane triacrylate (TMPTA)

3.5 Fabrication of 200-nm Trapezoidal Trimethylopropane Triacrylate (TMPTA) Particles A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Following this, 50 µL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light ($\lambda$=365 nm) for ten minutes while under a nitrogen purge. Particles are observed after separation of the PFPE mold and the treated silicon wafer using scanning electron microscopy (SEM) (see FIG. 18).

Figure 19:
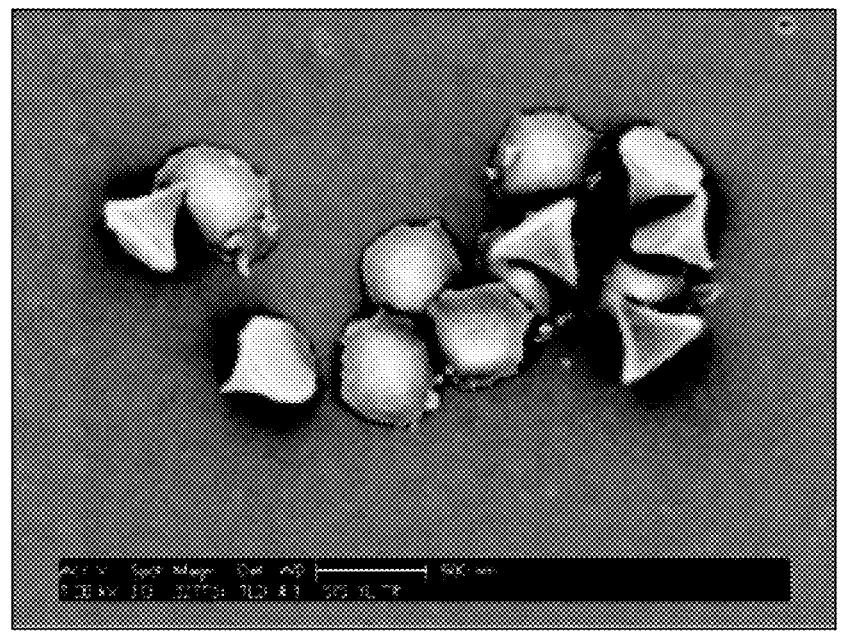
FIG. 19 is a scanning electron micrograph of 500-nm isolated conical particles of TMPTA.
Figure 20:
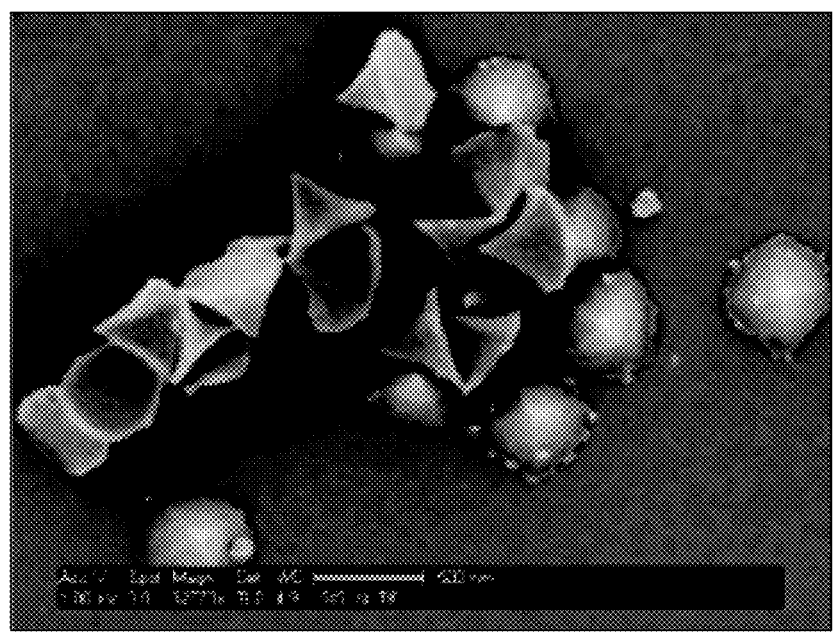
FIG. 20 is a scanning electron micrograph of 500-nm isolated conical particles of TMPTA, which have been printed using an embodiment of the presently described non-wetting imprint lithography method and harvested mechanically using a doctor blade.

3.6 Fabrication of 500-nm Conical Trimethylopropane Triacrylate (TMPTA) Particles A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 12). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Following this, 50 µL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light ($\lambda$=365 nm) for ten minutes while under a nitrogen purge. Particles are observed after separation of the PFPE mold and the treated silicon wafer using scanning electron microscopy (SEM) (see FIG. 19). Further, FIG. 20 shows a scanning electron micrograph of 500-nm isolated conical particles of TMPTA, which have been printed using an embodiment of the presently described non-wetting imprint lithography method and harvested mechanically using a doctor blade. The ability to harvest particles in such a way offers conclusive evidence for the absence of a "scum layer."

3.7 Fabrication of 3-µm Arrow-Shaped TMPTA Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 3-µm arrow shapes (see FIG. 11). A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Following this, 50 µL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light ($\lambda$=365 nm) for ten minutes while under a nitrogen purge. Particles are observed after separation of the PFPE mold and the treated silicon wafer using scanning electron microscopy (SEM).

3.8 Fabrication of 200-nm Trapezoidal Poly(Lactic Acid) (PLA) Particles

Figure 21:
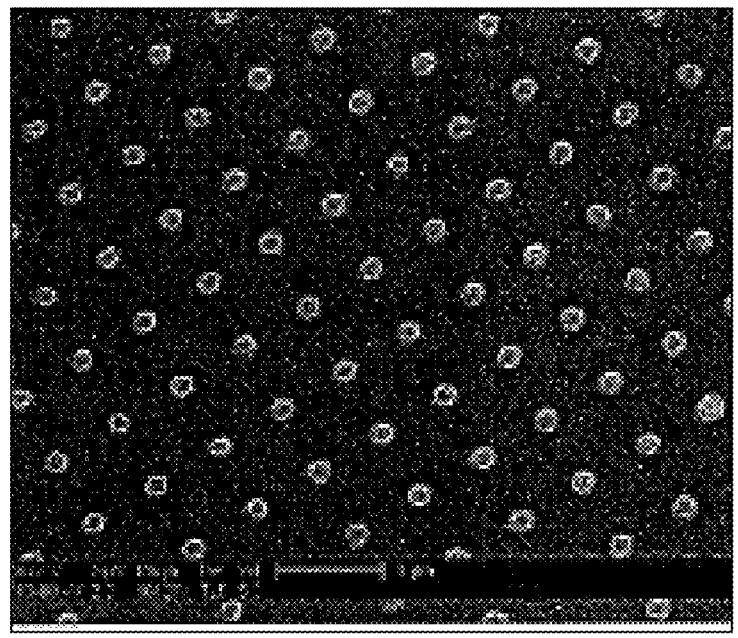
FIG. 21 is a scanning electron micrograph of 200-nm isolated trapezoidal particles of poly(lactic acid) (PLA)
Figure 22:
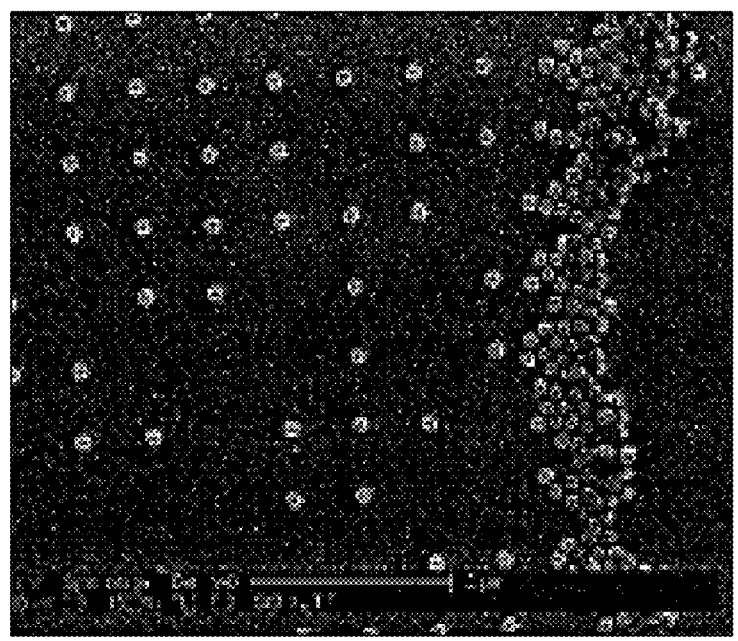
FIG. 22 is a scanning electron micrograph of 200-nm isolated trapezoidal particles of poly(lactic acid) (PLA), which have been printed using an embodiment of the presently described non-wetting imprint lithography method and harvested mechanically using a doctor blade.

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, one gram of (3S)-cis-3,6-dimethyl-1,4-dioxane-2,5-dione (LA) is heated above its melting temperature (92° C.) to 110° C. and approximately 20 µL of stannous octoate catalyst/initiator is added to the liquid monomer. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H, 2H-perfluorooctyl) silane via vapor deposition in a desiccator for 20 minutes. Following this, 50 µL of molten LA containing catalyst is then placed on the treated silicon wafer preheated to 110° C. and the patterned PFPE mold is placed on top of it. The substrate is then placed in a molding apparatus and a small pressure is applied to push out excess monomer. The entire apparatus is then placed in an oven at 110° C. for 15 hours. Particles are observed after cooling to room temperature and separation of the PFPE mold and the treated silicon wafer using scanning electron microscopy (SEM) (see FIG. 21). Further, FIG. 22 is a scanning electron micrograph of 200-nm isolated trapezoidal particles of poly (lactic acid) (PLA), which have been printed using an embodiment of the presently described non-wetting imprint lithography method and harvested mechanically using a doctor blade. The ability to harvest particles in such a way offers conclusive evidence for the absence of a "scum layer."

3.9 Fabrication of 3-μm Arrow-Shaped (PLA) Particles

Figure 23:
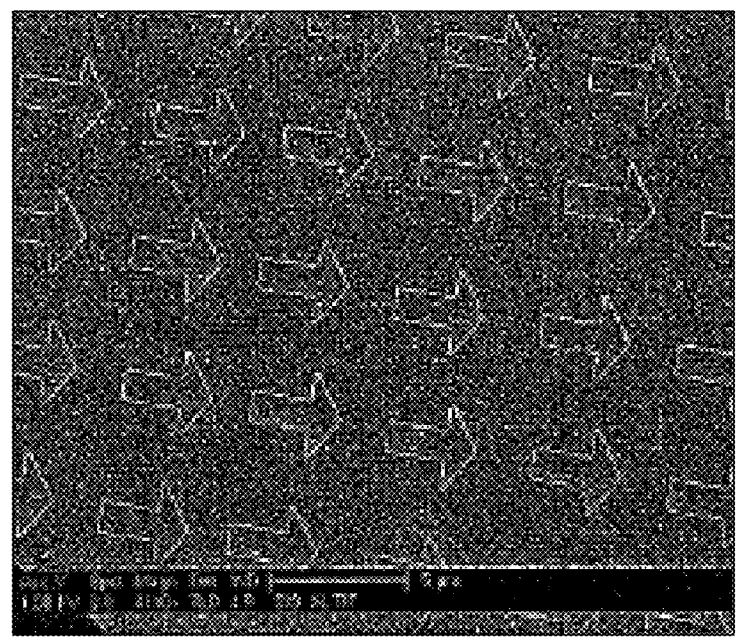
FIG. 23 is a scanning electron micrograph of 3-μm isolated arrow-shaped particles of PLA.

A patterned perfluoropolyether (PFPE) mold is generated by pouring a PFPE-dimethacrylate (PFPE-DMA) containing 1-hydroxycyclohexyl phenyl ketone over a silicon substrate patterned with 3-μm arrow shapes (see FIG. 11). A poly (dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Separately, one gram of (3S)-cis-3, 6-dimethyl-1,4-dioxane-2,5-dione (LA) is heated above its melting temperature (92° C.) to 110° C. and approximately 20 μL of stannous octoate catalyst/initiator is added to the liquid monomer. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Following this, 50 μL of molten LA containing catalyst is then placed on the treated silicon wafer preheated to 110° C. and the patterned PFPE mold is placed on top of it. The substrate is then placed in a molding apparatus and a small pressure is applied to push out excess monomer. The entire apparatus is then placed in an oven at 110° C. for 15 hours. Particles are observed after cooling to room temperature and separation of the PFPE mold and the treated silicon wafer using scanning electron microscopy (SEM) (see FIG. 23).

3.10 Fabrication of 500-nm Conical Shaped (PLA) Particles

Figure 24:
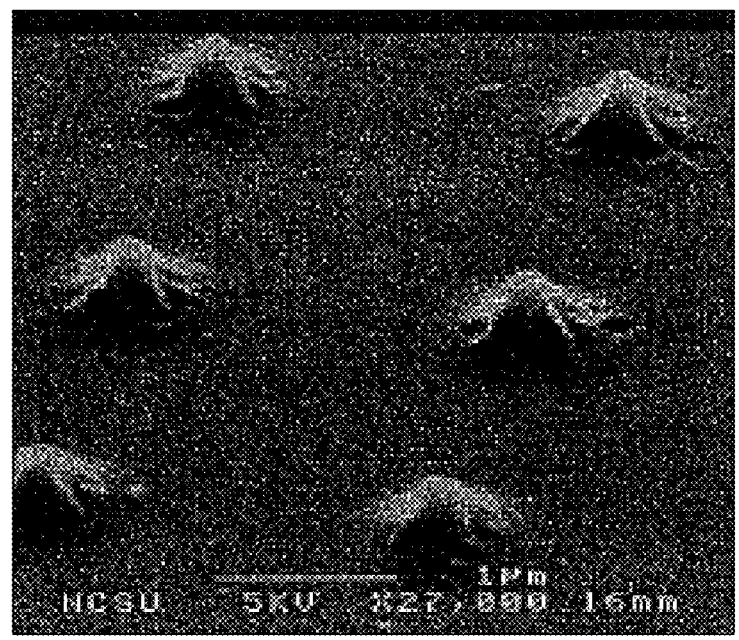
FIG. 24 is a scanning electron micrograph of 500-nm isolated conical-shaped particles of PLA.

A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 12). A poly(dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Separately, one gram of (3S)-cis-3,6-dimethyl-1,4-dioxane-2,5-dione (LA) is heated above its melting temperature (92° C.) to 110° C. and approximately 20 μL of stannous octoate catalyst/initiator is added to the liquid monomer. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H, 2H-perfluorooctyl) silane via vapor deposition in a desiccator for 20 minutes. Following this, 50 μL of molten LA containing catalyst is then placed on the treated silicon wafer preheated to 110° C. and the patterned PFPE mold is placed on top of it. The substrate is then placed in a molding apparatus and a small pressure is applied to push out excess monomer. The entire apparatus is then placed in an oven at 110° C. for 15 hours. Particles are observed after cooling to room temperature and separation of the PFPE mold and the treated silicon wafer using scanning electron microscopy (SEM) (see FIG. 24).

3.11 Fabrication of 200-nm Trapezoidal Poly(Pyrrole) (Ppy) Particles

Figure 25:
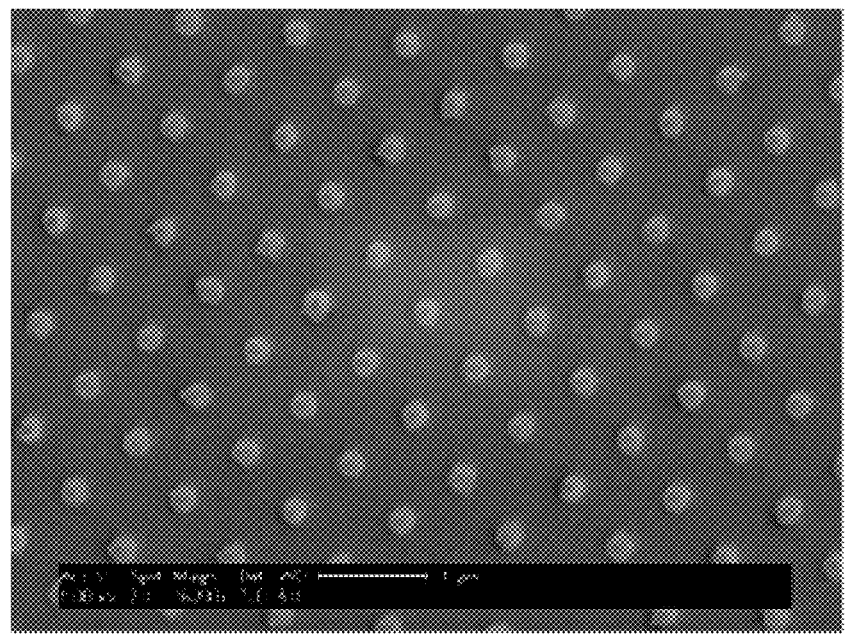
FIG. 25 is a scanning electron micrograph of 200-nm isolated trapezoidal particles of poly(pyrrole) (Ppy)

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro (1H,1H,2H,2H-perfluorooctyl) silane via vapor deposition in a desiccator for 20 minutes. Separately, 50 μL of a 1:1 v:v solution of tetrahydrofuran:pyrrole is added to 50 μL of 70% perchloric acid (aq). A clear, homogenous, brown solution quickly forms and develops into black, solid, polypyrrole in 15 minutes. A drop of this clear, brown solution (prior to complete polymerization) is placed onto a treated silicon wafer and into a stamping apparatus and a pressure is applied to remove excess solution. The apparatus is then placed into a vacuum oven for 15 h to remove the THF and water. Particles are observed using scanning electron microscopy (SEM) (see FIG. 25) after release of the vacuum and separation of the PFPE mold and the treated silicon wafer.

3.12 Fabrication of 3-μm Arrow-Shaped (Ppy) Particles

Figure 26:
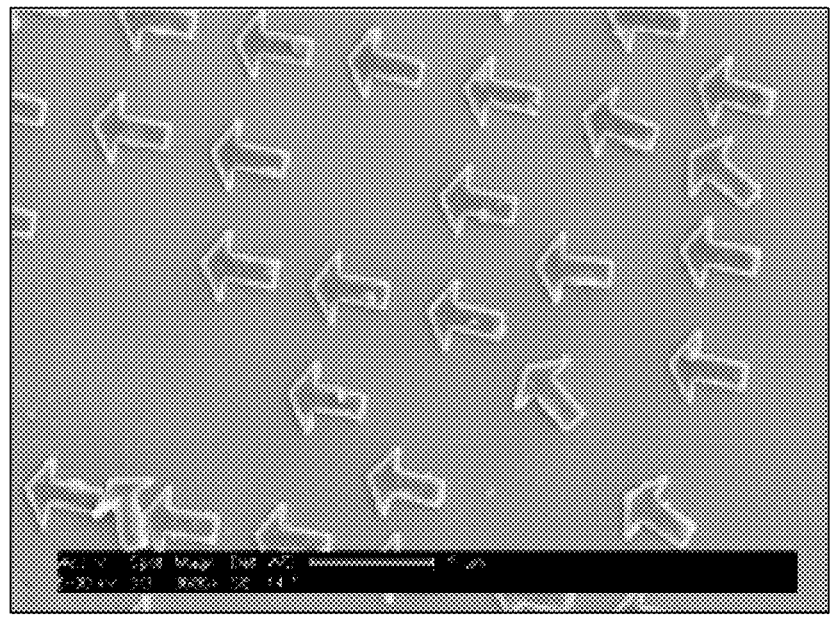
FIG. 26 is a scanning electron micrograph of 3-μm arrow-shaped Ppy particles.

A patterned perfluoropolyether (PFPE) mold is generated by pouring a PFPE-dimethacrylate (PFPE-DMA) containing 1-hydroxycyclohexyl phenyl ketone over a silicon substrate patterned with 3-μm arrow shapes (see FIG. 11). A poly (dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H, 2H-perfluorooctyl) silane via vapor deposition in a desiccator for 20 minutes. Separately, 50 μL of a 1:1 v:v solution of tetrahydrofuran:pyrrole is added to 50 μL of 70% perchloric acid (aq). A clear, homogenous, brown solution quickly forms and develops into black, solid, polypyrrole in 15 minutes. A drop of this clear, brown solution (prior to complete polymerization) is placed onto a treated silicon wafer and into a stamping apparatus and a pressure is applied to remove excess solution. The apparatus is then placed into a vacuum oven for 15 h to remove the THF and water. Particles are observed using scanning electron microscopy (SEM) (see FIG. 26) after release of the vacuum and separation of the PFPE mold and the treated silicon wafer.

3.13 Fabrication of 500-nm Conical (Ppy) Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 12). A poly(dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro (1H,1H,2H,2H-perfluorooctyl) silane via vapor deposition in a desiccator for 20 minutes. Separately, 50 μL of a 1:1 v:v solution of tetrahydrofuran:pyrrole is added to 50 μL of 70% perchloric acid (aq). A clear, homogenous, brown solution quickly forms and develops into black, solid, polypyrrole in 15 minutes. A drop of this clear, brown solution (prior to complete polymerization) is placed onto a treated silicon wafer and into a stamping apparatus and a pressure is applied to remove excess solution. The apparatus is then placed into a vacuum oven for 15 h to remove the THF and water. Particles are observed using scanning electron microscopy (SEM) (see FIG. 27) after release of the vacuum and separation of the PFPE mold and the treated silicon wafer.

3.14 Encapsulation of Fluorescently Tagged DNA Inside 200-nm Trapezoidal PEG Particles A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly (ethylene glycol) (PEG) diacrylate (n=9) is blended with 1 wt % of a photoinitiator, 1-hydroxycyclohexyl phenyl ketone. 20 μL of water and 20 μL of PEG diacrylate monomer are added to 8 nanomoles of 24 by DNA oligonucleotide that has been tagged with a fluorescent dye, CY-3. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Following this, 50 μL of the PEG diacrylate solution is then placed on the treated silicon wafer and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for ten minutes while under a nitrogen purge. Particles are observed after separation of the PFPE mold and the treated silicon wafer using confocal fluorescence microscopy (see FIG. 28). Further, FIG. 28A shows a fluorescent confocal micrograph of 200-nm trapezoidal PEG nanoparticles which contain 24-mer DNA strands that are tagged with CY-3. FIG. 28B is optical micrograph of the 200-nm isolated trapezoidal particles of PEG diacrylate that contain fluorescently tagged DNA. FIG. 28C is the overlay of the images provided in FIGS. 28A and 28B, showing that every particle contains DNA.

3.15 Encapsulation of Magnetite Nanoparticles Inside 500-nm Conical PEG Particles A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 12). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro (1H,1H,2H,2H-perfluorooctyl) silane via vapor deposition in a desiccator for 20 minutes. Separately, citrate capped magnetite nanoparticles were synthesized by reaction of ferric chloride (40 mL of a 1 M aqueous solution) and ferrous chloride (10 mL of a 2 M aqueous hydrochloric acid solution) which is added to ammonia (500 mL of a 0.7 M aqueous solution). The resulting precipitate is collected by centrifugation and then stirred in 2 M perchloric acid. The final solids are collected by centrifugation. 0.290 g of these perchlorate-stabilized nanoparticles are suspended in 50 mL of water and heated to 90° C. while stirring. Next, 0.106 g of sodium citrate is added. The solution is stirred at 90° C. for 30 min to yield an aqueous solution of citrate-stabilized iron oxide nanoparticles. 50 μL of this solution is added to 50 μL of a PEG diacrylate solution in a microtube. This microtube is vortexed for ten seconds. Following this, 50 μL of this PEG diacrylate/particle solution is then placed on the treated silicon wafer and the patterned PFPE mold placed on top of it. The substrate is then placed in a molding apparatus and a small pressure is applied to push out excess PEG-diacrylate/particle solution. The entire apparatus is then subjected to UV light ($\lambda$=365 nm) for ten minutes while under a nitrogen purge. Nanoparticle-containing PEG-diacrylate particles are observed after separation of the PFPE mold and the treated silicon wafer using optical microscopy.

3.16 Fabrication of Isolated Particles on Glass Surfaces Using "Double Stamping"

Figure 29:
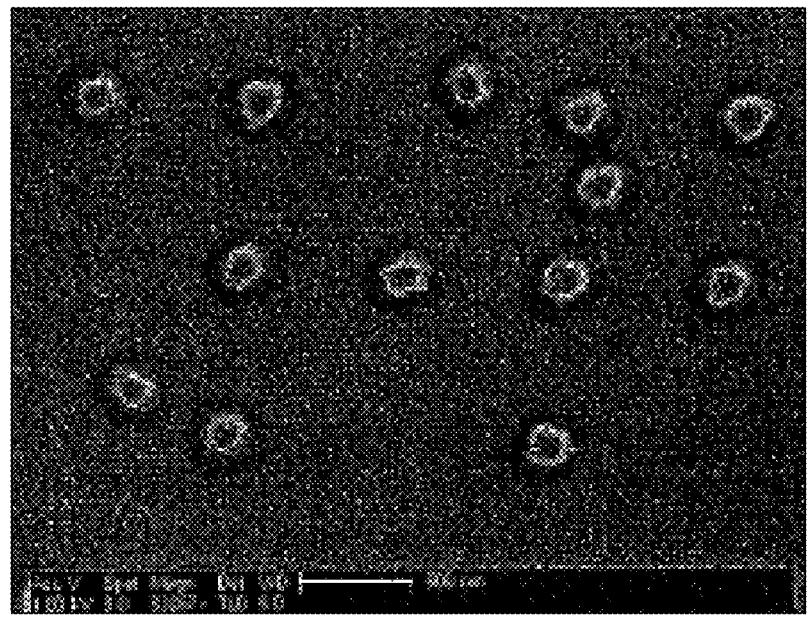
FIG. 29 is a scanning electron micrograph of fabrication of 200-nm PEG-diacrylate nanoparticles using "double stamping"

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly (ethylene glycol) (PEG) diacrylate (n=9) is blended with 1 wt % of a photoinitiator, 1-hydroxycyclohexyl phenyl ketone. A flat, non-wetting surface is generated by photocuring a film of PFPE-DMA onto a glass slide, according to the procedure outlined for generating a patterned PFPE-DMA mold. 5 μL of the PEG-diacrylate/photoinitiator solution is pressed between the PFPE-DMA mold and the flat PFPE-DMA surface, and pressure is applied to squeeze out excess PEG-diacrylate monomer. The PFPE-DMA mold is then removed from the flat PFPE-DMA surface and pressed against a clean glass microscope slide and photocured using UV radiation ($\lambda$=365 nm) for 10 minutes while under a nitrogen purge. Particles are observed after cooling to room temperature and separation of the PFPE mold and the glass microscope slide, using scanning electron microscopy (SEM) (see FIG. 29).

3.17 Encapsulation of Viruses in PEG-Diacrylate Nanoparticles.

A patterned perfluoropolyether (PFPE) mold is generated by pouring PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly (ethylene glycol) (PEG) diacrylate (n=9) is blended with 1 wt % of a photoinitiator, 1-hydroxycyclohexyl phenyl ketone. Fluorescently-labeled or unlabeled Adenovirus or Adeno-Associated Virus suspensions are added to this PEG-diacrylate monomer solution and mixed thoroughly. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Following this, 50 µL of the PEG diacrylate/virus solution is then placed on the treated silicon wafer and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for ten minutes while under a nitrogen purge. Virus-containing particles are observed after separation of the PFPE mold and the treated silicon wafer using transmission electron microscopy or, in the case of fluorescently-labeled viruses, confocal fluorescence microscopy.

3.18 Encapsulation of Proteins in PEG-Diacrylate Nanoparticles.

A patterned perfluoropolyether (PFPE) mold is generated by pouring PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly (ethylene glycol) (PEG) diacrylate (n=9) is blended with 1 wt % of a photoinitiator, 1-hydroxycyclohexyl phenyl ketone. Fluorescently-labeled or unlabeled protein solutions are added to this PEG-diacrylate monomer solution and mixed thoroughly. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Following this, 50 µL of the PEG diacrylate/virus solution is then placed on the treated silicon wafer and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for ten minutes while under a nitrogen purge. Protein-containing particles are observed after separation of the PFPE mold and the treated silicon wafer using traditional assay methods or, in the case of fluorescently-labeled proteins, confocal fluorescence microscopy.

3.19 Fabrication of 200-nm Titania Particles

A patterned perfluoropolyether (PFPE) mold can be generated by pouring a PFPE-dimethacrylate (PFPE-DMA) containing 1-hydroxycyclohexyl phenyl ketone over a silicon substrate patterned with 200-nm trapezoidal shapes, such as shown in FIG. 13. A poly(dimethylsiloxane) mold can be used to confine the liquid PFPE-DMA to the desired area. The apparatus can then be subjected to UV light ($\lambda$=365 nm) for 10 minutes while under a nitrogen purge. The fully cured PFPE-DMA mold is then released from the silicon master. Separately, 1 g of Pluronic P123 is dissolved in 12 g of absolute ethanol. This solution was added to a solution of 2.7 mL of concentrated hydrochloric acid and 3.88 mL titanium (IV) ethoxide. Flat, uniform, non-wetting surfaces can be generated by treating a silicon wafer cleaned with "piranha" solution (1:1 concentrated sulfuric acid: 30% hydrogen peroxide (aq) solution) with trichloro(1H,1H,2H, 2H-perfluorooctyl) silane via vapor deposition in a desiccator for 20 minutes. Following this, 50 µL of the sol-gel solution can then be placed on the treated silicon wafer and the patterned PFPE mold placed on top of it. The substrate is then placed in a molding apparatus and a small pressure is applied to push out excess sol-gel precursor. The entire apparatus is then set aside until the sol-gel precursor has solidified. After solidification of the sol-gel precursor, the silicon wafer can be removed from the patterned PFPE and particles will be present.

3.20 Fabrication of 200-nm Silica Particles

A patterned perfluoropolyether (PFPE) mold can be generated by pouring a PFPE-dimethacrylate (PFPE-DMA) containing 1-hydroxycyclohexyl phenyl ketone over a silicon substrate patterned with 200-nm trapezoidal shapes, such as shown in FIG. 13. A poly(dimethylsiloxane) mold can then be used to confine the liquid PFPE-DMA to the desired area. The apparatus can then be subjected to UV light ($\lambda$=365 nm) for 10 minutes while under a nitrogen purge. The fully cured PFPE-DMA mold is then released from the silicon master. Separately, 2 g of Pluronic P123 is dissolved in 30 g of water and 120 g of 2 M HCl is added while stirring at 35° C. To this solution, add 8.50 g of TEOS with stirring at 35° C. for 20 h. Flat, uniform, non-wetting surfaces can then be generated by treating a silicon wafer cleaned with "piranha" solution (1:1 concentrated sulfuric acid: 30% hydrogen peroxide (aq) solution) with trichloro (1H,1H,2H,2H-perfluorooctyl) silane via vapor deposition in a desiccator for 20 minutes. Following this, 50 µL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sol-gel precursor has solidified. Particles should be observed after separation of the PFPE mold and the treated silicon wafer using scanning electron microscopy (SEM).

3.21 Fabrication of 200-nm Europium-Doped Titania Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, 1 g of Pluronic P123 and 0.51 g of $EuCl_3.6H_2O$ are dissolved in 12 g of absolute ethanol. This solution is added to a solution of 2.7 mL of concentrated hydrochloric acid and 3.88 mL titanium (IV) ethoxide. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H, 2H-perfluorooctyl) silane via vapor deposition in a desiccator for 20 minutes. Following this, 50 µL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sol-gel precursor has solidified. Next, after the sol-gel precursor has solidified, the PFPE mold and the treated silicon wafer are separated and particles should be observed using scanning electron microscopy (SEM).

3.22 Encapsulation of CdSe Nanoparticles Inside 200-nm PEG Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro (1H,1H,2H,2H-perfluorooctyl) silane via vapor deposition in a desiccator for 20 minutes. Separately, 0.5 g of sodium citrate and 2 mL of 0.04 M cadmium perchlorate are dissolved in 45 mL of water, and the pH is adjusted to of the solution to 9 with 0.1 M NaOH. The solution is bubbled with nitrogen for 15 minutes. 2 mL of 1 M N,N-dimethylselenourea is added to the solution and heated in a microwave oven for 60 seconds. 50 of this solution is added to 50 µL of a PEG diacrylate solution in a microtube. This microtube is vortexed for ten seconds. 50 µL of this PEG diacrylate/CdSe particle solution is placed on the treated silicon wafer and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for ten minutes while under a nitrogen purge. PEG-diacrylate particles with encapsulated CdSe nanoparticles will be observed after separation of the PFPE mold and the treated silicon wafer using TEM or fluorescence microscopy.

3.23 Synthetic Replication of Adenovirus Particles Using Non-Wetting Imprint Lithography A template, or "master," for perfluoropolyether-dimethacrylate (PFPE-DMA) mold fabrication is generated by dispersing adenovirus particles on a silicon wafer. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Following this, 50 µL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light ($\lambda$=365 nm) for ten minutes while under a nitrogen purge. Synthetic virus replicates are observed after separation of the PFPE mold and the treated silicon wafer using scanning electron microscopy (SEM) or transmission electron microscopy (TEM).

3.24 Synthetic Replication of Earthworm Hemoglobin Protein Using Non-Wetting Imprint Lithography A template, or "master," for perfluoropolyether-dimethacrylate (PFPE-DMA) mold fabrication is generated by dispersing earthworm hemoglobin protein on a silicon wafer. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Following this, 50 µL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light ($\lambda$=365 nm) for ten minutes while under a nitrogen purge. Synthetic protein replicates are observed after separation of the PFPE mold and the treated silicon wafer using scanning electron microscopy (SEM) or transmission electron microscopy (TEM).

3.25 Combinatorial Engineering of 100-nm Nanoparticle Therapeutics

A patterned perfluoropolyether (PFPE) mold is generated by pouring a PFPE-dimethacrylate (PFPE-DMA) containing 1-hydroxycyclohexyl phenyl ketone over a silicon substrate patterned with 100-nm cubic shapes. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Other therapeutic agents (i.e., small molecule drugs, proteins, polysaccharides, DNA, etc.), tissue targeting agents (cell penetrating peptides and ligands, hormones, antibodies, etc.), therapeutic release/transfection agents (other controlled-release monomer formulations, cationic lipids, etc.), and miscibility enhancing agents (cosolvents, charged monomers, etc.) are added to the polymer precursor solution in a combinatorial manner. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl) silane via vapor deposition in a desiccator for 20 minutes. Following this, 50 µL of the combinatorially-generated particle precursor solution is then placed on the treated silicon wafer and the patterned PFPE mold placed on top of it. The substrate is then placed in a molding apparatus and a small pressure is applied to push out excess solution. The entire apparatus is then subjected to UV light ($\lambda$=365 nm) for ten minutes while under a nitrogen purge. The PFPE-DMA mold is then separated from the treated wafer, particles can be harvested, and the therapeutic efficacy of each combinatorially generated nanoparticle is established. By repeating this methodology with different particle formulations, many combinations of therapeutic agents, tissue targeting agents, release agents, and other important compounds can be rapidly screened to determine the optimal combination for a desired therapeutic application.

3.26 Fabrication of a Shape-Specific PEG Membrane

A patterned perfluoropolyether (PFPE) mold is generated by pouring a PFPE-dimethacrylate (PFPE-DMA) containing 1-hydroxycyclohexyl phenyl ketone over a silicon substrate patterned with 3-µm cylindrical holes that are 5 µm deep. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Following this, 50 µL of PEG diacrylate is then placed on the treated silicon wafer and the patterned PFPE mold placed on top of it. The substrate is then placed in a molding apparatus and a small pressure is applied to push out excess PEG-diacrylate. The entire apparatus is then subjected to UV light ($\lambda$=365 nm) for ten minutes while under a nitrogen purge. An interconnected membrane will be observed after separation of the PFPE mold and the treated silicon wafer using scanning electron microscopy (SEM). The membrane will release from the surface by soaking in water and allowing it to lift off the surface.

3.27 Harvesting of PEG Particles by Ice Formation

A patterned perfluoropolyether (PFPE) mold is generated by pouring a PFPE-dimethacrylate (PFPE-DMA) containing 1-hydroxycyclohexyl phenyl ketone over a silicon substrate patterned with 5-µm cylinder shapes. The substrate is then subjected to a nitrogen purge for 10 minutes, then UV light ($\lambda$=365 nm) is applied for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by coating a glass slide with PFPE-DMA containing 1-hydroxycyclohexyl phenyl ketone. The slide is then subjected to a nitrogen purge for 10 minutes, then UV light ($\lambda$=365 nm) is applied for 10 minutes while under a nitrogen purge. The flat, fully cured PFPE-DMA substrate is released from the slide. Following this, 0.1 mL of PEG diacrylate is then placed on the flat PFPE-DMA substrate and the patterned PFPE mold placed on top of it. The substrate is then placed in a molding apparatus and a small pressure is applied to push out excess PEG-diacrylate. The entire apparatus is then purged with nitrogen for 10 minutes, then subjected to UV light ($\lambda$=365 nm) for 10 minutes while under a nitrogen purge. PEG particles are observed after separation of the PFPE-DMA mold and substrate using optical microscopy. Water is applied to the surface of the substrate and mold containing particles. A gasket is used to confine the water to the desired location. The apparatus is then placed in the freezer at a temperature of −10° C. for 30 minutes. The ice containing PEG particles is peeled off the PFPE-DMA mold and substrate and allowed to melt, yielding an aqueous solution containing PEG particles.

3.28 Harvesting of PEG Particles with Vinyl Pyrrolidone

A patterned perfluoropolyether (PFPE) mold is generated by pouring a PFPE-dimethacrylate (PFPE-DMA) containing 1-hydroxycyclohexyl phenyl ketone over a silicon substrate patterned with 5-µm cylinder shapes. The substrate is then subjected to a nitrogen purge for 10 minutes, then UV light ($\lambda$=365 nm) is applied for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by coating a glass slide with PFPE-DMA containing 1-hydroxycyclohexyl phenyl ketone. The slide is then subjected to a nitrogen purge for 10 minutes, then UV light ($\lambda$=365 nm) is applied for 10 minutes while under a nitrogen purge. The flat, fully cured PFPE-DMA substrate is released from the slide. Following this, 0.1 mL of PEG diacrylate is then placed on the flat PFPE-DMA substrate and the patterned PFPE mold placed on top of it. The substrate is then placed in a molding apparatus and a small pressure is applied to push out excess PEG-diacrylate. The entire apparatus is then purged with nitrogen for 10 minutes, then subjected to UV light ($\lambda$=365 nm) for 10 minutes while under a nitrogen purge. PEG particles are observed after separation of the PFPE-DMA mold and substrate using optical microscopy. In some embodiments, the material includes an adhesive or sticky surface. In some embodiments, the material includes carbohydrates, epoxies, waxes, polyvinyl alcohol, polyvinyl pyrrolidone, polybutyl acrylate, polycyano acrylates, polymethyl methacrylate. In some embodiments, the harvesting or collecting of the particles includes cooling water to form ice (e.g., in contact with the particles) drop of n-vinyl-2-pyrrolidone containing 5% photoinitiator, 1-hydroxycyclohexyl phenyl ketone, is placed on a clean glass slide. The PFPE-DMA mold containing particles is placed patterned side down on the n-vinyl-2-pyrrolidone drop. The slide is subjected to a nitrogen purge for 5 minutes, then UV light ($\lambda$=365 nm) is applied for 5 minutes while under a nitrogen purge. The slide is removed, and the mold is peeled away from the polyvinyl pyrrolidone and particles. Particles on the polyvinyl pyrrolidone were observed with optical microscopy. The polyvinyl pyrrolidone film containing particles was dissolved in water. Dialysis was used to remove the polyvinyl pyrrolidone, leaving an aqueous solution containing 5 µm PEG particles.

3.29 Harvesting of PEG Particles with Polyvinyl Alcohol

A patterned perfluoropolyether (PFPE) mold is generated by pouring a PFPE-dimethacrylate (PFPE-DMA) containing 1-hydroxycyclohexyl phenyl ketone over a silicon substrate patterned with 5-µm cylinder shapes. The substrate is then subjected to a nitrogen purge for 10 minutes, then UV light ($\lambda$=365 nm) is applied for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by coating a glass slide with PFPE-DMA containing 1-hydroxycyclohexyl phenyl ketone. The slide is then subjected to a nitrogen purge for 10 minutes, then UV light ($\lambda$=365 nm) is applied for 10 minutes while under a nitrogen purge. The flat, fully cured PFPE-DMA substrate is released from the slide. Following this, 0.1 mL of PEG diacrylate is then placed on the flat PFPE-DMA substrate and the patterned PFPE mold placed on top of it. The substrate is then placed in a molding apparatus and a small pressure is applied to push out excess PEG-diacrylate. The entire apparatus is then purged with nitrogen for 10 minutes, then subjected to UV light ($\lambda$=365 nm) for 10 minutes while under a nitrogen purge. PEG particles are observed after separation of the PFPE-DMA mold and substrate using optical microscopy. Separately, a solution of 5 weight percent polyvinyl alcohol (PVOH) in ethanol (EtOH) is prepared. The solution is spin coated on a glass slide and allowed to dry. The PFPE-DMA mold containing particles is placed patterned side down on the glass slide and pressure is applied. The mold is then peeled away from the PVOH and particles. Particles on the PVOH were observed with optical microscopy. The PVOH film containing particles was dissolved in water. Dialysis was used to remove the PVOH, leaving an aqueous solution containing 5 µm PEG particles.

3.30 Fabrication of 200 nm Phosphatidylcholine Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to a nitrogen purge for 10 minutes followed by UV light ($\lambda$=365 nm) for 10 minutes while under a nitrogen purge. The fully cured PFPE-DMA mold is then released from the silicon master. Separately, flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Following this, 20 mg of the phosphatidylcholine was placed on the treated silicon wafer and heated to 60 degrees C. The substrate is then placed in a molding apparatus and a small pressure is applied to push out excess phosphatidylcholine. The entire apparatus is then set aside until the phosphatidylcholine has solidified. Particles are observed after separation of the PFPE mold and the treated silicon wafer using scanning electron microscopy (SEM).

3.31 Functionalizing PEG Particles with FITC

Poly(ethylene glycol) (PEG) particles with 5 weight percent aminoethyl methacrylate were created. Particles are observed in the PFPE mold after separation of the PFPE mold and the PFPE substrate using optical microscopy. Separately, a solution containing 10 weight percent fluorescein isothiocyanate (FITC) in dimethylsulfoxide (DMSO) was created. Following this, the mold containing the particles was exposed to the FITC solution for one hour. Excess FITC was rinsed off the mold surface with DMSO followed by deionized (DI) water. The tagged particles were observed with fluorescence microscopy, with an excitation wavelength of 492 nm and an emission wavelength of 529 nm.

3.32 Encapsulation of Doxorubicin Inside 500 nm Conical PEG Particles

Figure 42:
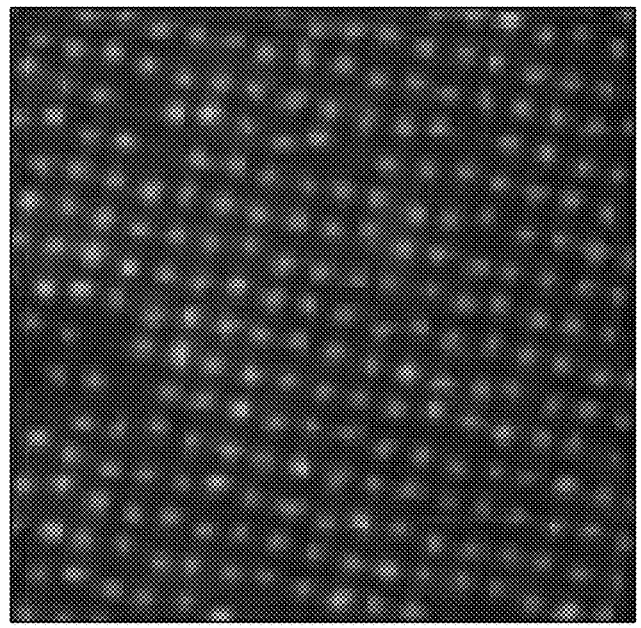
FIG. 42 shows doxorubicin containing particles after removal from a template according to an embodiment of the presently disclosed subject matter.

A patterned perfluoropolyether (PFPE) mold was generated by pouring a PFPE-dimethacrylate (PFPE-DMA) containing 1-hydroxycyclohexyl phenyl ketone over a silicon substrate patterned with 500-nm conical shapes (see FIG. 12). A poly(dimethylsiloxane) mold was used to confine the liquid PFPE-DMA to the desired area. The apparatus was then subjected to UV light ($\lambda$=365 nm) for 10 minutes while under a nitrogen purge. The fully cured PFPE-DMA mold was then released from the silicon master. Flat, uniform, non-wetting surfaces were generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Separately, a solution of 1 wt % doxorubicin in PEG diacrylate was formulated with 1 wt % photoinitiator. Following this, 50 µL of this PEG diacrylate/doxorubicin solution was then placed on the treated silicon wafer and the patterned PFPE mold placed on top of it. The substrate was then placed in a molding apparatus and a small pressure was applied to push out excess PEG-diacrylate/doxorubicin solution. The small pressure in this example was at least about 100 N/cm$^2$. The entire apparatus was then subjected to UV light ($\lambda$=365 nm) for ten minutes while under a nitrogen purge. Doxorubicin-containing PEG-diacrylate particles were observed after separation of the PFPE mold and the treated silicon wafer using fluorescent microscopy (FIG. 42).

3.33 Encapsulation of Avidin (66 kDa) in 160 nm PEG Particles

Figure 43:
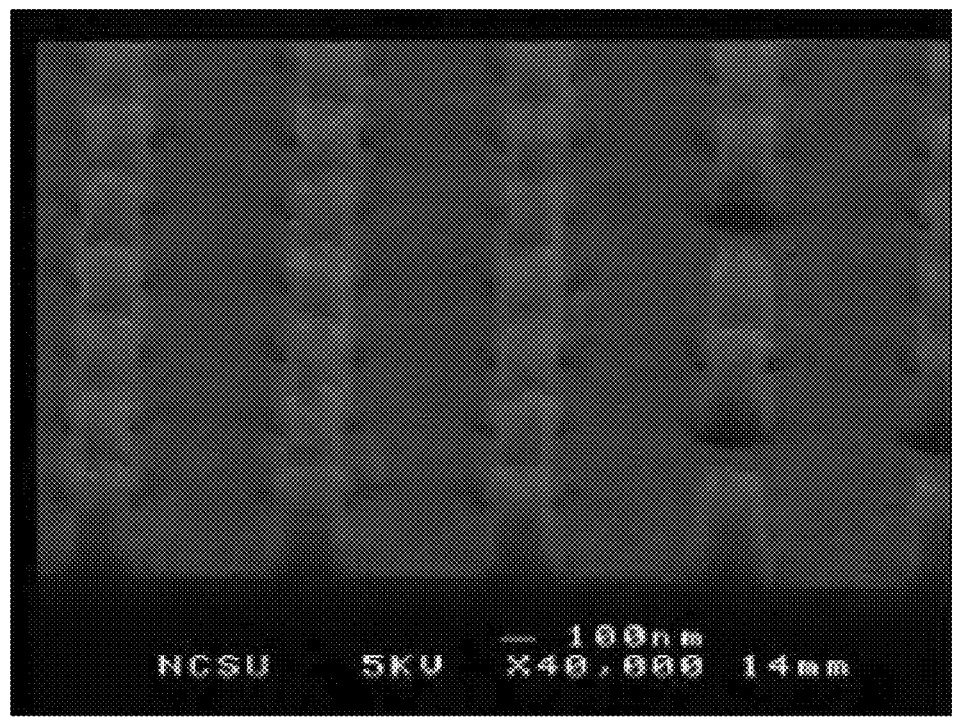
FIG. 43 shows a structure patterned with nano-cylindrical shapes according to an embodiment of the presently disclosed subject matter.

A patterned perfluoropolyether (PFPE) mold was generated by pouring a PFPE-dimethacrylate (PFPE-DMA) containing 1-hydroxycyclohexyl phenyl ketone over a silicon substrate patterned with 160-nm cylindrical shapes (see FIG. 43). A poly(dimethylsiloxane) mold was used to confine the liquid PFPE-DMA to the desired area. The apparatus was then subjected to UV light ($\lambda$=365 nm) for 10 minutes while under a nitrogen purge. The fully cured PFPE-DMA mold was then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Separately, a solution of 1 wt % avidin in 30:70 PEG monomethacrylate: PEG diacrylate was formulated with 1 wt % photoinitiator. Following this, 50 µL of this PEG/avidin solution was then placed on the treated silicon wafer and the patterned PFPE mold placed on top of it. The substrate was then placed in a molding apparatus and a small pressure is applied to push out excess PEG-diacrylate/avidin solution. The small pressure in this example was at least about 100 N/cm$^2$. The entire apparatus was then subjected to UV light ($\lambda$=365 nm) for ten minutes while under a nitrogen purge. Avidin-containing PEG particles were observed after separation of the PFPE mold and the treated silicon wafer using fluorescent microscopy.

3.34 Encapsulation of 2-Fluoro-2-Deoxy-d-Glucose in 80 nm PEG Particles

A patterned perfluoropolyether (PFPE) mold is generated by pouring a PFPE-dimethacrylate (PFPE-DMA) containing 1-hydroxycyclohexyl phenyl ketone over a 6 inch silicon substrate patterned with 80-nm cylindrical shapes. The substrate is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Separately, a solution of 0.5 wt % 2-fluoro-2-deoxy-d-glucose (FDG) in 30:70 PEG monomethacrylate:PEG diacrylate is formulated with 1 wt % photoinitiator. Following this, 200 µL of this PEG/FDG solution is then placed on the treated silicon wafer and the patterned PFPE mold placed on top of it. The substrate is then placed in a molding apparatus and a small pressure is applied to push out excess PEG/FDG solution. The small pressure should be at least about 100 N/cm$^2$. The entire apparatus is then subjected to UV light ($\lambda$=365 nm) for ten minutes while under a nitrogen purge. FDG-containing PEG particles will be observed after separation of the PFPE mold and the treated silicon wafer using scanning electron microscopy.

3.35 Encapsulated DNA in 200 nm×200 nm×1 µm Bar-Shaped Poly(Lactic Acid) Particles A patterned perfluoropolyether (PFPE) mold is generated by pouring a PFPE-dimethacrylate (PFPE-DMA) containing 1-hydroxycyclohexyl phenyl ketone over a silicon substrate patterned with 200 nm×200 nm×1 µm bar shapes. The substrate is then subjected to UV light ($\lambda$=365 nm) for 10 minutes while under a nitrogen purge. The fully cured PFPE-DMA mold is then released from the silicon master.

Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Separately, a solution of 0.01 wt % 24 base pair DNA and 5 wt % poly(lactic acid) in ethanol is formulated. 200 µL of this ethanol solution is then placed on the treated silicon wafer and the patterned PFPE mold placed on top of it. The substrate is then placed in a molding apparatus and a small pressure is applied to push out excess PEG/FDG solution. The small pressure should be at least about 100 N/cm$^2$. The entire apparatus is then placed under vacuum for 2 hours. DNA-containing poly(lactic acid) particles will be observed after separation of the PFPE mold and the treated silicon wafer using optical microscopy.

3.36 100 nm Paclitaxel Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 12). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro (1H,1H,2H,2H-perfluorooctyl) silane via vapor deposition in a desiccator for 20 minutes. Separately, a solution of 5 wt % paclitaxel in ethanol was formulated. Following this, 100 µL of this paclitaxel solution is then placed on the treated silicon wafer and the patterned PFPE mold placed on top of it. The substrate is then placed in a molding apparatus and a small pressure is applied to push out excess solution. The pressure applied was at least about 100 N/cm$^2$. The entire apparatus is then placed under vacuum for 2 hours. Separation of the mold and surface yielded approximately 100 nm spherical paclitaxel particles, which were observed with scanning electron microscopy.

3.37 Triangular Particles Functionalized on One Side

A patterned perfluoropolyether (PFPE) mold is generated by pouring a PFPE-dimethacrylate (PFPE-DMA) containing 1-hydroxycyclohexyl phenyl ketone over a 6 inch silicon substrate patterned with 0.6 µm×0.8 µm×1 µm right triangles. The substrate is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Separately, a solution of 5 wt % aminoethyl methacrylate in 30:70 PEG monomethacrylate:PEG diacrylate is formulated with 1 wt % photoinitiator. Following this, 200 µL of this monomer solution is then placed on the treated silicon wafer and the patterned PFPE mold placed on top of it. The substrate is then placed in a molding apparatus and a small pressure is applied to push out excess solution. The small pressure should be at least about 100 N/cm$^2$. The entire apparatus is then subjected to UV light ($\lambda$=365 nm) for ten minutes while under a nitrogen purge. Aminoethyl methacrylate-containing PEG particles are observed in the mold after separation of the PFPE mold and the treated silicon wafer using optical microscopy. Separately, a solution containing 10 weight percent fluorescein isothiocyanate (FITC) in dimethylsulfoxide (DMSO) is created. Following this, the mold containing the particles is exposed to the FITC solution for one hour. Excess FITC is rinsed off the mold surface with DMSO followed by deionized (DI) water. Particles, tagged only on one face, will be observed with fluorescence microscopy, with an excitation wavelength of 492 nm and an emission wavelength of 529 nm.

3.38 Formation of an Imprinted Protein Binding Cavity and an Artificial Protein.

The desired protein molecules are adsorbed onto a mica substrate to create a master template. A mixture of PFPE-dimethacrylate (PFPE-DMA) containing a monomer with a covalently attached disaccharide, and 1-hydroxycyclohexyl phenyl ketone as a photoinitiator was poured over the substrate. The substrate is then subjected to UV light ($\lambda$=365 nm) for 10 minutes while under a nitrogen purge. The fully cured PFPE-DMA mold is then released from the mica master, creating polysaccharide-like cavities that exhibit selective recognition for the protein molecule that was imprinted. The polymeric mold was soaked in NaOH/NaClO solution to remove the template proteins.

Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Separately, a solution of 25% (w/w) methacrylic acid (MAA), 25% diethyl aminoethylmethacrylate (DEAEM), and 48% PEG diacrylate was formulated with 2 wt % photoinitiator. Following this, 200 µL of this monomer solution is then placed on the treated silicon wafer and the patterned PFPE/disaccharide mold placed on top of it. The substrate is then placed in a molding apparatus and a small pressure is applied to push out excess solution. The entire apparatus is then subjected to UV light ($\lambda$=365 nm) for ten minutes while under a nitrogen purge. Removal of the mold yields artificial protein molecules which have similar size, shape, and chemical functionality as the original template protein molecule.

Example 4

Figure 30:
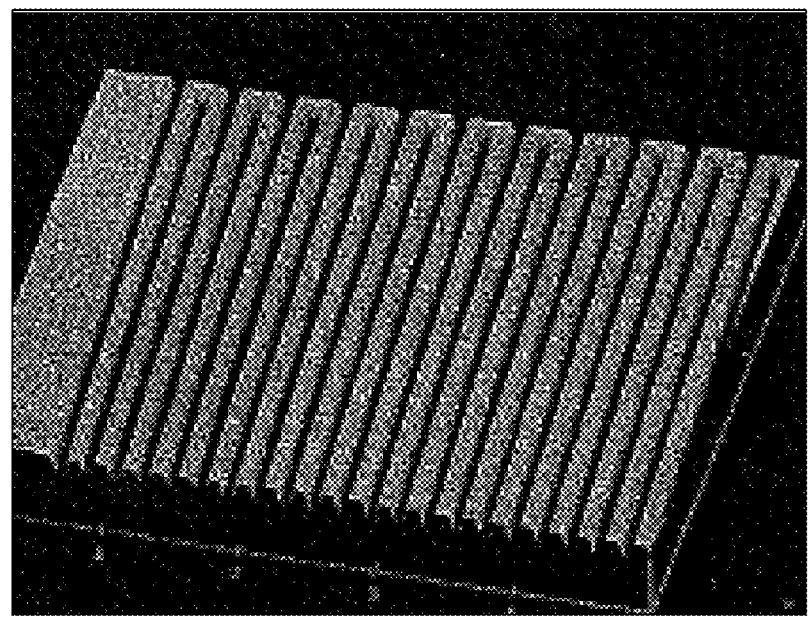
FIG. 30 is an atomic force micrograph image of 140-nm lines of TMPTA separated by distance of 70 nm that were fabricated using a PFPE mold.

Molding of Features for Semiconductor Applications 4.1 Fabrication of 140-nm Lines Separated by 70 nm in TMPTA A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. Flat, uniform, surfaces are generated by treating a silicon wafer cleaned with "piranha" solution (1:1 concentrated sulfuric acid:30% hydrogen peroxide (aq) solution) and treating the wafer with an adhesion promoter, (trimethoxysilyl propyl methacrylate). Following this, 50 µL of TMPTA is then placed on the treated silicon wafer and the patterned PFPE mold placed on top of it. The substrate is then placed in a molding apparatus and a small pressure is applied to ensure a conformal contact. The entire apparatus is then subjected to UV light ($\lambda$=365 nm) for ten minutes while under a nitrogen purge. Features are observed after separation of the PFPE mold and the treated silicon wafer using atomic force microscopy (AFM) (see FIG. 30).

4.2 Molding of a Polystyrene Solution

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, polystyrene is dissolved in 1 to 99 wt % of toluene. Flat, uniform, surfaces are generated by treating a silicon wafer cleaned with "piranha" solution (1:1 concentrated sulfuric acid:30% hydrogen peroxide (aq) solution) and treating the wafer with an adhesion promoter. Following this, 50 µL of polystyrene solution is then placed on the treated silicon wafer and the patterned PFPE mold is placed on top of it. The substrate is then placed in a molding apparatus and a small pressure is applied to ensure a conformal contact. The entire apparatus is then subjected to vacuum for a period of time to remove the solvent. Features are observed after separation of the PFPE mold and the treated silicon wafer using atomic force microscopy (AFM) and scanning electron microscopy (SEM).

4.3 Molding of Isolated Features on Microelectronics-Compatible Surfaces Using "Double Stamping"

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. A flat, non-wetting surface is generated by photocuring a film of PFPE-DMA onto a glass slide, according to the procedure outlined for generating a patterned PFPE-DMA mold. 50 µL of the TMPTA/photoinitiator solution is pressed between the PFPE-DMA mold and the flat PFPE-DMA surface, and pressure is applied to squeeze out excess TMPTA monomer. The PFPE-DMA mold is then removed from the flat PFPE-DMA surface and pressed against a clean, flat silicon/silicon oxide wafer and photocured using UV radiation ($\lambda$=365 nm) for 10 minutes while under a nitrogen purge. Isolated, poly(TMPTA) features are observed after separation of the PFPE mold and the silicon/silicon oxide wafer, using scanning electron microscopy (SEM).

4.4 Fabrication of 200-nm Titania Structures for Microelectronics

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, 1 g of Pluronic P123 is dissolved in 12 g of absolute ethanol. This solution was added to a solution of 2.7 mL of concentrated hydrochloric acid and 3.88 mL titanium (IV) ethoxide. Flat, uniform, surfaces are generated by treating a silicon/silicon oxide wafer with "piranha" solution (1:1 concentrated sulfuric acid:30% hydrogen peroxide (aq) solution) and drying. Following this, 50 µL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sol-gel precursor has solidified. Oxide structures will be observed after separation of the PFPE mold and the treated silicon wafer using scanning electron microscopy (SEM).

4.5 Fabrication of 200-nm Silica Structures for Microelectronics

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, 2 g of Pluronic P123 is dissolved in 30 g of water and 120 g of 2 M HCl is added while stirring at 35° C. To this solution, add 8.50 g of TEOS with stirring at 35° C. for 20 h. Flat, uniform, surfaces are generated by treating a silicon/silicon oxide wafer with "piranha" solution (1:1 concentrated sulfuric acid:30% hydrogen peroxide (aq) solution) and drying. Following this, 50 µL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sol gel precursor has solidified. Oxide structures will be observed after separation of the PFPE mold and the treated silicon wafer using scanning electron microscopy (SEM).

4.6 Fabrication of 200-nm Europium-Doped Titania Structures for Microelectronics A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, 1 g of Pluronic P123 and 0.51 g of $EuCl_3.6H_2O$ are dissolved in 12 g of absolute ethanol. This solution was added to a solution of 2.7 mL of concentrated hydrochloric acid and 3.88 mL titanium (IV) ethoxide. Flat, uniform, surfaces are generated by treating a silicon/silicon oxide wafer with "piranha" solution (1:1 concentrated sulfuric acid:30% hydrogen peroxide (aq) solution) and drying. Following this, 50 µL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sol-gel precursor has solidified. Oxide structures will be observed after separation of the PFPE mold and the treated silicon wafer using scanning electron microscopy (SEM).

4.7 Fabrication of Isolated "Scum Free" Features for Microelectronics

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. Flat, uniform, non-wetting surfaces capable of adhering to the resist material are generated by treating a silicon wafer cleaned with "piranha" solution (1:1 concentrated sulfuric acid:30% hydrogen peroxide (aq) solution) and treating the wafer with a mixture of an adhesion promoter, (trimethoxysilyl propyl methacrylate) and a non-wetting silane agent (1H,1H,2H,2H-perfluorooctyl trimethoxysilane). The mixture can range from 100% of the adhesion promoter to 100% of the non-wetting silane. Following this, 50 µL of TMPTA is then placed on the treated silicon wafer and the patterned PFPE mold placed on top of it. The substrate is then placed in a molding apparatus and a small pressure is applied to ensure a conformal contact and to push out excess TMPTA. The entire apparatus is then subjected to UV light ($\lambda$=365 nm) for ten minutes while under a nitrogen purge. Features are observed after separation of the PFPE mold and the treated silicon wafer using atomic force microscopy (AFM) and scanning electron microscopy (SEM).

Example 5

Figure 31A:
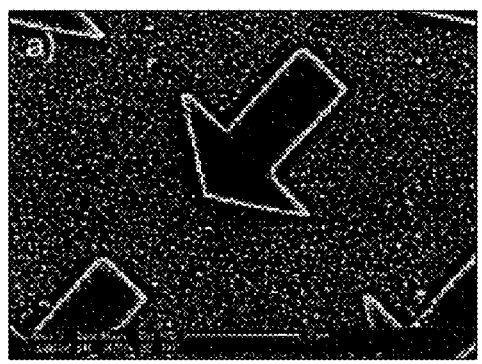
FIGS. 31A and 31B are a scanning electron micrograph of mold fabrication from electron-beam lithographically generated masters.
Figure 31B:
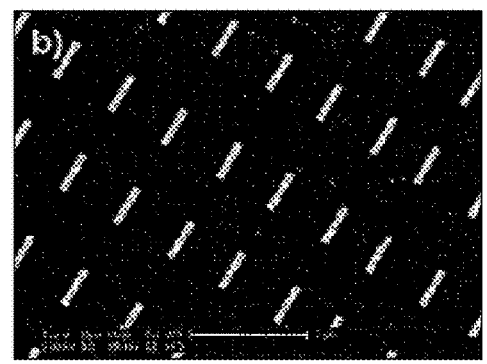

Molding of Natural and Engineered Templates 5.1. Fabrication of a Perfluoropolyether-Dimethacrylate (PFPE-DMA) Mold from a Template Generated Using Electron-Beam Lithography A template, or "master," for perfluoropolyether-dimethacrylate (PFPE-DMA) mold fabrication is generated using electron beam lithography by spin coating a bilayer resist of 200,000 MW PMMA and 900,000 MW PMMA onto a silicon wafer with 500-nm thermal oxide, and exposing this resist layer to an electron beam that is translating in a pre-programmed pattern. The resist is developed in 3:1 isopropanol:methyl isobutyl ketone solution to remove exposed regions of the resist. A corresponding metal pattern is formed on the silicon oxide surface by evaporating 5 nm Cr and 15 nm Au onto the resist covered surface and lifting off the residual PMMA/Cr/Au film in refluxing acetone. This pattern is transferred to the underlying silicon oxide surface by reactive ion etching with $CF_4/O_2$ plasma and removal of the Cr/Au film in aqua regia. (FIG. 31). This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. This mold can be used for the fabrication of particles using non-wetting imprint lithography as specified in Particle Fabrication Examples 3.3 and 3.4.

5.2 Fabrication of a Perfluoropolyether-Dimethacrylate (PFPE-DMA) Mold from a Template Generated Using Photolithography.

Figure 32A:
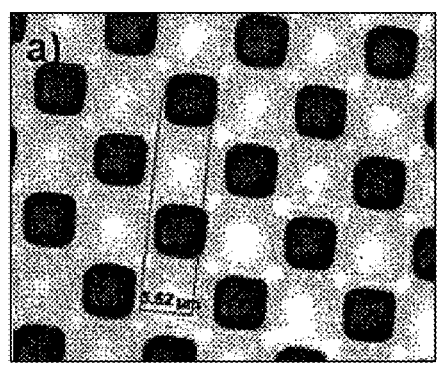
FIGS. 32A and 32B are an optical micrographic image of mold fabrication from photoresist masters.
Figure 32B:
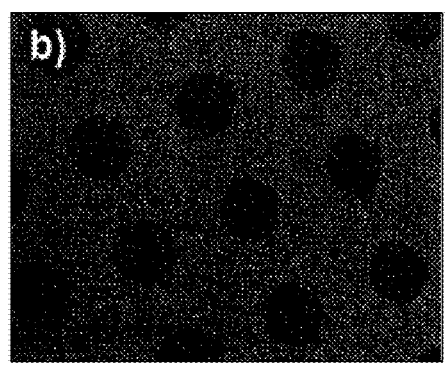

A template, or "master," for perfluoropolyether-dimethacrylate (PFPE-DMA) mold fabrication is generated using photolithography by spin coating a film of SU-8 photoresist onto a silicon wafer. This resist is baked on a hotplate at 95° C. and exposed through a pre-patterned photomask. The wafer is baked again at 95° C. and developed using a commercial developer solution to remove unexposed SU-8 resist. The resulting patterned surface is fully cured at 175° C. This master can be used to template a patterned mold by pouring PFPE-DMA containing 1-hydroxycyclohexyl phenyl ketone over the patterned area of the master. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master, and can be imaged by optical microscopy to reveal the patterned PFPE-DMA mold (see FIG. 32).

Figures 33A, 33B:
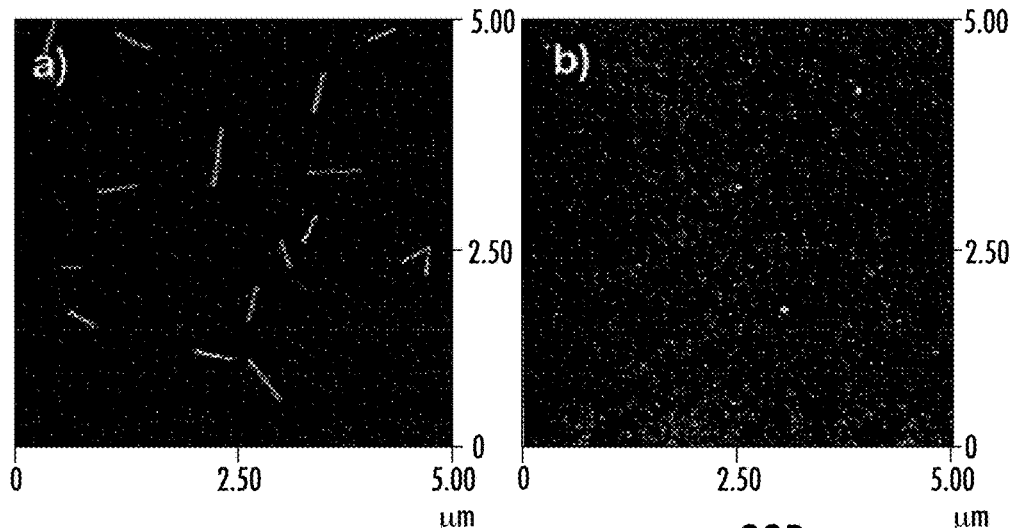
FIGS. 33A and 33B are an atomic force micrograph of mold fabrication from Tobacco Mosaic Virus templates.

5.3 Fabrication of a Perfluoropolyether-Dimethacrylate (PFPE-DMA) Mold from a Template Generated from Dispersed Tobacco Mosaic Virus Particles A template, or "master," for perfluoropolyether-dimethacrylate (PFPE-DMA) mold fabrication is generated by dispersing tobacco mosaic virus (TMV) particles on a silicon wafer (FIG. 33*a*). This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy (FIG. 33*b*).

Figures 34A, 34B:
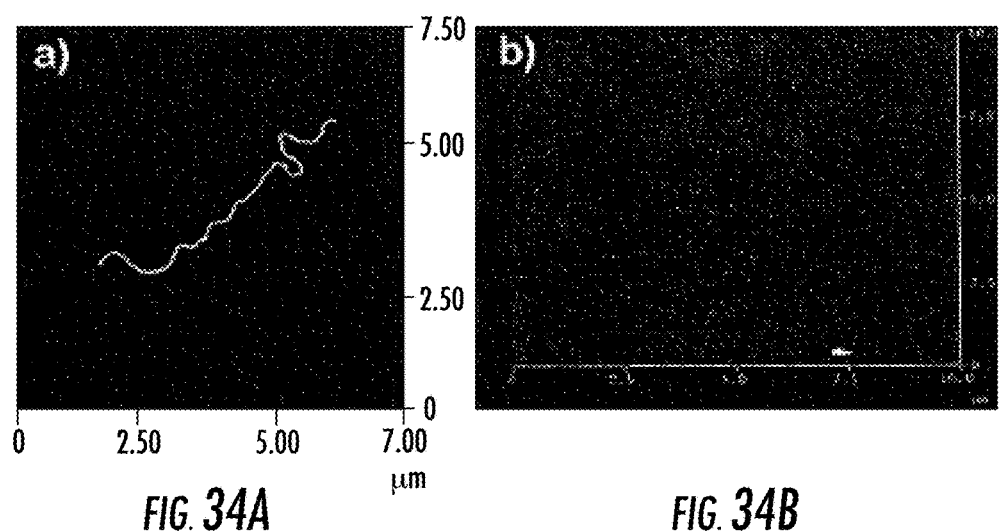
FIGS. 34A and 34B are an atomic force micrograph of mold fabrication from block copolymer micelle masters.
Figures 35A, 35B:
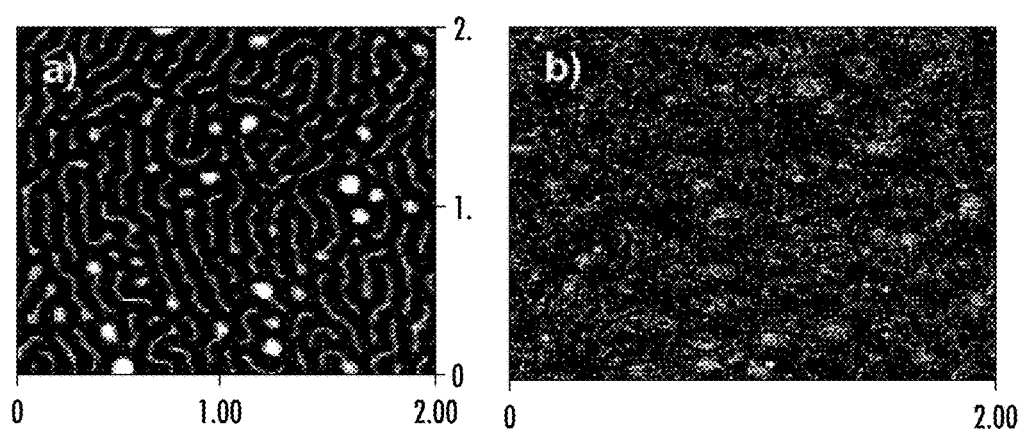
FIGS. 35A and 35B are an atomic force micrograph of mold fabrication from brush polymer masters.

5.4. Fabrication of a Perfluoropolyether-Dimethacrylate (PFPE-DMA) Mold from a Template Generated from Block-Copolymer Micelles A template, or "master," for perfluoropolyether-dimethacrylate (PFPE-DMA) mold fabrication is generated by dispersing polystyrene-polyisoprene block copolymer micelles on a freshly-cleaved mica surface. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy (see FIG. 34).

5.5 Fabrication of a Perfluoropolyether-Dimethacrylate (PFPE-DMA) Mold from a Template Generated from Brush Polymers.

A template, or "master," for perfluoropolyether-dimethacrylate (PFPE-DMA) mold fabrication is generated by dispersing poly(butyl acrylate) brush polymers on a freshly-cleaved mica surface. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy (FIG. 35).

5.6 Fabrication of a Perfluoropolyether-Dimethacrylate (PFPE-DMA) Mold from a Template Generated from Earthworm Hemoglobin Protein A template, or "master," for perfluoropolyether-dimethacrylate (PFPE-DMA) mold fabrication is generated by dispersing earthworm hemoglobin proteins on a freshly-cleaved mica surface. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy.

5.7 Fabrication of a Perfluoropolyether-Dimethacrylate (PFPE-DMA) Mold from a Template Generated from Patterned DNA Nanostructures A template, or "master," for perfluoropolyether-dimethacrylate (PFPE-DMA) mold fabrication is generated by dispersing DNA nanostructures on a freshly-cleaved mica surface. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy.

5.8 Fabrication of a Perfluoropolyether-Dimethacrylate (PFPE-DMA) Mold from a Template Generated from Carbon Nanotubes A template, or "master," for perfluoropolyether-dimethacrylate (PFPE-DMA) mold fabrication is generated by dispersing or growing carbon nanotubes on a silicon oxide wafer. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy.

Example 6

Method of Making Monodisperse Nanostructures Having a Plurality of Shapes and Sizes In some embodiments, the presently disclosed subject matter describes a novel "top down" soft lithographic technique; non-wetting imprint lithography (NoWIL) which allows completely isolated nanostructures to be generated by taking advantage of the inherent low surface energy and swelling resistance of cured PFPE-based materials.

The presently described subject matter provides a novel "top down" soft lithographic technique; non-wetting imprint lithography (NoWIL) which allows completely isolated nanostructures to be generated by taking advantage of the inherent low surface energy and swelling resistance of cured PFPE-based materials. Without being bound to any one particular theory, a key aspect of NoWIL is that both the elastomeric mold and the surface underneath the drop of monomer or resin are non-wetting to this droplet. If the droplet wets this surface, a thin scum layer will inevitably be present even if high pressures are exerted upon the mold. When both the elastomeric mold and the surface are non-wetting (i.e. a PFPE mold and fluorinated surface) the liquid is confined only to the features of the mold and the scum layer is eliminated as a seal forms between the elastomeric mold and the surface under a slight pressure. Thus, the presently disclosed subject matter provides for the first time a simple, general, soft lithographic method to produce nanoparticles of nearly any material, size, and shape that are limited only by the original master used to generate the mold.

Using NoWIL, nanoparticles composed of 3 different polymers were generated from a variety of engineered silicon masters. Representative patterns include, but are not limited to, 3-µm arrows (see FIG. 11), conical shapes that are 500 nm at the base and converge to <50 nm at the tip (see FIG. 12), and 200-nm trapezoidal structures (see FIG. 13). Definitive proof that all particles were indeed "scum-free" was demonstrated by the ability to mechanically harvest these particles by simply pushing a doctor's blade across the surface. See FIGS. 20 and 22.

Polyethylene glycol (PEG) is a material of interest for drug delivery applications because it is readily available, non-toxic, and biocompatible. The use of PEG nanoparticles generated by inverse microemulsions to be used as gene delivery vectors has previously been reported. K. McAllister et al., *Journal of the American Chemical Society* 124, 15198-15207 (Dec. 25, 2002). In the presently disclosed subject matter, NoWIL was performed using a commercially available PEG-diacrylate and blending it with 1 wt % of a photoinitiator, 1-hydroxycyclohexyl phenyl ketone. PFPE molds were generated from a variety of patterned silicon substrates using a dimethacrylate functionalized PFPE oligomer (PFPE DMA) as described previously. See J. P. Rolland, E. C. Hagberg, G. M. Denison, K. R. Carter, J. M. DeSimone, *Angewandte Chemie-International Edition* 43, 5796-5799 (2004). In one embodiment, flat, uniform, non-wetting surfaces were generated by using a silicon wafer treated with a fluoroalkyl trichlorosilane or by casting a film of PFPE-DMA on a flat surface and photocuring. A small drop of PEG diacrylate was then placed on the non-wetting surface and the patterned PFPE mold placed on top of it. The substrate was then placed in a molding apparatus and a small pressure was applied to push out the excess PEG-diacrylate. The entire apparatus was then subjected to UV light ($\lambda$=365 nm) for ten minutes while under a nitrogen purge. Particles were observed after separation of the PFPE mold and flat, non-wetting substrate using optical microscopy, scanning electron microscopy (SEM), and atomic force microscopy (AFM).

Poly(lactic acid) (PLA) and derivatives thereof, such as poly(lactide-co-glycolide) (PLGA), have had a considerable impact on the drug delivery and medical device communities because it is biodegradable. See K. E. Uhrich, S. M. Cannizzaro, R. S. Langer, K. M. Shakesheff, *Chemical Reviews* 99, 3181-3198 (November, 1999); A. C. Albertsson, I. K. Varma, *Biomacromolecules* 4, 1466-1486 (November-December, 2003). As with PEG-based systems, progress has been made toward the fabrication of PLGA particles through various dispersion techniques that result in size distributions and are strictly limited to spherical shapes. See C. Cui, S. P. Schwendeman, *Langmuir* 34, 8426 (2001).

The presently disclosed subject matter demonstrates the use of NoWIL to generate discrete PLA particles with total control over shape and size distribution. For example, in one embodiment, one gram of (3S)-cis-3,6-dimethyl-1,4-dioxane-2,5-dione was heated above its melting temperature to 110° C. and ~20 µL of stannous octoate catalyst/initiator was added to the liquid monomer. A drop of the PLA monomer solution was then placed into a preheated molding apparatus which contained a non-wetting flat substrate and mold. A small pressure was applied as previously described to push out excess PLA monomer. The apparatus was allowed to heat at 110° C. for 15 h until the polymerization was complete. The PFPE-DMA mold and the flat, non-wetting substrate were then separated to reveal the PLA particles.

To further demonstrate the versatility of NoWIL, particles composed of a conducting polymer polypyrrole (PPy) were generated. PPy particles have been formed using dispersion methods, see M. R. Simmons, P. A. Chaloner, S. P. Armes, *Langmuir* 11, 4222 (1995), as well as "lost-wax" techniques, see P. Jiang, J. F. Bertone, V. L. Colvin, *Science* 291, 453 (2001).

The presently disclosed subject matter demonstrates for the first time, complete control over shape and size distribution of PPy particles. Pyrrole is known to polymerize instantaneously when in contact with oxidants such as perchloric acid. Dravid et al. has shown that this polymerization can be retarded by the addition of tetrahydrofuran (THF) to the pyrrole. See M. Su, M. Aslam, L. Fu, N. Q. Wu, V. P. Dravid, *Applied Physics Letters* 84, 4200-4202 (May 24, 2004).

The presently disclosed subject matter takes advantage of this property in the formation of PPy particles by NoWIL. For example, 50 µL of a 1:1 v/v solution of THF:pyrrole was added to 50 µL of 70% perchloric acid. A drop of this clear, brown solution (prior to complete polymerization) into the molding apparatus and applied pressure to remove excess solution. The apparatus was then placed into the vacuum oven overnight to remove the THF and water. PPy particles were fabricated with good fidelity using the same masters as previously described.

Importantly, the materials properties and polymerization mechanisms of PLA, PEG, and PPy are completely different. For example, while PLA is a high-modulus, semicrystalline polymer formed using a metal-catalyzed ring opening polymerization at high temperature, PEG is a malleable, waxy solid that is photocured free radically, and PPy is a conducting polymer polymerized using harsh oxidants. The fact that NoWIL can be used to fabricate particles from these diverse classes of polymeric materials that require very different reaction conditions underscores its generality and importance.

In addition to its ability to precisely control the size and shape of particles, NoWIL offers tremendous opportunities for the *facile* encapsulation of agents into nanoparticles. As described in Example 3-14, NoWIL can be used to encapsulate a 24-mer DNA strand fluorescently tagged with CY-3 inside the previously described 200 nm trapezoidal PEG particles. This was accomplished by simply adding the DNA to the monomer/water solution and molding them as described. We were able to confirm the encapsulation by observing the particles using confocal fluorescence microscopy (see FIG. 28). The presently described approach offers a distinct advantage over other encapsulation methods in that no surfactants, condensation agents, and the like are required. Furthermore, the fabrication of monodisperse, 200 nm particles containing DNA represents a breakthrough step towards artificial viruses. Accordingly, a host of biologically important agents, such as gene fragments, pharmaceuticals, oligonucleotides, and viruses, can be encapsulated by this method.

The method also is amenable to non-biologically oriented agents, such as metal nanoparticles, crystals, or catalysts. Further, the simplicity of this system allows for straightforward adjustment of particle properties, such as crosslink density, charge, and composition by the addition of other comonomers, and combinatorial generation of particle formulations that can be tailored for specific applications.

Accordingly, NoWIL is a highly versatile method for the production of isolated, discrete nanostructures of nearly any size and shape. The shapes presented herein were engineered non-arbitrary shapes. NoWIL can easily be used to mold and replicate non-engineered shapes found in nature, such as viruses, crystals, proteins, and the like. Furthermore, the technique can generate particles from a wide variety of organic and inorganic materials containing nearly any cargo. The method is simplistically elegant in that it does not involve complex surfactants or reaction conditions to generate nanoparticles. Finally, the process can be amplified to an industrial scale by using existing soft lithography roller technology, see Y. N. Xia, D. Qin, G. M. Whitesides, *Advanced Materials* 8, 1015-1017 (December, 1996), or silk screen printing methods.

Example 7

Synthesis of Functional Perfluoropolyethers 7.1. Synthesis of Krytox® (DuPont, Wilmington, Del., United States of America) Diol to be Used as a Functional PFPE

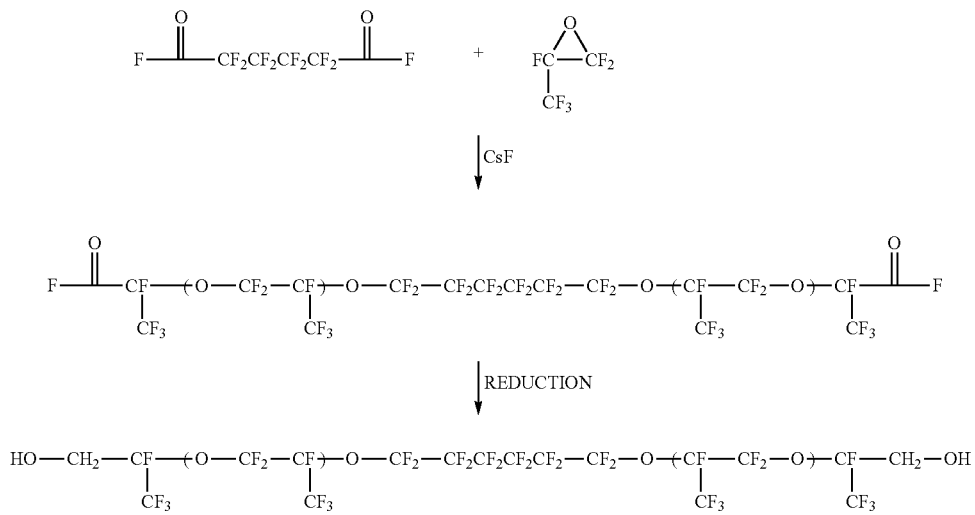

7.2 Synthesis of Krytox® (DuPont, Wilmington, Del., United States of America) Diol to be Used as a Functional PFPE

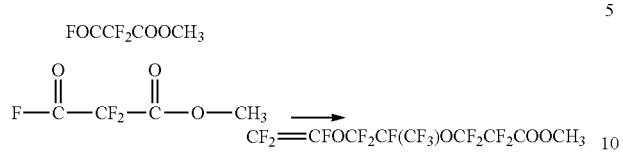

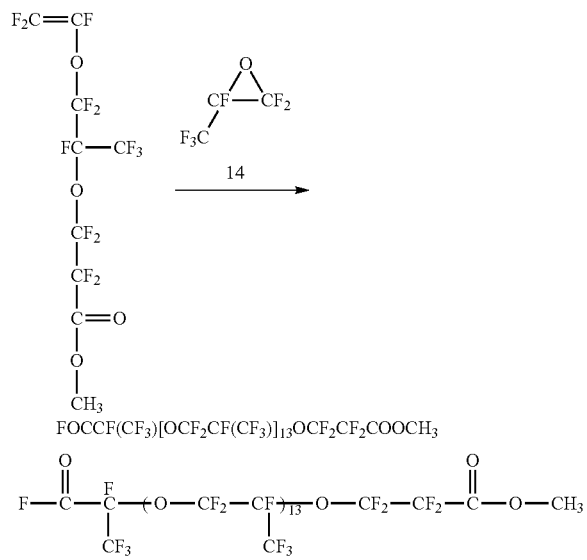

7.3 Synthesis of Krytox® (DuPont, Wilmington, Del., United States of America) Diol to be Used as a Functional PFPE

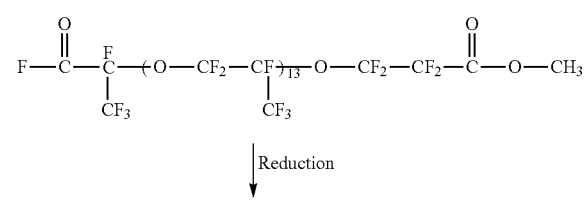

7.4 Example of Krytox® (DuPont, Wilmington, Del., United States of America) Diol to be Used as a Functional PFPE

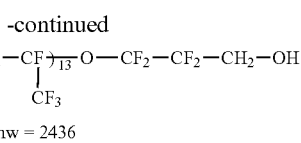

mw = 2436

7.5 Synthesis of a Multi-Arm PFPE Precursor

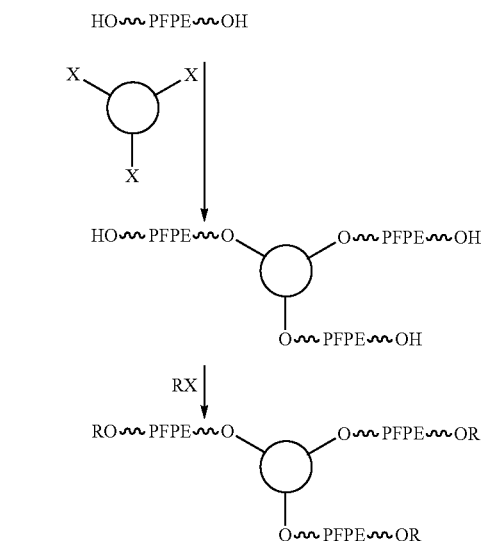

wherein, X includes, but is not limited to an isocyanate, an acid chloride, an epoxy, and a halogen; R includes, but is not limited to an acrylate, a methacrylate, a styrene, an epoxy, and an amine; and the circle represents any multifunctional molecule, such a cyclic compound. PFPE can be any perfluoropolyether material as described herein, including, but not limited to a perfluoropolyether material including a backbone structure as follows:

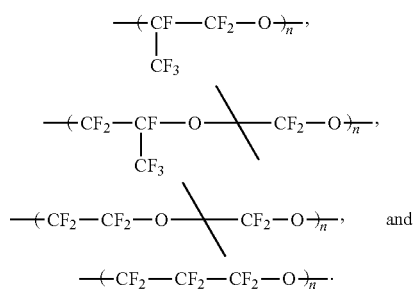

7.6 Synthesis of a Hyperbranched PFPE Precursor

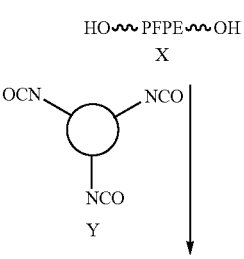

-continued

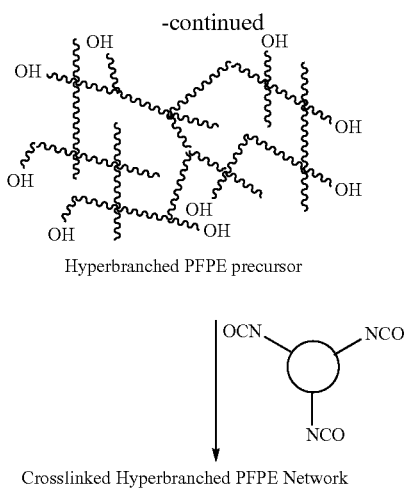

Hyperbranched PFPE precursor

Crosslinked Hyperbranched PFPE Network

∿∿ = PFPE Chain wherein, PFPE can be any perfluoropolyether material as described herein, including, but not limited to a perfluoropolyether material including a backbone structure as follows:

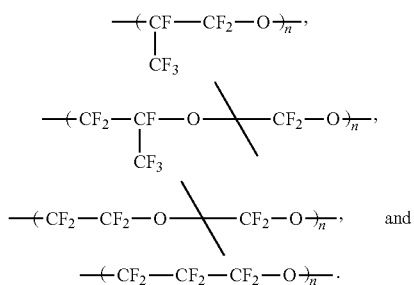

Example 8

Variability of Congruent Particle Fabrication 8.1 Fabrication of 200 nm Trapezoidal Particles from Various Matrix Materials To demonstrate the utility and flexibility of PRINT, shape specific organic particles composed of three different materials were generated from a commercially available silicon template (FIG. 49A) that is composed of a 2 dimensional array of 200 nm trapezoids. Elastomeric PFPE replica molds of the silicon master templates were generated by pouring a PFPE-dimethacrylate (PFPE-DMA) containing 1-hydroxycyclohexyl phenyl ketone over the silicon substrate patterned with 200-nm trapezoidal shapes. A poly(dimethylsiloxane) perimeter mold is used to confine the liquid PFPE-DMA to a desired area. The apparatus was then subjected to UV light ($\lambda$=365 nm) for 10 minutes while under a nitrogen purge. The fully cured PFPE-DMA mold was then released from the silicon master. This process was repeated to obtain several molds of the same master.

To fabricate monodisperse PLA particles using the PRINT™ process, one gram of (3S)-cis-3,6-dimethyl-1,4-dioxane-2,5-dione (melting point 92° C.) was heated to 110° C. and approximately 20 µL of stannous octoate catalyst/initiator is added to the liquid monomer. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Following this, 50 µL of molten Lactic acid containing catalyst is then placed on the treated silicon wafer preheated to 110° C. and the patterned PFPE mold is placed on top of it. A small pressure is applied to the top of the mold with a planar surface to push out excess monomer. The entire apparatus is then placed in an oven at 110° C. for 15 hours. After polymerization was achieved, the PFPE mold and the flat, nonwetting substrate were separated to reveal monodisperse 200 nm trapezoidal particles (FIG. 49B).

To further demonstrate the versatility and breadth of the PRINT technique, we chose to generate specifically shaped particles of 200 nm trapezoids from poly(pyrrole) (PPy). PPy has been used in a variety of applications, ranging from electronic devices and sensors to cell scaffolds. We fabricated PPy particles via one-step polymerization using the following method: flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl) silane via vapor deposition in a desiccator for 20 minutes. Separately, 50 µL of a 1:1 v:v solution of tetrahydrofuran:pyrrole is added to 50 µL of 70% perchloric acid (aq). A clear, homogenous, brown solution quickly forms and develops into black, solid, polypyrrole in 15 minutes. A drop of this clear, brown solution (prior to complete polymerization) is placed onto a treated silicon wafer, the PFPE mold is placed on top, and pressure is applied with a planar surface to remove excess solution. The apparatus is then placed into a vacuum oven for 15 h to remove the THF and water. Particles are observed using scanning electron microscopy (SEM) (see FIG. 49C) after release of the vacuum and separation of the PFPE mold and the treated silicon wafer.

Trapezoidal trimethylopropane triacrylate (TMPTA) particles were also generated using a photopolymerization technique. TMPTA is blended with 1 wt % of a photoinitiator, 1-hydroxycyclohexyl phenyl ketone. Uniform, non-wetting surfaces are generated by pouring a PFPE-dimethacrylate (PFPE-DMA) containing 1-hydroxycyclohexyl phenyl ketone over a silicon wafer. The wafer was then subjected to UV light ($\lambda$=365 nm) for 10 minutes while under a nitrogen purge. The fully cured PFPE-DMA substrate was then released from the silicon master. Following this, 50 µL of TMPTA is then placed on the PFPE substrate and the patterned PFPE mold placed on top of it. The substrate is then placed on a flat surface and a small pressure is applied to push out excess TMPTA. The entire apparatus is then subjected to UV light ($\lambda$=365 nm) for ten minutes while under a nitrogen purge. Particles are observed after separation of the PFPE mold and the treated silicon wafer using scanning electron microscopy (SEM). A flat blade was pushed along the surface to gather the fabricated 200 nm particles (see FIG. 49D).

Particles of the same unique dimensions made using these three different polymerization methods were evaluated using scanning electron microscopy and atomic force microscopy. The NIH Image program was used to measure the particle dimensions on the micrographs and compare them to images of the master template.

8.2 Fabrication of PEG Particles of Different Shapes and Sizes

Poly(ethylene glycol) (PEG) is a material of tremendous interest to the biotechnology community due to its commercial availability, nontoxic nature, and biocompatibility. Here, the PRINT was utilized to produce monodisperse, micro- and nanometer scale PEG particles in a variety of shapes by molding a PEG-diacrylate liquid monomer followed by room temperature photopolymerization. Because the morphology of the particles is controlled by the master, it is possible to generate complex particles on a variety of length scales.

A patterned perfluoropolyether (PFPE) molds are generated by pouring a PFPE-dimethacrylate (PFPE-DMA) containing 1-hydroxycyclohexyl phenyl ketone over a silicon substrate patterned with the desired shape. The silicon masters used include: 200 nm trapezoidal features (FIG. 50A); 200 nm×800 nm bars (FIG. 50B); 500 nm conical features that are <50 nm at the tip (FIG. 50C); 3 µm arrows (FIG. 50D); 10 µm boomerangs (FIG. 50E); and 600 nm cylinders (FIG. 50F). The master coated with uncured PFPE was then subjected to UV light ($\lambda$=365 nm) for 10 minutes while under a nitrogen purge. The fully cured PFPE-DMA mold was then easily released from the silicon master by peeling. Separately, a poly(ethylene glycol) (PEG) diacrylate (n=9) is blended with 1 wt % of a photoinitiator, 1-hydroxycyclohexyl phenyl ketone. Uniform, non-wetting surfaces are generated by pouring a PFPE-dimethacrylate (PFPE-DMA) containing 1-hydroxycyclohexyl phenyl ketone over a silicon wafer. The wafer was then subjected to UV light ($\lambda$=365 nm) for 10 minutes while under a nitrogen purge. The fully cured PFPE-DMA substrate was then released from the silicon master. Following this, 50 µL of PEG diacrylate is then placed on the PFPE film and the patterned PFPE mold placed on top of it. The substrate is then placed on a flat surface and a small pressure is applied to push out excess PEG-diacrylate. The pressure used was at least about 100 N/cm². The entire apparatus was then subjected to UV light ($\lambda$=365 nm) for ten minutes while under a nitrogen purge. Arrays of particles of different shapes and sizes are observed after separation of the PFPE mold and the treated silicon wafer using scanning electron microscopy (SEM). (See FIGS. 50A-50F)

Figure 51:
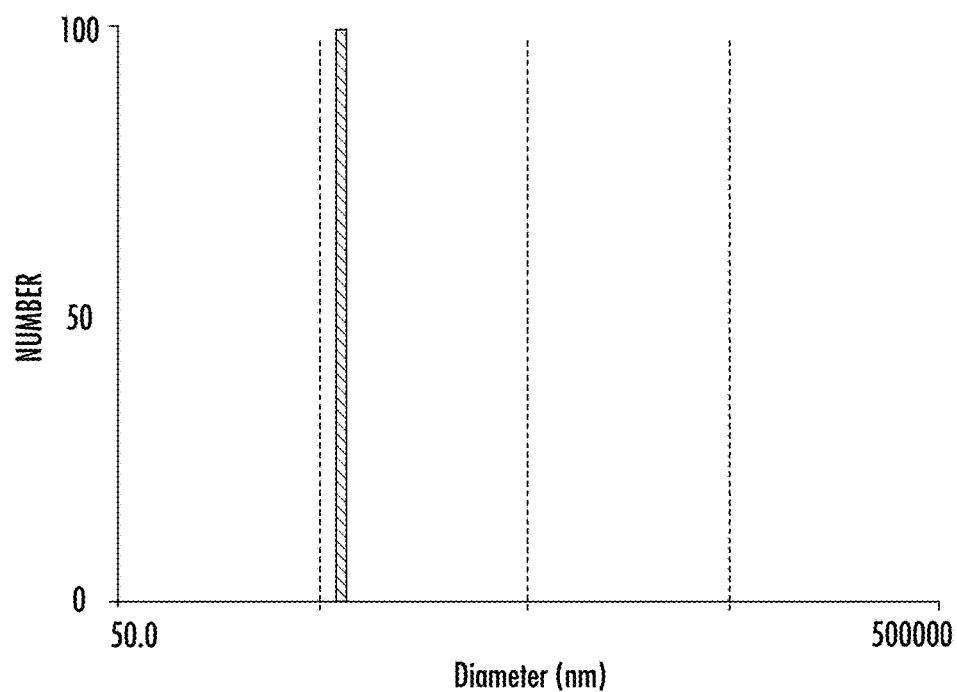
FIG. 51 shows a DLS trace showing congruent particles fabricated according to embodiments of the present invention.

Confirmation of the structural similarity between the silicon master and replicate PEG particles was confirmed via atomic force microscopy (AFM) and scanning electron microscopy (SEM). Atomic Force Microscopy was performed on a Nanoscope IIIa/Multimode AFM in tapping mode. Dynamic light scattering (DLS) is performed on particles suspended in phosphate buffered saline solution (PBS) to look for aggregation. This technique is designed for spherical particles; however, we can use the values empirically to look for large aggregates (some non-uniformity in size will be seen at a scale smaller than that of the particle diameter due to the non-spherical shapes of the particles) An example DLS trace is given in FIG. 51, with the value measured for the particle size as 0.62±0.2 µm. The line indicates monodispersity of the particles, with no aggregation occurring.

8.3 Utilizing PRINT Technology to Create Free-Flowing Particles, Particles on a Scum Layer, and Particles on a Film The PRINT technology can be used to generate a variety of products having varying forms, including free flowing particles and particles in an array on a film. The following example shows our ability to make poly(ethylene glycol) (PEG) based particles free flowing, as an array on a PEG film, and as an array on a different polymer film.

Figure 52A:
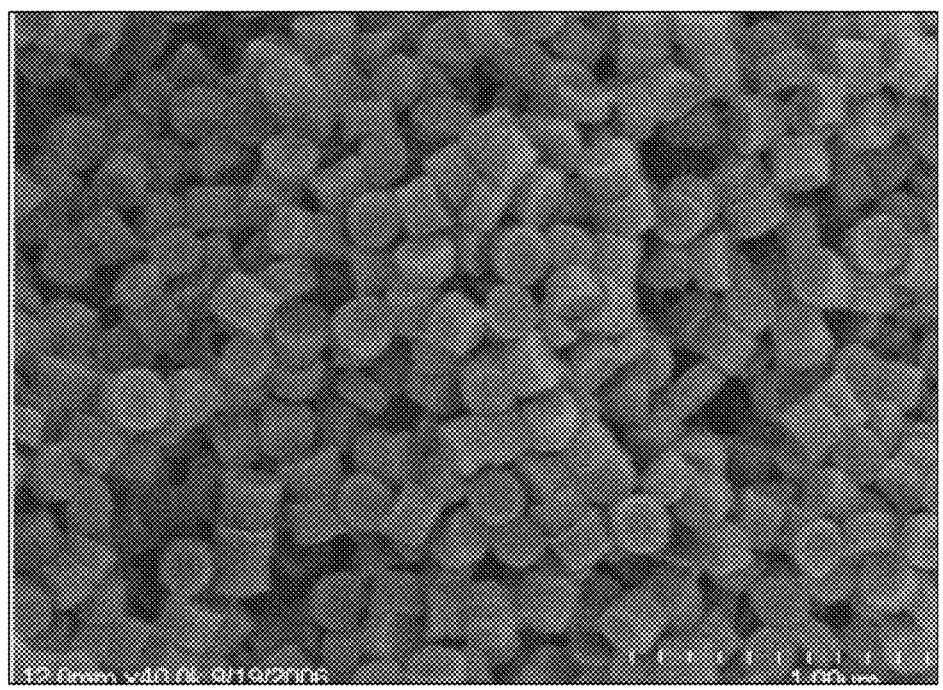
FIG. 52A shows discrete 200 nm PEG particles fabricated according to embodiments of the present invention.

Free-flowing Particles: A patterned perfluoropolyether (PFPE) mold was generated by pouring a PFPE-dimethacrylate (PFPE-DMA) containing 1-hydroxycyclohexyl phenyl ketone over a silicon substrate patterned with 200 nm tall×200 nm diameter cylinders. The PFPE-DMA covered master was then subjected to UV light ($\lambda$=365 nm) for 3 minutes while under a nitrogen purge. The fully cured PFPE-DMA mold was then released from the silicon master. Separately, a mixture of 790 mg trimethylolpropane ethoxylate triacrylate, 200 mg polyethylene glycol carbonylimidizole monomethacrylate, and 10 mg α-α-diethoxyacetophenone was prepared. This mixture was spotted directly onto the patterned PFPE-DMA mold and covered with an unpatterned polyethylene (PE) film. The monomer mixture was pressed between the two polymer sheets, and then the PE sheet was slowly peeled from the patterned PFPE-DMA to remove any excess monomer solution from the surface of the PFPE-DMA mold. The mold was then subjected to UV light ($\lambda$=365 nm) for 2 minutes while maintaining a nitrogen purge. The particles were harvested by placing 2 mL of DMSO on the mold and scrapping the surface with a glass slide. The particle suspension was transferred to a scintillation vial. One drop of the suspension was placed on a SEM stub and the solvent was allowed to evaporate. The stub was coated with approximately 10 angstroms of gold and imaged with SEM (FIG. 52A).

Figure 52B:
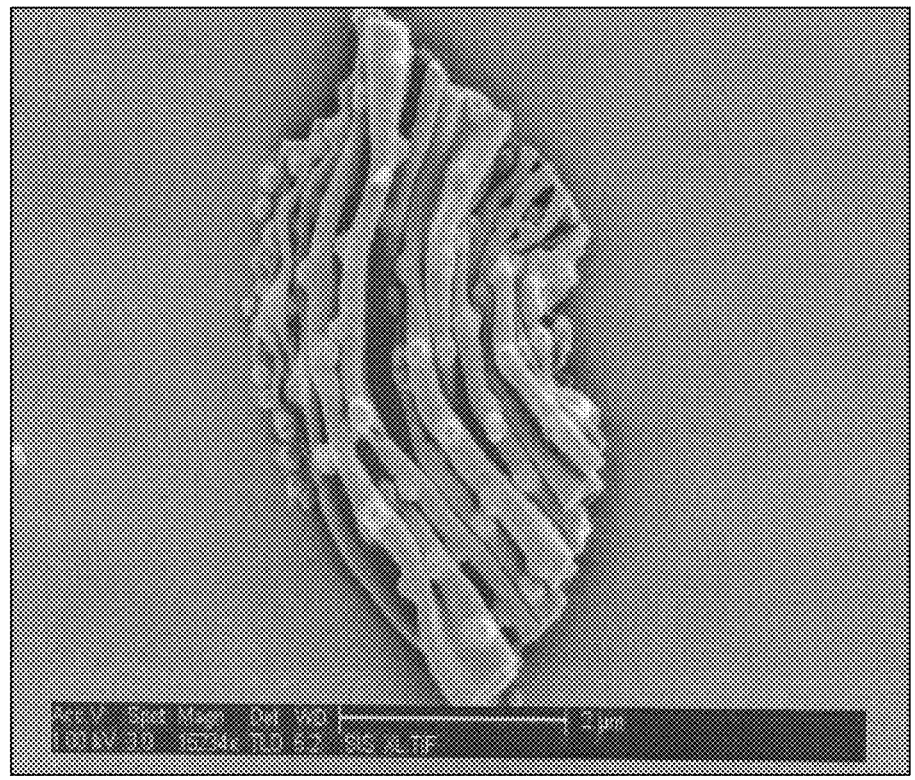
FIG. 52B shows 200 nm PEG particles connected by a PEG film after dragging a blade across a surface to roll up the film according to embodiments of the present invention.

Particles on a PEG film: A patterned perfluoropolyether (PFPE) mold is generated by pouring a PFPE-dimethacrylate (PFPE-DMA) containing 1-hydroxycyclohexyl phenyl ketone over a 6 inch silicon substrate patterned with 200-nm cylindrical shapes. The substrate is then subjected to UV light ($\lambda$=365 nm) for 10 minutes while under a nitrogen purge. The fully cured PFPE-DMA mold is then released from the silicon master. Separately, a solution of 30:70 PEG monomethacrylate:PEG diacrylate is formulated with 1 wt % photoinitiator. Following this, 200 µL of this PEG solution is then placed on an untreated silicon wafer and the patterned PFPE mold placed on top of it. The substrate is then placed on a flat substrate and a small pressure is applied to push out excess PEG solution. The entire apparatus is then subjected to UV light ($\lambda$=365 nm) for ten minutes while under a nitrogen purge. PEG particles connected by a PEG film will be observed after separation of the PFPE mold and the silicon wafer using scanning electron microscopy. Dragging a blade across the surface yields a rolled up film as shown in FIG. 52B.

Figure 52C:
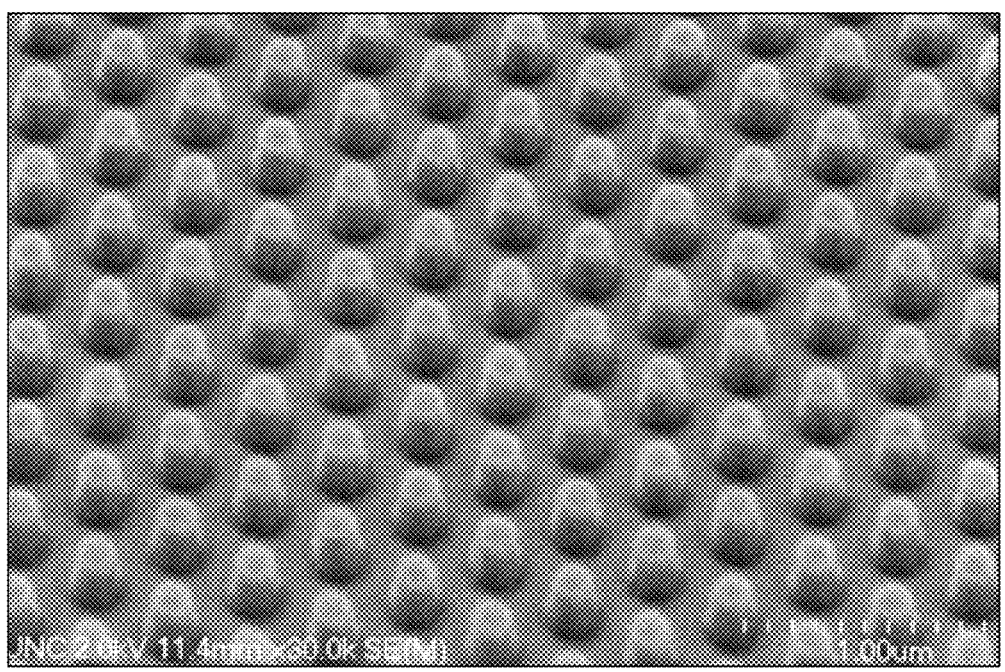
FIG. 52C shows 200 nm PEG particles coupled with a glass slide with a cyanoacrylate monomer according to embodiments of the present invention.

Particles on a cyanoacrylate film: A patterned perfluoropolyether (PFPE) mold is generated by pouring a PFPE-dimethacrylate (PFPE-DMA) containing 2,2-diethoxyacetophenone over a silicon substrate patterned with 200 nm cylindrical shapes. The apparatus is then subjected to a nitrogen purge for 10 minutes before the application of UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 28 wt % PEG methacrylate (n=9), 2 wt % azobisisobutyronitrile (AIBN), and 0.25 wt % rhodamine methacrylate. Flat, uniform, non-wetting surfaces are generated by coating a glass slide with PFPE-dimethacrylate (PFPE-DMA) containing 2,2-diethoxyacetophenone. The slide is then subjected to a nitrogen purge for 10 minutes, then UV light is applied ($\lambda$=365 nm) while under a nitrogen purge. The flat, fully cured PFPE-DMA substrate is released from the slide. Following this, 0.1 mL of the monomer blend is evenly spotted onto the flat PFPE-DMA surface and then the patterned PFPE-DMA mold placed on top of it. The surface and mold are then placed in a molding apparatus and a small amount of pressure is applied to remove any excess monomer solution. The entire apparatus is purged with nitrogen for 10 minutes, then subjected to UV light (λ=365 nm) for 10 minutes while under a nitrogen purge. Neutral PEG nanoparticles are observed after separation of the PFPE-DMA mold and substrate using scanning electron microscopy (SEM). A thin layer of cyanoacrylate monomer is sprayed onto the PFPE-DMA mold filled with particles. The PFPE-DMA mold is immediately placed onto a glass slide and the cyanoacrylate is allowed to polymerize in an anionic fashion for one minute. The mold is removed and the particles are embedded in the adhesive layer (see FIG. 52C).

8.4 Identification of PRINT Particles Using Nano-Scale "Defects"

Figures 53A, 53B:
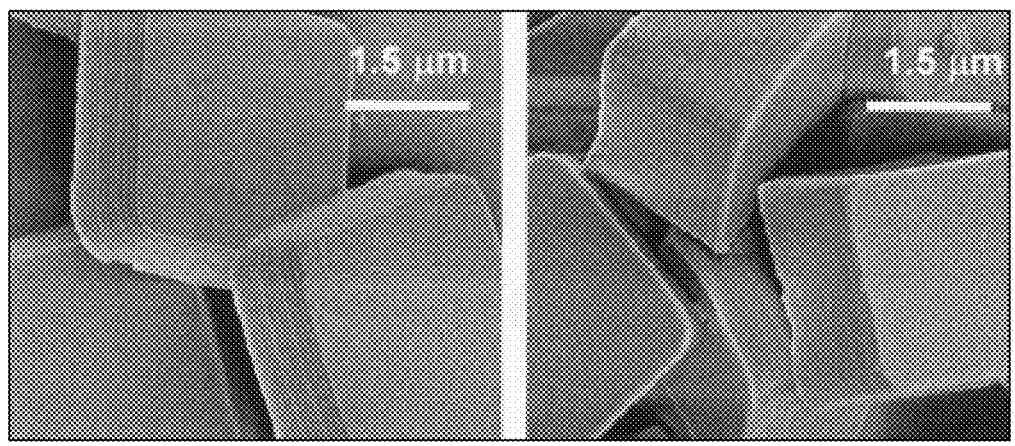
FIGS. 53A and 53B show 2 micrometer TMPTA particles having Bosch-type etch lines on sidewalls of the particles according to embodiments of the present invention.

The PRINT process inherently introduces structural features from the silicon masters that are transferred to the mold and subsequently to the particles during PRINT fabrication. Here, a Bosch-type etch is used to process a master which introduces a recognizable pattern ("Bosch etch lines") on the sidewalls of individual particles. Bosch etching is one of many techniques used to fabricate wafers, most of which leave residual "defects" on the sidewalls of the features or surface. FIGS. 53A and 53B shows distinct particles derived from the masters that show a similar sidewall pattern resulting from the specific Bosch-type etch process used on the master. In this case, this pattern can be recognized using SEM imaging and identifies these particles as originating from the same master.

A patterned perfluoropolyether (PFPE) mold is generated by pouring a PFPE-dimethacrylate (PFPE-DMA) containing 1-hydroxycyclohexyl phenyl ketone over a silicon substrate patterned with 3-μm cubical shapes at a 1 μm depth. The substrate is then subjected to a nitrogen purge for 10 minutes, then UV light (λ=365 nm) is applied for 10 minutes while under a nitrogen purge. The fully cured PFPE-DMA mold is then released from the silicon master. A PFPE-DMA mold is made from a master patterned with 2 μm deep cubical shapes Separately, TMPTA is blended with 1 wt % of a photoinitiator, 1-hydroxycyclohexyl phenyl ketone. Flat, uniform, non-wetting surfaces are generated by coating a glass slide with PFPE-DMA containing 1-hydroxycyclohexyl phenyl ketone. The slide is then subjected to a nitrogen purge for 10 minutes, then UV light (λ=365 nm) is applied for 10 minutes while under a nitrogen purge. The flat, fully cured PFPE-DMA substrate is released from the slide. Following this, 0.1 mL of TMPTA is then placed on the flat PFPE-DMA substrate and the patterned PFPE mold placed on top of it. The substrate is then placed in a molding apparatus and a small pressure is applied to push out excess TMPTA. The entire apparatus is then purged with nitrogen for 10 minutes, then subjected to UV light (λ=365 nm) for 10 minutes while under a nitrogen purge. TMPTA particles are observed after separation of the PFPE-DMA mold and substrate using optical microscopy. A drop of n-vinyl-2-pyrrolidone containing 5% photoinitiator, 1-hydroxycyclohexyl phenyl ketone, is placed on a clean glass slide. The PFPE-DMA mold containing particles is placed patterned side down on the n-vinyl-2-pyrrolidone drop. The slide is subjected to a nitrogen purge for 5 minutes, then UV light (λ=365 nm) is applied for 5 minutes while under a nitrogen purge. The slide is removed, and the mold is peeled away from the polyvinyl pyrrolidone and particles. Particles on the polyvinyl pyrrolidone were observed with optical microscopy. The polyvinyl pyrrolidone film containing particles was dissolved in water. Dialysis was used to remove the polyvinyl pyrrolidone, leaving an aqueous solution containing TMPTA particles. Samples dispersions from the 1 μm and 2 μm deep master are dropped on an SEM stub and the water allowed to evaporate in a vacuum oven. The particles were coated with ~10 Å gold-palladium and imaged with SEM (FIGS. 53A and 53B).

What is claimed is:

1. A delivery device, comprising:
   a dissolvable substrate of a first material, wherein the dissolvable substrate is dissolvable in biological fluids; and
   a plurality of substantially monodisperse particles configured from a second material;
   wherein, each particle of the plurality has (i) an engineered shape bounded by six substantially planar surfaces that each span respective entire sides of the particle and (ii) a maximum cross-sectional dimension of less than about 10 micrometers;
   wherein the plurality of substantially monodisperse particles are coupled with the dissolvable substrate in a substantially predetermined orientation; and
   wherein the second material comprises a therapeutically or pharmaceutically active agent dispersed throughout the entire particle.

2. The delivery device of claim 1, wherein the maximum cross-sectional dimension is between about 5 nanometers and about 5 micrometers.

3. The delivery device of claim 1, wherein the maximum cross-sectional dimension is less than about 500 nanometers.

4. The delivery device of claim 1, wherein said delivery device has a modulus from about 0.1 MPa to about 500 MPa.

5. The delivery device of claim 1, wherein the dissolvable substrate comprises a thickness of about twice a dimension of a particle of the plurality of particles.

6. The delivery device of claim 1, further comprising a second plurality of particles of a second size coupled with the dissolvable substrate.

7. The delivery device of claim 1, further comprising a second plurality of particles of a second shape coupled with the dissolvable substrate.

8. The delivery device of claim 1, further comprising an agent configured to couple the plurality of substantially monodisperse particles with the dissolvable substrate by interactions selected from the group consisting of covalent bonding, ionic bonding, electrostatic binding, surface energy, hydrogen bonding, van der Waals forces, other intra- and inter-molecular forces, adhesives, and a magnetic force.

9. The delivery device of claim 1, wherein said plurality of substantially monodisperse particles are arranged in a substantially ordered array.

10. The delivery device of claim 1, wherein said dissolvable substrate is a sugar-based dissolvable film.

11. The delivery device of claim 10, wherein said film is a sugar sheet comprising pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate and/or casein, or combinations thereof.

* * * * *